(12) United States Patent
Kennedy et al.

(10) Patent No.: US 7,622,271 B2
(45) Date of Patent: Nov. 24, 2009

(54) IDENTIFICATION OF AGING GENES THROUGH LARGE-SCALE ANALYSIS

(75) Inventors: Brian K. Kennedy, Redmond, WA (US); Matthew R. Kaeberlein, Kirkland, WA (US)

(73) Assignee: University of Washington, Seattle, WA (US)

( * ) Notice: Subject to any disclaimer, the term of this patent is extended or adjusted under 35 U.S.C. 154(b) by 510 days.

(21) Appl. No.: 11/107,542

(22) Filed: Apr. 15, 2005

(65) Prior Publication Data

US 2006/0068414 A1    Mar. 30, 2006

Related U.S. Application Data

(60) Provisional application No. 60/591,461, filed on Jul. 26, 2004.

(51) Int. Cl.
*G01N 33/53* (2006.01)
*A01N 63/00* (2006.01)
*G06F 19/00* (2006.01)

(52) U.S. Cl. .................. 435/7.31; 424/93.1; 702/19

(58) Field of Classification Search ................ None
See application file for complete search history.

(56) References Cited

OTHER PUBLICATIONS

Chen et al. (2003) Experimental Gerontology. vol. 38, pp. 1051-1063.*
Fabrizio et al. (2004) FEBS Letters. vol. 557, pp. 136-142.*
Itahana et al. (2003) Molecular and Cellular Biology. vol. 23, No. 1, pp. 389-401.*
Kapahi et al. (2004) Current Biology. vol. 14, pp. 885-890.*
Lin et al. (2000) Science. vol. 289, pp. 2126-2128.*
Vellai et al. (2003) Nature. vol. 426, pp. 620-621.*
Chen et al. Experimental Gerontology (2003) vol. 38, pp. 1051-1063.*
Abraham, R. T. et al., "Immunopharmacology of Rapamycin," *Annu. Rev. Immuno.* 14, 483, 1996.
Beretta, L. et al., "Rapamycin blocks the phosphorylation of 4E-BP1 and inhibits cap-dependent initiation of translation," *EMBO J.* 15(3), 658-664, 1996.
Brown, E. J. et al., "A mammalian protein targeted by G1-arresting rapamycin-receptor complex," *Nature* 369, 756-758, Jun. 30, 1994.
Dumont, F. J. et al., "Distinct Mechanisms of Supression of Murine T Cell Activation by the Related Macrolides FK-506 and Rapamycin," *J. Immunol* 144, 251-258, 1990.
Feldmann, H. et al., "Complete DNA sequence of yeast chromosome II," *EMBO J.* 13, 5795-5809, 1994.

(Continued)

*Primary Examiner*—Lori A Clow
(74) *Attorney, Agent, or Firm*—Fenwick & West LLP

(57) ABSTRACT

High throughput methods for screening genetic variants that are phenotypically distinguishable are provided. Methods for identifying "long-lived" genetic variants among a set of variants are also provided. Methods for identifying pharmaceutical compounds that can promote longevity in various subjects, including mammals, and that can delay the onset of various diseases associated with aging are also provided. Various vectors and host cells containing identified genes/gene products are useful for screening longevity-promoting compounds that can interact with life-span-regulating genes/gene products. Pharmaceutical compositions that can promote longevity are also provided.

10 Claims, 25 Drawing Sheets

Replicative Life Span (RLS) Analysis

OTHER PUBLICATIONS

Jefferies, H. B. J. et al., "Rapamycin suppresses 5' TOP mRNA translation through inhibition of p70$^{s6k}$," *EMBO J.* 16(12), 3693-3704, 1997.

Johnston, M. et al., "The nucleotide sequence of *Saccharomyces cerevisiae* chromosome XII," *Nature* 387(6632), 87-90, 1997.

Goffeau et al., "Life with 6000 Genes," *Science* 274, 546-547, 1996.

Huang, M-E. et al., "Analysis of a 62 kb DNA Sequence of Chromosome X Reveals 36 Open Reading Frames and a Gene Cluster with a Counterpart on Chromosome XI," *Yeast* 12, 869-875, 1996.

Kunz, J. et al., "Target of Rapamycin in Yeast, TOR2, Is an Essential Phosphatidylinositol Kinase Homolog Required for $G_1$ Progression," *Cell* 73, 585-596, 1993.

Philippsen, P. et al., "The nucleotide sequence of *Saccharomyces* XIV and its evolutionary implications," *Nature* 387(6632), 93-98, 1997.

Raught, B. et al., "The target of rapamycin (TOR) proteins," *Proc. Natl. Acad. Sci U.S.A..* 98(13), 7037-7044, 2001.

\* cited by examiner

Table 1. Probability of Type I and Type II Errors for Mean Threshold Values at Hypothetical Set Sizes

| Set Size | Mean Threshold Value | Probability of Correct Classification of LL when μRLS > Mean Threshold Value | Probability of Type II Error | Probability of Type I Error |
|---|---|---|---|---|
| 3 | 23 | 0.95 | 0.05 | 0.73 |
| 5 | 26 | 0.95 | 0.05 | 0.52 |
| 5 | 36 | 0.52 | 0.48 | 0.009 |
| 10 | 28 | 0.96 | 0.04 | 0.18 |
| 20 | 31 | 0.95 | 0.05 | 0.01 |

FIG. 11

IDENTIFICATION OF AGING GENES THROUGH LARGE-SCALE ANALYSIS

CROSS-REFERENCE TO RELATED APPLICATIONS

This application claims the benefit of U.S. Provisional Application No. 60/591,461, filed on Jul. 26, 2004, the disclosure of which is incorporated herein in its entirety.

STATEMENT OF GOVERNMENT SUPPORT

This invention was made by government support by Grant No. P30 AG0133280 from the National Institutes of Health. The Government has certain rights in this invention.

FIELD

The present invention relates to methods for identifying genes that confer longevity, methods for utilizing the identified genes to screen pharmacological agents useful for extending life spans, and related compositions comprising identified gene sequences.

BACKGROUND

In general, the life span of an organism is defined by measuring its chronological age. Alternatively, the life span of yeasts can be determined by measuring the number of mitotic divisions completed by a mother cell prior to senescence, defined as the replicative life span ("RLS"). To determine the RLS for a yeast mother cell, each daughter cell needs to be physically removed from a mother cell after each mitotic cycle. Yeast strains that are genetically predisposed to a long life span are identified, for example, by measuring a mean RLS for a statistically reliable number of mother cells for each strain, and by comparing the determined mean RLS value to a mean RLS value of a reference population. Alternatively, life spans can be measured by determining the median RLS value observed for a given strain, or by determining the maximum RLS value observed for a strain.

The labor-intensive nature of the RLS assay and the vast number of individual RLS determinations that need to be performed for a statistically significant set of each variant in a library have precluded attempts to comprehensively approach the identification of aging mutations by implementing a genome-wide characterization. For example, because laboratory yeast strains are highly variable, approximately 40 to 50 cells of each genotype are evaluated in order to determine a statistically reliable mean RLS for a particular strain of interest. When 50 cells of each genetic variant from a hypothetical genomic library containing 5,000 variants are used to determine the mean RLS, then a total number of 250,000 RLS determinations would need to be performed. Determinations of such large numbers of RLSs is impractical, and, therefore, comprehensive analysis of a large collection of strains representing variants of a yeast genome have not been carried out.

Prior to the present invention, RLS determinations have been made utilizing yeast strains of highly disparate backgrounds, including different short-lived strains that have a mean RLS less than the mean RLS of other wildtype yeast strains. Since laboratory yeast strains are highly divergent at the genomic level, many mutations identified from these variant strains may affect RLS in a strain-specific manner. For example, mutations that increase the life span of short-lived strains may result from suppression or reversion events that compensate for strain-specific mutations, and such longevity-promoting mutations may be specific to only that particular strain.

FIG. 1 illustrates aging regulatory pathways in eukaryotes. In yeast, at least two biological pathways that regulate life spans are known, a pathway mediated by the SIR2 gene and a pathway responsive to calorie restriction ("CR"). The Sir2 gene product is a NAD-dependent histone deacetylase that regulates the rate at which extra-chromosomal ribosomal DNA circles (ERCs) are formed in the nucleus of a mother cell. The accumulation of ERCs within a mother cell with each successive mitotic event is one mechanism by which yeast cells age. Deletion of Sir2 decreases life span by approximately 50%, and over-expression of Sir2 increases lifespan by approximately 30-40%. The Sir2 ortholog, Sir-2.1, regulates aging in *C. elegans* through a pathway dependent on the Daf-16 transcription factor. In mammals, a similar pathway exists, in which the Sir2 ortholog, SirT1, regulates the activity of FOXO3a, a Daf-16 ortholog. Although life-span-regulating mechanisms of most eukaryotic organisms, including yeast, worms, and mammals, are highly responsive to calorie restriction (CR), gene products that regulate the CR pathway are, as yet, poorly characterized.

Analysis of yeast variants that are predisposed to longevity can yield previously uncharacterized genes that confer long life spans. An improved method for efficiently evaluating a large collection of genetic variants with differential life spans in order to identify genes that confer longevity is highly desirable. Gene products that regulate the life spans of eukaryotes can be targeted by pharmaceutical agents in order to decrease the rate of aging. Pharmaceutical agents and methods for screening such pharmaceutical agents that can increase the life expectancy of mammals, including humans, are highly desirable. In addition, by slowing the rate of aging, it may be possible to delay the onset of various diseases/conditions associated with aging, including various types of cancers, diabetes, cataracts, heart diseases, and neurodegenerative diseases, such as Parkinson's disease, Huntington disease, and amyloid diseases.

SUMMARY

In one aspect, the present invention provides a high throughput method for screening genetic variants that are phenotypically distinguishable. Various embodiments of the present invention are directed to methods for identifying "long-lived" genetic variants among a set of variants. Each variant of a set is evaluated, in turn, to determine whether the variant exhibits a long life span based on a phenotypic measurement. Long-lived variants identified by various methods of the present invention enable the identification of life-span-regulating genes conserved among eukaryotes.

In another aspect, the present invention relates to methods for identifying pharmaceutical compounds that are useful for prolonging the life spans of mammals and for delaying the onset of various mammalian diseases. Various vectors and host cells containing identified genes and gene products of the present invention are useful as an assay for screening compounds that can suppress, inactivate, or modulate the expression of identified genes. In another aspect, the present invention relates to pharmaceutical compositions that can modulate the activities of identified genes/gene products of the present invention.

The present invention therefore provides nucleic acids encoding replicative life span proteins. The invention therefore provides methods of screening for variants. The invention further provides compounds, e.g., small organic molecules, antibodies, peptides, lipids, peptides, cyclic peptides, nucleic acids, antisense molecules, RNAi molecules, and ribozymes, that are capable of modulating replicative life span genes and gene products, e.g., inhibiting replicative life span genes. Therapeutic and diagnostic methods and reagents are also provided.

In one aspect, a method for screening and for sorting a set of genetic variants to determine whether a genetic variant within the set of genetic variants exhibits a phenotype of interest, the method comprising: providing a set of genetic variants; iteratively for each genetic variant in the set of genetic variants, selecting a number N of cells for the genetic variant; quantitatively measuring a phenotype for the N cells of the genetic variant; classifying the genetic variant as positive, negative, or ambiguous based on quantitatively measuring the phenotype; and removing the genetic variant from the set of genetic variants, when the genetic variant is classified as positive or negative; and incrementing a number of iterations until either the number of iterations equals a maximum number of iterations or the set of genetic variants is empty. In some aspects, the N is same for each variant. In other aspects, the N is variable for different variants selected. In another aspect, the classifying the variant further comprises: establishing a positive threshold value; establishing a negative threshold value; comparing the phenotypic measurement to the positive threshold value and to the negative threshold value; evaluating whether the determined phenotypic measurement is greater than the positive threshold value, or less than the negative threshold value; classifying the variant as positive when the determined phenotypic measurement is greater than the positive threshold value; classifying the variant as negative when the determined phenotypic measurement is less than the negative threshold value; and classifying the variant as ambiguous when the determined phenotypic measurement is not greater than the positive threshold value nor less than the negative threshold value. In some aspects, the measuring a phenotype is determining a mean replicative life span for N cells of the variant. In some such aspects, the negative threshold value is established by determining the mean life span value of a statistically reliable set of a wildtype reference, and wherein the positive threshold value is established by determining the mean life span value of a statistically reliable set of variants exhibiting a life span substantially greater than that of the wildtype reference. In some methods, the sample size N is an integer greater than 3 and less than 20, when the variant is a yeast strain containing a mutation that affects the expression of at least one gene, and wherein the maximum number of iterations is between 2 and 5. In some aspects, the positive variant has a mean replicative life span substantially greater than the mean replicative life span of a wildtype reference, and wherein the negative variant has a mean replicative life span less than the mean replicative life span of the wildtype reference. In some such methods, the mean replicative life span of the positive variant is at least about 20% greater than the mean replicative life span of the wildtype reference. In some such aspects, the determining the N further comprises minimizing the misclassification of variants that further includes: minimizing the classification of a positive variant having a mean replicative life span substantially greater than that of a wildtype reference as a negative variant; and minimizing the classification of a negative variant having a mean replicative life span less than that of the wildtype reference as a positive variant. In some aspects, measuring a phenotype further comprises: establishing a first dataset that includes replicative life span values for N cells of a variant, wherein the replicative life span value for each cell of N is included; establishing a second dataset by selecting a subset of the first dataset, wherein the second dataset includes highest replicative life span values observed for the first dataset; determining a mean replicative life span from values included in the second dataset; and utilizing the determined mean replicative life span as the phenotypic measurement for the classification of variants. In some aspects, the classifying the variant further comprises: iteratively for each variant of the set, computing a mean replicative life span for each variant; computing a median replicative life span for the set of variants; computing an average median mean replicative life span for the set; and normalizing the mean replicative life span for each variant. In other such aspects, the normalizing further includes multiplying the computed mean replicative life span for each variant by a coefficient value, wherein the coefficient value is computed by dividing the median replicative life span for the set of variants by the average median mean replicative life span for the set.

In another aspect, the invention provides a method for identifying genes having life-span-regulating activity, the method comprising: identifying a variant having substantially greater life span than the life span of a wildtype reference, according to the method of described herein; and identifying a gene having life-span-regulating activity from the variant.

In another aspect, the invention provides a method for inhibiting the activity of a replicative life span protein, wherein the replicative life span protein is a gene product of a gene set forth in Table 5 or ortholog thereof, or a fragment thereof, the method comprising binding an inhibitor to the replicative life span protein. In some aspects the replicative life span genes identified by the methods of the invention include BRE5, FOB1, IDH2, REI1. ROM2, RPL31A, RPL6B, TOR1, YBR238C, YBR255W, YBR266C, YOR135C, SCH9, or URE2 or any ortholog thereof, or fragment thereof.

In another aspect, the invention provides a vector comprising: a sequence having a life-span-regulating activity, and encoding a polypeptide that has at least about 40% sequence similarity to at least one at least one sequence for a gene indicated in Table 5 or ortholog thereof; and a promoter operably-linked to the sequence. In some aspects, the sequence hybridizes to at least one of the sequences for the genes indicated in Table 5 or ortholog thereof, or complementary sequences of at least one sequence for a gene indicated in Table 5 or ortholog thereof, under moderately stringent hybridization conditions. In some such aspects the sequence is mammalian. In other such aspects, the sequence comprises at least one of sequence for a gene indicated in Table 5 or ortholog thereof. In some aspects, a host cell comprising the vector discussed above.

In another aspect, the invention provides a method for identifying a compound that prolongs a life span of a host, the method comprising: providing a set of target molecules that includes one or more sequences having life-span-regulating activity, and the target molecules having at least about 40% sequence similarity to the sequences for the genes indicated in Table 5 or 6, or having a complementary sequence to molecules that have 40% sequence similarity the sequences for the genes indicated in Table 5 or 6; exposing a library of compounds to the set of target molecules; determining an experimental value correlating with the extent of a biochemical reaction between the compound and the target molecule; comparing the experimental value against a pre-established threshold value; and determining that the compound has a longevity-promoting activity when the experimental value exceeds the pre-established threshold value. In some aspects, the target molecules have at least about 70% sequence similarity to the sequences for the genes indicated in Table 5 or 6, or is a complementary sequence to molecules having 70% sequence similarity to the sequences for the genes indicated in Table 5 or 6.

In another aspect, the invention provides a method for identifying a compound that prolongs a life span of a host, the method comprising: providing a first eukaryotic host deficient in the expression of sir2 and fob1; determining a life span of the first host that has, not been exposed to a test compound; exposing the test compound to a second eukaryotic host of the same genotype as the first host; determining a life span of the second host that has been exposed to the test compound; comparing the life spans of the first and second hosts; and determining that the compound has a longevity-promoting activity when the life span of the second host exceeds the life span of the first host.

In another aspect, the invention provides a compound that increases a life span of a host, the compound comprising an oligonucleotide that interacts with a gene having at least about 40% sequence similarity to at least one of the sequences for the genes indicated in Table 5 or 6, or a gene having at least 70% sequence similarity to at least one the sequences for the genes indicated in Table 5 or 6. In some aspects, the oligonucleotide interacts with a gene product encoded by the gene having at least about 40% sequence similarity to at least one of the sequences for the genes indicated in Table 5 or 6. In some such aspects, the oligonucleotide interacts with a gene product encoded by the gene having at least about 70% sequence similarity to at least one of the sequences for the genes indicated in Table 5 or 6. In other such aspects, the compound is at least one of: a single-stranded DNA oligonucleotide, double-stranded DNA oligonucleotide, a single-stranded RNA oligonucleotide, double-stranded RNA oligonucleotide, and modified variants of these. In some such aspects, the compound includes an anti-sense strand that hybridizes to an endogenous messenger RNA that encodes a protein having life-span-regulating activity, and that inhibits the translation of the messenger RNA.

In another aspect, the invention provides an antibody that increases a life span of a host, the antibody comprising: an antigen-binding domain that reacts with a polypeptide having at least about 40% sequence similarity to at least one least one of the sequences for the genes indicated in Table 5 or 6; and a constant region. In some aspects, the antigen-binding domain reacts with a polypeptide having at least about 70% sequence similarity to at least one least one of the sequences for the genes indicated in Table 5 or 6.

In another aspect, the invention provides a ribozyme that increases a life span of a host, the ribozyme comprising a sub-sequence that is complementary to a target molecule encoded by a gene having at least about 40% sequence similarity to at least one least one of the sequences for the genes indicated in Table 5 or 6. In some aspects, the target molecule is encoded by a gene having at least about 70% sequence similarity to at least one least one of the sequences for the genes indicated in Table 5 or 6.

In another aspect, the invention provides a pharmaceutical composition comprising: a compound as described herein; and a pharmaceutical carrier.

In another aspect, the invention provides a method for extending the life span of a eukaryotic organism, the method comprising administering to a subject, a pharmaceutical composition of as described herein containing an effective dose of a compound determined to have longevity-promoting activity.

In another aspect, the invention provides a non-human transgenic animal that exhibits a life span longer than a non-transgenic reference animal, and that has a genome comprising an inactivated or suppressed endogenous gene having at least about 40% sequence similarity to at least one least one of the sequences for the genes indicated in Table 5 or 6, or a gene having at least about 70% sequence similarity to at least one least one of the sequences for the genes indicated in Table 5 or 6.

In another aspect, the invention provides a method of evaluating the effect of a replicative life span bioactive agent comprising: a) administering the bioactive agent to a mammal; b) removing a cell sample from the mammal; and c) determining the expression profile of the cell sample. In some aspects, the method further comprises comparing the expression profile to an expression profile of a healthy individual. In other aspects, the expression profile includes at least one BRE5, FOB1, IDH2, REI1. ROM2, RPL31A, RPL6B, TOR1, YBR238C, YBR255W, YBR266C, YOR135C, SCH9, or URE2 gene, or ortholog thereof.

In another aspect, the invention provides an array of probes, comprising a support bearing a plurality of nucleic acid probes complementary to a plurality of mRNAs fewer than 1000 in number, wherein the plurality of mRNA probes includes an mRNA expressed by at least one BRE5, FOB1, IDH2, REI1. ROM2, RPL31A, RPL6B, TOR1, YBR238C, YBR255W, YBR266C, YOR135C, SCH9, or URE2 gene, or ortholog thereof. In some aspects, the invention provides a replicative mRNA expressed by akt-1, a homolog of sch9. In some aspects, the probes are cDNA sequences. In some such aspects, the array comprises a plurality of sets of probes, each set of probes complementary to subsequences from a mRNA.

In another aspect, the invention provides a biochip comprising one or more nucleic acid segments encoding the genes as shown in Table 5 or ortholog thereof, or a fragment thereof, wherein the biochip comprises fewer than 1000 nucleic acid probes. In some aspects, probes are cDNA sequences. In some aspects, biochip comprises a plurality of sets of probes, each set of probes complementary to subsequences from a mRNA.

In another aspects, the invention provides a replicative life span nucleic acid having a sequence at least 95% homologous to a sequence of a nucleic acid of Table 5 or ortholog thereof, or its complement. In some aspects, the a vector is provided comprising the nucleic acid molecule described above. In other aspects, the invention provides an isolated host cell comprising the vector described above.

In another aspect, the invention provides a method for producing a replicative life span protein, the method comprising the steps of: a) culturing the host cell as described above under conditions suitable for the expression of the polypeptide; and b) recovering the polypeptide from the host cell culture. In some aspects the host cell is a eukaryotic cell. In other aspects the host cell is a prokaryotic cell.

BRIEF DESCRIPTION OF THE DRAWINGS

FIG. 11 provides probabilities for Type I and Type II errors as a function of sample size and threshold values, in Table 1.

DETAILED DESCRIPTION

I. Introduction

Figure 1:
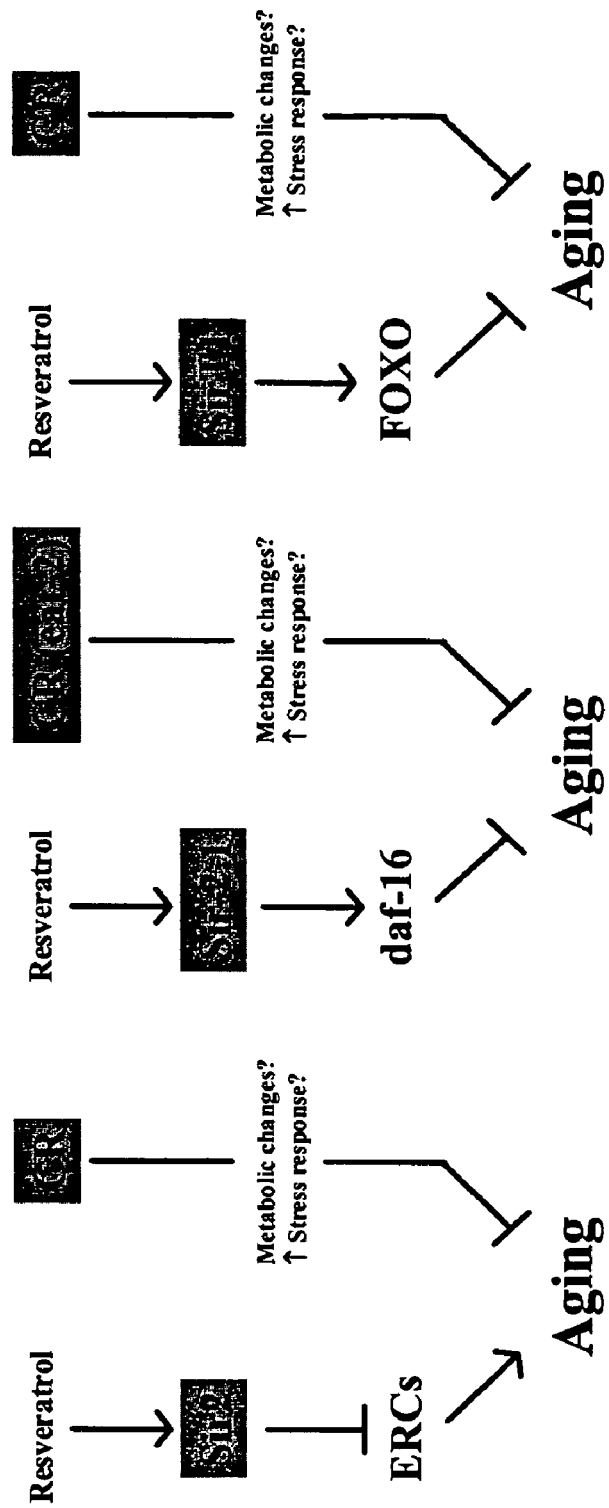
FIG. 1 illustrates aging-regulatory pathways in eukaryotes.

The invention provides a number of methods, reagents, and compounds that can be used either for the treatment of a replicative life span disease or disorder or a disease or disorder associated with aging (e.g., various types of cancers, diabetes mellitus, cataracts, heart diseases, and neurodegenerative diseases, such as Alzheimer's disease, Pick's disease, Huntington's disease, Parkinson's disease, adult onset myotonic dystrophy, multiple sclerosis, and adult onset leukodystrophy disease), the development of treatments for life span disorders or related disorders (e.g., various types of cancers, diabetes mellitus, cataracts, heart diseases, and neurodegenerative diseases, such as Alzheimer's disease, Pick's disease, Huntington's disease, Parkinson's disease, adult onset myotonic dystrophy, multiple sclerosis, and adult onset leukodystrophy disease), the practice of the other inventive methods described herein, or for a variety of other purposes.

It is to be understood that this invention is not limited to particular methods, reagents, compounds compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Replicative life span," abbreviated as "RLS," refers to a total number of mitotic divisions completed by a cell of interest prior to senescence or death. The determination of replicative life span is one measure of a yeast life span. An "RLS assay" is typically used to determine "replicative life spans." Replicative capacity of mammalian cell cultures can be estimated in vitro by enumerating the number of population doublings completed by a population of cells prior to mitotic arrest. Typically, cells of a known population are cultured under conditions that encourage cell division. For example, one method for determining life span of mammalian cultures is to count the number of times that such a population that has been reduced to half-density can mitotically divide to produce the original population density.

"Replicative life span protein" or "RLS" protein or fragment thereof, or nucleic acid encoding "replicative life span" or "RLS" or a fragment thereof refer to nucleic acids and polypeptide polymorphic variants, alleles, mutants, and interspecies homologs that: (1) have an amino acid sequence that has greater than about 40% amino acid sequence identity, 45%, 50%, 60%, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by a RLS nucleic acid or amino acid sequence of an RLS protein, e.g., a RLS protein as shown in Table 5 or ortholog as shown Table 6; (2) specifically bind to antibodies, e.g., polyclonal antibodies, raised against an immunogen comprising an amino acid sequence of a RLS protein, e.g., a RLS protein as shown in Table 5 or ortholog as shown Table 6, immunogenic fragments thereof, and conservatively modified variants thereof; (3) specifically hybridize under stringent hybridization conditions to an anti-sense strand corresponding to a nucleic acid sequence encoding a RLS protein, e.g., RLS protein (Table 5) or ortholog as shown Table 6, and conservatively modified variants thereof; (4) have a nucleic acid sequence that has greater than about 40% sequence identity, 45%, 50%, 60%, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to a RLS nucleic acid, e.g., a RLS protein as shown in Table 1 or ortholog as shown Table 2.

A RLS polynucleotide or polypeptide sequence is typically from a mammal including, but not limited to, primate, e.g., human; rodent, e.g., rat, mouse, hamster; cow, pig, horse, sheep, or any mammal. Other RLS polynucleotide or polypeptide sequences are from other organisms, including yeast (e.g., *Saccharomyces cerevisiae*; also referred to as *S. cerevisiae*), worms, and insects. The nucleic acids and proteins of the invention include both naturally occurring or recombinant molecules.

The terms "RLS" protein or a fragment thereof, or a nucleic acid encoding "RLS" protein or a fragment thereof refer to nucleic acid and polypeptide polymorphic variants, alleles, mutants, and interspecies homologs that: (1) have an amino acid sequence that has greater than about 40% amino acid sequence identity, 45%, 50%, 60%, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by as shown in Table 5 or Table 6; (2) specifically bind to antibodies, e.g., polyclonal antibodies, raised against an immunogen comprising an amino acid sequence encoded by a RLS protein as shown in Table 5 or ortholog as shown Table 6, immunogenic fragments thereof, and conservatively modified variants thereof; (3) specifically hybridize under stringent hybridization conditions to an antisense strand corresponding to a nucleic acid sequence encoding a RLS protein, e.g., a RLS protein as shown in Table 5 or ortholog as shown Table 6, or their complements, and conservatively modified variants thereof; (4) have a nucleic acid sequence that has greater than about 40% sequence identity, 45%, 50%, 60%, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to the genes and their representative sequences as a RLS protein as shown in Table 5 or ortholog as shown Table 6 or their complements.

Exemplary replicative life span genes are listed in Table 5 and interspecies orthologs for these genes are listed in Table 6.

The phrases "identified sequences of the present invention" and "identified genes of the present invention" are used interchangeably in this disclosure. Such "identified sequences" are identified by methods of the present invention, which include genes and gene products; fragments of genes and gene products; sequences of genes and gene products, and any modifications of these genes and gene products that have life-span-regulating function. Such "identified sequences" that regulate eukaryotic life spans, includes yeast genes/gene products identified in "long-lived" variants, and related orthologous genes/gene products having conserved life-span-regulating activity. Such "identified sequences" include yeast gene sequences, corresponding yeast polypeptide sequences, and mammalian orthologous gene sequences; and corresponding mammalian polypeptide sequences, as can be determined by the referenced genes in Table 5 and 6 disclosed herein. Exemplary set of mammalian orthologs is provided in Tables 6 and in Example 3.

"Ortholog" refers to an evolutionarily conserved bio-molecule represented in a species other than the organism in which a reference sequence is identified, and contains a nucleic-acid or amino-acid sequence that is homologous to the reference sequence. To determine the degree of homology between a reference sequence and a sequence in question, two nucleic-acid sequences or two amino-acid sequences are compared. Homology can be defined by percentage identity or by percentage similarity. Percentage identity correlates with the proportion of identical amino-acid residues shared between two sequences compared in an alignment. Percentage similarity correlates with the proportion of amino-acid residues having similar structural properties that is shared between two sequences compared in an alignment. Percentages of similarity and identity can be calculated over a portion of the primary structure and not over the entire gene/protein sequence. For example, amino-acid residues having similar structural properties can be substituted for one another, such as the substitutions of analogous hydrophilic amino-acid residues, and the substitution of analogous hydrophobic amino-acid residues. Percentages of similarity and identity can be calculated over a portion of the primary structure and not over the entire gene/protein sequence. For the present disclosure, an ortholog or an orthologous sequence is defined as a homologous molecule or a sequence having life-span-regulating activity and a sequence identity of at least about 20%, 25%, 30%, 35%, 40%, 45%, 50%, 55%, 60%, 65%, 70%, 75%, 80%, 85%, 90%, and 95%. Alternatively, an ortholog is defined as a homologous molecule or sequence having life-span-regulating activity and a sequence similarity of at least about 40%, 40%, 45%, 50%, 55%, 60%, 65%, 70%, 75%, 80%, 85%, 90%, and 95%.

It is further contemplated that "ortholog" is a polypeptide or nucleic acid molecule of an organism that is highly related to a reference protein, or nucleic acid sequence, from another organism. An ortholog is functionally related to the reference gene, protein or nucleic acid sequence. In other words, the ortholog and its reference molecule would be expected to fulfill similar, if not equivalent, functional roles in their respective organisms. It is not required that an ortholog, when aligned with a reference sequence, have a particular degree of amino acid sequence identity to the reference sequence. A protein ortholog might share significant amino acid sequence identity over the entire length of the protein, for example, or, alternatively, might share significant amino acid sequence identity over only a single functionally important domain of the protein. Such functionally important domains may be defined by genetic mutations or by structure-function assays. Orthologs can be identified using methods provided herein. The functional role of an ortholog may be assayed using methods well known to the skilled artisan, and described herein. For example, function might be assayed in vivo or in vitro using a biochemical, immunological, or enzymatic assay; transformation rescue, or for example, in a nematode bioassay for the effect of gene inactivation on nematode phenotype. Alternatively, bioassays may be carried out in tissue culture; function can also be assayed by gene inactivation (e.g., by RNAi, siRNA, or gene knockout), or gene overexpression, as well as by other methods. Exemplary orthologs for the genes of the invention are shown in Table 6.

"Paralogs" are distinct but structurally related proteins made by an organism. Paralogs are believed to arise through gene duplication.

The GenPept accession number for bre5 is CAA96332.1, and GenBank accession number for exemplary nucleotide and amino acid sequences is Z71666.1.

The GenPept accession number for fob1 is CAA88664.1, and GenBank accession number for exemplary nucleotide and amino acid sequences is Z48758.1.

The GenPept accession number for idh2 is CAA99335.1, and GenBank accession number for exemplary nucleotide and amino acid sequences is Z75043.1.

The GenPept accession number for rei1 is CAA85229.1, and GenBank accession number for exemplary nucleotide and amino acid sequences is Z36135.1. (see, e.g., Feldmann et al., *EMBO J.* 13: 5795-5809, 1994).

The GenPept accession number for rom2 is AAB67564.1, and GenBank accession number for exemplary nucleotide and amino acid sequences is U19103.1. (see, e.g., Johnston et al., *Nature* 387(6632): 87-90, 1997).

The GenPept accession number for rpl31a is CAA98641.1, and GenBank accession number for exemplary nucleotide and amino acid sequences is Z74123.1.

The GenPept accession number for rpl6b is AAB67529.1, and GenBank accession number for exemplary nucleotide and amino acid sequences is U22382.1 (see, e.g., Johnston et al. 1997, supra).

The GenPept accession number for tor1 is AAB39292.1, and GenBank accession number for exemplary nucleotide and amino acid sequences is L47993.1. (see, e.g., Huang et al., *Yeast* 12: 869-875, 1996). "TOR" refers to a 280-300 kD peptide belonging to the phosphoinositide (PI) 3-kinase family, which phosphorylate proteins on serine or threonine residues. TOR is a highly conserved protein kinase found in both prokaryotes and eukaryotes. For example, Raught et al., *Proc. Natl. Acad. Sci U.S.A.* 98: 7037, 2001, describe homologues of TOR protein found in *Saccharomyces cerevisiae*, *Schizosaccharomyces pombe*, *Drosophila melanogaster* and other *Metazoans*, and mammals. A single mammalian TOR protein has been cloned from several species. (Raught et al., *Proc. Natl. Acad. Sci U.S.A.* 98: 7037, 2001). In a preferred embodiment, TOR is isolated from rat brain tissue using an ion-exchange column, and fraction purification. However, native TOR is easily isolated from a variety of tissues using a variety of techniques by those of skill in the art. By way of example only, bovine testes is another source for isolating native TOR protein. Additionally, one of skill in the art will readily isolate TOR proteins from other species for use within the spirit of the present invention. As used in the following description, "TOR" refers to any and all proteins in this described family, including but not limited to dTOR, mTOR, TOR1, TOR2, RAFT and others. Many key signaling molecules are conserved from yeast to man. mTOR is a protein kinase involved in nutrient and growth factor signaling in humans. Signaling downstream of the TOR kinase pathways in yeast and humans regulates the nuclear localization of several transcription factors in response to the carbon and nitrogen sources in the nutritional environment.

The GenPept accession number for ybr238c is CAA85201.1, and GenBank accession number for exemplary nucleotide and amino acid sequences is Z36107.1. (see, e.g., Feldmann et al., 1994, supra).

The GenPept accession number for ybr255w is CAA85218.1, and GenBank accession number for exemplary nucleotide and amino acid sequences is Z36124.1. (see, e.g., Feldmann et al., 1994, supra).

The GenPept accession number for ybr266c is CAA85230.1, and GenBank accession number for exemplary nucleotide and amino acid sequences is Z36135.1.

The GenPept accession number for yor135c is CAA99334.1, and GenBank accession number for exemplary nucleotide and amino acid sequences is Z75043.1.

The GenPept accession number for sch9 is NP_012075.1, and GenBank accession number for exemplary nucleotide and amino acid sequences is NC_001140.4. (see, e.g., Goffeau et al., *Science* 274: 546-547, 1996). A preferred ortholog of this gene is akt-1.

The GenPept accession number for ure2 is NP_014170.1, and GenBank accession number for exemplary nucleotide and amino acid sequences is NC_001146.3. (see, e.g., Philippsen et al., *Nature* 387(6632): 93-98, 1997).

"Senescence" refers to a mitotically-arrested state in which a cell or an organism may be metabolically active but is incapable of further cell division. In yeast, one cause of senescence is the accumulation of ribosomal DNA ("rDNA") circles. In mammals, telomere shortening is one mechanism by which cells senesce. Markers for senescence in multicellular organisms include: increase in cell size, shortening in telomere-length, increase in senescence-associated beta-galactosidase ("SA-beta-gal") expression, and altered patterns of gene expression. Assays that can detect such markers are well-known in the art. For example, senescence can be detected in cultured cells and tissue sections of organisms at pH 6 by histochemical detection of SA-beta-gal activity present only in senescent cells and not in pre-senescent, quiescent, or immortal cells. Various methods for detecting telomeres and for measuring telomere length are known, including Southern analysis of terminal restriction fragments ("TRF") obtained by digestion of genomic DNA using frequently cutting restriction enzymes. The TRFs containing DNA with uniform telomeric repeats (TTAGGG) and degenerate repeats are separated by gel electrophoresis, blotted, and visualized directly or indirectly by hybridization with labeled oligonucleotides complementary to the telomeric-repeat sequence. "Quiescence," differs from "senescence" in that cells can retain the ability to re-enter the cell cycle during quiescence.

"Cell culture" refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

"Standard growth conditions", as used herein, refers to culturing of cells (e.g., mammalian cells) at 37° C., in a standard atmosphere comprising 5% $CO_2$. Relative humidity is maintained at about 100%. While the foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like. For example, "standard growth conditions" for yeast (e.g., *S. cerevisiae*) include 30° C. and generally under regular atmospheric conditions (less than 0.5% $CO_2$, approximately 20% $O_2$, approximately 80% $N_2$) at a relative humidity at about 100%.

"Gene" refers to a unit of inheritable genetic material found in a chromosome, such as in a human chromosome. Each gene is composed of a linear chain of deoxyribonucleotides which can be referred to by the sequence of nucleotides forming the chain. Thus, "sequence" is used to indicate both the ordered listing of the nucleotides which form the chain, and the chain which has that sequence of nucleotides. The term "sequence" is used in the same way in referring to RNA chains, linear chains made of ribonucleotides. The gene includes regulatory and control sequences, sequences which can be transcribed into an RNA molecule, and can contain sequences with unknown function. Some of the RNA products (products of transcription from DNA) are messenger RNAs (mRNAs) which initially include ribonucleotide sequences (or sequence) which are translated into a polypeptide and ribonucleotide sequences which are not translated. The sequences which are not translated include control sequences, introns and sequences with unknowns function. It can be recognized that small differences in nucleotide sequence for the same gene can exist between different persons, or between normal cells and cancerous cells, without altering the identity of the gene.

"Gene expression pattern" means the set of genes of a specific tissue or cell type that are transcribed or "expressed" to form RNA molecules. Which genes are expressed in a specific cell line or tissue can depend on factors such as tissue or cell type, stage of development or the cell, tissue, or target organism and whether the cells are normal or transformed cells, such as cancerous cells. For example, a gene can be expressed at the embryonic or fetal stage in the development of a specific target organism and then become non-expressed as the target organism matures. Alternatively, a gene can be expressed in liver tissue but not in brain tissue of an adult human.

"Differential expression" refers to both quantitative as well as qualitative differences in the temporal and tissue expression patterns of a gene or a protein. For example, a differentially expressed gene can have its expression activated or completely inactivated in normal versus disease conditions. Such a qualitatively regulated gene can exhibit an expression pattern within a given tissue or cell type that is detectable in either control or disease conditions, but is not detectable in both. Differentially expressed genes can represent "profile genes," or "target genes" and the like.

Similarly, a differentially expressed protein can have its expression activated or completely inactivated in normal versus disease conditions. Such a qualitatively regulated protein can exhibit an expression pattern within a given tissue or cell type that is detectable in either control or disease conditions, but is not detectable in both. Moreover, differentially expressed genes can represent "profile proteins", "target proteins" and the like.

Differentially expressed genes can represent "expression profile genes", which includes "target genes". "Expression profile gene," as used herein, refers to a differentially expressed gene whose expression pattern can be used in methods for identifying compounds useful in the modulation of lifespan extension or activity, or the treatment of disorders, or alternatively, the gene can be used as part of a prognostic or diagnostic evaluation of lifespan disorders, e.g., diseases or disorders associated with aging including various types of cancers, diabetes mellitus, cataracts, heart diseases, and neurodegenerative diseases, such as Alzheimer's disease, Pick's disease, Huntington's disease, Parkinson's disease, adult onset myotonic dystrophy, multiple sclerosis, and adult onset leukodystrophy disease. For example, the effect of the compound on the expression profile gene normally displayed in connection with a particular state, for example, can be used to evaluate the efficacy of the compound to modulate that state, or preferably, to induce or maintain that state. Such assays are further described below. Alternatively, the gene can be used as a diagnostic or in the treatment of lifespan disorders as also further described below. In some instances, only a fragment of an expression profile gene is used, as further described below.

"Expression profile," as used herein, refers to the pattern of gene expression generated from two up to all of the expression profile genes which exist for a given state. As outlined above, an expression profile is in a sense a "fingerprint" or "blueprint" of a particular cellular state; while two or more states have genes that are similarly expressed, the total expression profile of the state will be unique to that state. A "fingerprint pattern", as used herein, refers to a pattern generated when the expression pattern of a series (which can range from two up to all the fingerprint genes that exist for a given state) of fingerprint genes is determined. A fingerprint pattern also can be referred to as an "expression profile". A fingerprint pattern or expression profile can be used in the same diagnostic, prognostic, and compound identification methods as the expression of a single fingerprint gene. The gene expression profile obtained for a given state can be useful for a variety of applications, including diagnosis of a particular disease or condition and evaluation of various treatment regimes. In addition, comparisons between the expression profiles of different lifespan disorders can be similarly informative. An expression profile can include genes which do not appreciably change between two states, so long as at least two genes which are differentially expressed are represented. The gene expression profile can also include at least one target gene, as defined below. Alternatively, the profile can include all of the genes which represent one or more states. Specific expression profiles are described below.

Gene expression profiles can be defined in several ways. For example, a gene expression profile can be the relative transcript level of any number of particular set of genes. Alternatively, a gene expression profile can be defined by comparing the level of expression of a variety of genes in one state to the level of expression of the same genes in another state. For example, genes can be either upregulated, downregulated, or remain substantially at the same level in both states.

Figure 3:
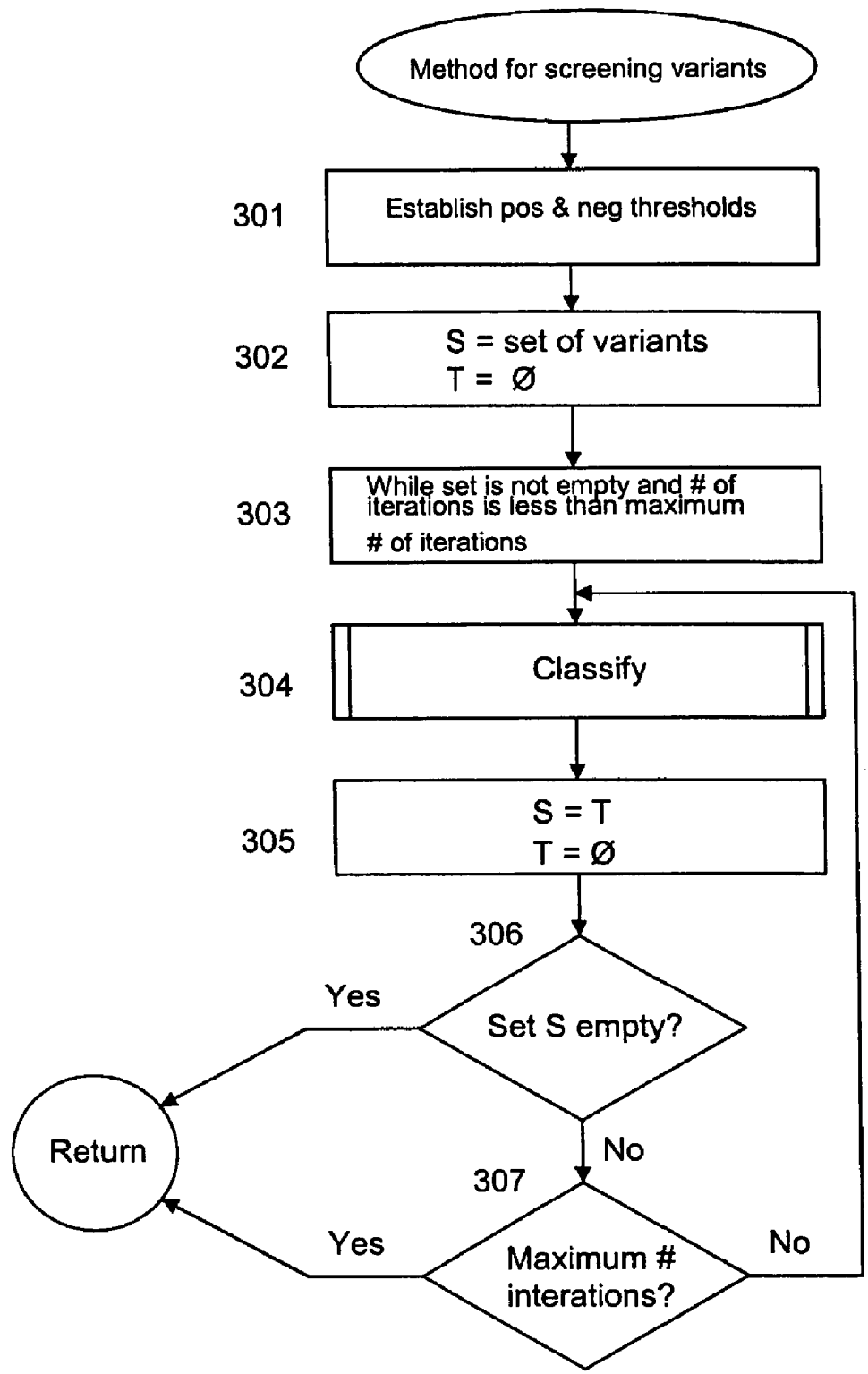
FIG. 3 is a control-flow diagram illustrating a high throughput method for screening genetic variants exhibiting a phenotypic measurement of interest that represents one embodiment of the present invention.

A "target gene" refers to a nucleic acid, often derived from a biological sample, to which an oligonucleotide probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The target nucleic acid can also refer to the specific subsequence of a larger nucleic acid to which the probe is directed or to the overall sequence (e.g., gene or mRNA) whose expression level it is desired to detect. A "target gene", therefore, refers to a differentially expressed gene in which modulation of the level of gene expression or of gene product activity prevents and/or ameliorates a lifespan disease or disorder. Thus, compounds that modulate the expression of a target gene, the target gene, or the activity of a target gene product can be used in the diagnosis, treatment or prevention lifespan diseases. Particular target genes of the present invention is shown in FIG. 3 or in the Examples.

A "target protein" refers to an amino acid or protein, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid can also refer to the specific substructure of a larger protein to which the protein-capture agent is directed or to the overall structure (e.g., gene or mRNA) whose expression level it is desired to detect.

A "differentially expressed gene transcript", as used herein, refers to a gene, including an chronological life span gene, transcript that is found in different numbers of copies in different cell or tissue types of an organism having a chronological life span disease or disorder or a disease or disorder associated with aging, including various types of cancers, diabetes mellitus, cataracts, heart diseases, and neurodegenerative diseases, such as Alzheimer's disease, Pick's disease, Huntington's disease, Parkinson's disease, adult onset myotonic dystrophy, multiple sclerosis, and adult onset leukodystrophy, compared to the numbers of copies or state of the gene transcript found in the cells of the same tissue in a healthy organism, or in the cells of the same tissue in the same organism. Multiple copies of gene transcripts can be found in an organism having a chronological life span disease or disorder or a disease or disorder associated with aging, while fewer copies of the same gene transcript are found in a healthy organism or healthy cells of the same tissue in the same organism, or vice-versa.

A "differentially expressed gene," can be a target, fingerprint, or pathway gene. For example, a "fingerprint gene", as used herein, refers to a differentially expressed gene whose expression pattern can be used as a prognostic or diagnostic marker for the evaluation of chronological life span diseases or disorders, or which can be used to identify compounds useful for the treatment of such diseases or disorders or a disease or disorder associated with aging. For example, the effect of a compound on the fingerprint gene expression pattern normally displayed in connection with chronological life span diseases or disorders or diseases or disorders associated with aging, can be used to evaluate the efficacy, such as potency, of the compound as chronological life span treatment, or can be used to monitor patients undergoing clinical evaluation for the treatment of such a disease or disorder.

"variant" may refer to an organism with a particular genotype in singular form, a set of organisms with different genotypes in plural form, and also to alleles of any gene identifiable by methods of the present invention. For example, the term "variants" includes various alleles that may occur at high frequency at a polymorphic locus, and includes organisms containing such allelic variants. The term "variant" includes various "strains" and various "mutants."

"Strains" refers to genetic variants that arise in a population, spontaneously and non-spontaneously, by acquiring a mutation or change in genomic DNA. Different strains are genotypically different with respect to at least one gene, gene regulatory element, or other non-coding element. The term "strain" can be used to refer to different laboratory-generated strains and to various mutant lines that arise spontaneously in a population.

"Wildtype" refers to a reference genotype, which is arbitrarily defined by a practitioner of the invention. For screening a large collection of genetic variants to identify long-lived variants, the BY4742 strain may be defined as a "wildtype" to screen a deletion variant set as one example. For screening longevity-promoting compounds that interact with components of the CR pathway, a sir2-fob1-double-deletion strain that is unexposed to a test compound may be employed as a "wildtype" reference strain.

"positive" refers to a variant exhibiting a life span greater than a positive threshold, established according to statistical methods of the present invention.

"Pegative" refers to a variant exhibiting a life span less than a negative threshold, established according to statistical methods of the present invention.

"Ambiguous" refers to a variant that cannot be classified as "positive" or "negative." An example of an "ambiguous" variant is a variant that cannot be classified as "long-lived" or "not-long-lived."

"Sample size" or "N" refers to a number of genetically identical cells of a variant of interest for which a phenotypic measurement is determined. As an example, for yeast life span determinations, the term "sample size" or "N" refers to genetically identical mother cells of a variant for which µRLS is determined. Suitable values for N depend on a particular organism of interest for which mean life spans are determined.

"Mean replicative life span," "µRLS," and "µRLS$_v$," refer to a computed average for RLS values determined for a given N-cell variant set.

"Median mean replicative life span" or "MµRLS" refers to a computed median for µRLS values of a set, where the µRLS is determined for each variant of a set.

"Average median mean replicative life span" or "AvMµRLS" refers to a computed average for MµRLS values determined for each set.

"Substantially greater" refers to a measured life span of an organism, such as a variant, that is at least 20%, 25%, 30%, 35%, 40%, 45%, 50%, 55%, 60%, 65%, 70%, 75%, 80%, 85%, 90%, 95%, or 100% greater than that of a reference organism, such as a wildtype. "Substantially less" refers to a measured life span of an organism, such as a variant, that is at least 20%, 25%, 30%, 35%, 40%, 45%, 50%, 55%, 60%, 65%, 70%, 75%, 80%, 85%, 90%, 95%, or 100% less than that of a reference organism, such as a wildtype.

"Longevity-promoting" can refer to a substantial increase in a life span of an organism by at least 10%, 15%, 20%, 25%, 30%, 35%, 40%, 45%, 50%, 55%, 60%, 65%, 70%, 75%, 80%, 85%, 90%, 95%, or 100%, from an exposure to a compound. "Longevity-inhibiting" can refer to a substantial decrease in a life span of an organism by at least 10%, 15%, 20%, 25%, 30%, 35%, 40%, 45%, 50%, 55%, 60%, 65%, 70%, 75%, 80%, 85%, 90%, 95%, or 100%, from an exposure to a compound.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the compositions, compounds or agents of the present invention to prevent or delay the onset of the symptoms, complications, or biochemical indicia of a disease, alleviating or ameliorating the symptoms or arresting or inhibiting further development of the disease, condition, or disorder (e.g., diseases/conditions associated with aging, including various types of cancers, diabetes mellitus, cataracts, heart diseases, and neurodegenerative diseases, such as Alzheimer's disease, Pick's disease, Huntington's disease, Parkinson's disease, adult onset myotonic dystrophy, multiple sclerosis, and adult onset leukodystrophy disease). "Treating" further refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a replicative life span disease or related disease or a disease or disorder associated with aging. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with aging but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

"Concomitant administration" of a known drug with a compound of the present invention means administration of the drug and the compound at such time that both the known drug and the compound will have a therapeutic effect or diagnostic effect. Such concomitant administration can involve concurrent (i.e., at the same time), prior, or subsequent administration of the drug with respect to the administration of a compound of the present invention. A person of ordinary skill in the art, would have no difficulty determining the appropriate timing, sequence and dosages of administration for particular drugs and compounds of the present invention.

In general, the phrase "well tolerated" refers to the absence of adverse changes in health status that occur as a result of the treatment and would affect treatment decisions.

"Inhibitors," "activators," and "modulators" of replicative life span genes and their gene products in cells are used to refer to inhibitory, activating, or modulating molecules, respectively, identified using in vitro and in vivo assays for binding or signaling, e.g., ligands, agonists, antagonists, and their homologs and mimetics. The term "modulator" includes inhibitors and activators. Inhibitors are agents that, e.g., bind to, partially or totally block stimulation, decrease, prevent, delay activation, inactivate, desensitize, or down regulate the activity of replicative life span genes, e.g., antagonists. Activators are agents that, e.g., bind to, stimulate, increase, open, activate, facilitate, enhance activation, sensitize or up regulate the activity of replicative life span genes, e.g., agonists. Modulators include agents that, e.g., alter the interaction of replicative life span gene or gene product with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring activated replicative life span disorder ligands, e.g., with altered activity, as well as naturally occurring and synthetic ligands, antagonists, agonists, small chemical molecules and the like. Such assays for inhibitors and activators include, e.g., applying putative modulator compounds to a cell expressing a replicative life span receptor and then determining the functional effects on replicative life span receptor signaling. Samples or assays comprising activated replicative life span receptor that are treated with a potential activator, inhibitor, or modulator are compared to control samples without the inhibitor, activator, or modulator to examine the extent of inhibition. Control samples (untreated with inhibitors) can be assigned a activity value of 100%. Inhibition of activated samples is achieved when the activity value relative to the control is about 80%, optionally 50% or 25-0%. Activation of sample is achieved when the activity value relative to the control is 110%, optionally 150%, optionally 200-500%, or 1000-3000% higher.

An intact "antibody" comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) through cellular receptors such as Fc receptors (e.g., FcγRI, FcγRIIa, FcγRIIb, FcγRIII, and FcRη) and the first component (Clq) of the classical complement system. The term antibody includes antigen-binding portions of an intact antibody that retain capacity to bind the antigen. Examples of antigen binding portions include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341: 544-546, 1989), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., *Science* 242: 423-426, 1988; and Huston et al., *Proc. Natl. Acad. Sci. U.S.A.* 85: 5879-5883, 1988). Such single chain antibodies are included by reference to the term "antibody" Fragments can be prepared by recombinant techniques or enzymatic or chemical cleavage of intact antibodies.

"Human sequence antibody" includes antibodies having variable and constant regions (if present) derived from human immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). However, the term "human sequence antibody", as used herein, is not intended to include antibodies in which entire CDR sequences sufficient to confer antigen specificity and derived from the germline of another mammalian species, such as a mouse, have been grafted onto human framework sequences (i.e., humanized antibodies).

"Monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

"Diclonal antibody" refers to a preparation of at least two antibodies to an antigen. Typically, the different antibodies bind different epitopes.

"Oligoclonal antibody" refers to a preparation of 3 to 100 different antibodies to an antigen. Typically, the antibodies in such a preparation bind to a range of different epitopes.

"Polyclonal antibody" refers to a preparation of more than 1 (two or more) different antibodies to an antigen. Such a preparation includes antibodies binding to a range of different epitopes.

"Recombinant human antibody" includes all human sequence antibodies of the invention that are prepared, expressed, created or isolated by recombinant means, such as antibodies isolated from an animal (e.g., a mouse) that is transgenic for human immunoglobulin genes (described further below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human gerinline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

A "heterohybrid antibody" refers to an antibody having a light and heavy chains of different organismal origins. For example, an antibody having a human heavy chain associated with a murine light chain is a heterohybrid antibody.

"Substantially pure" or "isolated" means an object species (e.g., an antibody of the invention) has been identified and separated and/or recovered from a component of its natural environment such that the object species is the predominant species present (i.e., on a molar basis it is more abundant than any other individual species in the composition); a "substantially pure" or "isolated" composition also means where the object species comprises at least about 50 percent (on a molar basis) of all macromolecular species present. A substantially pure or isolated composition can also comprise more than about 80 to 90 percent by weight of all macromolecular species present in the composition. An isolated object species (e.g., antibodies of the invention) can also be purified to essential homogeneity (contaminant species cannot be detected in the composition by conventional detection methods) wherein the composition consists essentially of derivatives of a single macromolecular species. For example, an isolated antibody to any one chronological gene product as shown in FIG. 1 can be substantially free of other antibodies that lack binding to that particular gene product and bind to a different antigen. Further, an isolated antibody that specifically binds to an epitope, isoform or variant of a chronological life span protein may, however, have cross-reactivity to other related antigens, e.g., from other species (e.g., chronological life span species homologs). Moreover, an isolated antibody of the invention be substantially free of other cellular material (e.g., non-immunoglobulin associated proteins) and/or chemicals.

"Specific binding" refers to preferential binding of an antibody to a specified antigen relative to other non-specified antigens. The phrase "specifically (or selectively) binds" to an antibody refers to a binding reaction that is determinative of the presence of the protein in a heterogeneous population of proteins and other biologics. Typically, the antibody binds with an association constant ($K_a$) of at least about $1 \times 10^6$ $M^{-1}$ or $10^7$ $M^{-1}$, or about $10^8$ $M^{-1}$ to $10^9$ $M^{-1}$, or about $10^{10}$ $M^{-1}$ to $10^{11}$ $M^{-1}$ or higher, and binds to the specified antigen with an affinity that is at least two-fold greater than its affinity for binding to a non-specific antigen (e.g., BSA, casein) other than the specified antigen or a closely-related antigen. The phrases "an antibody recognizing an antigen" and "an antibody specific for an antigen" are used interchangeably herein with the term "an antibody which binds specifically to an antigen". A predetermined antigen is an antigen that is chosen prior to the selection of an antibody that binds to that antigen.

"Specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions can require a binding moiety that is selected for its specificity for a particular target antigen. A variety of assay formats can be used to select ligands that are specifically reactive with a particular protein. For example, solid-phase ELISA immunoassays, immunoprecipitation, Biacore and Western blot are used to identify peptides that specifically react with the antigen. Typically a specific or selective reaction will be at least twice background signal or noise and more typically more than 10 times background.

"High affinity" for an antibody refers to an equilibrium association constant ($K_a$) of at least about $10^7 M^{-1}$, at least about $10^8 M^{-1}$, at least about $10^9 M^{-1}$, at least about $10^{10} M^{-1}$, at least about $10^{11} M^{-1}$, or at least about $10^{12} M^{-1}$ or greater, e.g., up to $10^{13} M^{-1}$ or $10^{14} M^{-1}$ or greater. However, "high affinity" binding can vary for other antibody isotypes.

"$K_a$", as used herein, is intended to refer to the equilibrium association constant of a particular antibody-antigen interaction. This constant has units of 1/M.

"$K_d$", as used herein, is intended to refer to the equilibrium dissociation constant of a particular antibody-antigen interaction. This constant has units of M.

The term "$k_a$", as used herein, is intended to refer to the kinetic association constant of a particular antibody-antigen interaction. This constant has units of 1/Ms.

The term "$k_d$", as used herein, is intended to refer to the kinetic dissociation constant of a particular antibody-antigen interaction. This constant has units of 1/s.

"Particular antibody-antigen interactions" refers to the experimental conditions under which the equilibrium and kinetic constants are measured.

"Isotype" refers to the antibody class that is encoded by heavy chain constant region genes. Heavy chains are classified as gamma, mu, alpha, delta, or epsilon, and define the antibody's isotype as IgG, IgM, IgA, IgD and IgE, respectively. Additional structural variations characterize distinct subtypes of IgG (e.g., $IgG_1$, $IgG_2$, $IgG_3$ and $IgG_4$) and IgA (e.g., $IgA_1$ and $IgA_2$)

"Isotype switching" refers to the phenomenon by which the class, or isotype, of an antibody changes from one Ig class to one of the other Ig classes/

"Nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching can occur by, for example, homologous recombination between human $\sigma_\mu$ and human $\Sigma_\mu$ (δ-associated deletion). Alternative non-classical switching mechanisms, such as intertransgene and/or interchromosomal recombination, among others, can occur and effectuate isotype switching.

"Switch sequence" refers to those DNA sequences responsible for switch recombination. A "switch donor" sequence, typically a μ switch region, are 5' (i.e., upstream) of the construct region to be deleted during the switch recombination. The "switch acceptor" region are between the construct region to be deleted and the replacement constant region (e.g., γ, ε, and alike). As there is no specific site where recombination always occurs, the final gene sequence is not typically predictable from the construct.

"Glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

"Naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Immunoglobulin locus" refers to a genetic element or set of linked genetic elements that comprise information that can be used by a B cell or B cell precursor to express an immunoglobulin peptide. This peptide can be a heavy chain peptide, a light chain peptide, or the fusion of a heavy and a light chain peptide. In the case of an unrearranged locus, the genetic elements are assembled by a B cell precursor to form the gene encoding an immunoglobulin peptide. In the case of a rearranged locus, a gene encoding an immunoglobulin peptide is contained within the locus.

"Rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus has at least one recombined heptamer/nonamer homology element.

"Unrearranged" or "germline configuration" in reference to a V segment refers to the configuration wherein the V segment is not recombined so as to be immediately adjacent to a D or J segment.

"Nucleic acid" or "nucleic acid molecule" refer to a deoxyribonucleotide or ribonucleotide polymer in either single- or double-stranded form, and unless otherwise limited, can encompass known analogs of natural nucleotides that can function in a similar manner as naturally occurring nucleotides.

"Isolated nucleic acid" in reference to nucleic acids encoding antibodies or antibody portions (e.g., VH, VL, CDR3) that bind to the antigen, is intended to refer to a nucleic acid in which the nucleotide sequences encoding the antibody or antibody portion are free of other nucleotide sequences encoding antibodies or antibody portions that bind antigens other than which other sequences can naturally flank the nucleic acid in human genomic DNA.

The nucleic acids of the invention be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (See, e.g., Sambrook, Tijssen and Ausubel discussed herein and incorporated by reference for all purposes). The nucleic acid sequences of the invention and other nucleic acids used to practice this invention, whether RNA, cDNA, genomic DNA, or hybrids thereof, can be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, ☐ adioimmunoassay (RIAs), enzyme-linked immunosorbent assays (ELISAs), immunofluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The nucleic acid compositions of the present invention, while often in a native sequence (except for modified restriction sites and the like), from either cDNA, genomic or mixtures can be mutated, thereof in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

"Recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IWPAC-IUB Biochemical Nomenclature Comrnrission. Nucleotides, likewise, can be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine.

Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a kinase domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are contemplated here.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

"Rapamycin" is a bacterial macrolide and a potent immunosuppressant with realized or potential clinical applications in the prevention of graft rejection after organ transplantation and the treatment of autoimmune disorders. This drug acts by forming a complex with the immunophillin FKBP12, and then inhibiting activity of TOR. (Abraham et al., *Annu. Rev. Immuno.* 14: 483, 1996). Rapamycin treatment of cells has been shown to lead to the dephosphorylation and inactivation of TOR substrates such as P70 S6 Kinase and 4E-BP1/PHAS1. (Dumont et al., *J. Immunol* 144: 251, 1990; Brown et al., *Nature* 369: 756, 1994; Kunz et al., *Cell* 73: 585, 1993; Jefferies et al., *EMBO J.* 15: 3693, 1997; Beretta et al., *EMBO J.* 15: 658, 1996). Numerous derivatives of rapamycin are known. Certain 40-O-substituted rapamycins are described in, e.g., in U.S. Pat. No. 5,258,389 and WO 94/09010 (O-alkyl rapamycins); WO 92/05179 (carboxylic acid esters), U.S. Pat. No. 5,118,677 (amide esters), U.S. Pat. No. 5,118,678 (carbamates), U.S. Pat. No. 5,100,883 (fluorinated esters), U.S. Pat. No. 5,151,413 (acetals), and U.S. Pat. No. 5,120,842 (silyl ethers). As described herein, rapamycin (or a rapamycin analog, derivative or related compound thereof) is shown to extend life span by inhibiting the TOR pathway.

This invention relies on routine techniques in the field of recombinant genetics. Basic texts disclosing the general methods of use in this invention include Sambrook et al., *Molecular Cloning, A Laboratory Manual*, 2$^{nd}$ ed., 1989; Kriegler, *Gene Transfer and Expression: A Laboratory Manual*, 1990; and Ausubel et al., eds., *Current Protocols in Molecular Biology*, 1994; all of which are herein incorporated by reference for all purposes.

In the following, aspects of the present invention are directed to: (1) high throughput methods for classifying genetic variants, and for identifying "long-lived" variants; (2) methods for identifying genes that regulate eukaryotic life spans; (3) various vectors and host cells comprising the identified genes, related orthologs, and related gene products; and (4) pharmaceutical compositions that can modulate, or modify, the function of the identified genes/gene products.

Figure 2:
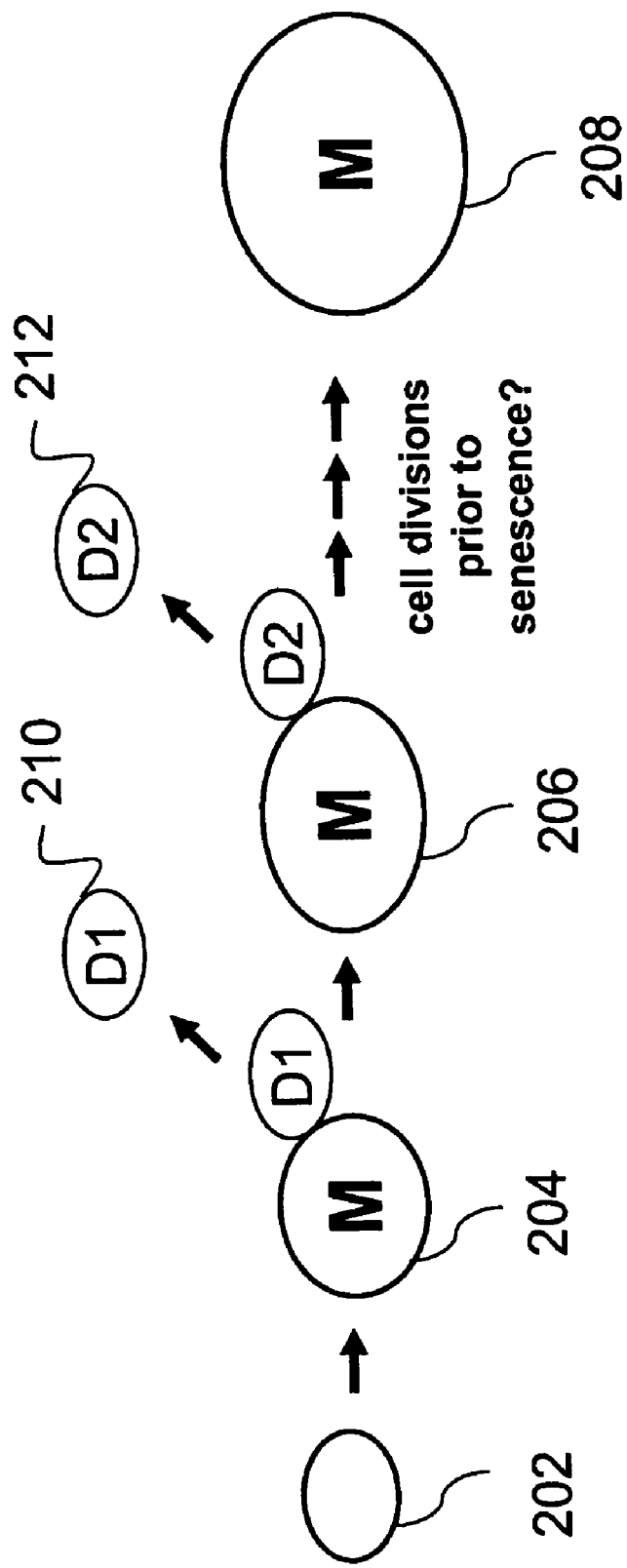
FIG. 2 illustrates replicative-life-span ("RLS") analysis in yeast.

II. High throughput Methods for Identifying Yeast Sequences that Regulate Life Spans A. Replicative Life Span (RLS) Assay FIG. 2 illustrates replicative life span ("RLS") analysis in yeast. In FIG. 2, a virgin yeast cell 202, which is a cell that has not produced any daughter cells, is isolated and allowed to undergo cell division under conditions favorable for growth. After the first division, the cell 202 is defined as a mother cell 204, and the first daughter cell "D1" 210 is physically removed from the mother cell. A mother cell is a yeast cell that has produced one or more daughter cells. After the second division of mother cell 206, a second daughter cell "D2" 212 is again physically removed from the same mother cell, and all daughter cells produced by a mother cell under analysis are, in turn, physically removed and enumerated. The total number of mitotic divisions completed by a given mother cell is the replicative life span for that mother cell. One indicator of senescence in yeast is the inability to produce daughter cells. In general, aged mothers 208 exhibit phenotypic changes, including morphological changes, protracted cell division, increased size, and nucleolar fragmentation.

B. A High throughput Method for Identifying Long-Lived Mutants

1. Screening a Large Set of Genetic Variants by Minimizing Sample Size (N)

The RLS assay described in FIG. 2 is used in various context of the present invention. In one embodiment, a RLS assay is combined with various statistical methods of the present invention for screening a large number of genetic variants in order to identify "long-lived" ("LL") variants that exhibit a life span substantially longer than a reference strain. Generally, since substantial variance is commonly observed for any given set of genotypically identical mother cells, a statistically reliable number of cells for a given variant should be analyzed.

Various statistical methods of the present invention can be used to classify genetic variants of any organism, by measuring a phenotype of interest (referred to as "a phenotypic measurement"). As examples, various embodiments of the present invention described below are directed to statistical methods for the classification of "long-lived" ("LL") variants and "not-long-lived" ("NLL") variants in an unsorted set. The methods of the present invention can be used to determine a minimal sample size that needs to be evaluated for determining a statistically significant phenotypic measurement.

Various statistical methods of the present invention are useful for making phenotypic analysis of an organism for which a phenotypic measurement requires a statistically significant number of organisms, and assays for measuring a phenotype are inherently labor-intensive and/or costly. For example, methods of the present invention are well-suited for life span determinations that require a statistically significant number of organisms and life-span-determinative assays that are inherently labor-intensive. Examples of suitable hosts include various plants, various fungi, such as yeasts, various invertebrate organisms, such as worms and flies, and various vertebrates, such as mammals. For the present disclosure, embodiments of the present invention will be described in the context of yeast variants to describe unique features of the invention. Exemplary data include life span determinations for yeast variants, however, the present invention is not intended to be limited only to the analysis of yeast variants.

2. Classification Based on Determination of a Mean Replicative Life Span (μRLS) for N Cells of Each Variant In one embodiment, the present invention provides a statistical method for screening a large number of genetic variants in order to identify "long-lived" ("LL") variants by distinguishing variants based on calculated mean RLS ("μRLS") as a phenotypic measurement. LL variants exhibit μRLS substantially greater than the μRLS of a "wildtype" reference strain.

One embodiment of the present invention provides a high throughput method for classifying genetic variants that exhibit long life spans based on calculated μRLS values. Described below is an exemplary high throughput method for efficiently screening a large collection of variants, including a large genomic library of genetic variants. Identified LL variants enable the identification of genes that affect life-span regulation. In the following, various embodiments relating to the methods of the present invention for classifying genetic variants are described in a computational-like manner to facilitate comprehension of inter-related processes. The automation of the following methods, in part or in whole, is contemplated.

FIG. 3 is a control-flow diagram illustrating a high throughput method for screening genetic variants exhibiting a phenotypic measurement of interest. In step 301 of the high throughput method ("HTM"), a positive and negative threshold is determnined. A variant with a phenotypic measurement greater than the positive threshold can be classified as "positive." A variant with a phenotypic measurement less than the negative threshold can be classified as "negative." A variant with a phenotypic measurement equal to or greater than a negative threshold and less than or equal to the positive threshold cannot be classified, and is considered "ambiguous." Next, in step 302, the HTM assigns an initial set of variants to the set variable S and sets the set variable T to the empty set. The HTM attempts to classify every variant in the set of variants represented by set variable S, placing any unclassifiable, "ambiguous" variants into T. Steps 303-307 together compose a while-loop in which the HTM iteratively classifies variants, in step 304. The while-loop of steps 303-307 continues until either all variants are classified, as detected in step 306, or until a maximum number of iterations have been carried out, as detected in step 307. Following classification of all variants currently represented by set variable S, in step 304, the HTM sets S to contain any unclassified variants in set variable T to the empty set, in step 305, in preparation for a subsequent iteration of the while-loop comprising steps 303-307.

Figure 4:
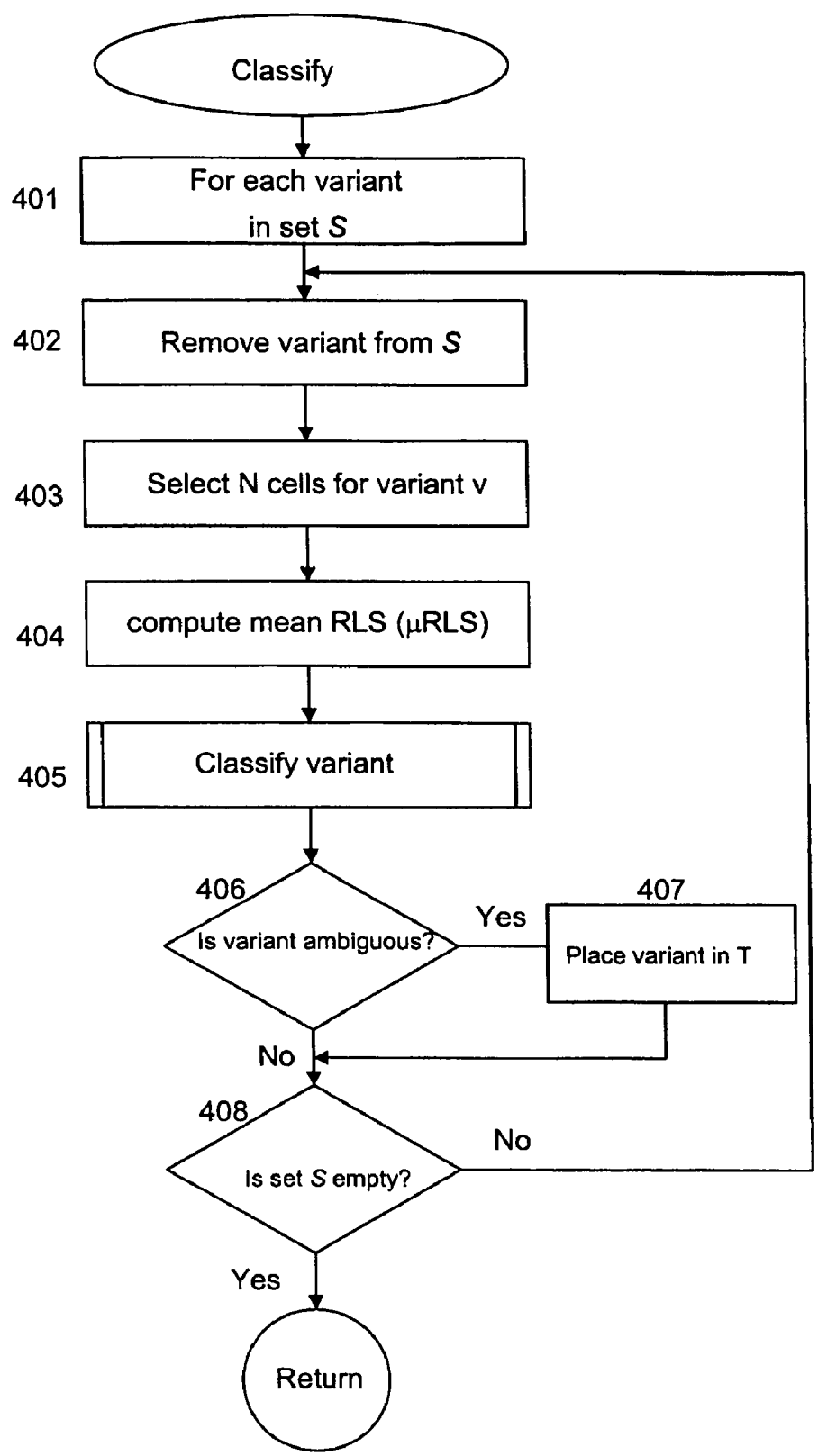
FIG. 4 is a control-flow diagram of one embodiment of the step "classify" iteratively called in step 304 of the high throughput method (HTM) diagramed in FIG. 3, according to one embodiment of the present invention.

If the phenotypic measurement described, in step 301 of FIG. 3, is mean RLS (μRLS) for each variant of a set of variants S, then "positive" variants are "long-lived" and "negative" variants are "not-long-lived." Thus, the classification step of FIG. 3 includes the following embodiment. FIG. 4 is a control-flow diagram of one embodiment of the step "classify" iteratively called in step 304 of the high throughput method (HTM) diagramed in FIG. 3. Steps 401-408 represent a for-loop in which each variant, currently contained in the set variable S, is classified by carrying out steps 402-405. First, in step 402, a next variant is removed from the set of variants S for consideration in the current iteration of the for-loop of steps 401-408. Next in step 403, a number of cells N are chosen for the currently considered variant. Then, in step 404, a μRLS is computed from the RLS determined for each of the N variant cells, in which, a $$\mu RLS = \frac{\sum_{i=1}^{N} RLS}{N}.$$

In step 405, the variant is classified as "positive," "negative," or "ambiguous," depending on the μRLS computed in step 404. If the variant has been classified as ambiguous, as determined in step 406, then the variant is placed into the set of ambiguous variants T in step 407. The for-loop of steps 401-408 continues until the set S is empty, as determined in step 408, indicating that all variants initially present in set S at the beginning of the for-loop have been classified.

Figure 5:
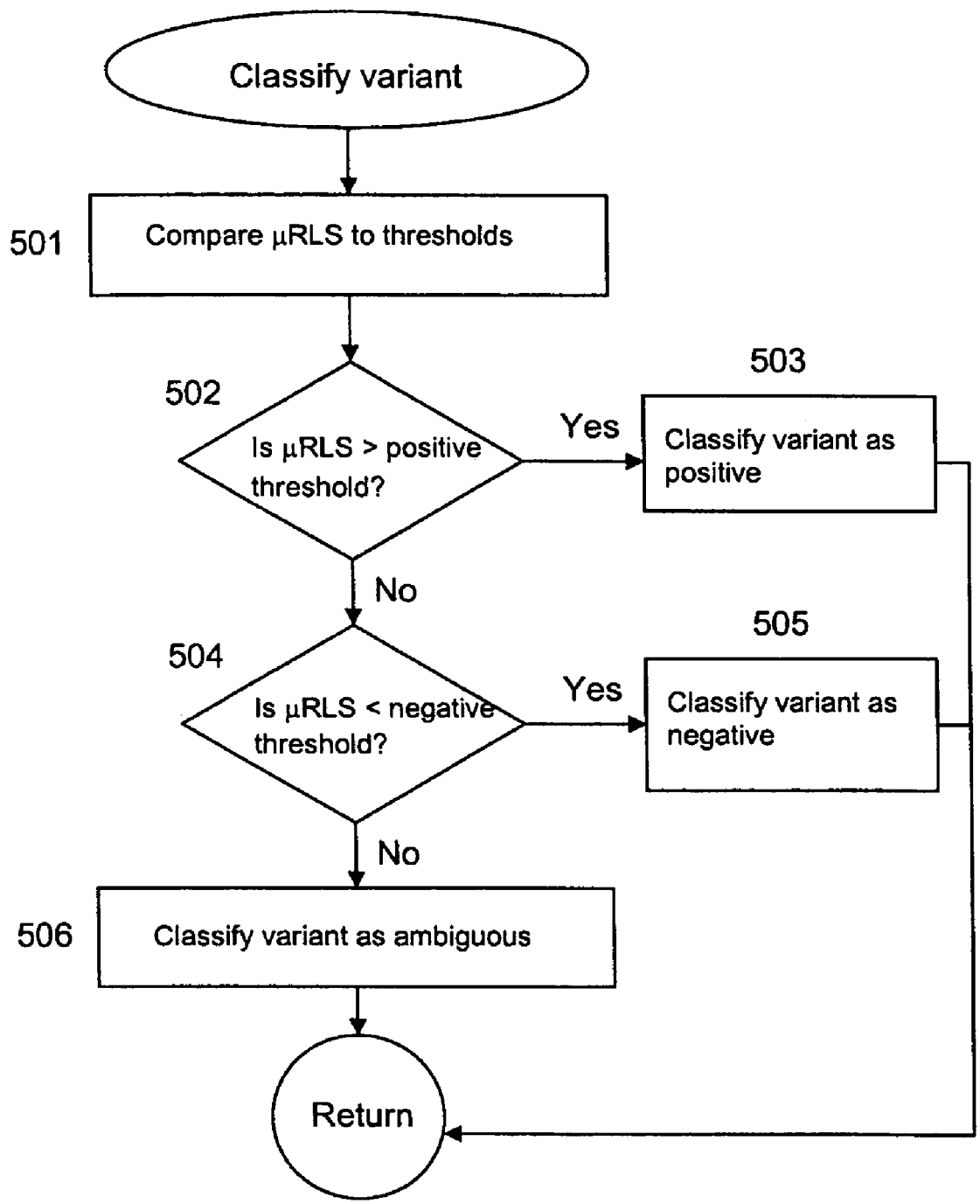
FIG. 5 is a control-flow diagram for the method "classified variant" called in step 405 of the method "classify" diagrammed in FIG. 4, according to one embodiment of the present invention.

FIG. 5 is a control-flow diagram for the method "classify variant" called in step 405 of the method "classify" diagrammed in FIG. 4. In step 501, the μRLS computed for a variant in step 404 of FIG. 4 is compared to the positive and negative threshold values, determined in step 301 of FIG. 3, in order to classify the variant. If the μRLS of the variant is greater than the positive threshold, as determined in step 502, then the variant is classified as "positive," or "long-lived," in step 503. If, on the other hand, the μRLS for the variant is less than the negative threshold, as determined in step 504, then the variant is classified as "negative," or "not-long-lived" in step 505. Otherwise, in step 506, the variant is considered to be "ambiguous," or currently unclassifiable.

3. Classification Based on Determination of a Mean RLS for a Subset of N-Cell Set Exhibiting Maximum RLS for Each Variant Alternatively, in another embodiment, the present invention provides a statistical method for screening a large number of genetic variants in order to identify "long-lived" variants by distinguishing variants, based on μRLS determined for a subset of N cells of a variant, that exhibit the highest RLS values for the N-cell set. As previously described in FIG. 4, for each variant in a set S, N cells for each variant are selected to determine a μRLS value for each variant. In step 404, a μRLS is computed by averaging RLS values for N cells, in which, a $$\mu RLS = \frac{\sum_{i=1}^{N} RLS}{N}.$$

Alternatively, μRLS may be computed by selecting the highest RLS values for a given N-cell set, excluding the lowest RLS values of the N-cell set. For example, RLS values for a subset of N cells that are less than optimal in shape, size, or fitness may be excluded for μRLS determinations. As N value decreases, each cell of a N-cell set is more likely to increase the variance for the set. A classification method that can selectively exclude individual RLS values determined for a N-cell set that vary substantially from a computed μRLS based on N cells, for example, should increase the statistical reliability of a computed μRLS based on a smaller subset of the N-cell set.

Figure 6:
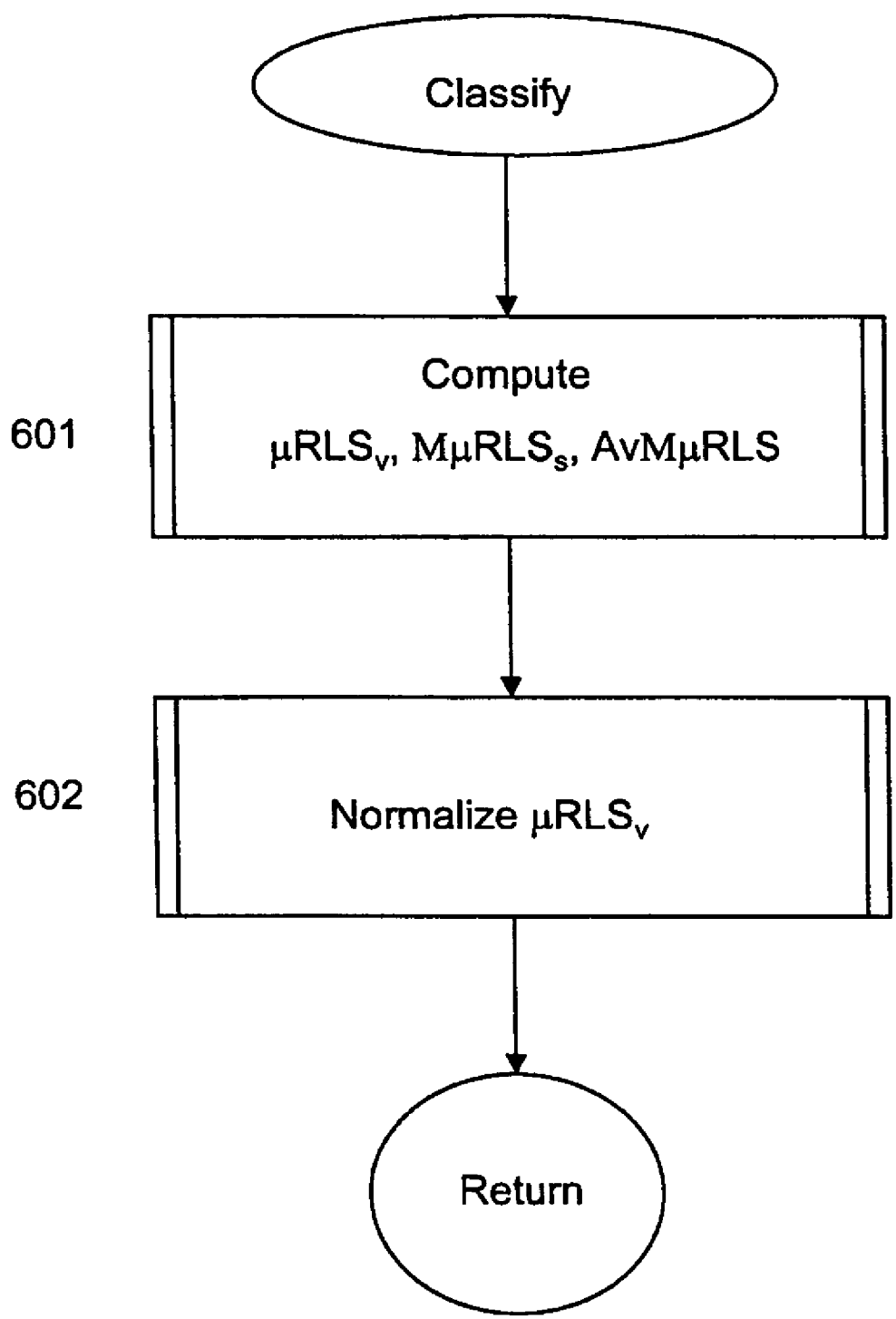
FIG. 6 is a high-level control-flow diagram for an alternative version of the method "classify," diagrammed in FIG. 4, according to one embodiment of the present invention.

4. Classification Based on Determination of a Normalized μRLS for Each Variant of Set S Alternatively, a classification scheme can be based on the computation of a mean RLS ("μRLS$_v$") for a variant, a median mean RLS ("MμRLS$_S$") for a set of variants in Set S, and an average median mean RLS ("AvMμRLS") for multiple sets of variants, that can be utilized to normalize the mean RLS ("μRLS$_v$") for each variant. FIG. 6 is a high-level control-flow diagram for an alternative version of the method "classify," diagrammed in FIG. 4. The alternative version of the method "classify" computes a μRLS$_v$, MμRLS$_S$, and AvMμRLS, in step 601, and then, in step 602, normalizes the μRLS$_v$ values for each variant using the computed MμRLS$_S$ and AvMμRLS, and then classifies each variant using the normalized μRLS$_v$ for that variant. The following FIGS. 7-8 describes each set of steps.

Figure 7:
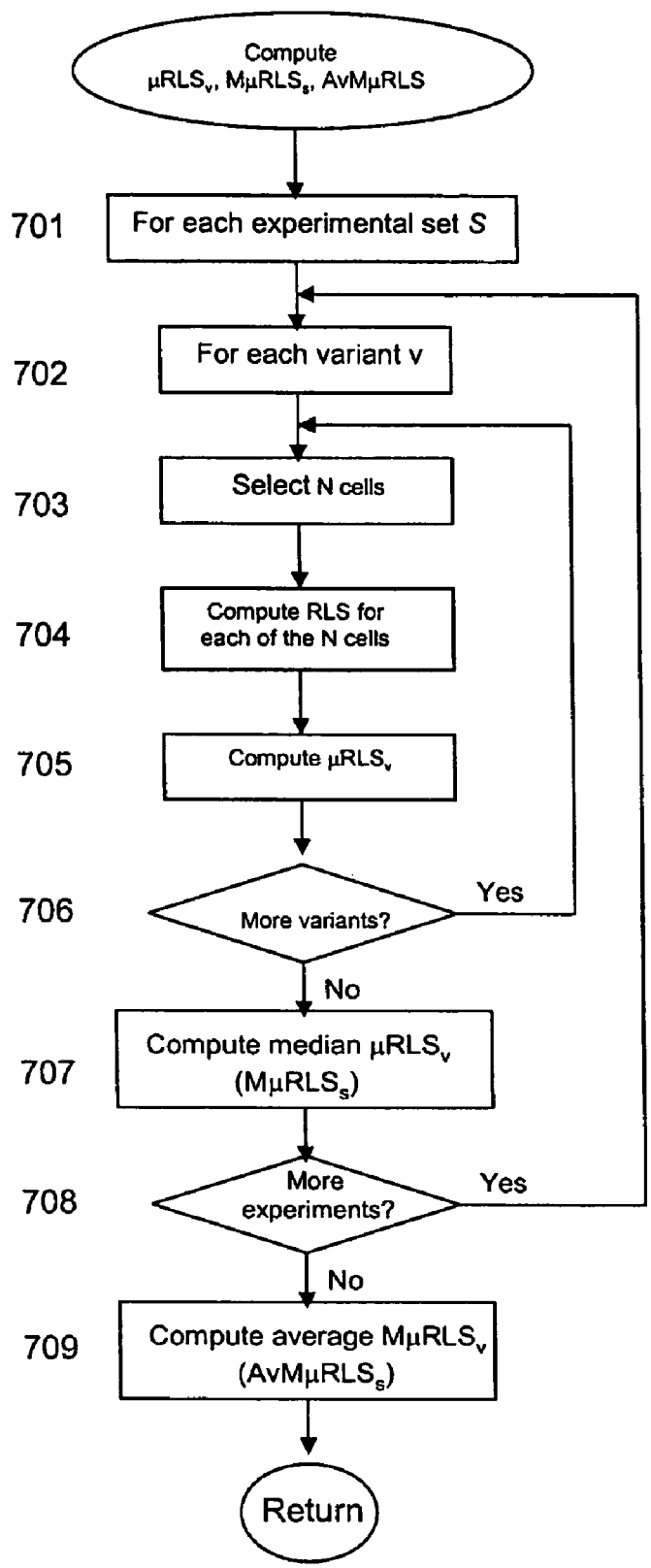
FIG. 7 is a control-flow diagram for the method carried out in step 601 of FIG. 6, according to one embodiment of the present invention.

FIG. 7 is a control-flow diagram for the method carried out in step 601 of FIG. 6. Steps 701-708 that together compose an outer for-loop, in which μRLS$_v$ values are computed for each variant v in each of experimental set S. Step 702-706 is an inner for-loop in which the RLS for each variant v in a particular set of variants S is computed. Thus, the μRLS$_v$ values are computed set-by-set for S different sets, corresponding to collections of variants analyzed in a single experiment. Steps 703-705 of the inner-for-loop are equivalent to steps 402-404 of FIG. 4, discussed above. Once μRLS$_v$ values are computed for each variant in a particular set of variants S, MµRLS$_S$ for the set S is computed in step 707. Finally, in step 709, an AvMµRLS for all of the sets S is computed, in which, a $$AvM\mu RLS = \frac{\sum_{i=1}^{S} M\mu RLS}{S}.$$

Figure 8:
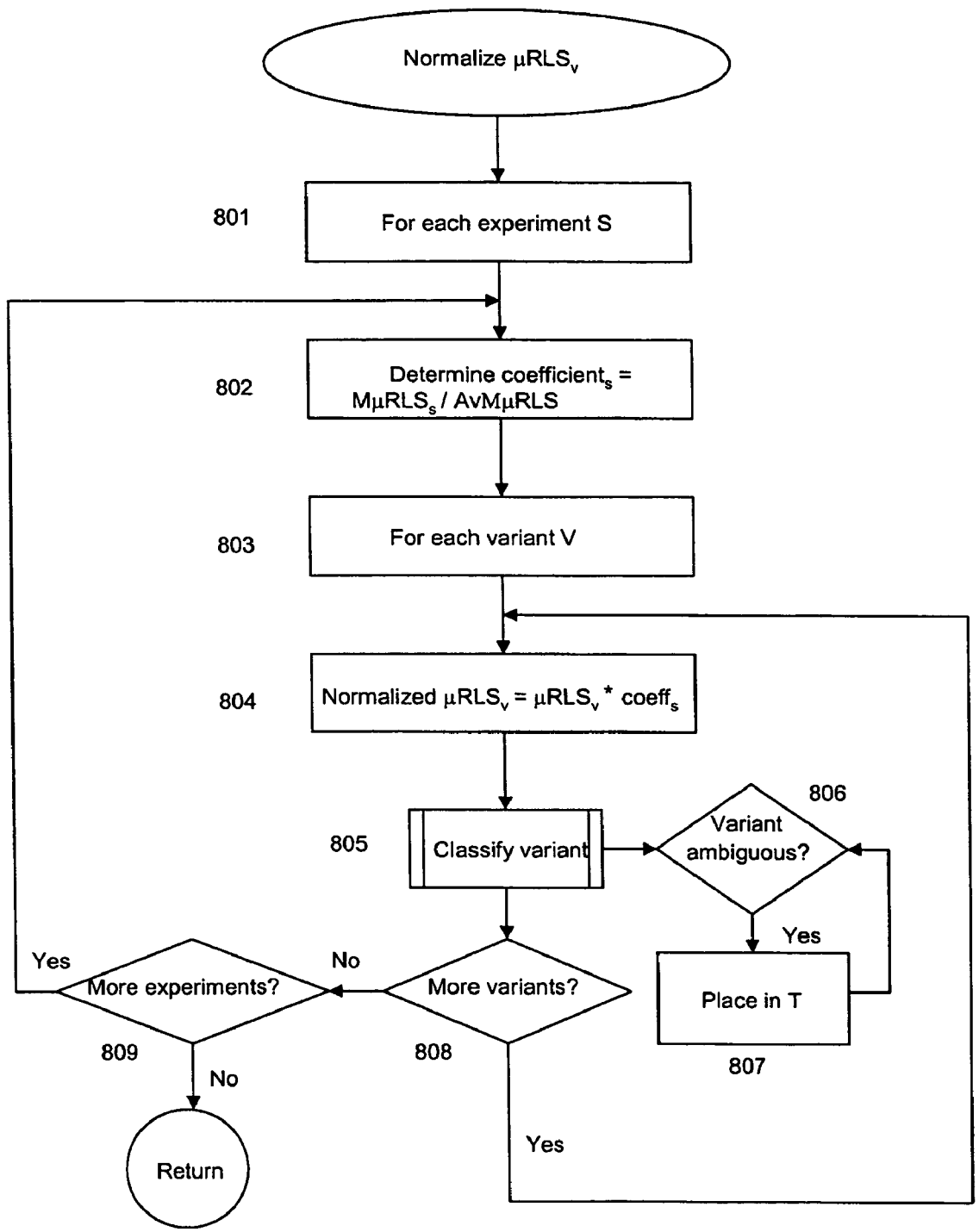
FIG. 8 is a control-flow diagram for the method carried out in step 602 of FIG. 6, according to one embodiment of the present invention.

FIG. 8 is a control-flow diagram for the method carried out in step 602 of FIG. 6. Steps 801-809 that together compose an outer for-loop, in which each set of variants S is considered. Steps 803-808 together compose an inner for-loop in which a normalized µRLS is computed for each variant of a particular set of variants S. In step 802, a coefficient$_s$ for the currently considered set of variants S is computed by dividing the MµRLS$_S$ for the set S by the AvMµRLS computed in step 709 of FIG. 7. In step 804, the normalized µRLS$_v$ for a particular variant v is computed by multiplying the µRLS$_v$ computed for the variant v in step 705 of FIG. 7 by the coefficient$_s$ for the set of variants in which v is included, computed above in step 802. Then, in steps 805-807, the variant is classified, using the computed, normalized µRLS$_v$ value, in a similar fashion to the classification of variants in step 405-407 of FIG. 4.

Statistical methods for establishing thresholds and for reducing a sample size are provided below.

5. Determining Thresholds as a Function of Sample Size (N)

One embodiment of the present invention provides a statistical method for determining a minimal number of cells ($N_{min}$) that need to be evaluated to obtain a statistically reliable mean RLS (µRLS) value for a given variant. In another embodiment, the present invention provides a statistical method for establishing threshold values that may be used to discriminate LL and NLL variants. Positive and negative thresholds described in FIGS. 3-8 are established by the following method.

Figure 9:
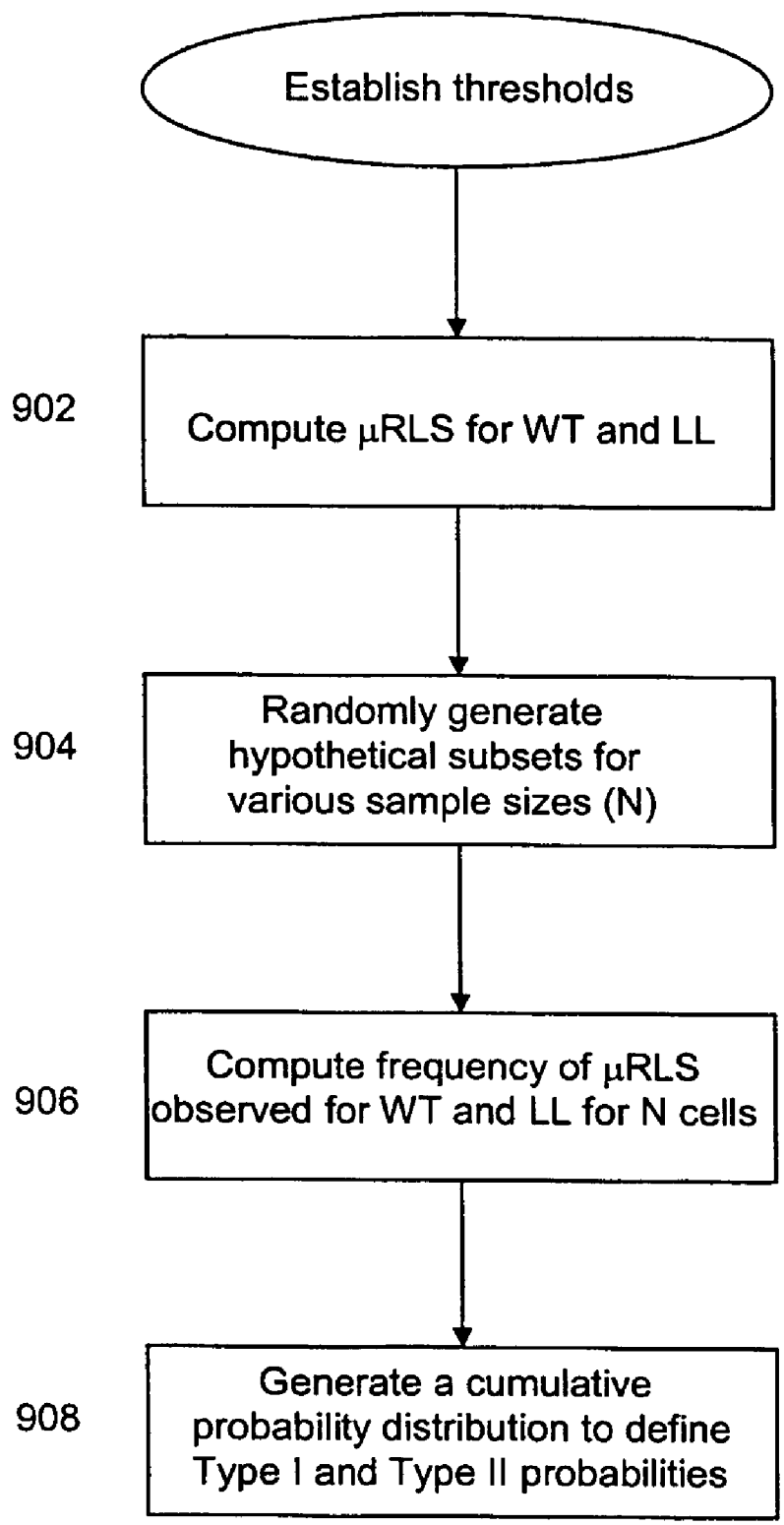
FIG. 9 provides an exemplary method for determining threshold values that may be used to discriminate LL variants from NLL variants that represent one embodiment of the present invention.

FIG. 9 provides an exemplary method for determining threshold values that may be used to discriminate LL variants from NLL variants. In step 902, RLS values are determined for a statistically reliable number of wildtype (WT) cells and long-lived (LL) variants determined to exhibit long life spans. In step 904, subsets of various sample size of N cells are randomly generated by a computational algorithm, from a RLS dataset established in step 902, and subsets are used to compute µRLS for various sets. A suitable sample size range includes a range of N values from about 3 to 20 cells per hypothetical µRLS determination. In step 906, computed µRLS values, from step 904, are used to calculate the frequency at which a given µRLS at a particular sample size is observed for WT and LL cells. In step 908, a cumulative probability distribution is generated to define the probabilities for Type I and Type II error that correlate with each hypothetical positive threshold value. An exemplary set of positive threshold values and associated probabilities for Type I and Type II error for various sample sizes (N=3, 5, 10, and 20) are shown in Table 1 of FIG. 11.

In step 902 of FIG. 9, any reference population may be used to compile a "wildtype" RLS dataset, including haploid and diploid variant backgrounds. For the identification of LL yeast variants, BY4741 (MATa), BY4742 (MATα), and BY4743 (MATa/MATα) strains that exhibit relatively longer mean life spans compared to other spontaneous and laboratory-generated variants that are generally available, may be preferred. (Winzeler et al., *Science Vol.* 285: 901-906, 1999).

Thus, the BY4742 strain, BY4741 strain, and equivalent variant strains may be preferred. Variant strains, such as BKY4-14c, PSY316AT, and W303R, that exhibit a relatively shorter life spans may contain deletions that are unrelated to aging pathways, making RLS interpretations generally more difficult, and should be avoided. Table 1 in Example 1 provides exemplary mean RLSs (µRLS) for various strains that may be employed for selecting a "wildtype" reference strain.

In step 902 of FIG. 9, variants that exhibit longer mean life spans by at least 20% compared to a "wildtype" strain may be employed for compiling a RLS dataset for LL variants ("LL-RLS data set"). Any variant determined to be long-lived by a statistically reliable method may be used to compile a LL-RLS data set, including single-gene-deletion variants, such as fob1Δ, gpa2Δ, gpr1Δ, and Δhxk2-deletion strains. Other functionally equivalent variants that exhibit a long-lived phenotype may be used as well, including double-deletion and triple-deletion variants. Examples of various mutations that are possible in a given variant set are provided in subsection C.

Figure 10:
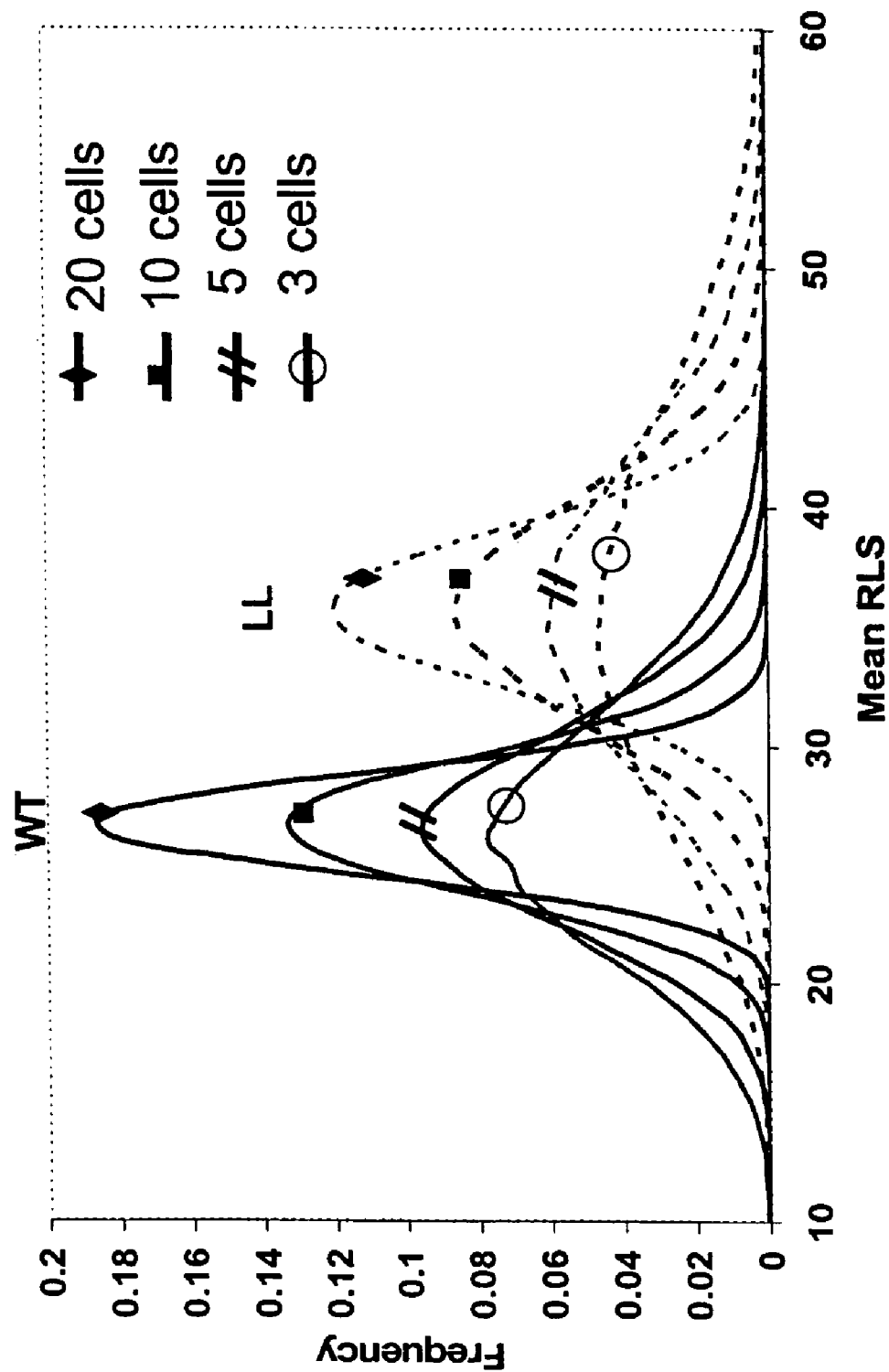
FIG. 10 provides eight theoretical distribution curves for wildtype and long-lived variants plotted for various sample sizes.

FIG. 10 provides eight theoretical distribution curves for "wildtype" and "long-lived" variants plotted for various sample sizes. In FIG. 10, various frequencies of µRLS values observed for a wildtype (WT) reference (solid lines) corresponding to exemplary N-cell sample sizes (N=3, 5, 10, and 20) that are computationally selected ("WT-µRLS distributions"), in step 904 of FIG. 9, are shown. Similarly, FIG. 10 shows a frequency of µRLS values observed for LL variants (broken lines) corresponding to exemplary N-cell sample sizes (N=3, 5, 10, and 20) that are computationally selected ("LL-µRLS distributions"), in step 904 of FIG. 9. In general, as the sample size increases from N=3 to N=20, the distribution curves for both WT and LL variants demonstrate less variance as expected. In general, for each sample-size set, "LL-µRLS distribution" curves show greater variance than "WT-µRLS distribution" curves. A µRLS value for a "LL-µRLS distribution" curve for a particular sample-size set can be used as a positive threshold. A µRLS value for a "WT-µRLS distribution" curve for a particular sample-size set can be used as a negative threshold.

Threshold values established according to a method described in FIG. 9, and referred to in step 301 of FIG. 3 and in steps 501-506 of FIG. 5 can be employed for classifying variants of an unknown life-span phenotype. As described in steps 502-503 of FIG. 5 above, evaluated variants can be classified as "positive" when the determined µRLS is greater than a positive threshold value. As described in steps 504-505 of FIG. 5 above, evaluated variants can be classified as "negative" when the determined µRLS is less than a negative threshold value. "Positive" variants represent LL variants, and "negative" variants represent NLL variants. Probabilities for correctly classifying variants and probabilities for misclassifying variants with respect to variable sample sizes are discussed below.

6. Determining Thresholds as a Function of Probabilities for Misclassification of Variants In FIGS. 3-8, µRLS for each variant of a provided set is compared to statistically established threshold values in order to classify a given variant as "long-lived" (LL) or "not-long-lived" (NLL). In one embodiment, for a given RLS data set corresponding to N cells of a variant, variants are classified as either LL or NLL, while minimizing probabilities for Type I error, Type II error, or both Type I and Type II errors. Type I error is defined as an error resulting from misclassification of a NLL variant as LL. Type II error is defined as an error resulting from misclassification of a LL variant as NLL.

FIG. 11 provides probabilities for Type I and Type II errors as a function of sample size and threshold values, in Table 1. In Table 1 of FIG. 11, based on cumulative probability distributions generated in step 908 of FIG. 9, hypothetical μRLS threshold values (column 2) that include 95% of LL variants are computed for each sample size (N) (column 1) when probabilities for Type II error are <5% (column 4). Corresponding to a given sample size and threshold value, calculated probabilities for Type I error (column 5) are shown.

Probability distributions may be used to predict probabilities for Type I and Type II errors associated with a hypothetical sample size. For example, when N=3, and the determined μRLS>23, then the probability that a variant would be correctly classified as LL is approximately 95% (column 3). However, when sample size is very small, such as N=3, then it is predicted that approximately 73% of NLL variants are likely to be misclassified as LL. Since numbers of NLL variants are likely to be substantially greater than numbers of LL variants, generally in any given population of naturally-occurring variants and in any randomly-generated variant library, the frequency of Type I error for this sample size is not desirable.

Although increasing a sample size is one way to decrease Type I error, total number of N cells that need to be analyzed can be reduced to enable more efficient identification of LL variants. In one embodiment, it is desirable to select a sample size and a threshold value that would enable the correct classification of LL variants at frequencies of at least 50%. In another embodiment, it is also desirable to select a sample size and a negative threshold value that would enable the correct classification of NLL variants at frequencies of at least 95%. In the preferred embodiment, sample size (N) of yeast mother cells of any strain is 5. An exemplary method for classifying variants when sample size equals five is described in Example 2.

7. High Throughput Format

An assay performed in a "homogeneous format" means that the assay can be performed in a single container, with no manipulation or purification of any components being required to determine the result of the assay, e.g., a test agent can be added to an assay system and any effects directly measured. Often, such "homogeneous format" assays will comprise at least one component that is "quenched" or otherwise modified in the presence or absence of a test agent.

A "secondary screening step" refers to a screening step whereby a test agent is assessed for a secondary property in order to determine the specificity or mode of action of a compound identified using the methods provided herein. Such secondary screening steps can be performed on all of the test agents, or, e.g., on only those that are found to be positive in a primary screening step, and can be performed subsequently, simultaneously, or prior to a primary screening step.

"High throughput screening" refers to a method of rapidly assessing a large number of test agents for a specific activity. Typically, the plurality of test agents will be assessed in parallel, for example by simultaneously assessing 96 or 384 agents using a 96-well or 384-well plate, 96-well or 384-well dispensers, and detection methods capable of detecting 96 or 384 samples simultaneously. Often, such methods will be automated, e.g., using robotics.

"Robotic high throughput screening" refers to high throughput screening that involves at least one robotic element, thereby eliminating a requirement for human manipulation in at least one step of the screening process. For example, a robotic arm can dispense a plurality of test agents to a multi-well plate.

A "multi-well plate" refers to any container, receptacle, or device that can hold a plurality of samples, e.g., for use in high throughput screening. Typically, such "multi-well plates" will be part of an integrated and preferably automated system that enables the rapid and efficient screening or manipulation of a large number of samples. Such plates can include, e.g., 24, 48, 96, 384, or more wells, and are typically used in conjunction with a 24, 48, 96, 384, or more tip pipettors, samplers, detectors, and the like.

In some assays, it will be desirable to have positive controls to ensure that the components of the assays are working properly.

In the high throughput assays of the invention, it is possible to screen up to several thousand different modulators in a single day. In particular, each well of a microtiter plate can be used to run a separate assay against a selected potential modulator, or if concentration or incubation time effects are to be observed, every 5-10 wells can test a single modulator. Thus, a single standard microtiter plate can assay about 100 (96) modulators. If 1536 well plates are used, then a single plate can easily assay from about 100 to about 1500 different compounds. It is possible to assay many different plates per day; assay screens for up to about 6,000-20,000, and even up to about 100,000-1,000,000 different compounds are possible using the integrated systems of the invention.

8. Solid State and Soluble High throughput Assays

The invention provides soluble assays using a replicative life span gene or gene product, or a cell or tissue expressing a replicative life span gene product, either naturally occurring or recombinant. The invention further provides solid phase based in vitro assays in a high throughput format, where a replicative life span protein or fragment thereof, is attached to a solid phase substrate.

In the high throughput assays of the invention, either soluble or solid state, it is possible to screen up to several thousand different modulators or ligands in a single day. This methodology can be used for the replicative life span proteins in vitro, or for cell-based or membrane-based assays comprising a replicative life span protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the replicative life span protein of interest or a fragment thereof as part of a fusion protein can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, and the like) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, and the like), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85: 2149-2154, 1963 (describing solid phase synthesis of, e.g., peptides); Geysen et al., *J. Immun. Meth.* 102: 259-274, 1987 (describing synthesis of solid phase components on pins); Frank & Doring, *Tetrahedron* 44:60316040 (1988) (describing synthesis of various peptide sequences on cellulose disks); Fodor et al., *Science,* 251: 767-777, 1991; Sheldon et al., *Clinical Chemistry* 39(4): 718-719, 1993; and Kozal et al., *Nature Medicine* 2(7):753-759, 1996 (all describing arrays of biopolymers fixed to solid substrates). Non-chemical approaches for fixing tag binders to substrates include other common methods, such as heat, cross-linking by UV radiation, and the like.

C. Mutations and Libraries

For the analysis of yeast variants, examples of suitable libraries include various yeast haploid deletion collections, such as ORF-deletion collections made in various suitable backgrounds. For example, a *S. cerevisiae* Genome Deletion and Parallel collection ("SCGDP") contains an almost complete set of genetic variants in which a single-ORF is replaced with a KanMX selectable marker. Several isogenic, S288C-derived, designer deletion variants containing different genetic backgrounds for SCGDP exists, including the BY4741 (MATa), BY4742 (MATα), and BY4743 (MATa/MATα) strains. (Winzeler et al., *Science Vol.* 285: 901-906, 1999). Four deletion collections (haploid MATa, haploid MATα, heterozygous diploid, and homozygous diploid) representing greater than 6000 unique gene disruptions may be employed for the identification of any subset exhibiting a phenotype of interest, including a long life span.

Variants for analysis by methods of the present invention include naturally occurring variants that arise spontaneously in a laboratory and in nature, and genetic variants that are generated in a laboratory using various mutation-inducing methods known to persons skilled in the art. Variants can be generated in any gene, by various methods, including chemical mutagenesis induced by exposure to a mutagen, such as ethane methyl sulfonate ("EMS"), radiation-induced mutagenesis, and various genetic-engineering techniques, such as PCR-mediated mutations, transposon mutagenesis, site-directed mutagenesis, or gene over-expression techniques. Suitable mutations include point mutations, gene deletions, gene insertions, and any modification of genomic sequences that results in a change in gene expression, such as the over-expression, modification, or inactivation of at least one gene or gene product. Contemplated variants include various species of plants; invertebrates, such as yeasts, insects, and worms; and vertebrates, such as mammals or mammalian cells.

III. Isolation of Life-Span Regulating Yeast Genes and Functionally-Related Orthologs A. General Techniques The nucleic acids used to practice this invention, whether RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams, *J. Am. Chem. Soc.* 105: 661, 1983; Belousov, *Nucleic Acids Res.* 25: 3440-3444, 1997; Frenkel, *Free Radic. Biol. Med.* 19: 373-380, 1995; Blommers, *Biochemistry* 33: 7886-7896, 1994; Narang, *Meth. Enzymol.* 68: 90, 1979; Brown *Meth. Enzymol.* 68: 109, 1979; Beaucage, *Tetra. Lett.* 22: 1859, 1981; U.S. Pat. No. 4,458,066.

The invention provides oligonucleotides comprising sequences of the invention, e.g., subsequences of the exemplary sequences of the invention. Oligonucleotides can include, e.g., single stranded poly-deoxynucleotides or two complementary polydeoxynucleotide strands which can be chemically synthesized.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL ($2^{ND}$ ED.), Vols. 1-3, Cold Spring Harbor Laboratory, 1989; CURRENT PROTOCOLS IN MOLECULAR BIOLOGY, Ausubel, ed. John Wiley & Sons, Inc., New York, 1997; LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y., 1993.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be done by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld, *Nat. Genet.* 15: 333-335, 1997; yeast artificial chromosomes (YAC); bacterial artificial chromosomes (BAC); P1 artificial chromosomes, see, e.g., Woon, *Genomics* 50: 306-316, 1998; P1-derived vectors (PACs), see, e.g., Kern, *Biotechniques* 23: 120-124, 1997; cosmids, recombinant viruses, phages or plasmids.

The invention provides fusion proteins and nucleic acids encoding them. A chronological life span polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego, Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams, *Biochemistry* 34: 1787-1797, 1995; Dobeli, *Protein Expr. Purif* 12: 404-414, 1998). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll, *DNA Cell. Biol.* 12: 441-53, 1993.

B. Verification of Genes Isolated from LL Variants

Genes that confer longevity within identified LL variants can be functionally retested to determine whether the longevity effect observed in LL-classified variants is reproducible. For example, new deletion strains can be re-created by standard homologous recombination methods, and mean RLS for re-created deletion strains can be determined. If a deletion of the gene in question results in life spans substantially higher than that of a "wildtype" reference, then the deleted gene is correctly identified. If the re-created deletion strain is determined to exhibit a life span similar to that of a "wildtype" reference, then it is possible that a genetic change unrelated to a particular known deletion mutation may cause a "long-lived" phenotype observed initially in a variant classified as LL. Various methods known to persons skilled in the art can be utilized to confirm bonafide genes that regulate life spans, and exclude genes that are not related to life-span regulation but are falsely detected.

C. Cloning Genes of Interest from Selected LL Variants

In one aspect, methods of the present invention can be employed for the identification, isolation, and cloning of genes of interest. In one embodiment, methods of the present invention, such as methods described in FIGS. 3-8, enable the identification, isolation, and cloning of genes that regulate life spans. For example, yeast variants classified as "long-lived" (LL) can be employed for isolating genes that regulate life spans in yeasts and in other eukaryotes.

Various methods for gene isolation and gene cloning are well-known by persons skilled in the art that enable the identification of a gene of interest having an unknown sequence that may be expressed in one variant and not expressed in a reference variant, or that may not be expressed in one variant and expressed in a reference variant. Exemplary methods for gene isolation and gene cloning include: subtractive or differential hybridization, RT-PCR-mediated differential display (U.S. Pat. No. 5,599,672), and other functionally-equivalent or related methods for gene-cloning known by persons skilled in the art. These methods and many others enable the synthesis of cDNAs corresponding to desirable mRNA transcripts that encode life-span-regulating proteins. Cloned cDNAs of interest can be sequenced so that the determined sequence can be entered into a genomic database in order to identify the gene. In particular, polymerase chain reaction ("PCR") or other in vitro amplification methods may be used for cloning nucleic acid sequences of interest when a partial or complete sequence is known, as in the characterization of mutants from a known "bar-coded" genomic library.

For in vivo amplification, genes of interest may be subcloned into suitable vectors, such as phage vectors and prokaryotic vectors. Exemplary components of a suitable cloning vector include a replicon recognizable by a prokaryotic host, a gene encoding antibiotic resistance to permit selection of recombinant hosts, and a multiple cloning region containing unique restriction sites within non-essential regions of a plasmid vector so that a gene of interest may be inserted or removed. Examples of cloning plasmids include pBR322-derived plasmids, pSKF, and pET23D.

D. Identification of Life-Span-Regulating Orthologs
 1. By Screening Libraries Containing Genomic Sequences
  a. Hybridization Conditions Identified yeast sequences of the present invention can be employed for identifying homologous sequences contained within various invertebrates, such as worms and flies; and vertebrates, including mammals, such as mice, rats, dogs, cats, cows, pigs, horses, and humans. For example, the nucleic acid sequences derived from identified "long-lived" variants can be used as probes for identifying homologous nucleic acid sequences derived from various organisms of diverse species. Identified sequences include genes having at least about 40% sequence similarity to the sequences for the genes indicated in Table 5 or 6, or at least about 70% sequence similarity to these genes. Various methods for assaying sequence homology include hybridization techniques conducted at variable degrees of stringency. To assay for highly-conserved sequences with substantial homology, hybridizations may be conducted under stringent conditions. Under stringent conditions, hybridized pairs of nucleic acids molecules having high thermodynamic stability are selected, in which the hybridized pairs usually consist of highly complementary subsequences. Exemplary stringent hybridization conditions include 50% formamide, 5×SSC and 1% SDS incubated at 42° C., or 5×SSC and 1% SDS incubating at 65° C., which is followed by a wash in 0.2×SSC and 0.1% SDS at 65° C.

For identification of orthologous sequences, including polymorphic alleles and non-polymorphic alleles, that are related to the identified yeast sequences, hybridization conditions that are within a range of low-to-moderately stringent may be more suitable since the percentage of sequence similarity shared between orthologous sequences can be as low as 35%, especially if entire lengths of compared gene sequences are considered. Examples of moderately stringent hybridization conditions include hybridizations performed at 40% formamide, 1 M NaCl, 1% SDS at 37° C., followed by a wash in 1×SSC at 45° C. Generally, decreasing the concentrations of salt, SDS, formamide, and temperature will decrease the stringency of hybridization conditions. Alternative hybridization buffers, wash conditions, and temperature parameters are known by persons skilled in the art of Southern and Northern techniques, and general molecular biology. A hybridization signal intensity of at least twice the intensity of a control probe can be interpreted as a positive identification. Sambrook et al., Molecular Cloning, A Laboratory Manual (2nd ed. 1989) is incorporated by reference in its entirety.

b. Nucleic-Acid Libraries

By utilizing a sub-sequence derived from the identified yeast sequences as probe molecules, various libraries containing desired sequences may be screened. For example, human-derived cellular mRNAs, or human cDNA libraries derived from cellular mRNAs, that presumably contain human orthologous sequences can be screened with a probe containing complementary yeast sequence. Methods for making and screening cDNA libraries are known by persons skilled in the art. Alternatively, a human genomic library presumably containing human orthologous sequences can be screen by utilizing the identified yeast sequence as a probe. Methods for making and screening a genomic library, and methods for sequencing nucleic acid molecules are well-established and known by persons skilled in the art. Although the present examples are based on human libraries, analogous libraries and reagents can be constructed for any organism of interest, including various mammals, such as mice, rats, dogs, cats, cows, pigs, sheep, horses, and other primates. For example, analogous libraries and reagents can be used to identify life-span regulating orthologous sequences represented in various endangered species of fishes, amphibians, reptiles, birds, and mammals. Screening genomic libraries of live-stock animals that are substantially valuable for agricultural use and for recombinant-protein production are also contemplated.

c. Expression Libraries

Alternatively, expression libraries presumably containing orthologs of interest, such as polypeptides having at least about 40% sequence similarity to the sequences for the genes indicated in Table 5 or 6, or at least about 70% sequence similarity to the sequences for the genes indicated in Table 5 or 6, can be screened by utilizing antibodies made against identified yeast homologs, such as the sequences for the genes indicated in Table 6. Orthologs generally contain one or more sub-regions, including regulatory domains and catalytic domains, that are highly-conserved. Antibodies that recognize such highly conserved, functional domains of a conserved homolog are likely to recognize similar domains within a related ortholog. Orthologs identified by such antibodies can be sequenced by various methods known in the art in order to determine the corresponding polypeptide sequences. Expression libraries can be constructed for any organism of interest, including mammalian species, such as mice, rats, dogs, cows, pigs, horses, primates, and human.

d. Degenerate Primers

Alternatively, by utilizing degenerate-oligonucleotide primers based on identified yeast sequences, such as the sequences for the genes indicated in Table 5, various nucleic-acid-amplification techniques, such as polymerase-chain-reaction (PCR), can be used to amplify orthologous sequences from various libraries containing nucleic-acid molecules, including mRNAs, cDNAs, genomic DNA, organelle-specific DNA, and others, that are derived from cells of any organism of interest, including mammalian species, such as mice, rats, dogs, cows, pigs, horses, primates, and human. Various methods for utilizing degenerate-oligonucleotide primers to amplify desired sequences are well-known in the art.

2. By Searching Databases and by Sequence Alignments

Alternatively, genomic databases for model organisms of various species can be employed for conducting multi-genome-wide sequence alignments in order to identify homologous sequences of interest. For each identified yeast sequence, such as the sequences for the genes indicated in Table 5, related orthologous sequences can be determined by searching composite genomic databases. The breath of a database search is limited by the scope of representative model organisms for which sequence data is available.

Homology can be determined by various methods, including alignments of open-reading-frames ("ORFs") contained in private and/or public databases. Any suitable mathematical algorithm may be used to determine percent identities and percent similarities between any two sequences being compared. For example, nucleic acid and protein sequences of the present invention can be used as a "query sequence" to perform a search against sequences deposited within various public databases to identify other family members or evolutionarily-related sequences. Genomic sequences for various organisms are currently available, including fungi, such as the budding yeast, or *Saccharomyces cerevisiae*; invertebrates, such as *Caenorhabditis elegans* and *Drosophila melangaster*; and mammals, such as the mouse, rat, and human. Exemplary databases for identifying orthologs of interest include Genebank, Swiss Protein, EMBL, and National Center for Biotechnology Information ("NCBI"), and many others known in the art. These databases enable a user to set various parameters for a hypothetical search according to the user's preference, or to utilize default settings. Example 3 provides a table of identified sequences, including various exemplary mammalian orthologs.

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media can be a hard disk, a floppy disk, a magnetic tape, CD-ROM, Digital Versatile Disk (DVD), Random Access Memory (RAM), or Read Only Memory (ROM) as well as other types of other media known to those skilled in the art.

As used herein, the terms "computer," "computer program" and "processor" are used in their broadest general contexts and incorporate all such devices.

E. Functional Confirmation of Orthologs

Various genes and gene products isolated from LL variants, and orthologous genes/gene products are useful for identifying pharmaceutical agents that can modulate the activities of these genes/gene products. Prior to utilizing orthologous genes/gene products for screening compounds, the life-span-regulating properties of orthologs can be confirmed by various methods known in the art, which are provided below.

Figure 14:
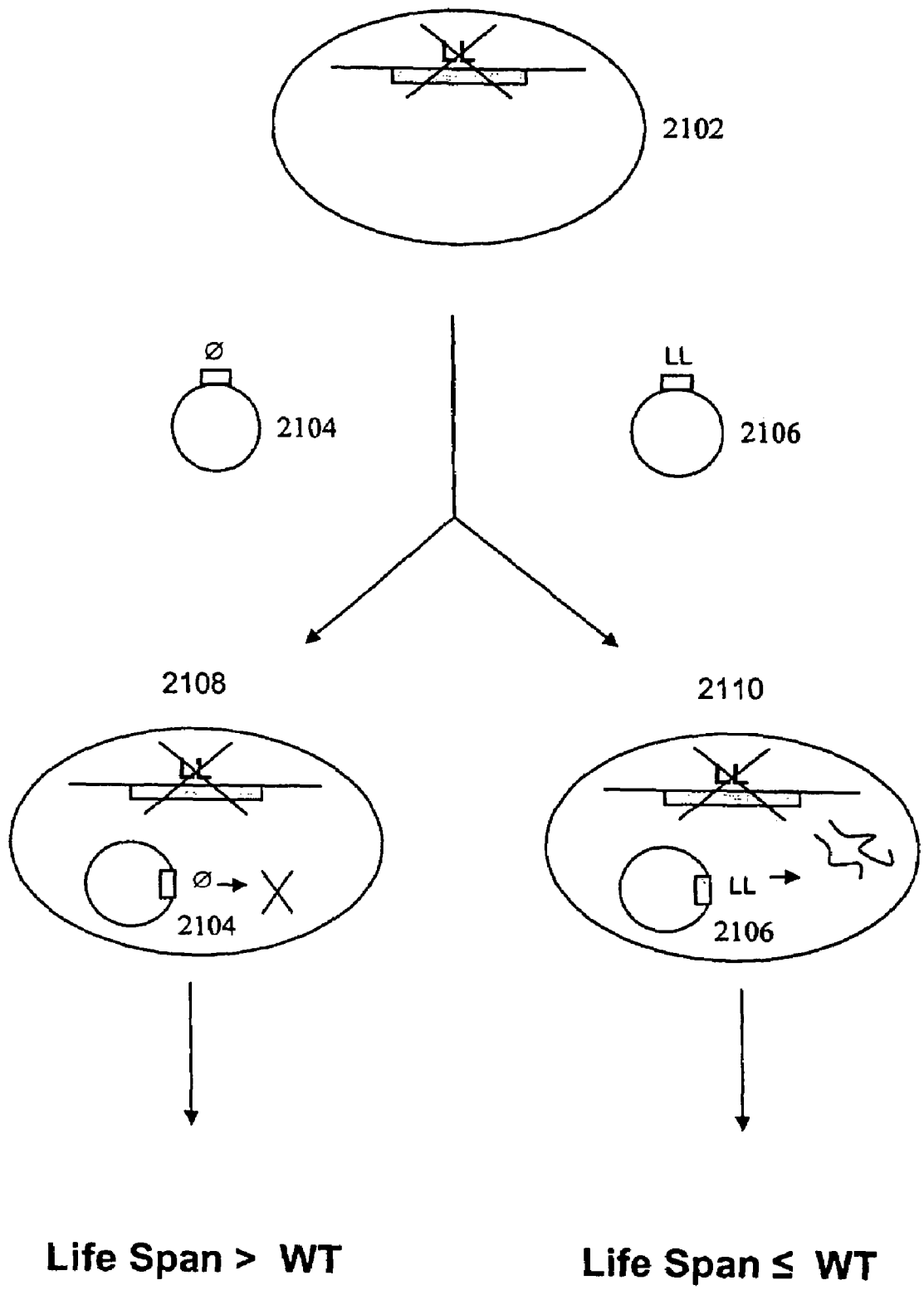
FIG. 14 illustrates an exemplary genetic complementation assay for assaying orthologs utilizing LL variants.

1. Genetic Complementation of Long-Lived Variants by Over-Expression of Orthologs FIG. 14 illustrates an exemplary genetic complementation assay for assaying orthologs utilizing LL variants. In FIG. 14, a hypothetical "long-lived" (LL) variant 2102 is shown. A hypothetical LL variant includes LL variants identifiable by methods of the present invention, and LL variants identifiable by alternative methods known in the art. A suitable LL variant, in this context, is any organism that exhibits a life span longer than that of a reference organism by at least 20%, 25%, 30%, 35%, 40%, 45%, 50%, 55%, 60%, 65%, 70%, 75%, 80%, 85%, 90%, 95%, or 100%. For example, a suitable LL variant is deficient in a gene that confers a long life span ("LL-gene"), such as genes having at least about 40% sequence similarity to the sequences for the genes indicated in Table 5 or 6, or at least about 70% sequence similarity to the sequences for the genes indicated in Table 5 or 6. A suitable "wildtype" reference is able to express a corresponding endogenous gene. As a negative control, a LL variant 2102 can be transformed with either a control expression vector that does not contain a gene insert 2104, or that contains a gene insert unrelated to life-span regulation, or that contains a non-functional mutated allele of the gene of interest. To assay the effect of a "LL-gene" ortholog on the life span of a particular LL variant, a LL variant deficient in a particular "LL-gene" can be transformed with an expression vector containing a gene insert 2106 that encodes the related ortholog. The life span of a transformed cell 2108 containing the control expression vector 2104 is expected to be greater than that of a "wildtype" reference. However, a life span of a transformed cell 2110 containing the expression vector 2106 is expected to be less than the transformed cell containing the control expression vector and approximately equal to a life span of a "wildtype" reference if sufficient amount of an ortholog under evaluation is produced and recognized by cellular proteins. In these cases, the over-expression of a "LL gene" ortholog should reverse the longevity effect observable in the absence or suppression of an endogenous LL gene. Methods for transforming various organisms and methods for constructing suitable expression vectors are known by persons skilled in the art.

2. Suppression of Orthologs by RNA Interference

Figure 15:
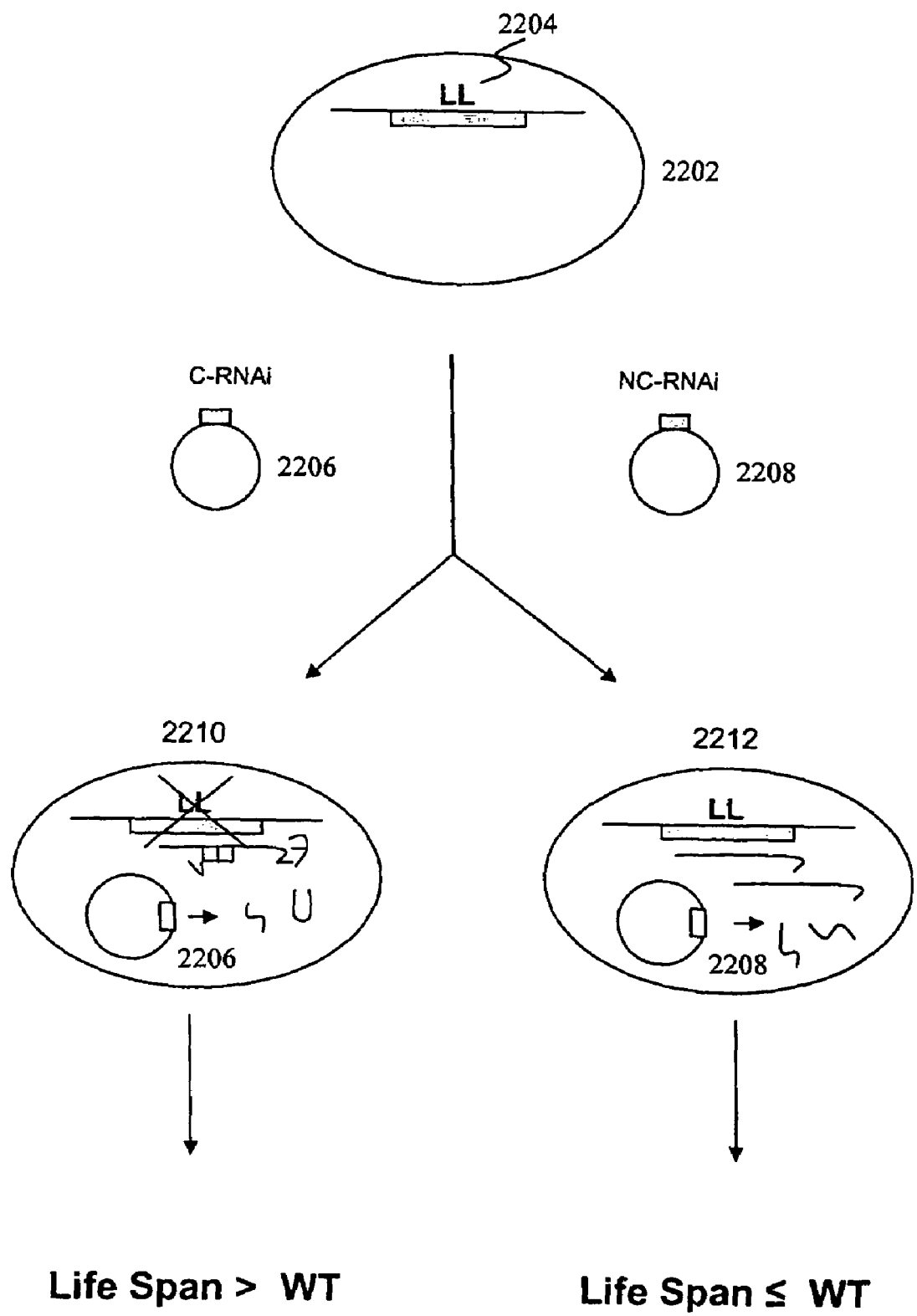
FIG. 15 illustrates exemplary methods for suppressing gene expression of endogenous orthologous sequences using RNA interference in various hosts.

FIG. 15 illustrates exemplary methods for suppressing the gene expression of endogenous orthologous sequences using RNA interference in various hosts. In FIG. 15, a hypothetical host 2202 is shown, in which the host is transcriptionally-competent for an endogenous "LL" 2204 gene expression. Suitable hosts include various invertebrates, such as worms; vertebrates, such as mammals; and host cell cultures derived from any multicellular eukaryote. A suitable "LL" gene 2204 includes identified sequences of the present invention, including various orthologs related to identified yeast genes, and determined to increases life span by at least 20%, 25%, 30%, 35%, 40%, 45%, 50%, 55%, 60%, 65%, 70%, 75%, 80%, 85%, 90%, 95%, or 100% relative to that of a reference cell or a reference organism. Identified sequences include genes having at least about 40% sequence similarity to the sequences for the genes indicated in Table 6, or at least about 70% sequence similarity to the sequences for the genes indicated in Table 6. For example, a host cell 2202 can be transformed with either an expression vector that expresses a short-interfering RNA molecules "C-RNAi" 2206 which is complementary to mRNA encoded by a given "LL" gene 2204, or a control expression vector that encodes a non-complementary RNAi molecules, such as "NC-RNAi" 2208. Exemplary complementary sequences include anti-sense polynucleotides that can hybridize to sequences having at least about 40% sequence similarity to the sequences for the genes indicated in Table 5 or 6, or at least about 70% sequence similarity to the sequences for the genes indicated in Table 5 or 6. The life span of a transformed cell 2210 that expresses complementary RNAi molecules, such as "C-RNAi" 2206, is expected to be greater than the life span of a reference host. Suitable reference hosts include comparable "wildtype" (WT) host cells that have not been exposed to RNAi molecules. In this case, if a complementary RNAi "C-RNAi" 2206 can sufficiently inactivate a LL-gene product, a longevity effect should be observed. However, the life span of a transformed cell 2210 that expresses non-complementary RNAi molecules, such as "NC-RNAi" 2208, is expected to be less than or approximately equal to that of a "wildtype" reference. Methods for constructing suitable expression vectors and methods for transforming various organisms are known by persons skilled in the art. Exemplary methods are provided in section IV below.

Anti-sense RNAi molecules that contain a sequence complementary to a target mRNA, such as "C-RNAi" 2206, includes various forms of RNAi molecules, such as short-interfering RNAs ("siRNAs") and short-hairpin RNAs ("shRNAs") that can be introduced into cellular hosts in various ways. For example, if the host is a worm or a fly, then target-specific RNAi can be introduced as double-stranded RNAs via integrated transposons or by replicating viruses. Double-stranded RNAs can be processed in vivo into siRNAs that can activate RNA-induced silencing complexes ("RISCs") and degrade homologous mRNA molecules resulting in post-transcriptional gene silencing. For gene inactivation in mammalian cells, introduction of long double-stranded RNA molecules results in nonspecific toxicity due to the activation of the gamma-interferon pathway. Thus, for the identified genes/gene products of the present invention having life-span-regulating activity, various siRNAs of 21-23 base-pairs, may be chemically synthesized and introduced into mammalian host cells by various methods, including transfection, without activating the gamma-interferon pathway.

Alternatively, expression vectors that produce siRNA-like molecules in vivo can be constructed so that promoters, such as RNA-polymerase-II and RNA-polymerase-III, are operably-linked to sequences encoding shRNA molecules. Such shRNAs are processed intracellularly into siRNA-like molecules by "Dicer," a RNase III family member. These siRNAs are incorporated into RNA-inducing silencing complexes ("RISCs"), in which siRNA duplexes are unwound so that single-stranded siRNA molecules can guide RISC to complementary sub-sequences within target MRNA, resulting in endonucleolytic cleavage of target mRNA. Designing effective siRNA and shRNA are known in the art, and are discussed further in section IV.

Alternative methods for achieving gene inactivation are also known, which can be applied in this assay. For example, genetic suppressor elements ("GSE") are short and biologically-active cDNA fragments that can interfere with the function of an endogenous gene. GSEs can inactivate a target gene by encoding anti-sense RNA molecules that interfere with the function of the complementary mRNA, and by encoding peptide fragments that act as dominant-negative inhibitors of the full-length target protein. In one embodiment, the present invention is directed to compounds that increase a life span of a host, the compounds comprising an oligonucleotide that interacts with a gene having at least about 40% sequence similarity to at least one of the sequences for the genes indicated in Table 5 or 6, or a gene having at least 70% sequence similarity to at least one of the sequences for the genes indicated in Table 5 or 6. Such DNA oligonucleotide compounds can be single-stranded or double-stranded. In another embodiment, the oligonucleotide compound interacts with a coding strand of a gene. In another embodiment, the oligonucleotide compound interacts with a non-coding strand of a gene.

Alternatively, ribozymes, which are catalytic RNA molecules that can cleave RNA targets containing complementary subsequences, can be used for gene inactivation. A discussion of ribozymes that can inactivate life-span-regulatory genes/gene products are discussed further in section IV.

In addition, non-human transgenic animals in which endogenous genes having life-span-regulating activity are inactivated within somatic and/or germ-line cells can be generated by methods known in the art. In one embodiment, the present invention is directed to these "knock-out" animals that cannot produce gene products encoded by genes having life-span regulating activity, and having at least about 40% sequence similarity to the sequences for the genes indicated in Table 5 or 6, or at least about 70% sequence "similarity" to the sequences for the genes indicated in Table 5 or 6. Exemplary non-human transgenic animals include various flies, worms, and mammals, such as rodents and rabbits.

Figure 16A:
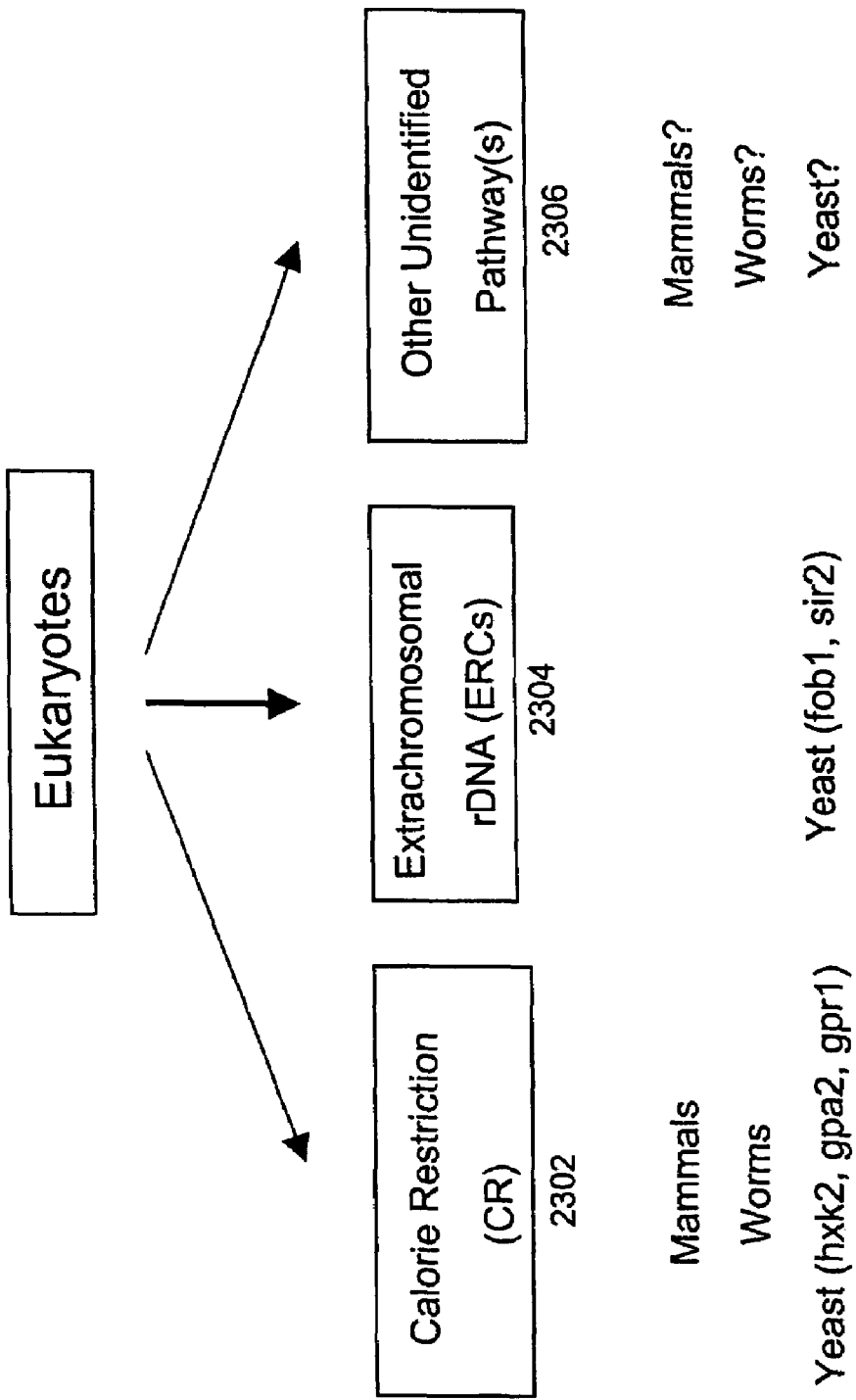
FIG. 16A illustrates two pathways known to regulate life spans in yeast.

F. Epistasis Analysis of LL Variants to Identify Mammalian Components Acting in Calorie Restriction (CR) Pathway FIG. 16A illustrates two pathways known to regulate life spans in yeast. The calorie-restriction (CR) pathway 2302 is highly conserved among various eukaryotes, including yeasts. The CR pathway in yeast can be activated either by: (1) enforcing calorie restrictions, such as reductions in glucose intake, or (2) deleting genes known to act in the CR pathway, including genes such as HXK2, GPA2, or GPR1. Activation of the CR pathway by either method results in 30-40% increase in yeast life spans. HXK2 encodes a hexokinase that converts glucose to glucose-6-phosphate during glycolysis. GPA2 and GPR1 decrease cAMP-dependent protein kinase ("PKA") activity.

Second, the ERC-regulation pathway 2304 controls the rate of extra-chromosomal rDNA (ERCs) formation, involving life-span-regulatory proteins, such as Fob1 and Sir2 that act antagonistically. Fob1 is a replication-fork-barrier protein, and Sir2 is a NAD-dependent-histone deacetylase. ERCs formed by recombination within an rDNA repeat continue to replicate through out the life span of a given mother cell, and partition with the mother cell instead of emerging daughter cells. After successive rounds of mitosis, nuclear accumulation of ERCs in mother cells reaches toxic levels that restrict further cell divisions.

Figure 16B:
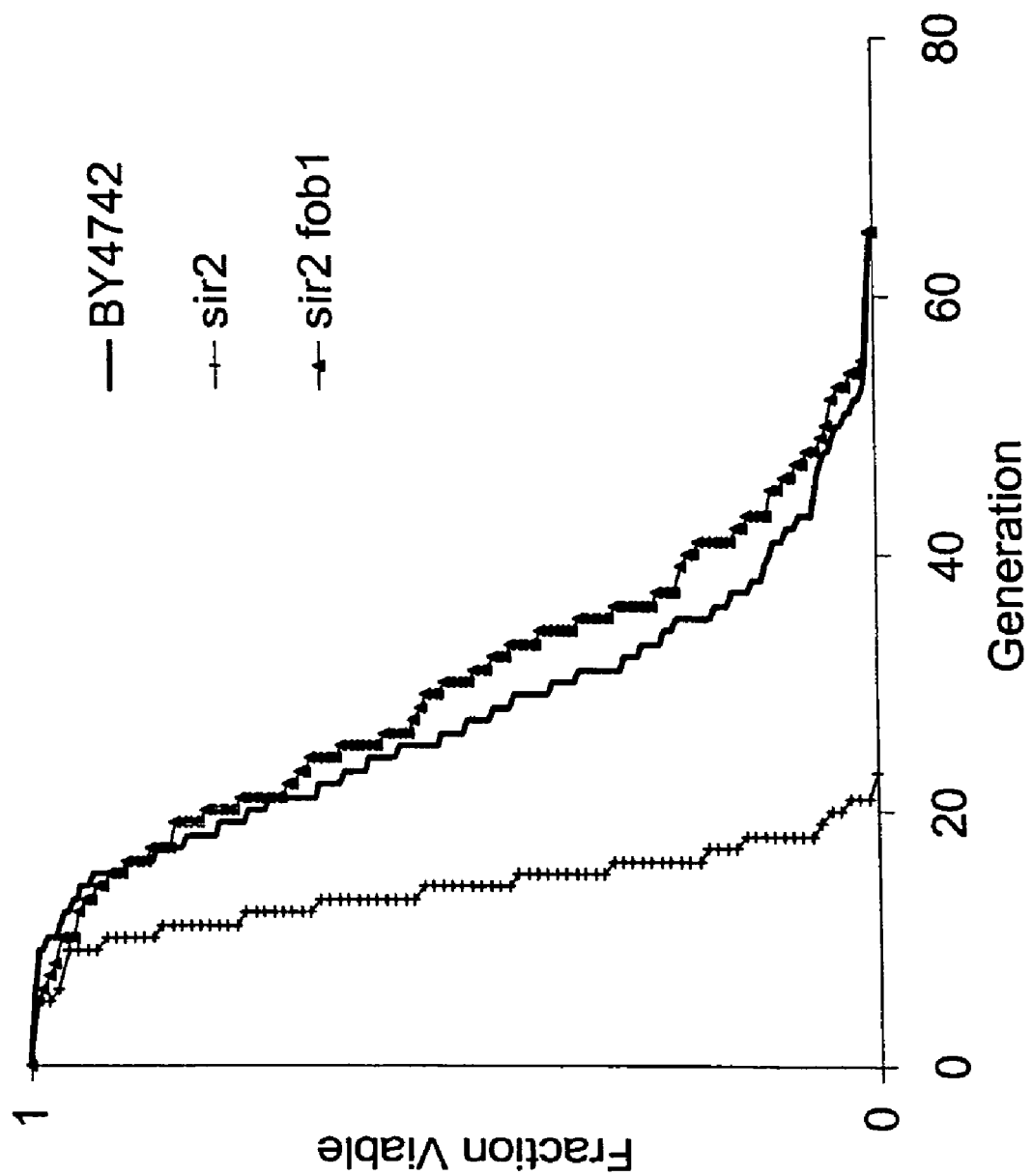
FIG. 16B compares mortality curves of a fob1-sir2-double deletion mutant, fob1 deletion mutant, and sir2 deletion mutant.

FIG. 16B compares mortality curves of a fob1-sir2-double deletion mutant, fob1-deletion mutant, and sir2-deletion mutant. Sir2 can delay the onset of senescence by inhibiting ERC formation, and sir2Δ strains generally exhibit a shorter RLS than a "wildtype" reference strain. In contrast, Fob1 can accelerate aging by promoting ERC formation, and fob1Δ strains generally exhibit a longer RLS than a "wildtype" reference strain. However, over-expression of sir2 in the context of a FOB1 deletion does not further increase life span, demonstrating that sir2 and fob1 operate in the same pathway. Furthermore, fob1Δ-sir2Δ-double-deletion strains generally demonstrate life spans comparable to a "wildtype" reference strain, such as the BY4742 strain.

The present inventors are the first to identify a Sir2-independent calorie restriction (CR) pathway in yeast, which may be conserved in a broad range of eukaryotes. Data supporting the characterization of this novel pathway, is provided in Example 4. Example 5 provides an exemplary method utilizing epigenetic analysis to identify mammalian genes/gene products that act either in: (1) the Sir2-independent CR pathway, and (2) other putatively uncharacterized life-span-regulatory pathways 2306. In one embodiment, variants deficient in FOB1 and SIR2, such as fob1Δ-sir2Δ-double-deletion strains, can be used in cell-based assays to identify longevity-promoting compounds that can interact with components of the calorie restriction (CR) pathway in mammals. Drug-screening methods utilizing fob-sir2-deficient strains are further described in section IV.

IV. Methods for Identifying Compounds that Promote Life-Span Extension

Genes sequences identified by present methods can be subcloned into various prokaryotic and eukaryotic vectors for various uses. Various embodiments are directed to prokaryotic expression vectors comprising identified sequences of the present invention, including related orthologs of yeast sequences that have life-span-regulating activities. Various embodiments are directed to eukaryotic expression vectors comprising identified sequences of the present invention, including related orthologs of yeast sequences that have life-span-regulating activities. These expression vectors comprising life-span-regulating sequences (referred to as "present expression vectors") can be used, for example: (1) to assay identified orthologs to confirm life-span-regulating activities, as described in section III, and (2) to screen compounds in order to identify those that can promote life-span extension, or promote longevity.

Various methods for screening such longevity-promoting compounds include: (1) in vitro screening methods, and (2) in vivo screening methods, provided below. For implementing these methods, identified sequences of the present invention, including related orthologs of yeast sequences, need to be expressed within various cellular hosts. Suitable expression vectors and host cells are provided before discussion of screening methods to facilitate discussion.

A. Expression Vectors

Construction of prokaryotic expression systems that are operable in various prokaryotic cells, and eukaryotic expression systems that are operable in yeast, insects, worms, and various mammalian cells are well-known by persons skilled in the art. Generally, suitable expression vectors include a transcriptional regulatory element operably-linked to a transcriptional unit comprising a gene of interest, such as the gene sequences identified by methods of the present invention that regulate eukaryotic-aging processes, including genes having at least about 40% sequence similarity to the sequences for the genes indicated in Table 5 or 6, or at least about 70% sequence similarity to the sequences for the genes indicated in Table 5 or 6. Suitable gene sequences include double-stranded DNA sequence, such as fragments of genomic DNA, cDNAs, or cDNA fragments, that encode any portion of life-span-regulating polypeptides. A gene of interest can be a chimeric molecule, comprising two or more distinct polynucleotide sequences that together encodes a fusion protein. For example, epitope tags can be optionally added to recombinant proteins of interest in order to provide a molecular label, to facilitate isolation, or other uses. Examples of recombinant techniques can be found in various sources, such as standard laboratory molecular biology treatises, such as Sambrook et al., Molecular Cloning: A Laboratory Manual, 3d ed., 2001, Cold Spring Harbor, which is incorporated in its entirety. Conventional techniques for DNA engineering, including restriction-enzyme digestion, nucleic-acid ligation, and PCR are known by persons skilled in the art.

A transcriptional regulatory element of a transcriptional unit may include one or more promoters and enhancers. Generally, a promoter is positioned upstream of a gene of interest. In contrast, an enhancer can be placed upstream, downstream, or both upstream and down stream of a gene of interest. With respect to a gene of interest, promoter and enhancer elements may be derived from a homologous source, for example, derived from a native gene locus. For example, an endogenous promoter of gene A may be operably-linked to gene A within a vector. Alternatively, promoter and enhancer elements may be derived from a heterologous source, such as from the same gene locus of a different species, from a different gene locus of the same species, or from a different gene locus of a different species.

Various constitutive and inducible promoters that are suitable for either prokaryotic or eukaryotic expression vectors are generally known by persons skilled in the art. Constitutive promoters are transcriptionally activated at steady-state. Inducible promoters are transcriptionally activated upon proper stimulus. Examples of constitutive eukaryotic promoters include various promoters derived from infectious viruses, such as retroviruses, herpes virus, lentivirus, adenovirus and adenovirus variants, and mumps and poliovirus viruses. Promoter and enhancer selections are generally independent of a particular gene of interest, and are dependent on the presence or absence of host-specific factors, such as tissue-specific regulatory factors that are present within a host cell. Promoter and enhancer selections can vary depending on the type of eukaryotic host cell in which the present expression vectors need to be operable. Thus, operable promoters of the present invention include a broad range of constitutive, inducible, tissue-specific, non-tissue-specific, and developmentally-specific promoters and enhancers that can be derived from various viruses, prokaryotes, and eukaryotes.

Optionally, the present expression vectors may include one or more additional sequences that can enhance gene expression. For example, the present expression vectors may include a 3' untranslated sequence ("UTS"), such as a polyadenylation site that can be derived from the 3' end of most eukaryotic genes. Various polyadenylation sites may be positioned downstream of the gene of interest, including the 3' UTS derived from any gene locus, including homologous polyadenylation site and heterologous polyadenylation sites. In addition, a 5' UTS element may be optionally positioned upstream of a gene of interest to enhance long-term gene expression.

The present expression constructs may also include genes that encode a selectable marker that confers a selectable phenotype upon introduction into various mammalian cells. For example, a selectable marker which confers a selectable phenotype, such as drug resistance, nutritional auxotrophy, resistance to a cytotoxic agent, or expression of a surface protein, may be used. Examples of suitable selectable markers include genes that confer resistance to neomycin, dihydrofolate, puromycin, hygromycin, and histidine D. A selectable marker can be introduced into host cells by incorporating the selectable marker gene within present expression vectors comprising identified sequences having life-span-regulating activities, or by incorporating the marker gene into a distinct vector than can be co-transfected with the present expression vectors.

B. Host Cells

The present expression vectors may be introduced into various host cells that include various cell-lines, primary cells, and secondary cells, known by persons skilled in the art. Methods for gene-delivery include receptor-mediated gene delivery, microinjection, protoplast fusion, and conventional methods of transfection, such as liposome fusion, electroporation, calcium-phosphate precipitation, and other methods known in the art. For protein production using insect cell-lines such as the Hi-fives and Sf-9 cells, viral infection is a preferred method for gene delivery. Vectors designed to target insect tissues for making recombinant proteins are contemplated. (Wurm, *Nature Biotechnology* 21: 34-35, 2003). To produce recombinant proteins using various mammalian cell lines, transfection and receptor-mediated gene delivery methods, such as virus infection, may be preferred.

C. In Vitro Biochemical Screening Assays

Figure 19:
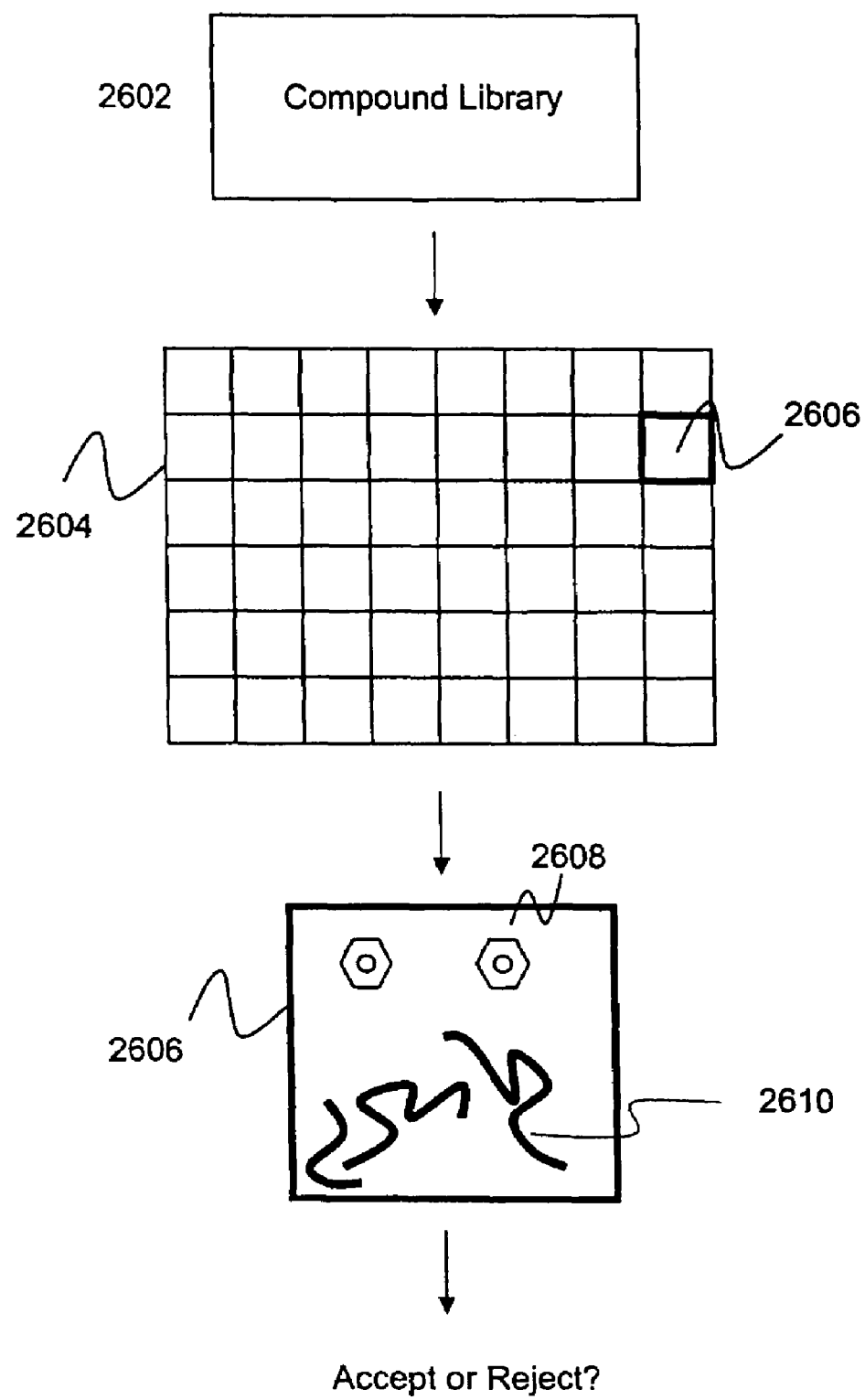
FIG. 19 illustrates an exemplary high throughput screening method for identifying longevity-promoting compounds.

In one embodiment, the present invention is directed to high throughput screening methods to screen longevity-promoting compounds by utilizing identified genes/gene products having life-span-regulating activities as target molecules. FIG. 19 illustrates an exemplary high throughput screening method for identifying longevity-promoting compounds. In FIG. 19, a hypothetical compound library 2602 containing a large number of candidate compounds is provided. Suitable libraries of compounds include compounds derived by various combinatorial-chemistry methods and by isolating natural products. Methods for generating such libraries are known in the art. Next, candidate compounds of a library are exposed to target molecules. For convenience, target molecules may be assayed together in an array-like format 2604. Target molecules of interest 2610 may be placed into discrete analytical chambers 2606. Suitable target molecules of interest include gene products encoded by genes having at least about 40% sequence similarity to the sequences for the genes indicated in Table 5 or 6, or at least about 70% sequence similarity to the sequences for the genes indicated in Table 5 or 6. Target molecules can be provided either in soluble form or can be attached to a physical substrate. In one embodiment, a single-type of target molecule is placed into multiple analytical chambers so that reactivities against a panel of candidate compounds can be determined. In an alternative embodiment, different target molecules are placed together in a single chamber, such as chamber 2606, so that combinations of different target molecules can be tested together against a panel of candidate compounds, such as compound 2608. Each reaction chamber can be evaluated in order to quantify the extent of a biochemical reaction under analysis. The type of biochemical reaction under evaluation depends on the function of the target molecule of interest. Lastly, compounds can be accepted or rejected by comparing experimental value to a pre-established threshold, or cut-off, value. Accepted compounds may be further evaluated for solubility, bioavailability, potency, and other relevant parameters. An effective compound can increase the life span of a host by at least 10%, 15%, 20%, 25%, 30%, 35%, 40%, 45%, 50%, 55%, 60%, 65%, 70%, 75%, 80%, 85%, 90%, 95%, or 100%.

In one embodiment, target molecules of interest are coding and/or non-coding strands of DNA molecules, such as genes, or gene fragments, having at least about 40% sequence similarity to the sequences for the genes indicated in Table 5 or 6, or at least about 70% sequence similarity to the sequences for the genes indicated in Table 5 or 6. In another embodiment, target molecules of interest are proteins, such as polypeptides encoded by genes having at least about 40% sequence similarity to the sequences for the genes indicated in Table 5 or 6, or at least about 70% sequence similarity to the sequences for the genes indicated in Table 5 or 6. In another embodiment, target molecules of interest are RNA molecules, such as RNA sequences encoded by genes having at least about 40% sequence similarity to the sequences for the genes indicated in Table 5 or 6, or at least about 70% sequence similarity to the sequences for the genes indicated in Table 5 or 6. In another embodiment, target molecules of interest are sequences that are complementary to messenger RNAs encoded by genes having at least about 40% sequence similarity to the sequences for the genes indicated in Table 5 or 6, or at least about 70% sequence similarity to the sequences for the genes indicated in Table 5 or 6.

In various embodiments discussed above, various assays, including homogenous assays and separation-based assays, may be employed for detecting products derived from various biochemical reactions. Examples of homogeneous assays, in which the detection of the product does not require a separation step, includes: fluorescence polarization assays, time-resolved-fluorescence-energy-transfer ("HTRF/LANCE™") assays, conventional fluorescence-resonance-energy-transfer ("FRET") assays, SPA/flashplate assays, alpha screen assays, and coupled-enzyme assays. Examples of separation-based assays, in which the reaction product is detected after separation from starting reagents, includes: filter-binding assays, precipitation/filtration assays, and enzyme-linked-immunosorbent assays ("ELISA"). These methods and others are known in the art, and reviewed in Walters et al., *Nature Reviews* 2: 259-266, 2003, which is incorporated by reference.

Other embodiments are directed to virtual-screening methods to identify longevity-promoting compounds by utilizing identified genes/gene products having life-span-regulating activities as target molecules. Virtual libraries are structural databases containing candidate compounds. In virtual screening, at the first-dimensional level, a generic filter is first applied to eliminate chemical structures having properties that are statistically predicted to be unlikely drug candidates. At the second and third dimensional levels, additional levels of filters are applied, which takes into consideration ligand information and conformation, respectively. At the highest dimensional level, various highest-ranking molecules are selected for biostructure-based "docking and scoring," determined with respect to a binding site of a target protein. These and other related methods are known by persons skilled in the art.

D. Screening Longevity-Promoting Compounds in Sir2-Fob1-Deficient Cells

Figure 20:
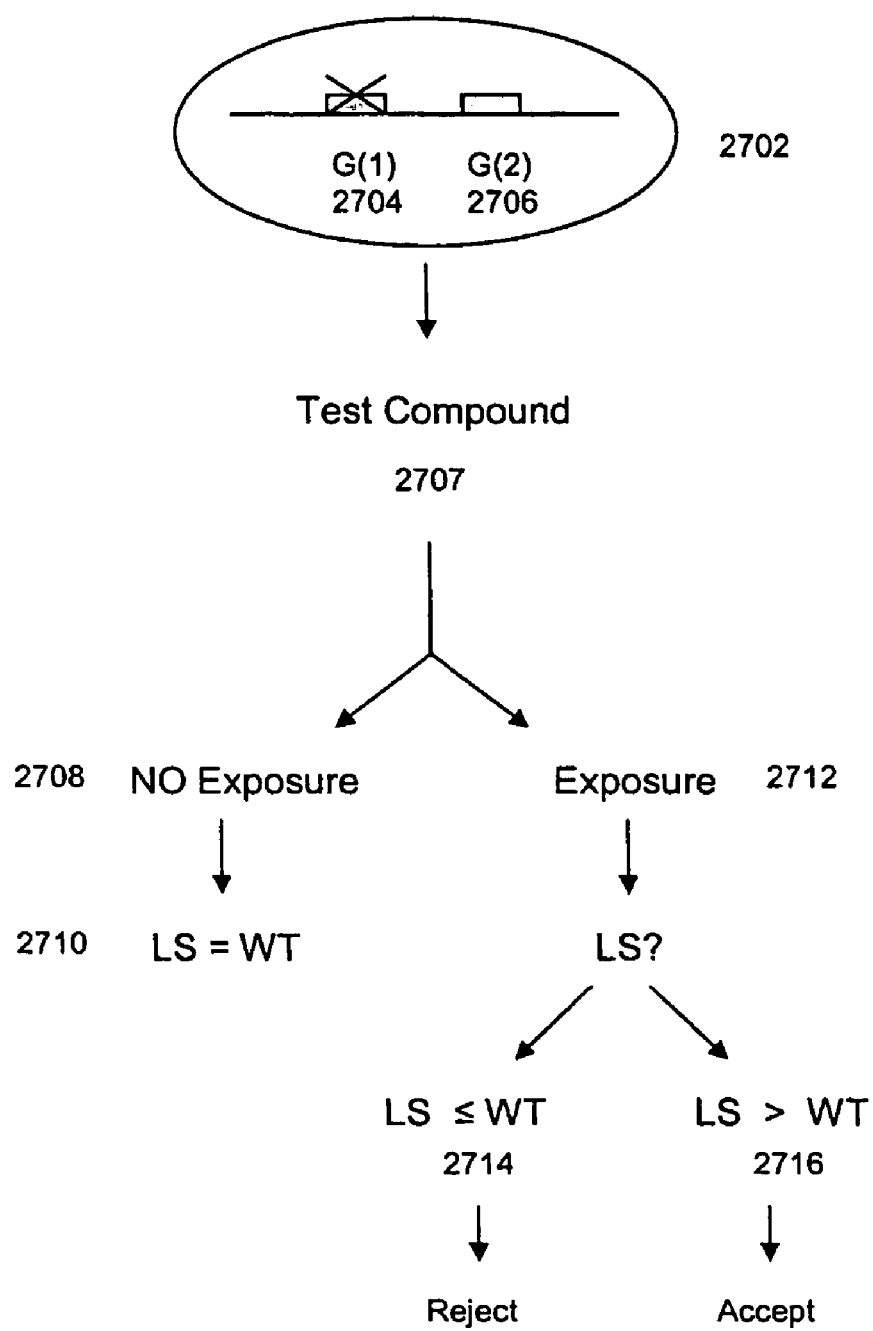
FIG. 20 illustrates an exemplary method for screening longevity-promoting compounds utilizing sir2-fob1-deficient variants.

In another embodiment, genetic variants deficient in sir2 and fob1 may be utilized as hosts for screening longevity-promoting compounds that can modulate regulatory proteins in the Calorie Restriction (CR) pathway. FIG. 20 illustrates an exemplary method for screening longevity-promoting compounds utilizing sir2-fob1-deficient variants. In FIG. 20, an exemplary host cell 2702 is shown, in which "G(1)" 2704 representing one or more genes in the ERC-dependent pathway has been inactivated or suppressed, and "G(2)" 2706 represents one or more genes in the CR pathway. Suitable host cells include variants, for example, deficient in SIR2 and FOB1 expression. The gene products of both are known to act in the ERC-dependent pathway. The life span of "G(1)"-deficient host cells 2702 that have not been exposed to a test compound 2708 can be determined in order to establish a reference life span "WT" 2710. The effect of a test compound 2707 on the life span of "G(1)"-deficient host cells 2702, such as sir2-fob1-double-deletion mutants, can be tested by exposing host cells 2712 to the test compound and determining a statistically-reliable RLS value. If the life span "LS" is approximately less than or equal to that of a "WT" reference 2710, then the compound is ineffective in extending life span 2714, and should be rejected. If the life span "LS" is approximately greater than that of the "WT" reference 2716, then the compound is effective in extending life span, and should be accepted. An effective compound can increase the life span of a host by at least 10%, 15%, 20%, 25%, 30%, 35%, 40%, 45%, 50%, 55%, 60%, 65%, 70%, 75%, 80%, 85%, 90%, 95%, or 100% relative to a reference organism unexposed to the compound.

Various embodiments are directed to high throughput screening methods for evaluating candidate compounds having longevity-promoting properties. In the above method, life spans for "G(1)"-deficient host cells can be determined by applying the various statistical methods used to screen genetic variants described in FIGS. 3-8. For example, a minimum number ($N_{min}$) of G(1)-deficient mother cells can be efficiently evaluated to determine a statistically-reliable RLS. Similar to methods described for classifying variants as "long-lived" or "not-long-lived," the threshold values for determining whether a compound should be accepted or rejected can be established using comparable statistical methods.

When a test compound is determined to be effective in life-span extension, gene products encoded by "G(2)" 2906 that act in the yeast CR pathway are presumably targeted. Such compounds with specificity for yeast components of the CR pathway have high probability of reacting with conserved domains of orthologous eukaryotic sequences. The identification of lead candidate compounds with known structures and known life-span-prolonging activities should facilitate rational-drug design, which is preferred over methods involving randomly-selected compounds. Methods for designing pharmaceutical compounds based on pre-selected lead structures are known by persons skilled in the art.

E. Functional Assays

When the function of a gene product encoded by a gene having at least about 40% sequence similarity the sequences for the genes indicated in Table 5 or 6, or at least about 70% sequence similarity to the sequences for the genes indicated in Table 5 or 6 is known, a function-based assay can be designed. For example, if a gene of interest encodes a transcriptional activator, a reporter construct containing binding-sites specific for the transcriptional activator can be positioned upstream of a reporter gene. The effect of a compound on reporter gene expression can be used to assay for altered function of the transcriptional activator. If a compound is able to interact with the transcriptional activator, the level of reporter-protein production should decrease. In contrast, if a compound cannot interact with the transcriptional activator, the level of reporter-protein production should not decrease, and should be comparable to control levels observed in the absence of the compound.

However, if a function is not known, then compounds that can physically interact with gene products encoded by genes having at least about 40% sequence similarity to the sequences for the genes indicated in Table 5 or 6, or at least about 70% sequence similarity to the sequences for the genes indicated in Table 5 or 6 can be identified by employing, for example, an assay described in FIG. 19. The effect of the compound on the life span of a "wildtype" host cell that can produce gene products encoded by genes having at least about 40% sequence similarity to the sequences for the genes indicated in Table 5 or 6, or at least about 70% sequence similarity to the sequences for the genes indicated in Table 5 or 6 can be determined by various methods taught by the present invention.

F. Arrays or "Biochips"

The invention provides methods for identifying/screening for modulators (e.g., inhibitors, activators) of a chronological life span activity, e.g., chronological life span-signaling activity, using arrays. Potential modulators, including small molecules, nucleic acids, polypeptides (including antibodies) can be immobilized to arrays. Nucleic acids or polypeptides of the invention can be immobilized to or applied to an array. Arrays can be used to screen for or monitor libraries of compositions (e.g., small molecules, antibodies, nucleic acids, and the like) for their ability to bind to or modulate the activity of a nucleic acid or a polypeptide of the invention, e.g., a chronological life span activity. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays can be used to simultaneously quantify a plurality of proteins. Small molecule arrays can be used to simultaneously analyze a plurality of chronological life span modulating or binding activities.

The present invention can be practiced with any known "array," also referred to as a "microarray" or "nucleic acid array" or "polypeptide array" or "antibody array" or "biochip," or variation thereof. Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts. In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston, *Curr. Biol.* 8: R171-R174, 1998; Schummer, *Biotechniques* 23: 1087-1092, 1997; Kern, *Biotechniques* 23: 120-124, 1997; Solinas-Toldo, *Genes, Chromosomes & Cancer* 20: 399-407, 1997; Bowtell, *Nature Genetics Supp.* 21: 25-32, 1999. See also published U.S. patent application Nos. 20010018642; 20010019827; 20010016322; 20010014449; 20010014448; 20010012537; 20010008765.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface.

G. Pharmaceutical Compounds that Promote Longevity

Various genes/gene products isolated from "long-lived" (LL) variants, and related orthologous genes/gene products can be targeted for modulation by pharmaceutical agents. Pharmaceutical agents and methods for screening such pharmaceutical agents that can increase the life expectancy of an organism are highly desirable for decreasing the rate of metabolic aging in humans. In addition, by slowing the rate of aging, it may be possible to delay the onset of a variety of diseases associated with the aging process, including various types of cancers, diabetes, cataracts, heart diseases, and neurodegenerative diseases, such as Parkinson's disease, Huntington disease, amyloid diseases, and others. An effective compound can increase the life span of a host by at least 10%, 15%, 20%, 25%, 30%, 35%, 40%, 45%, 50%, 55%, 60%, 65%, 70%, 75%, 80%, 85%, 90%, 95%, or 100%.

1. Sequence-Specific Compounds a. RNAi Compounds

In one embodiment, various siRNAs that are complementary to identified sequences of the present invention, including mammalian orthologs, can be employed by persons skilled in the art in order to prevent or to decrease the expression of life-span-regulating genes/gene products. Identified sequences include genes having at least about 40% sequence similarity to having at least about 40% sequence similarity the sequences for the genes indicated in Table 5 or 6, or at least about 70% sequence similarity to the sequences for the genes indicated in Table 5 or 6. Silencing or inactivation of life-span-regulating genes/gene products within selective tissues of a host receiving such RNAi compounds can increase the longevity of the host. As discussed briefly in section III, because introduction of double-stranded RNA ("dsRNA") that are longer than 30 nucleotides into mammalian cells induces a sequence-nonspecific interferon response, alternative methods for delivery of interfering RNA molecules ("RNAi") may be suitable. For example, most common form of RNAi molecules are short-interfering RNAs ("siRNAs") of 21-23 base-pairs that are chemically or enzymatically synthesized, which can be introduced into mammalian host cells by various methods, including transfections. However, unlike fungi, plants, and worms that can replicate siRNAs in vivo, transfection of siRNA produces only transient gene-silencing effect in mammalian cells. As an alternative, DNA vectors encoding precursor-like forms of siRNAs may be used for stable production of siRNAs in vivo in various hosts, including mammalian cells.

In one embodiment, the present invention is directed to compounds that increase a life span of a host, the compounds comprising an oligonucleotide that interacts with a gene product encoded by the gene having at least about 40% sequence similarity to at least one the sequences for the genes indicated in Table 5 of 6, or a gene having at least 70% sequence similarity to at least one the sequences for the genes indicated in Table 5 or 6. Such RNA oligonucleotide compounds can be single-stranded or double-stranded. Suitable lengths of RNA oligonucleotides include molecules containing 15-20 nucleotides, 20-30 nucleotides, 30-50 nucleotides, 50-75 nucleotides, 75-100 nucleotides, 100-150 nucleotides, 150-200 nucleotides, and 200-300 nucleotides. In another embodiment, the present invention is directed to compounds that increase a life span of a host, the compounds comprising an oligonucleotide that interacts with sequences that are complementary to gene products encoded by a gene having at least about 40% sequence similarity to at least one the sequences for the genes indicated in Table 5 or 6, or a gene having at least 70% sequence similarity to at least one the sequences for the genes indicated in Table 5 or 6. In another embodiment, the present invention is directed to compounds that increase a life span of a host, the compounds include an anti-sense strand that hybridizes to an endogenous messenger RNA that encodes a protein having life-span-regulating activity, and that inhibits the translation of the messenger RNA.

Selection of efficient siRNAs is an empirical process, but certain rules governing optimal selection of siRNAs are known. The sequence selected for a siRNA appears to be critical. For example, siRNAs containing sequence motifs, such as $AAN_{19}TT$, $NAN_{19}NN$, $NARN_{17}YNN$, and $NANN_{17}YNN$, are effective, in which N is any nucleotide, R is a purine, and Y is a pyrimidine. In addition, regions of complementary DNA should have non-repetitive sequences, and should avoid intronic sequences. Suitable siRNAs contain approximately 30-70% GC content, contain even representation of all nucleotides on the anti-sense strand, and do not contain stretches of single nucleotide, especially stretches of Gs.

Although any region of mRNA can be theoretically targeted, certain sequences that are known binding sites for mRNA-binding proteins should be avoided, including untranslated regions, such as the "5'UTR" and "3'UTR," start-codons, and exon-exon boundaries. For some mRNA targets, siRNA-directed silencing may be more effective if the siRNA sequence is selected at least 50-100 nucleotides downstream of a start codon, and preferably directed towards the 3' end of a target mRNA. In addition, the conformation of a mRNA recognition site within an mRNA target is preferably RNAse-H-sensitive, and preferably not within a highly-structured RNA region. These guidelines are generally applicable since the choice of a siRNA depends on the target mRNA sequence, and persons skilled in the art would need to synthesize several siRNAs to validate the efficiency of each. The specificity of a siRNA for a single gene can be ascertained by performing a multiple-genome-sequence alignment, such as a BLAST search of the selected sequence against sequence databases, including "Unigene" libraries associated with National Center for Biotechnology Information (NCBI). Potential off-target silencing by siRNA may be minimized by choosing a siRNA sequence with maximum sequence divergence from a list of genes with partial-sequence identity to the intended mRNA target. General principles for siRNA selection are taught by the following two review articles, which are incorporated by reference. (Dorsett and Tuschl, *Nature Reviews* 3: 318-329, 2004; Dykxhoorn et al., *Nature Reviews* 4: 457-467, 2003).

Various expression vectors can be constructed to enable stable production of siRNA-like molecules in vivo. For example, RNA-pol II promoters may be operably-linked to a hairpin precursor of a siRNA sequence of interest. RNA-pol II promoters represent a broad range of promoters that enable substantial control over parameters governing RNA expression, such as inducible, constitutive, tissue-specific, or developmentally-regulated RNA expression. Alternatively, RNA-pol III promoters may be used to produce short RNA species that do not activate the interferon pathway. Suitable RNA-pol III promoters include class III promoters that lack essential transcriptional elements downstream of a transcription initiation site, such as U6 and H1 promoters, which may be operably-linked to a siRNA-encoding sequence.

Figure 21A:
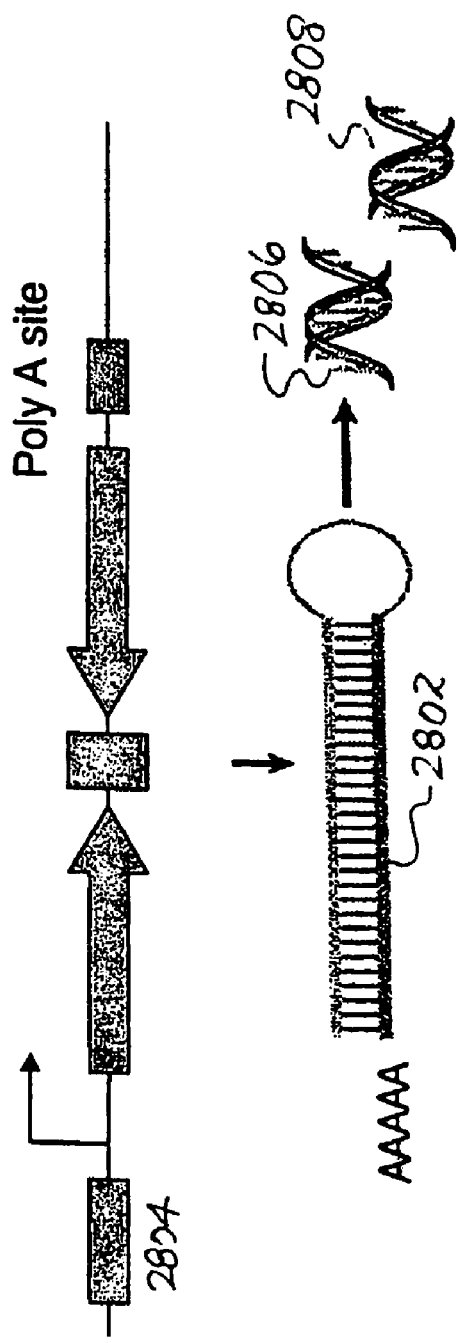
FIGS. 21A-D illustrate various exemplary methods for generating RNAi compounds that interfere with the expression of life-span-regulating genes identified by the present invention.
Figure 21B:
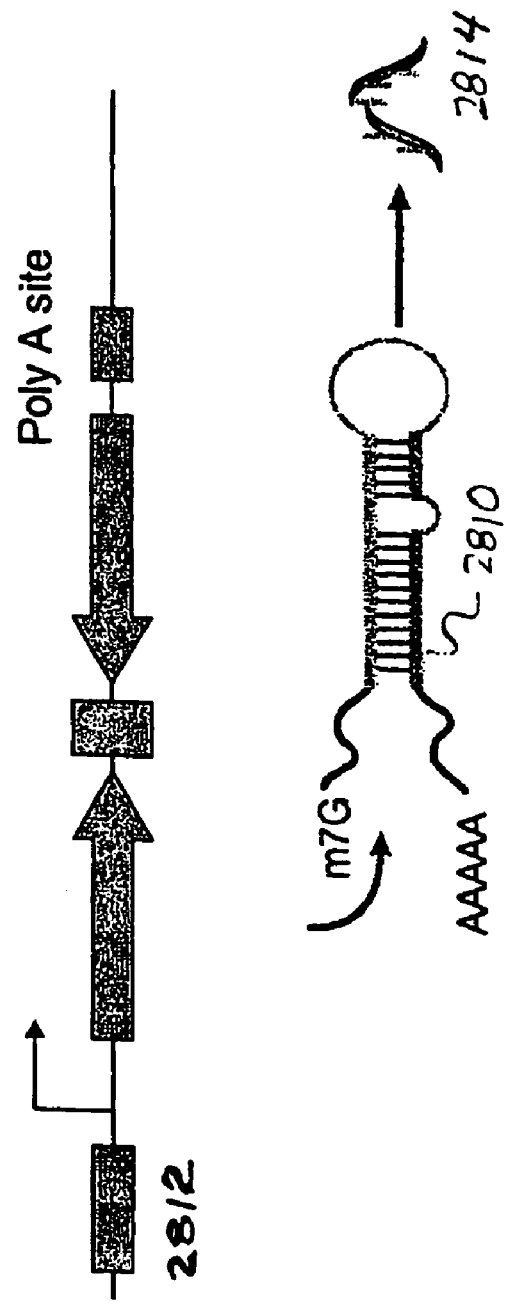
Figures 21C, 21D:
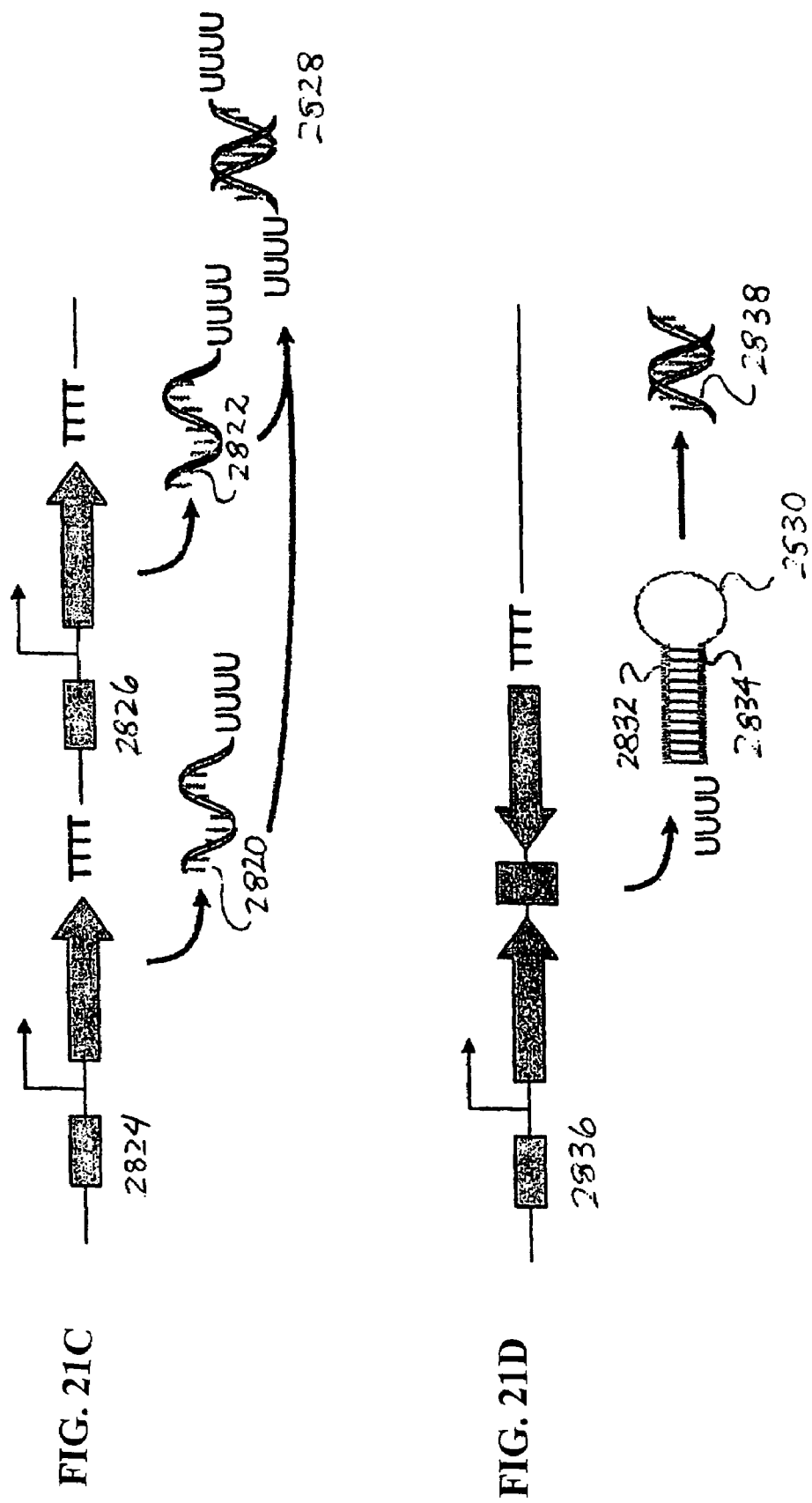

FIGS. 21A-D illustrate various exemplary methods for generating RNAi compounds that interfere with the expression of life-span-regulating genes identified by the present invention. In FIG. 21A, a hypothetical long-hairpin RNA, such as 2802, is produced from a transcriptional unit regulated by an RNA-pol-II promoter, such as 2804. The long-hairpin RNA 2802 is processed into a diverse population of siRNAs, such as 2806 and 2808, with different sequence specificities against a target mRNA. In FIG. 21B, an imperfect short-hairpin RNA ("shRNA"), such as 2810, is produced from a transcriptional unit regulated by a RNA-pol II promoter, such as 2812, and processed into mature form of micro RNA ("miRNA"), such as 2814, that can target a particular mRNA species. In FIG. 21C, a "sense" strand, such as 2820, and "anti-sense" strand, such as 2822, of a hypothetical siRNA, such as 2828, is produced from a transcriptional unit regulated by tandem pol III promoters, such as 2824 and 2826. The "sense" strand 2820 and "anti-sense" strand 2822 associate in trans as shown. In FIG. 21D, a hypothetical short-hairpin RNA molecule ("shRNA"), such as 2830, containing both "sense" 2832 and "anti-sense" 2834 strands, is produced from a transcriptional unit regulated by a pol III promoter, such as 2836. The "sense" 2832 and "anti-sense" 2834 strands associate together in cis as shown, to produce siRNA, such as 2838.

In the above, long-hairpin RNAs, imperfect shRNAs, miRNAs, and siRNAs, can be designed as follows. For example, a sub-sequence of a messenger RNA encoded by a gene, including genes having at least about 40% sequence similarity to the sequences for the genes indicated in Table 5 or 6, or at least about 70% sequence similarity to the sequences for the genes indicated in Table 5 or 6, may be selected for targeting. For example, an anti-sense strand of shRNA can be designed by selecting a sub-sequence portion of a complementary RNA sequence to a messenger RNA sequence of interest, which is encoded by any gene having at least about 40% sequence similarity to the sequences for the genes indicated in Table 5 or 6, or at least about 70% sequence similarity to the sequences for the genes indicated in Table 5 or 6.

For designing shRNA, the composition and size of the loop and length of the stem of a hairpin duplex should be considered. Suitable stem lengths for efficient silencing include a broad range, including stem lengths of 19-29 nucleotides. Suitable loop lengths for efficient silencing include a broad range, including loop lengths of 4-23 nucleotides. In certain context, hairpin structures with duplexed regions that are longer than 21 nucleotides may promote effective siRNA-directed silencing, regardless of loop sequence and length.

Various gene-delivery vectors that are practiced by persons skilled in the art can be used to introduce the present expression vectors. Examples of viral vectors that may be used to infect host cells include: improved adenoviral vectors that can target pulmonary tissues (Reynold et al., *Nature Biotechnology* 19: 838-842, 2001); gene-deleted adenovirus-transposon vectors that can stably maintain virus-encoded gene of interests in vivo through integration into host chromosomes (Yant et al., *Nature Biotechnology* 20: 999-1005, 2002); recombinant adenoviruses that can target rat brain neurons (Bilang-Bleuel et al., *Proc. Natl. Acad. Sci. U.S.A.* 94: 8818-8823, 1997); the Moloney-murine-leukemia-virus ("Mo-MuLV") based retroviral vectors that can target CD4+ and CD+8 Tcells and monocyte-macrophages (Auten et al., *Human Gene Therapy* 10: 1389-99, 2003); and poliovirus-replicon-based vectors that can target tissues of the central nervous tissue (Bledsoe et al., *Nature Biotechnology* 18: 964-969, 2000). Examples of other suitable viral vectors include: herpes virus, mumps virus, Sindbis virus, vaccinia virus, such as the canary pox virus, and lentivirus. The usage of viral vectors is well known by persons skilled in the art, and for gene therapy uses, viral infection is preferred generally. Robbins and Ghizzani, *Mol. Med. Today* 1: 410-417, 1995) is incorporated by reference.

b. Chemically Modified Anti-Sense Oligodeoxyribonucleic Acids ("ODNs")

In one embodiment, various ODN molecules that are complementary to endogenous mRNA transcripts identified as having life-span-regulating activity, and having at least about 40% sequence similarity to the sequences for the genes indicated in Table 5 or 6, or at least about 70% sequence similarity to the sequences for the genes indicated in Table 5 or 6, can be employed by persons skilled in the art in order to prevent or to decrease the expression of life-span-regulating genes/gene products. Silencing or inactivation of life-span-regulating genes/gene products within selective tissues of a host receiving such ODN compounds can increase the longevity of the host. Various ODN compounds can be screened in assays comparable to the assays described in FIGS. 27-29. Oligodeoxyribonucleic acid molecules ("ODNs") are short polynucleotides of approximately 20 nucleotides in length, that hybridize with pre-mRNA and mRNA to form RNA-DNA duplexes, which are degraded by ribonuclease H ("RNase H"). Such ODNs can be chemically modified to prevent the action of RNase H, to inhibit translation of mRNA by steric hindrance, to inhibit splicing of pre-mRNAs, and to inhibit transcription by the formation of triple helices. Kurreck et al., *Eur. J. Biochem.,* 270: 1628-1644, 2003; Baker et al., *J. Biol. Chem.,* 272: 11994-2000, 1997; Lu et al, *Nature Med.* 9: 1009-1014, 2003; and Uil et al., *Nucleic Acids Res.* 31: 6064-6078, 2003 are incorporated by reference.

c. Ribozymes

In one embodiment, various ribozymes containing sequences that are complementary to mRNAs encoded by genes having at least about 40% sequence similarity to the sequences for the genes indicated in Table 5 or 6, or at least about 70% sequence similarity to the sequences for the genes indicated in Table 5 or 6, can be employed by persons skilled in the art in order to prevent or to decrease the expression of life-span-regulating genes/gene products. Silencing or inactivation of life-span-regulating genes/gene products within selective tissues of a host receiving such ribozyme compounds can increase the longevity of the host. Ribozymes, including the "hammer-head" ribozyme, are RNA molecules that bind target mRNA by assuming a unique secondary structure when hybridized to target mRNA, which enables catalytic hydrolysis of a phosphodiester bond within in the backbone of target mRNA. Efficient cleavage by a ribozyme requires the presence of divalent ions, such as magnesium, and is also dependent on target RNA structure, and relative proximity between ribozyme and target molecule. RNA-localization signals or RNA chaperones may be used so that low concentrations of ribozymes are sufficiently effective in silencing a gene of interest. Ribozymes can be chemically synthesized in vitro, and can be transcribed from expression vectors in vivo. Methods for ribozyme construction and utilization are known by persons skilled in the art. Doudna and Cech, *Nature,* 418: 222-228, 2002; Kuwabara et al, *J. Biochem.* 132: 149-155, 2002; Michienzi and Rossi, *Methods Enzymol.* 341: 581-596, 2001; and Good et al., *Gene Ther.,* 4: 45-54, 1997 are incorporated by reference.

d. Full and Partial Length Antisense RNA Transcripts

Antisense RNA transcripts have a base sequence complementary to part or all of any other RNA transcript in the same cell. Such transcripts have been shown to modulate gene expression through a variety of mechanisms including the modulation of RNA splicing, the modulation of RNA transport and the modulation of the translation of mRNA (Denhardt, *Ann N Y Acad. Sci.* 660: 70, 1992; Nellen, *Trends Biochem. Sci.* 18: 419, 1993; Baker and Monia, *Biochem. Biophys. Acta,* 1489: 3, 1999; Xu et al., *Gene Therapy* 7: 438, 2000; French and Gerdes, *Curr. Opin. Microbiol.* 3: 159, 2000; Terryn and Rouze, *Trends Plant Sci.* 5: 1360, 2000).

2. Other Compounds

In one embodiment, non-sequence-specific compounds that can interact with identified genes/gene products having at least about 40% sequence similarity to the sequences for the genes indicated in Table 5 or 6, or at least about 70% sequence similarity to the sequences for the genes indicated in Table 5 or 6, can be employed by persons skilled in the art in order to prevent or to decrease the expression of life-span-regulating genes/gene products. In addition, compounds that can interact with RNA and DNA molecules that are complementary to sequences having at least about 40% sequence similarity to the sequences for the genes indicated in Table 5 or 6, or at least about 70% sequence similarity to the sequences for the genes indicated in Table 5 or 6 may be used. Silencing or inactivation of life-span-regulating genes/gene products within selective tissues of a host receiving such compounds can increase the longevity of the host. Longevity-promoting compounds can be either naturally-occurring or synthetically-produced. Large combinatorial libraries of chemical/biological compounds can be generated by various chemical and biological synthesis methods known in the art. Such combinatorial chemical libraries include: small organic molecule libraries (benzodiazepines, Baum, *C&EN* 33, 1993); (Chen et al., *J. Amer. Chem. Soc.,* 116: 2661, 1994,) such as isoprenoids (U.S. Pat. No. 5,569,588), thiazolidinones and metathiazanones (U.S. Pat. No. 5,549,974), pyrrolidines (U.S. Pat. Nos. 5,525,735 and 5,519,134), morpholino compounds (U.S. Pat. No. 5,506,337), and benzodiazepines (U.S. Pat. No. 5,288,514), oligocarbamates (Cho et al., *Science* 261: 1303, 1993), and peptidyl phosphonates (Campbell et al., *J. Org. Chem.*

59: 658, 1994). Exemplary combinatorial libraries include: various peptide libraries (U.S. Pat. No. 5,010,175; Furka, *Int. J. Pept. Prot. Res.* 37: 487-493, 1991); Houghton et al., *Nature* 354: 84-88, 1991); peptoid libraries (PCT Publication No. WO 91/19735); encoded peptides (PCT Publication No. WO 93/20242); random bio-oligomers (PCT Publication No. WO 92/00091); benzodiazepines (U.S. Pat. No. 5,288,514); diversomers such as hydantoins, benzodiazepines and dipeptides (Hobbs et al., Proc. *Nat. Acad. Sci. USA* 90: 6909-6913, 1993); vinylogous polypeptides (Hagihara et al., *J. Amer. Chem. Soc.* 114: 6568, 1992); nonpeptidal peptidomimetics with glucose scaffolding (Hirschmann et al., *J. Amer. Chem. Soc.* 114: 9217-9218, 1992); various nucleic-acid libraries; various peptide-nucleic acid libraries (U.S. Pat. No. 5,539, 083); various carbohydrate libraries (Liang et al., *Science* 274: 1520-1522, 1996); (U.S. Pat. No. 5,593,853); and various antibody libraries (Vaughn et al., *Nature Biotechnology* 14: 309-314, 1996).

3. Therapeutic Antibodies

In another embodiment, various antibodies that bind specifically to proteins of the present invention having at least about 40% sequence similarity to the sequences for the genes indicated in Table 5 or 6, or at least about 70% sequence similarity to the sequences for the genes indicated in Table 5 or 6, can be employed by persons skilled in the art in order to prevent or to decrease the expression of life-span-regulating genes/gene products. Suitable antibodies have antigen-binding domains that can react with polypeptides having at least about 40% sequence similarity to the sequences for the genes indicated in Table 5 or 6, or at least about 70% sequence similarity to the sequences for the genes indicated in Table 5 or 6. In addition, constant regions of such antibodies include various isotypic variants, such as kappa and lambda isotypes. Antibodies of the present invention include IgG, IgM, IgA, IgD, and IgE molecules containing different Fc regions that can interact with different effector cells of an immune system. Inactivation of life-span-regulating gene products within selective tissues of a host receiving such antibodies can increase the longevity of the host. Methods for producing polyclonal and monoclonal antibodies that can react specifically with life-span-regulating proteins are well-known in the art. Any fragment of such proteins may be used as an immunogen to produce antibodies with specificity for life-span-regulating proteins identified by the present invention. For example, suitable immunogens can be derived from an isolated endogenous protein or an antigenic fragment thereof, an isolated recombinant protein or an antigenic fragment thereof, and a synthetic peptide representing a portion of a life-span-regulating protein conjugated to a carrier protein. Methods for the preparation of various forms of immunogen are known by persons skilled in the art. In general, immunogens formulated in a standard adjuvant, such as Freund's adjuvant, are injected into warm-blooded animals capable of producing antibodies, such as mice, rabbits, and goats. Methods for polyclonal antibody production are known to persons skilled in the art, in which blood containing high titers of polyclonal antibodies are collected, including antisera enriched for immunogen-specific antibodies. Methods for monoclonal antibody production are known in the art, in which spleen cells that are removed from an animal immunized with an immunogen of interest are fused with an immortalized cell, such as a myeloma cell (Kohler & Milstein, *Eur. J. Immunol.* 6: 511-519, 1976) or may be transformed with viruses, such as retroviruses containing oncogenes, such as the Epstein Barr Virus. Individual hybridoma cells are screened to identify monoclonal antibodies having desired specificity and affinity. Alternatively, chimeric forms of antibodies containing mouse and human sequences that have specificity to life-span-regulating proteins of the present invention having at least about 40% sequence similarity to the sequences for the genes indicated in Table 5 or 6, or at least about 70% sequence similarity to the sequences for the genes indicated in Table 5 or 6, may be produced (Harlow and Lane Antibodies: A Laboratory Manual, Cold Spring Harbor Laboratory (1988) is incorporated by reference). Alternatively, humanized antibodies, containing selective amino-acid residues derived from non-human sources, that have specificity to life-span-regulating proteins of the present invention may be produced. (Verhoeyen et al., *Science* 239: 1534-1536, 1988). Alternatively, large libraries of human Fabs generated by various combinatorial methods using recombinant molecular biology and phage-display methods can be screened to identify antibodies that have high specificity and affinity for life-span-regulating proteins of the present invention. (de Haard et al., *J. Biol. Chem.* 274: 18218-18230, 1999).

4. Replicative Life Span Transgenic and "Knockout" Non-Human Animals

The invention provides transgenic non-human animals comprising a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA can encode mammalian kinases. Native expression in an animal can be reduced by providing an amount of antisense RNA or DNA effective to reduce expression of the receptor.

These animals can be used, e.g., as in vivo models to study which is modulators of a replicative life span-signaling activity, or, as models to screen for agents that change the replicative life span-signaling activity in vivo.

In one aspect, the inserted transgenic sequence is a sequence of the invention designed such that it does not express a functional replicative life span polypeptide. The defect can be designed to be on the transcriptional, translational and/or the protein level.

The coding sequences for the polypeptides, the replicative life span polypeptides, or mutant polypeptide to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111, 166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock, *J. Immunol. Methods* 231: 147-157, 1999, describing the production of recombinant proteins in the milk of transgenic dairy animals; Baguisi, *Nat. Biotechnol.* 17: 456-461, 1999, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No.

6,187,992, describes making and using a transgenic mouse whose genome comprises a disruption of the gene encoding amyloid precursor protein (APP). One exemplary method to produce genetically altered non-human animals is to genetically modify embryonic stem cells. The modified cells are injected into the blastocoel of a blastocyst. This is then grown in the uterus of a pseudopregnant female. In order to readily detect chimeric progeny, the blastocysts can be obtained from a different parental line than the embryonic stem cells. For example, the blastocysts and embryonic stem cells can be derived from parental lines with different hair color or other readily observable phenotype. The resulting chimeric animals can be bred in order to obtain non-chimeric animals which have received the modified genes through germ-line transmission. Techniques for the introduction of embryonic stem cells into blastocysts and the resulting generation of transgenic animals are well known.

Because cells contain more than one copy of a gene, the cell lines obtained from a first round of targeting are likely to be heterozygous for the targeted allele. Homozygosity, in which both alleles are modified, can be achieved in a number of ways. In one approach, a number of cells in which one copy has been modified are grown. They are then subjected to another round of targeting using a different selectable marker. Alternatively, homozygotes can be obtained by breeding animals heterozygous for the modified allele, according to traditional Mendelian genetics. In some situations, it may be desirable to have two different modified alleles. This can be achieved by successive rounds of gene targeting or by breeding heterozygotes, each of which carries one of the desired modified alleles. See, e.g., U.S. Pat. No. 5,789,215.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division. (Brinster et al., *Proc. Nat. Acad. Sci. USA* 82: 4438-4442, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), and the like The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897-905, 1991. Other procedures for introduction of DNA into tissues of animals are described in U.S. Pat. No. 4,945,050 (Sanford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. (Hammer et al., *Cell* 63: 1099-1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art (Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. (Capecchi, *Science* 244: 1288-1292, 1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153-156, 1989, the teachings of which are incorporated herein in their entirety including any drawings. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. (Houdebine and Chourrout, supra; Pursel et al., *Science* 244: 1281-1288, 1989; and Simms et al., *Bio/Technology* 6: 179-183, 1988).

5. Replicative Life Span Functional Knockouts

The invention provides non-human animals that do not express their endogenous replicative life span polypeptides, or, express their endogenous replicative life span polypeptides at lower than wild type levels (thus, while not completely "knocked out" their replicative life span activity is functionally "knocked out"). The invention also provides "knockout animals" and methods for making and using them. For example, in one aspect, the transgenic or modified animals of the invention comprise a "knockout animal," e.g., a "knockout mouse," engineered not to express an endogenous gene, e.g., an endogenous replicative life span gene, which is replaced with a gene expressing a polypeptide of the invention, or, a fusion protein comprising a polypeptide of the invention. Thus, in one aspect, the inserted transgenic sequence is a sequence of the invention designed such that it does not express a functional replicative life span polypeptide. The defect can be designed to be on the transcriptional, translational and/or the protein level. Because the endogenous replicative life span gene has been "knocked out," only the inserted polypeptide of the invention is expressed.

A "knock-out animal" is a specific type of transgenic animal having cells that contain DNA containing an alteration in the nucleic acid sequence that reduces the biological activity of the polypeptide normally encoded therefrom by at least 80% compared to the unaltered gene. The alteration can be an insertion, deletion, frameshift mutation, missense mutation, introduction of stop codons, mutation of critical amino acid residue, removal of an intron junction, and the like. Preferably, the alteration is an insertion or deletion, or is a frameshift mutation that creates a stop codon. Typically, the disruption of specific endogenous genes can be accomplished by deleting some portion of the gene or replacing it with other sequences to generate a null allele. Cross-breeding mammals having the null allele generates a homozygous mammals lacking an active copy of the gene.

A number of such mammals have been developed, and are extremely helpful in medical development. For example, U.S. Pat. No. 5,616,491 describes knock-out mice having suppression of CD28 and CD45. Procedures for preparation and manipulation of cells and embryos are similar to those described above with respect to transgenic animals, and are well known to those of ordinary skill in the art.

A knock out construct refers to a uniquely configured fragment of nucleic acid which is introduced into a stem cell line and allowed to recombine with the genome at the chromosomal locus of the gene of interest to be mutated. Thus, a given knock out construct is specific for a given gene to be targeted for disruption. Nonetheless, many common elements exist among these constructs and these elements are well known in the art. A typical knock out construct contains nucleic acid fragments of about 0.5 kb to about 10.0 kb from both the 5' and the 3' ends of the genomic locus which encodes the gene to be mutated. These two fragments are typically separated by an intervening fragment of nucleic acid which encodes a positive selectable marker, such as the neomycin resistance gene. The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for the gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug.

Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of the polypeptide product of the wild-type gene from which it was derived.

Each knockout construct to be inserted into the cell must first be in the linear form. Therefore, if the knockout construct has been inserted into a vector, linearization is accomplished by digesting the DNA with a suitable restriction endonuclease selected to cut only within the vector sequence and not within the knockout construct sequence. For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion can be accomplished in a variety of ways known to the skilled artisan, however a preferred method is by microinjection. For microinjection, about 10-30 cells are collected into a micropipette and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan. After the ES cell has been introduced into the embryo, the embryo can be implanted into the uterus of a pseudopregnant foster mother for gestation as described above.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a target gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The functional replicative life span "knockout" non-human animals of the invention are of several types. Some non-human animals of the invention that are functional replicative life span "knockouts" express sufficient levels of a replicative life span inhibitory nucleic acid, e.g., antisense sequences or ribozymes of the invention, to decrease the levels or knockout the expression of functional polypeptide. Some non-human animals of the invention that are functional replicative life span "knockouts" express sufficient levels of a replicative life span dominant negative polypeptide such that the effective amount of free endogenous active replicative life span is decreased. Some non-human animals of the invention that are functional replicative life span "knockouts" express sufficient levels of an antibody of the invention, e.g., a replicative life span antibody, such that the effective amount of free endogenous active replicative life span protein is decreased. Some non-human animals of the invention that are functional replicative life span "knockouts" are "conventional" knockouts in that their endogenous replicative life span gene has been disrupted or mutated.

Functional replicative life span "knockout" non-human animals of the invention also include the inbred mouse strain of the invention and the cells and cell lines derived from these mice.

The invention provides methods for treating a subject with a replicative life span related disease or disorder. The method comprises providing an inhibitor of a replicative life span activity, e.g., a nucleic acid (e.g., antisense, ribozyme) or a polypeptide (e.g., antibody or dominant negative) of the invention. The inhibitor is administered in sufficient amounts to the subject to inhibit the expression of replicative life span polypeptides.

6. Replicative Life Span Inbred Mouse Strains

The invention provides an inbred mouse and an inbred mouse strain that can be generated as described herein and bred by standard techniques, see, e.g., U.S. Pat. Nos. 6,040,495; 5,552,287.

In order to screen for mutations with recessive effects a number of strategies can be used, all involving a further two generations. For example, male G1 mice can be bred to wild-type female mice. The resulting progeny (G2 mice) can be interbred or bred back to the G1 father. The G3 mice that result from these crosses will be homozygotes for mutations in a small number of genes (3-6) in the genome, but the identity of these genes is unknown. With enough G3 mice, a good sampling of the genome should be present.

7. Pharmaceutical Compositions and Therapeutic Dosage and Administration

Pharmaceutical formulations for effective delivery of pharmaceutical compounds of the present invention will vary depending on the pharmaceutical compound of interest and mode of administration. Suitable pharmaceutical carriers are known by persons skilled in the art (Remington's Pharmaceutical Sciences (1989), which is incorporated in its entirety). Pharmaceutical compounds described above can be administered by various methods, including by injection, oral administration, inhalation, transdermal application, or rectal administration. For oral administration, suitable formulations containing a pharmaceutical compound and pharmaceutically-compatible carriers can be delivered in various forms, such as tablets or capsules, liquid solutions, suspensions, emulsions, and the like. For inhalation, suitable formulations containing a pharmaceutical compound and pharmaceutically-compatible carriers can be delivered as aerosol formulations that can be placed into pressurized propellants, such as dichlorodifluoromethane, propane, nitrogen, and the like. For parenteral administration, suitable formulations containing a pharmaceutical compound and pharmaceutically-compatible carriers can be delivered by intra-articular, intra-venous, intramuscular, intra-dermal, intra-peritoneal, and sub-cutaneous routes.

8. Toxicity

Pharmaceutical compositions suitable for use in the present invention include compositions containing active ingredients in an effective amount to achieve its intended purpose. More specifically, a therapeutically-effective amount means an amount effective to prevent pre-mature aging or to delay aging-process in subjects exposed to pharmaceutical compositions of the present invention. Determination of the effective amounts is well within the capability of persons skilled in the art. For example, a therapeutically-effective dose can be estimated initially from cell culture assays described above. A dose can be formulated in animal models to achieve a circulating concentration range that includes IC50 value, defined as a dose in which 50% of cells of a culture show an effect due to the test compound. Such information can be used to more accurately determine useful doses in human subjects.

Toxicity and therapeutic efficacy of such compounds can be determined by standard pharmaceutical procedures utilizing cell cultures or experimental animals in order to determine a LD50 value, the dose determined to be lethal to 50% of the exposed population, and to determine a ED50 value, the dose determined to be therapeutically effective in 50% of the exposed population. A dose ratio between toxic effect and therapeutic effect is referred to as the "therapeutic index," or it can be expressed as the ratio of the LD50 value over the ED50 value. Compounds which exhibit high therapeutic indices are preferred. The data obtained from cell culture assays and animal studies can be used in formulating a range of effective dosage for human usage. Optimal dosage range includes a ED50 dose with minimal toxicity, although the dosage may vary within this range depending on a given pharmaceutical formulation and route of administration. Dosage administered to a subject should be adjusted according to the age of the subject, the weight of the subject, the manner of administration, and other circumstances unique to each subject.

9. Kits

The invention provides kits comprising the compositions, e.g., the differentially expressed protein, agonist or antagonist of the present invention or their homologs and are useful tools for examining expression and regulation of, for example, the genes as disclosed herein. Reagents that specifically hybridize to nucleic acids encoding differentially expressed proteins of the invention (including probes and primers of the differentially expressed proteins), and reagents that specifically bind to the differentially expressed proteins, e.g., antibodies, are used to examine expression and regulation.

Also within the scope of the invention are kits comprising the compositions (e.g., monoclonal antibodies, human sequence antibodies, human antibodies, multispecific and bispecific molecules, nucleic acid compositions, e.g., antisense oligonucleotides, double stranded RNA oligonucleotides (RNAi), or DNA oligonucleotides (vectors) containing nucleotide sequences encoding for the transcription of shRNA molecules) of the invention and instructions for use. The kit can further contain a least one additional reagent, or one or more additional human antibodies of the invention (e.g., a human antibody having a complementary activity which binds to an epitope in the antigen distinct from the first human antibody).

Nucleic acid assays for the presence of differentially expressed proteins in a sample include numerous techniques are known to those skilled in the art, such as Southern analysis, northern analysis, dot blots, RNase protection, S1 analysis, amplification techniques such as PCR and LCR, high density oligonucleotide array analysis, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4: 230-250, 1986; Haase et al., *Methods in Virology* 7: 189-226, 1984; and Nucleic Acid Hybridization: A Practical Approach (Hames et al., eds. 1987). In addition, a differentially expressed protein can be detected with the various immunoassay techniques described above. The test sample is typically compared to both a positive control (e.g., a sample expressing recombinant differentially expressed protein) and a negative control.

The present invention also provides for kits for screening drug candidates for treatment of replicative life span diseases or disorders or diseases or disorders associated with aging such as various types of cancers, diabetes mellitus, cataracts, heart diseases, and neurodegenerative diseases, such as Alzheimer's disease, Pick's disease, Huntington's disease, Parkinson's disease, adult onset myotonic dystrophy, multiple sclerosis, and adult onset leukodystrophy disease. Such kits can be prepared from readily available materials and reagents. For example, such kits can comprise any one or more of the following materials: the differentially expressed proteins, agonists, or antagonists of the present invention, pharmaceutical compositions that can modulate, or modify, the function of the identified genes and gene products, reaction tubes, and instructions for testing the activities of differentially expressed genes. A wide variety of kits and components can be prepared according to the present invention, depending upon the intended user of the kit and the particular needs of the user. For example, the kit can be tailored for in vitro or in vivo assays for measuring the activity of drug candidates for treatment of replicative life span diseases or disorders or related to diseases or conditions associated with aging as described herein.

The invention further provides kits comprising probe arrays as described above. The invention further provides oligonucleotide arrays comprising one or more of the inventive probes described above. In particular, the invention provides an oligonucleotide array comprising oligonucleotide probes that are able to detect polymorphic variants of the genes defined and disclosed herein. In a preferred embodiment the genes are defined in FIG. 3 or in the Examples. Such arrays can be provided in the form of kits for diagnostic and/or research purposes. Kits can include any of the components mentioned above, in addition to further components specific for hybridization and processing of oligonucleotide arrays. Appropriate software (i.e., computer-readable instructions stored on a computer-readable medium) for analyzing the results obtained by scanning the arrays can be provided by the invention. Such software can, for example, provide the user with an indication of the genotype of a sample and/or provide an assessment of the degree of susceptibility of the subject to replicative life span diseases or disorders or related to diseases or conditions associated with aging as described herein. According to certain embodiments of the invention, the kits are manufactured in accordance with good manufacturing practices (GMP) as required for FDA-approved diagnostic kits.

Optional additional components of the kit include, for example, other restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kits of the present invention also contain instructions for carrying out the methods.

The invention further provides compositions, kits and integrated systems for practicing the assays described herein. For example, an assay composition having a source of cells. Additional assay components as described above are also provided. For instance, a solid support or substrate in which the assays can be carried out can also be included. Such solid supports include membranes (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper. Most commonly, the assay will use 96, 384 or 1536 well microtiter plates.

The kits can include any of the compositions noted above, and optionally further include additional components such as instructions to practice a high throughput method of screening for replicative life span modulators, one or more containers or compartments (e.g., to hold the cells, test agents, controls, dyes, and the like), a control activity modulator, a robotic armature for mixing kit components, and the like.

The invention further provides compositions, kits and integrated systems for practicing the assays described herein. For example, an assay composition having a source of cells. Additional assay components as described above are also provided. For instance, a solid support or substrate in which the assays can be carried out can also be included. Such solid supports include membranes (e.g., nitrocellulose or nylon), a microtiter dish (e.g., PVC, polypropylene, or polystyrene), a test tube (glass or plastic), a dipstick (e.g., glass, PVC, polypropylene, polystyrene, latex, and the like), a microcentrifuge tube, or a glass, silica, plastic, metallic or polymer bead or other substrate such as paper. Most commonly, the assay will use 96, 384 or 1536 well microtiter plates.

The kits can include any of the compositions noted above, and optionally further include additional components such as instructions to practice a high throughput method of screening for chronological life span modulators, one or more containers or compartments (e.g., to hold the cells, test agents, controls, dyes, and the like), a control activity modulator, a robotic armature for mixing kit components, and the like.

The invention also provides integrated systems for high throughput screening of potential modulators of chronological life span extension. Such systems typically include a robotic armature which transfers fluid from a source to a destination, a controller which controls the robotic armature, a label detector, a data storage unit which records label detection, and an assay component such as a microtiter dish.

A number of well-known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. Any of the assays for compounds that modulate activity, as described herein, are amenable to high throughput screening. High throughput screening systems are commercially available (see, e.g., Zymark Corp. (Hopkinton, Mass.); Air Technical Industries (Mentor, Ohio); Beckman Instruments, Inc. (Fullerton, Calif.); Precision Systems, Inc., (Natick, Mass.), and the like). Such systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols for the various high throughput systems.

Optical images viewed (and, optionally, recorded) by a camera or other recording device (e.g., a photodiode and data storage device) are optionally further processed in any of the embodiments described herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT® or WINDOWS95® based machines), MACINTOSH®, or UNIX based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

EXEMPLARY EMBODIMENTS

Example 1

Establishing WT-μRLS Distributions and LL-μRLS Distributions

A comprehensive yeast-ORF-deletion collection ("SCGDP") provided an exemplary yeast variant library for conducting a genome-wide screen for long-lived variants. As an exemplary set, the BY4742-derived MATα deletion collection containing approximately 4800 unique single-ORF deletion variants are subjected to RLS analysis to generate a dataset of mean RLS values for each variant. RLS assays are performed to determine mean replicative life span for 42 different deletion variants reported by others to affect either replicative life span (RLS) or chronological life span (CLS) when respective genes are deleted in shorter-lived background variants. In terms of replicative aging, the BY4742 background is the longest-lived, "wildtype" variant tested by the present inventors, and therefore, yeast variants having a BY4742 background, or the equivalent, may be preferred for identifying genes that are involved in the regulation of life span. To generate the data set shown in Table 1-5 described below, over 130,000 daughter cells were removed or approximately 5,000 life spans for various mother cells were determined. The sample size (N) for each variant assayed is provided in the last column.

Table 1 provides mean replicative life spans (μRLS) determined for various exemplary background variants commonly available. All variants are identified by randomly assigned numbers to eliminate any potential bias during the RLS assay. All life spans are performed in sets of 10 cells per variant, with the BY4742 variant, defined as "wildtype" (WT) control, included in each experiment. In total, at least 4 independent 10-cell sets are analyzed for each variant. For this particular set of backgrounds evaluated, the BY4742 and BY4741 backgrounds demonstrate longest life spans with μRLSs of 27.4 and 26.4, respectively. ΔRLS refers to the strain RLS relative to pair-matched BY4742 cells assayed in the same experiment. N is the number of cells assayed.

TABLE 1

Exemplary Yeast Variant Backgrounds

| Variant | Mean RLS | Pair-matched BY4742 (WT) RLS | ΔRLS (%) | N |
|---|---|---|---|---|
| BY4742 | 27.4 | 27.4 | 0 | 250 |
| BY4741 | 26.4 | 25.8 | 2 | 50 |
| BKY4-14c | 17.6 | 29.7 | −41 | 40 |
| PSY316AT | 21.4 | 29.7 | −28 | 40 |
| W303R | 21.4 | 29.7 | −28 | 40 |

Table 2 provides mean replicative life span (μRLS) determined for various exemplary single-gene-deletion stains assayed that are reported to have long life spans. The BY4742 variant defined as a "wildtype" (WT) control is included in each experiment. For this particular set, the fob1-deletion variant exhibited the longest life span having a μRLS of 37.5.

TABLE 2

Exemplary Single-Gene Deletion Variants

| Variant | Mean RLS | Pair-matched BY4742 (WT) RLS | ΔRLS (%) | N |
|---|---|---|---|---|
| cdc73 | 22.4 | 26.1 | −14 | 40 |
| Cpr1 | 28.2 | 30.4 | −7 | 20 |
| Cpr2 | 27.3 | 30.4 | −10 | 20 |
| Cpr3 | 21.4 | 30.4 | −30 | 20 |
| Cpr5 | 30.3 | 30.4 | 0 | 20 |
| Cpr6 | 26.3 | 30.4 | −13 | 20 |
| Cpr7 | 30.3 | 26.3 | 15 | 80 |
| Cpr8 | 28.4 | 30.4 | −7 | 20 |
| Fob1 | 37.5 | 26.6 | 41 | 120 |
| Gpa2 | 34.9 | 25.8 | 35 | 40 |
| Gpr1 | 34.3 | 25.8 | 33 | 40 |
| Hog1 | 24.2 | 27.6 | −12 | 40 |
| Hpr1 | 9.8 | 26.1 | −63 | 40 |
| hsc82 | 25.1 | 30.4 | −17 | 20 |
| Hst1 | 26.2 | 27.6 | −5 | 40 |
| Hst2 | 26.2 | 27.6 | −5 | 40 |
| Hst3 | 18.8 | 27.6 | −32 | 40 |
| Hst4 | 25.8 | 27.6 | −7 | 40 |
| Hst1 | 26.2 | 27.6 | −5 | 40 |
| Hxk2 | 36.7 | 26.5 | 39 | 120 |
| Lag1 | 27.8 | 26.1 | 6 | 40 |
| Lag2 | 28.8 | 26.1 | 10 | 40 |
| Pde2 | 18.6 | 26.1 | −29 | 40 |
| Phb1 | 13.8 | 26.1 | −47 | 40 |
| Phb2 | 14.3 | 26.1 | −45 | 40 |
| Pnc1 | 26.5 | 26.1 | 1 | 40 |
| rad16 | 24.0 | 26.1 | −8 | 40 |
| rad52 | 9.9 | 26.1 | −62 | 40 |
| Ras1 | 28.4 | 26.1 | 9 | 40 |
| Ras2 | 18.1 | 26.1 | −31 | 40 |
| Rpd3 | 25.5 | 27.0 | −5 | 60 |
| Rtg3 | 23.7 | 26.7 | −11 | 50 |
| Sgs1 | 32.5 | 26.1 | 25 | 40 |
| Sin3 | 18.9 | 27.0 | −30 | 60 |
| Sip2 | 28.5 | 26.3 | 8 | 60 |
| sir2 | 14.0 | 27.5 | −49 | 60 |
| sir3 | 23.8 | 26.1 | −9 | 40 |
| sir4 | 24.3 | 26.1 | −7 | 40 |
| slt2 | 24.3 | 27.6 | −12 | 40 |
| Sod1 | 2.8 | 24.8 | −89 | 20 |
| Sod2 | 28.6 | 26.1 | 9 | 40 |
| Soh1 | 20.2 | 26.1 | −22 | 40 |
| Srs2 | 16.1 | 27.6 | −42 | 40 |
| Ssd1 | 24.8 | 25.6 | −3 | 60 |
| Uth1 | 29.4 | 27.1 | 8 | 40 |
| Zds1 | 27.7 | 26.1 | 6 | 40 |
| Zds2 | 29.5 | 26.1 | 13 | 40 |

Table 3 provides mean replicative life span (µRLS) determined for a selective set of exemplary single-gene-deletion haploids constructed in BY4742 background. The BY4742 variant defined as a "wildtype" (WT) control is included in each experiment. For this particular set, the cpr7::URA3a deletion variant exhibited the longest life span having a µRLS of 33.9. Unexpectedly, several deletions do not exhibit RLS phenotypes similar to those reported in the literature from experiments performed in short-lived variants. In order to address the possibility that the deletion set variants may contain other genetic anomalies such as aneuploidy, new deletion alleles for several genes are generated in the "wildtype" BY4742 variant, including SGS1, CPR7, RAS2, and RPD3. In every case, except SGS1, the newly created deletion variants behave identically to the variants from the deletion set when analyzed by RLS assay. Surprisingly, many of the gene deletions reported to extend RLS have minimal or no effect in a long-lived variant background.

TABLE 3

Exemplary Variants Constructed in BY4742 Background

| Variant | Mean RLS | Pair-matched BY4742 (WT) RLS | ΔRLS (%) | N |
|---|---|---|---|---|
| cpr7::URA3a | 33.9 | 26.3 | 29 | 20 |
| cpr7::URA3 alpha | 32.5 | 26.3 | 24 | 20 |
| mpt5::URA3 | 17.8 | 27.5 | −35 | 40 |
| ras2::URA3 | 18.8 | 26.3 | −29 | 20 |
| rho0 | 27.1 | 27.1 | 0 | 40 |
| sgs1::URA3 | 10.9 | 27.1 | −60 | 40 |
| sir3 SIR3S275A | 24.0 | 27.6 | −13 | 40 |
| sir3 SIR3-WT | 24.2 | 26.8 | −10 | 20 |

Table 4 provides mean replicative life span (µRLS) determined for a selective set of exemplary multipe-gene deletion variants constructed in the BY4742 background. The BY4742 variant defined as a "wildtype" (WT) control is included in each experiment. For this particular set, the fob1-gpa2-double-deletion variant exhibited the longest life span having a µRLS of 54.5.

TABLE 4

Exemplary Multiple Deletion Variants

| Variant | Mean RLS | Pair-matched BY4742 (WT) RLS | ΔRLS (%) | N |
|---|---|---|---|---|
| fob1 gpa2 | 54.5 | 28.2 | 93 | 40 |
| fob1 hxk2 | 48.6 | 26.0 | 87 | 100 |
| hxk2 sir2 | 12.4 | 26.4 | −53 | 30 |
| cpr7 sir2 | 12.0 | 30.4 | −61 | 20 |
| sir2 fob1 | 29.9 | 26.9 | 11.3 | 80 |
| sir2 fob1 hxk2 | 45.3 | 27.6 | 64 | 60 |
| mpt5 ssd1 | 14.4 | 24.6 | −41 | 20 |

Figure 12:
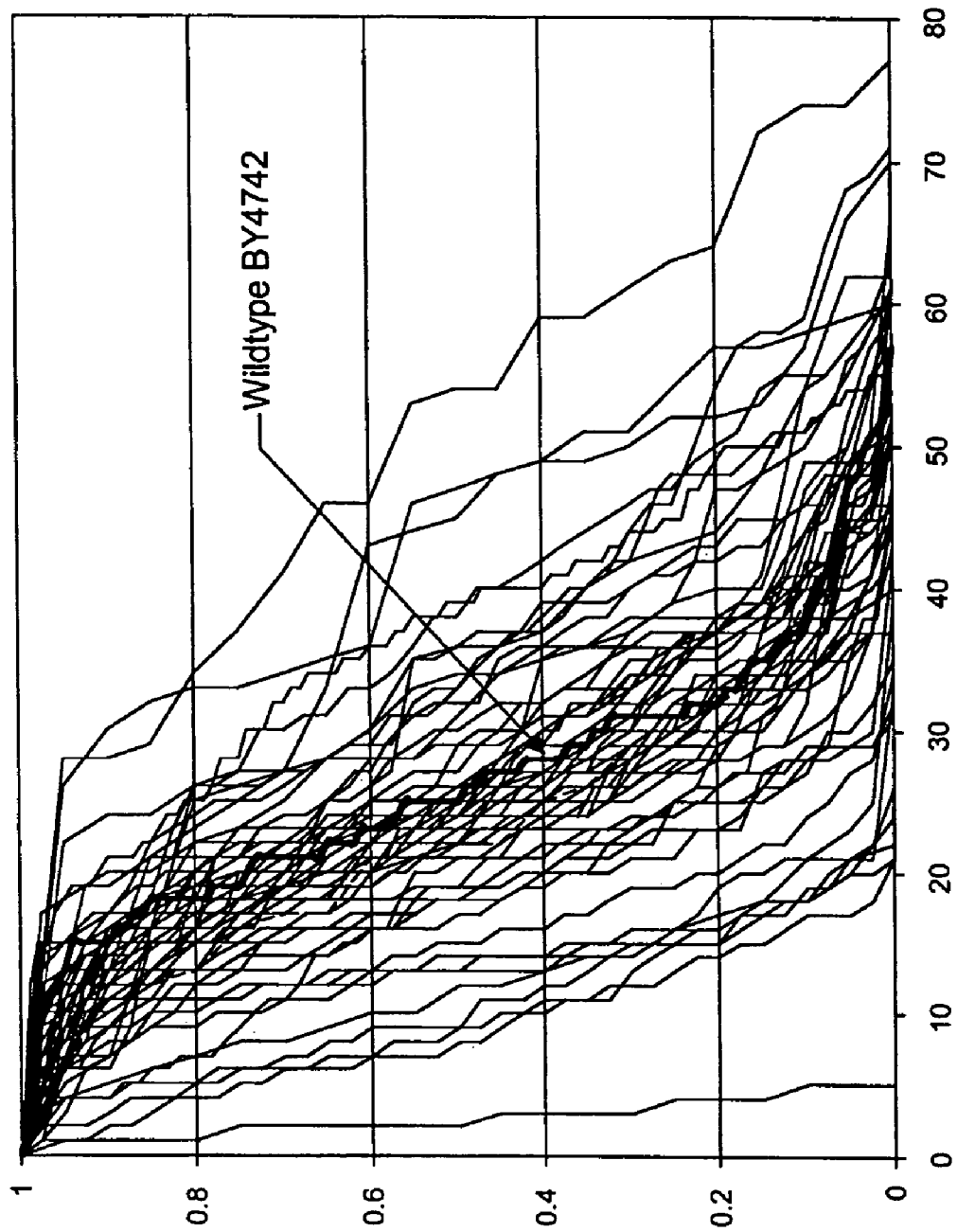
FIG. 12 illustrates mortality curves for various variants assayed.

FIG. 12 illustrates mortality curves for various variants assayed. Mortality curves for deletion variants assayed by RLS analysis are graphed relative to the pooled data for 250 "wildtype" BY4742 cells. For each deletion variant, the mean RLS for the deletion variant is compared to pair-matched BY4742 cells analyzed within the same experiment, with divergence from the computed mean RLSs compared to the published mean RLSs. Many gene deletions reported to lengthen RLS in short-lived-variant backgrounds do not have a similar effect in the BY4742 strain. Of those examined, only gene deletions variants resulting in statistically significant increases in mean life span, determined by Sign-Wilcoxson mean rank test, are the Δgpa1, Δgpr2, Δhxk2, Δcpr7, and Δfob1. Each of these deletion variants can extend mean life span from 20-40%, and can extend maximum life span to a similar extent. Among these, the Δcpr7 result is unexpected. In previous reports, Δgpa1, Δgpr2, and Δhxk2 variants are described as genetic models of CR, and it is known that FOB1 is required for the formation of ERCs. Also consistent with the ERC model of replicative aging, deletion of SIR2 results in drastically reduced replicative potential although deletions of SIR3 and SIR4 produce negligible effects. Several other deletions can extend mean life span by 10% or less (Table 2).

Example 2

Identification Long-Lived Yeast Variants by Screening a Single-Gene Deletion Library in BY4742 Background from a Small Sample Size (N=5)

As proof of principle, approximately 5,000 mother cells are assayed to establish statistically reliable replicative life span (RLS) data sets for wildtype ("WT-RLS data set") and for long-lived variants ("LL-RLS data set"). Exemplary LL-RLS data set includes RLS values determined for deletion variants fob1Δ, gpa2Δ, gpr1Δ, and Δhxk2 cells that live, on average, 30% longer than a "wildtype" reference (Table 2, Example 1). A WT-RLS data set can be complied from 250 discrete RLS determinations for "wildtype" BY4742 cells.

A large-scaled, life-span analysis is performed as follows. Approximately three days before initiating a life-span-determination assay, a set of 95 strains contained in a yeast alpha-haploid-deletion collection (Open Biosystems), is transferred to a 96-well plate containing YPDagar using a FX robot, so that each strain occupies one well of a 96-well plate. Concurrently, "wildtype" reference cells (BY4742) are plated within an empty well of the 96-well test plate. For 1-2 days, plated cells are allowed to grow on rich medium, such as YPD, at 30° C. Cells are patched onto life-span-measuring plates containing YPD so that approximately 12 strains are plated per plate the night, or approximately 12 hours, before initiating life-span analysis. A life-span experiment is initiated by gridding a region of the plate distal to growing cells, to which 5 cells of each strain of 12 strains are transferred by micromanipulation. Cells are incubated for two hours at 30° C. Then, virgin daughter cells of each deletion variant cell are selected, and original mother cells are removed. Such virgin daughter cells are monitored for de novo production of daughters at 2-3 hour intervals. Produced daughters are individually removed, and tabulated. Mother cells are placed back at 30° C. to allow continued growth. During evening hours, cells are moved to 4° C. so that the cell division rate is reduced to one cell division per evening. The following day, cells are placed at 30° C. to resume growth. This process is continued for a period of time, approximately two weeks, to allow cells of each variant strain to exhaust its proliferative potential. The total number of daughter cells produced by each mother variant cell is tabulated, and determined RLS values are entered into a database.

A computational algorithm can be designed to randomly extract a large number of hypothetical RLS datasets. For example, 100,000 hypothetical subsets can be computationally selected from a WT-RLS data set and LL-RLS data set, as a function of hypothetical sample sizes (N). As exemplary sample sizes, four N values are selected where N=3, 5, 10, and 20. For each wildtype or LL hypothetical subsets selected at a particular N value, the mean RLS (µRLS) is calculated. The calculated µRLS values for thousands of subsets determined for 8 groups ("wildtype" at N=3, 5, 10, and 20; "long-lived" at N=3, 5, 10, and 20) are plotted to determine the frequency of mean RLS observed for WT and LL cells for each hypothetical sample size. A cumulative probability distribution curve that defines the probabilities for Type I and Type II error that correlate with a particular μRLS for a particular sample size N is generated. See Table 1 in FIG. 11.

In this example, in order to completely evaluate 4800 deletion variants present in the BY4742-derived-MATα-deletion collection, an RLS assay described in FIG. 2 needs to be performed on ~4800×$N_{min}$ mother cells, in which $N_{min}$ is the minimum number of mother cells for a given deletion variant to be evaluated for reliably determining μRLS.

As a preferred embodiment, methods of the present invention are employed for identifying yeast variants exhibiting a long life span by selecting a sample size N=5 cells of each variant, as in step 403 of FIG. 4. In step 404, a μRLS is computed for each variant using a 5-cell sample size N. In step 405, each variant is classified according to steps in FIG. 5. In step 501 of FIG. 5, the computed μRLS for a variant is compared to threshold values established in step 301 of FIG. 3. In steps 502-503, variants exhibiting μRLS>a positive threshold, such as "36" is classified as "positive" or LL. In steps 504-505, variants exhibiting μRLS<a negative threshold, such as "26" is classified as "negative" or NLL. The probability that the negative variant is "short-lived" ("SL") relative to a "wildtype" reference can be assigned based on a cumulative probability distribution. If the computed μRLS of a deletion variant is not >36, and not <26, then μRLS is greater than 26 and less than 36. Such variants are classified as "ambiguous," and additional sample sets of N cells of the "ambiguous" variant can be reevaluated to determine whether the variant is LL or NLL.

RESULT: As an example, μRLS values for each deletion variant from a MATα-haploid-deletion set, contained in one 96-well plate (~2% of the entire set), is determined. Based on the cumulative probability distribution for N=5 (Table 1, FIG. 11), approximately 52% of true LL variants are predicted to be correctly classified, with less than 1% of NLL variants misclassified as LL. From this limited analysis of the genome, of the 96 strains tested, 4 LL variants (ΔYBR255W, ΔYDR124W, ΔYBR266C, and ΔYBR267W) exhibit μRLS>36. Approximately 20% (21/96) of the deletions variants exhibit a mean life span significantly shorter than the "wildtype" reference (p<0.05). Thirty variants that demonstrated 5-cell μRLS between 26 and 36, are classified as "ambiguous." The remaining 62 variants that exhibited μRLS<26 are characterized as NLL (41 variants) or "short-lived" ("SL") (21 variants).

For this initial dataset, μRLS for 5 additional cells for all 96 variants present in the test plate are evaluated, instead of analyzing only 30 variants classified as "ambiguous" after the first round, in order to determine the efficiency of the sorting algorithm, and to verify that a substantial fraction of LL variants are not being wrongly classified as NLL in the first round. Of the 4 variants classified as LL in the first set, 3 variants are independently scored as LL and the fourth variant (ΔYBR255W) scored as "ambiguous" in the second set. In contrast, only 1 variant out of 62 variants that initially scored as NLL retested as LL in the second round. Of the 30 deletion variants categorized as "ambiguous" in the first round, 4 are classified as LL and 14 are classified as NLL in the second round, leaving 12 variants that require further RLS analysis after two rounds. For each 96-well-plate-deletion collection assayed, one empty well contained a "wildtype" reference control. The "wildtype" control classified as "ambiguous" in the first round is correctly classified as NLL in the second round.

Figure 13:
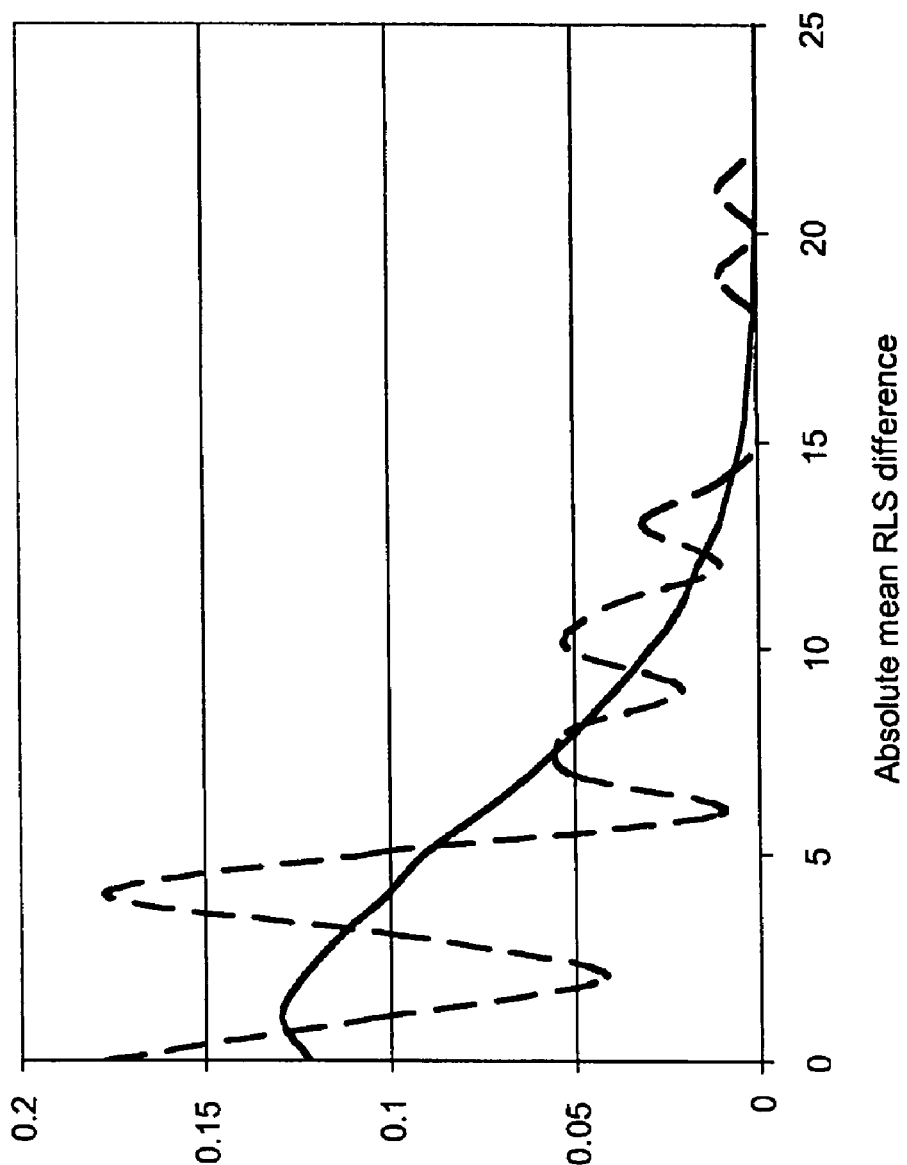
FIG. 13 is a comparison of a histogram of observed differences for 5-cell μRLS values calculated for each variant assayed in replicate, against a histogram of predicted differences for 5-cell μRLS values randomly generated from a WT-RLS data set.

FIG. 13 is a comparison of a histogram of observed differences for 5-cell μRLS values calculated for each variant assayed in replicate, against a histogram of predicted differences for 5-cell μRLS values randomly generated from a WT-RLS data set. The theoretical distribution can be generated by a computer algorithm that randomly selects two 5-cell sets from a WT-RLS data set, computes the μRLS for each pair, and computes the absolute difference of the μRLSs. This process is repeated 100,000 times, and a histogram of the difference frequency is generated. Although a relatively small number of data points (96) are analyzed initially, the observed μRLS difference frequency fits the theoretical distribution, demonstrating the reproducibility of the classification methods described.

Example 3

Exemplary Orthologous Sequences Identified by Database Search

Approximately 14 unique open reading frames ("ORFs") of yeast sequences are identified from long-lived variants classified by methods of the present invention. For each yeast sequence identified as conferring "long-lived" or life-span-regulating, the amino-acid sequence of the corresponding protein is used as a "query sequence" to perform a search against sequences deposited within various public databases to identify evolutionarily-related sequences. Coding sequences for each yeast ORF are obtained from a genomic database for *Saccharomyces cerevisiae*.

A BLAST search of the NCBI database resulted in the identification of various mammalian orthologs that are related to fourteen of these ORFs listed in Table 5. Tables 6 lists exemplary sets of conserved orthologs that correspond to the yeast homolog. For each identified yeast ORF, the respective percent identities, percent similarities, and E values are shown. Default parameters were used to perform the search.

For the present invention, an ortholog is defined as a homologous molecule or sequence having life-span-regulating activity and a sequence identity of at least 20%, 25%, 30%, 35%, 40%, 45%, 50%, 55%, 60%, 65%, 70%, 75%, 80%, 85%, 90%, and 95%. Alternatively, an ortholog is defined as a homologous molecule or sequence having life-span-regulating activity and a sequence similarity of at least about 40%, 45%, 50%, 55%, 60%, 65%, 70%, 75%, 80%, 85%, 90%, and 95%:

TABLE 5

| Genes that increase replicative life span |
| --- |
| bre5 |
| fob1 |
| idh2 |
| rei1 |
| rom2 |
| rpl31a |
| rpl6b |
| tor1 |
| ybr238c |
| ybr255w |
| ybr266c |
| yor135c |
| sch9 |
| ure2 |

TABLE 6

| Gene | GenBank | Synonyms/Description | Match Length | % Iden | % Sim | High Score | E Val |
|---|---|---|---|---|---|---|---|
| | | BRE5 - CAA96332.1 BRE5 blast vs human | | | | | |
| G3BP2 | NP_987101.1 | G3BP2; KIAA0660; (G3BP) Ras-GTPase activating protein SH3 domain-binding protein 2, putative RNA binding protein that possesses ATPase activity, is phosphorylated and activated by heregulin (NRG1) and overexpressed in breast tumors that also overexpress HER2 (ERBB2) | 344 | 23% | 40% | 136 | 7e−04 |
| ASXL2 | NP_060733.2 | ASXL2; ASXH2; FLJ10898; KIAA1685; Hs.13801 Additional sex combs like 2, a putative Polycomb group protein, may function in both the activation and repression of transcription, possibly involved in embryogenesis and carcinogenesis | 270 | 20% | 41% | 102 | 7e−04 |
| | | Compared with *M. musculus* protein sequences (Documentation) | | | | | |
| E430034L04Rik | NP_035946.2 | E430034L04Rik; (G3BP); G3BP2; G3bp2; Mm.2411; (G3bp) Ras-GTPase activating protein SH3 domain-binding protein 2, may transduce signals from receptor tyrosine kinases, associates with polyA mRNA; human G3BP2 is overexpressed in breast tumors that also overexpress HER2 (ERBB2) | 344 | 22% | 38% | 128 | 7e−04 |
| | | Compared with *C. elegans* protein sequences (Documentation) | | | | | |
| ptl-1 | AAK70646.1 | ptl-1; F42G9.9B; (tau-1); F42G9.3; F42G9.9 Protein with tau-like repeats 1, tau repeat-containing protein that promotes microtubule assembly | 283 | 23% | 40% | 114 | 5e−04 |
| | | FOB1 - CAA88664.1 FOB1 blast vs human - | | | | | |
| LOC124751 | NP_998762.1 | LOC124751 Member of the KRAB box family | 393 | 19% | 41% | 128 | 6e−05 |
| | | IDH2 - CAA99335.1 IDH2 blast vs human - | | | | | |
| IDH3A | NP_005521.1 | IDH3A; IDHalpha Isocitrate dehydrogenase 3 (NAD+) alpha, catalytic subunit of the mitochondrial enzyme that catalyzes the oxidative decarboxylation of isocitrate to form alpha-ketoglutarate in the tricarboxylic acid cycle | 337 | 55% | 70% | 883 | 5e−87 |
| IDH3G | NP_004126.1 | IDH3G; H-IDH_gamma; IDHgamma; H-IDHG NAD(+)-dependent isocitrate dehydrogenase gamma subunit, catalyzes the oxidative decarboxylation of isocitrate into alpha-ketoglutarate in the TCA cycle | 339 | 41% | 63% | 629 | 9e−61 |
| IDH3B | NP_008830.2 | IDH3B; IDHbeta; H-IDHB; MGC903; FLJ11043 Isocitrate dehydrogenase 3 (NAD+) beta, a putative regulatory subunit of mitochondrial isocitrate dehydrogenase, which catalyzes the oxidative decarboxylation of isocitrate to form alpha-ketoglutarate in the tricarboxylic acid cycle | 339 | 40% | 62% | 614 | 1e−60 |
| | | Compared with *M. musculus* protein sequences (Documentation) | | | | | |
| Idh3a | NP_083849.1 | Idh3a; 1500012E04Rik; 1110003P10Rik Protein with very strong similarity to isocitrate dehydrogenase 3 (NAD+) alpha (human IDH3A), which is the catalytic subunit of a key enzyme of the tricarboxylic acid cycle, contains an isocitrate or isopropylmalate dehydrogenase domain | 337 | 56% | 71% | 888 | 9e−88 |
| Idh3g | NP_032349.1 | Idh3g; Mm.14825 NAD(+)-dependent isocitrate dehydrogenase gamma subunit, catalyzes the oxidative decarboxylation of isocitrate into alpha-ketoglutarate in the TCA cycle | 339 | 40% | 63% | 626 | 1e−60 |
| Idh3b | NP_570954.1 | Idh3b; Mm.29590 Protein with high similarity to NAD(+)-dependent isocitrate dehydrogenase gamma subunit (human IDH3G), which catalyzes the oxidative decarboxylation of isocitrate into alpha-ketoglutarate, contains an isocitrate or isopropylmalate dehydrogenase domain | 339 | 40% | 63% | 626 | 2e−59 |
| 4933405O20Rik | NP_766489.1 | 4933405O20Rik; 4933405O20 Protein with high similarity to NAD(+)-dependent isocitrate dehydrogenase gamma subunit (human IDH3G), which catalyzes the oxidative decarboxylation of isocitrate into alpha-ketoglutarate, contains an isocitrate or isopropylmalate dehydrogenase domain | 351 | 38% | 63% | 591 | 1e−54 |
| | | Compared with *C. elegans* protein sequences (Documentation) | | | | | |
| F43G9.1 | CAB02111.2 | F4379.1 Putative NAD+ isocitrate dehydrogenase that functions in embryogenesis and regulation of DNA transposition | 332 | 59% | 72% | 943 | e−103 |

TABLE 6-continued

| Gene | GenBank | Synonyms/Description | Match Length | % Iden | % Sim | High Score | E Val |
|---|---|---|---|---|---|---|---|
| C30F12.7 | AAK85453.1 | C30F12.7 Protein with high similarity to *C. elegans* F35G12.2, which is involved in gametogenesis, larval development, and embryogenesis or morphogenesis, contains an isocitrate or isopropylmalate dehydrogenase domain | 337 | 39% | 61% | 618 | 3e−59 |
| F35G12.2 | CAA86325.2 | F35G12.2 Putative NAD+-isocitrate dehydrogenase | 379 | 36% | 58% | 593 | 1e−55 |
| C37E2.1 | CAB02822.1 | C37E2.1 Protein with high similarity to NAD(+)-dependent isocitrate dehydrogenase gamma subunit (human IDH3G), which catalyzes the formation of alpha-ketoglutarate in the tricarboxylic acid cycle, contains an isocitrate or isopropylmalate dehydrogenase domain | 366 | 38% | 60% | 600 | 2e−55 |
| F59B8.2 | CAA92778.1 | F59B8.2 Protein with high similarity to cytosolic NADP(+)-dependent isocitrate dehydrogenase (rat Idh1), which catalyzes the oxidative decarboxylation of isocitrate into alpha-ketoglutarate, contains an isocitrate or isopropylmalate dehydrogenase domain | 196 | 29% | 43% | 107 | 2e−04 |

REI1 - CAA85229.1
REI1 blast vs human -

| Gene | GenBank | Synonyms/Description | Match Length | % Iden | % Sim | High Score | E Val |
|---|---|---|---|---|---|---|---|
| ZNF622 | NP_219482.1 | ZNF622; ZPR9; MGC2485; MGC17552; Hs.60300 Zinc finger-like protein 9, homodimeric transcription factor that binds human MYBL2 and enhances transcriptional activity, may enhance apoptosis induced by various extracellular signals, associates with human MELK and is a substrate of mouse Melk | 414 | 31% | 46% | 441 | 5e−31 |
| FLJ10415 | NP_060559.1 | FLJ10415 Protein of unknown function | 80 | 34% | 58% | 135 | 6e−06 |

Compared with *M. musculus* protein sequences (Documentation)

| Gene | GenBank | Synonyms/Description | Match Length | % Iden | % Sim | High Score | E Val |
|---|---|---|---|---|---|---|---|
| Zfp622 | NP_653106.1 | Zfp622; ZPR9; D15Ertd806e; 1110033B05Rik Protein with strong similarity to zinc finger-like protein 9 (human ZNF622), which is a homodimeric transcription factor that binds human MELK and human MYBL2 and enhances transcriptional activity and may enhance apoptosis induced by extracellular signals | 412 | 30% | 45% | 426 | 2e−31 |

Compared with *C. elegans* protein sequences (Documentation)

| Gene | GenBank | Synonyms/Description | Match Length | % Iden | % Sim | High Score | E Val |
|---|---|---|---|---|---|---|---|
| C16A3.4 | AAB47598.1 | C16A3.4 NADH-ubiquinone oxidoreductase B22-protein involved in reproduction, embryogenesis, and positive growth regulation, putative target of DAF-16 | 406 | 30% | 50% | 431 | 2e−24 |

ROM2 - AAB67564.1
ROM2 blast vs human -

| Gene | GenBank | Synonyms/Description | Match Length | % Iden | % Sim | High Score | E Val |
|---|---|---|---|---|---|---|---|
| NET1 | NP_005854.2 | NET1; NET1A; ARHGEF8 Neuroepithelial cell transforming gene 1, a guanine nucleotide exchange factor for the Rho subfamily of GTPases, involved in actin filament organization; overexpression induces oncogenic transformation | 297 | 24% | 48% | 217 | 1e−16 |
| ARHGEF12 | NP_056128.1 | ARHGEF12; KIAA0382; LARG; Hs.6582; PRO2792 Rho guanine nucleotide exchange factor (GEF) 12, a Rho GEF that homo-oligomerizes and hetero-oligomerizes with PDZ-RhoGEF (ARHGEF11) and binds IGF1R, mediates actin stress fiber formation and is associated with some cases of acute myeloid leukemia | 305 | 26% | 52% | 215 | 8e−16 |
| ARHGEF3 | NP_062455.1 | ARHGEF3; STA3; GEF3; DKFZP434F2429; XPLN; Hs.25951 Rho guanine nucleotide exchange factor (GEF) 3, a guanine nucleotide exchange factor specific for RhoA (ARHA) and RhoB (ARHB), involved in Rho protein signaling; corresponding gene maps to a chromosomal region that is sometimes deleted in tumors | 385 | 21% | 44% | 209 | 2e−15 |
| ITSN1 | NP_003015.2 | ITSN1; ITSN; SH3P17; SH3D1A Intersectin 1, regulator of the actin cytoskeleton, acts as a guanine nucleotide exchange factor for CDC42, putative scaffold protein in endocytosis, may be misexpressed in Down syndrome | 336 | 24% | 46% | 206 | 3e−13 |
| ARHGEF11 | NP_937879.1 | ARHGEF11; KIAA0380; GTRAP48; PDZ-RHOGEF; PDZ-RhoGEF Rho guanine nucleotide exchange factor (GEF) 11, a guanine nucleotide exchange factor for Rho GTPases that also forms stable complexes with Galpha12 (human GNA12) and Galpha13 (human GNA13) | 392 | 23% | 46% | 200 | 6e−13 |
| ARHGEF1 | NP_945353.1 | ARHGEF1; P115-RHOGEF; SUB1.5; LBCL2; GEF1; p115RhoGEF Rho guanine nucleotide exchange factor 1, involved in cell cycle control and cell proliferation, may modulate HIV1 replication; overproduction induces cellular transformation | 305 | 26% | 49% | 219 | 2e−12 |

TABLE 6-continued

| Gene | GenBank | Synonyms/Description | Match Length | % Iden | % Sim | High Score | E Val |
|---|---|---|---|---|---|---|---|
| SGEF | NP_056410.2 | SGEF; CSGEF; DKFZP434D146; Hs.240845; HMFN1864 DKFZP434D146 protein, exists in at least two alternative forms that are differentially expressed, one of which may act as a regulator of Rho GTPases in all tissues, and the other may act as an androgen-induced regulator specific to prostate epithelium | 404 | 22% | 42% | 180 | 6e−12 |
| ARHGEF15 | NP_776089.2 | ARHGEF15; KIAA0915; FLJ13791; Hs.16714; MGC44868; Vsm-RhoGEF; ARGEF15 Protein containing a RhoGEF (GTPase exchange factor) domain, has a region of moderate similarity to neuronal guanine nucleotide exchange factor (mouse Ngef), which transforms cells and induces tumors in nude mice | 244 | 25% | 49% | 177 | 2e−11 |
| AKAP13 | NP_006729.4 | AKAP13; HT31; BRX; FLJ11952; LBC; PROTO-LBC; AKAP-Lbc; c-lbc; PROTO-LB; NIH_MGC_8; NIH_MGC_16; NIH_MGC_19; Ht31; HA-3 A kinase anchor protein 13, an anchor protein that regulates the subcellular localization of cAMP-dependent protein kinase (PRKA) by binding the type II regulatory subunit (PRKAR2A), likely Rho guanyl-nucleotide exchange factor that may act in signaling | 449 | 22% | 44% | 173 | 1e−10 |
| NGEF | NP_062824.1 | NGEF; EPHEXIN Neuronal guanine nucleotide exchange factor, member of the Dbl family of proteins that function as guanine nucleotide exchange factors for Rho-type GTPases, prominently expressed in the brain | 350 | 22% | 45% | 162 | 1e−10 |
| ARHGEF5 | NP_005426.2 | ARHGEF5; (TIM); (TIM1); (P60); GEF5; Hs.334; LOC7984 Rho guanine nucleotide exchange factor (GEF) 5, putative regulator of Rac/Rho proteins that induces stress fiber disassembly, membrane ruffling and filopodia formation, catalytically inactive variants are expressed in aggressive primary breast carcinomas | 310 | 23% | 43% | 158 | 4e−10 |
| ITSN2 | NP_006268.1 | ITSN2; KIAA1256; SH3D1B; (SWAP); SH3P18; SWA Intersectin 2, protein containing two EH domains, five Src homology 3 (SH3) domains, as well as C-terminal Dbl homology (DH), pleckstrin homology (PH) and C2 calcium binding domains, predicted to have roles in endocytosis and guanine nucleotide exchange | 303 | 22% | 47% | 165 | 6e−10 |
| DEPDC2 | NP_079146.2 | DEPDC2; DEP.2; FLJ12987; FLJ14017; PREX2; P-REX2 DEP domain containing 2, a Rac guanyl-nucleotide exchange factor, links Rac activation to the phosphatidylinositol-3 kinase pathway, highly expressed in skeletal muscle, may play a role in skeletal muscle development | 277 | 22% | 47% | 157 | 2e−09 |
| ARHGEF4 | NP_056135.2 | ARHGEF4; KIAA1112; STM6; ASEF; GEF4; DKFZp434G2016 APC-stimulated guanine nucleotide exchange factor, a brain-specific RAC guanine nucleotide exchange factor that plays a role in cytoskeletal reorganization, interacts with and may be stimulated by adenomatous polyposis coli protein (human APC) | 288 | 21% | 44% | 153 | 5e−09 |
| ARHGEF2 | NP_004714.2 | ARHGEF2; LFP40; GEF-H1; KIAA0651; (P40); (GEF); DKFZp547L106; GEFH1 Rho-Rac guanine nucleotide exchange factor 2, an exchange factor specific for Rho and Rac GTPases, mediates Rho-regulated cell shape control and Rho activation by colchicine and nocodazole, activity is reduced by microtubule binding | 316 | 21% | 46% | 150 | 3e−08 |
| FGD3 | NP_149077.1 | FGD3; FLJ00004; ZFYVE5 Protein with high similarity to faciogenital dysplasia homolog 3 (mouse Fgd3), which is involved in cell shape and size control, contains a RhoGEF (GTPase exchange factor) domain, a FYVE zinc finger, and a pleckstrin homology (PH) domain | 401 | 22% | 41% | 139 | 7e−08 |
| ARHGEF19 | NP_694945.2 | ARHGEF19; FLJ33962; WGEF Protein with strong similarity to mouse Arhgef19, which is a guanine nucleotide exchange factor for RhoA (mouse Rhoa), mouse Cdc42, and mouse Rac1, contains pleckstrin homology (PH), RhoGEF, Src homology 3 (SH3) and variant SH3 domains | 280 | 21% | 47% | 155 | 1e−07 |
| FGD4 | NP_640334.1 | FGD4; FRABP; FRABIN; ZFYVE6; LOC121512 FYVE RhoGEF and PH domain containing 4 (frabin), a protein that likely plays a role in actin cytoskeletal arrangement and is required for Cryptosporidium parvum invasion of epithelial cells | 266 | 22% | 42% | 140 | 2e−07 |
| ARHGEF10 | NP_055444.1 | ARHGEF10; KIAA0294; GEF10 Rho guanine nucleotide exchange factor 10, a putative Rho-specific guanine-nucleotide exchange factor, may act in peripheral nerve myelination; gene mutation is | 271 | 22% | 46% | 139 | 2e−07 |

TABLE 6-continued

| Gene | GenBank | Synonyms/Description | Match Length | % Iden | % Sim | High Score | E Val |
|---|---|---|---|---|---|---|---|
| | | associated with slowed nerve conductance and thin peripheral nerve myelination | | | | | |
| FGD2 | NP_775829.1 | FGD2; LOC221472; ZFYVE4 FGD1 family member 2, a putative rho guanine nucleotide exchange factor, has a rho guanine nucleotide exchange factor domain, two pleckstrin homology domains, and an FYVE domain | 283 | 23% | 43% | 160 | 3e−07 |
| FGD6 | NP_060821.2 | FGD6; ZFYVE24; FLJ11183 Protein containing two pleckstrin homology domains, which mediate protein-protein and protein-lipid interactions, a RhoGEF domain, and a FYVE zinc finger domain, which bind phosphatidylinositol 3-phosphate, has a region of low similarity to rat Fgd4 | 316 | 22% | 41% | 140 | 3e−07 |
| CIT | NP_009105.1 | CIT; KIAA0949; STK21; CRIK Citron Rho interacting kinase, a serine/threonine protein kinase that binds to Rho and Rac and mediates the regulation of cytokinesis in neuronal precursor cells | 140 | 31% | 48% | 131 | 4e−07 |
| HAPIP | NP_003938.1 | HAPIP; DUO; HS.8004; duo Huntington-associated protein interacting protein, a putative guanyl nucleotide exchange factor, binds Huntington-associated protein (HAP-1), may be involved in vesicle trafficking and cytoskeletal function | 223 | 26% | 45% | 135 | 5e−07 |
| TRIO | NP_009049.2 | TRIO; Hs.367689; tgat Triple functional domain, RAC and RHO guanine nucleotide exchange factor, interacts with filamin during actin cytoskeleton remodeling and with the tyrosine phosphatase LAR, involved in neurite outgrowth, contains a serine/threonine kinase domain | 259 | 22% | 46% | 136 | 1e−06 |
| PREX1 | NP_065871.2 | PREX1; KIAA1415; PRex1; P-Rex1 Phosphatidylinositol 3,4,5-trisphosphate-dependent RAC exchanger 1, a guanyl-nucleotide exchange factor that mediates formation of reactive oxygen species in neutrophils | 264 | 23% | 45% | 135 | 1e−06 |
| TRAD | NP_008995.1 | TRAD; DUET; Hs.162189 Duet, a serine/threonine kinase with Dbl and pleckstrin homology domains, expressed only in skeletal muscle, and localizes to the actin cytoskeleton | 251 | 24% | 44% | 132 | 1e−06 |
| ARHGEF9 | NP_056000.1 | ARHGEF9; KIAA0424; PEM-2; HPEM-2; COLLYBISTIN; Hs.54697; PEM2 Cdc42 guanine nucleotide exchange factor (GEF) 9 (ascidian protein posterior end mark-2), a putative guanyl-nucleotide exchange factor which specifically activates human CDC42, induces filopodia formation and actin polymerization | 267 | 22% | 43% | 124 | 1e−06 |
| ECT2 | NP_060568.3 | ECT2; FLJ10461 Epithelial cell transforming sequence 2 oncogene, a guanine nucleotide exchange factor for Rho GTPases that is active during the G2 and M phases of the cell cycle and is required for cytokinesis and for cytokinetic RhoA (ARHA) activity | 199 | 26% | 42% | 127 | 2e−06 |
| ARHGEF16 | NP_055263.1 | ARHGEF16; NBR; Hs.87435; GEF16 Protein containing a pleckstrin homology (PH) domain, a RhoGEF (GTPase exchange factor) domain, and a Src homology 3 (SH3) domain, has moderate similarity to neuronal guanine nucleotide exchange factor (mouse Ngef) | 187 | 21% | 48% | 124 | 4e−06 |
| SPATA13 | NP_694568.1 | SPATA13; FLJ31208 Protein with high similarity to human ARHGEF4, which is a guanine nucleotide exchange factor that acts in cytoskeletal organization, contains a RhoGEF (GTPase exchange factor), pleckstrin homology (PH), Src homology 3 (SH3), and variant SH3 domain | 308 | 22% | 40% | 128 | 5e−06 |
| CDC42BPB | NP_006026.2 | CDC42BPB; MRCKB; KIAA1124 CDC42 binding protein kinase beta, putative protein kinase of the myotonic dystrophy kinase family | 158 | 22% | 47% | 132 | 7e−06 |
| TIAM1 | NP_003244.1 | TIAM1 T lymphoma invasion and metastasis 1, RAC1 and RHO guanine nucleotide exchange factor that is involved in lamellipodium formation and apoptosis | 233 | 21% | 44% | 121 | 1e−05 |
| FGD1 | NP_004454.2 | FGD1; AAS; FGDY; ZFYVE3 Faciogenital dysplasia, guanine nucleotide exchange factor for CDC42, involved in actin cytoskeletal rearrangement and possibly in G1 cell cycle progression and ossification; variants cause faciogenital dysplasia, non-syndromal X-linked mental retardation | 295 | 23% | 43% | 125 | 2e−05 |
| CDC42BPA | NP_003598.2 | CDC42BPA; MRCKA; MRCK; PK428; KIAA0451; FLJ23347 CDC42 binding protein kinase alpha, a protein kinase that binds granulocyte-macrophage colony-stimulating factor receptor alpha subunit (CSF2RA), capable of autophosphorylation, may act in muscle physiology | 147 | 20% | 43% | 114 | 3e−05 |

TABLE 6-continued

| Gene | GenBank | Synonyms/Description | Match Length | % Iden | % Sim | High Score | E Val |
|---|---|---|---|---|---|---|---|
| FARP2 | NP_055623.1 | FARP2; (FIR); KIAA0793; FRG FERM RhoGEF and pleckstrin domain protein 2, a guanyl-nucleotide exchange factor with reported specificity for RAC1 or CDC42, may be involved in actin cytoskeleton organization, axonogenesis, and regulation of cell shape and motility | 418 | 20% | 39% | 120 | 1e−04 |
| ARHGEF18 | NP_056133.2 | ARHGEF18; KIAA0521; MGC15913; P114-RHO-GEF; Hs.6150 Rho-specific guanine nucleotide exchange factor (GEF) p114, a Dbl homology (DH) and pleckstrin homology (PH) domain-containing GEF involved in Rac- and Rho-mediated G protein signaling, plays a role in regulating actin organization and cell shape | 311 | 23% | 45% | 163 | 2e−04 |
| CDC42BPG | NP_059995.1 | CDC42BPG; HSMDPKIN; MRCKgamma; DMPK2; KAPPA-200 Member of the citron homology and protein kinase C-terminal domain-containing families, contains pleckstrin homology, protein kinase, and phorbol ester or diacylglycerol binding domains, has moderate similarity to rat Pk428, which is a protein kinase | 178 | 25% | 39% | 115 | 2e−04 |
| TIAM2 | NP_036586.2 | TIAM2; STEF; KIAA2016 T-cell lymphoma invasion and metastasis 2, a guanyl-nucleotide exchange factor, contains multiple domains (EX domain, PDZ domain, DHR domain, DH domain, and PH domain); gene maps to region commonly deleted in nasal T-cell lymphoma | 205 | 20% | 45% | 115 | 2e−04 |
| MCF2 | NP_005360.2 | MCF2; DBL MCF.2 cell line derived transforming sequence, oncoprotein and RHO guanyl-nucleotide exchange factor, functions in cytoskeleton organization cell growth and proliferation | 224 | 23% | 45% | 111 | 2e−04 |
| RGNEF | BAC04405.1 | RGNEF; FLJ21817; KIAA1998 Protein containing a phorbol ester or diacylglycerol binding domain, which bind two zinc ions, has strong similarity to a region of Rho interacting protein 2 (mouse Rgnef), which is a putative Rho guanyl-nucleotide exchange factor that binds GTP-Rho | 123 | 24% | 50% | 107 | 2e−04 |
| BCR | NP_004318.2 | BCR; CML; PHL; BCR1; D22S11; D22S662; ALL Breakpoint cluster region, GTPase-activating protein for p21rac with serine/threonine kinase activity; inhibition or decreased expression of BCR-ABL chimeric protein may be therapeutic for Philadelphia chromosome-positive leukemias | 262 | 18% | 42% | 102 | 3e−04 |
| Compared with *M. musculus* protein sequences (Documentation) | | | | | | | |
| Net1 | NP_062645.1 | Net1; Net1a; mNET1; Mm.22261; 0610025H04Rik; 9530071N24Rik Neuroepithelial cell transforming gene 1, a guanine nucleotide exchange factor for the Rho subfamily of GTPases, involved in actin filament organization and acts in signaling pathways from Rho and stress activated kinases | 297 | 24% | 49% | 224 | 1e−17 |
| Arhgef1 | NP_032514.1 | Arhgef1; Mm.3181; Lbcl2; Lsc Rho guanine nucleotide exchange factor 1, involved in cell proliferation and probably cell cycle control; human ARHGEF1 may modulate HIV1 replication | 305 | 26% | 48% | 213 | 1e−15 |
| Arhgef3 | NP_082147.1 | Arhgef3; 1200004I24Rik; C76747; Xpln; Mm.248606; 9830169H03Rik Protein with strong similarity to rho guanine nucleotide exchange factor 3 (human ARHGEF3), which is a guanine nucleotide exchange factor specific for RhoA (human ARHA) and RhoB (human ARHB), contains a RhoGEF domain and a pleckstrin homology (PH) domain | 367 | 22% | 46% | 209 | 2e−15 |
| Itsn1 | NP_034717.1 | Itsn1; Ese1; Itsn; EHSH1; Sh3p17; Intersectin Intersectin 1, an adaptor and scaffold protein that plays a role in endocytosis; human ITSN1 may be misexpressed in Down syndrome | 336 | 24% | 46% | 207 | 5e−15 |
| Arhgef11 | NP_001003912.1 | Arhgef11; (RhoGEF); B930073M02; E130307F09; PDZ-RhoGEF; MGC90827 Rho guanine nucleotide exchange factor 11, may regulate neuronal morphogenesis by signaling through G protein-coupled receptors | 392 | 23% | 46% | 217 | 5e−14 |
| Arhgef15 | NP_808234.2 | Arhgef15; D530030K12Rik; LOC442801; D130071N09; MGC102247 Protein containing a RhoGEF (GTPase exchange factor) domain, has low similarity to rho guanine nucleotide exchange factor 19 (mouse Arhgef19), which is | 245 | 26% | 49% | 181 | 1e−11 |

TABLE 6-continued

| Gene | GenBank | Synonyms/Description | Match Length | % Iden | % Sim | High Score | E Val |
|---|---|---|---|---|---|---|---|
| Rgnef | NP_036156.1 | a Rho guanine nucleotide exchange factor that induces rearrangement of the actin cytoskeleton Rgnef; (RIP2); (RhoGEF); D13Bwg1089e; Rhoip2; Mm.4620; 9230110L08Rik Rho interacting protein 2, a putative Rho guanyl-nucleotide exchange factor that binds GTP-Rho, induces cytoskeletal contraction in neuronal cells, inhibits neurite outgrowth | 339 | 24% | 45% | 171 | 1e−10 |
| Arhgef16 | AAH20030.1 | Arhgef16; LOC230972 Protein containing a pleckstrin homology (PH) domain, a Src homology 3 (SH3) domain, a variant SH3 domain, and a RhoGEF (GTPase exchange factor) domain, has moderate similarity to neuronal guanine nucleotide exchange factor (mouse Ngef) | 218 | 23% | 48% | 161 | 2e−10 |
| 2310014B11Rik | NP_081420.1 | 2310014B11Rik; Larg; Mm.101659; Mm.275266; (Arhgef12); mKIAA0382 Protein with strong similarity to rho guanine nucleotide exchange factor 12 (human ARHGEF12), which is a Rho GTPase activator that binds human IGF1R and is associated with acute myeloid leukemia, contains a PDZ, DHR, or GLGF domain and a RhoGEF domain | 309 | 27% | 52% | 216 | 3e−10 |
| Arhgef18 | NP_598723.3 | Arhgef18; D030053O22Rik; Mm.170461 Protein with strong similarity to rho-specific guanine nucleotide exchange factor p114 (human ARHGEF18), which is a Rho guanyl-nucleotide exchange factor, contains a RhoGEF (GTPase exchange factor) domain and a pleckstrin homology (PH) domain | 312 | 22% | 45% | 170 | 4e−10 |
| Arhgef19 | NP_766108.1 | Arhgef19; 6030432F23; 6430573B13Rik; WGEF Rho guanine nucleotide exchange factor 19, a Rho guanine nucleotide exchange factor, activates Rhoa, Cdc42, and Rac1, induces rearrangement of actin cytoskeleton, may play a role in heart, kidney, and intestine development or function | 280 | 21% | 46% | 158 | 8e−10 |
| Ngef | NP_063920.1 | Ngef; ephexin; Tims2 Neuronal guanine nucleotide exchange factor, member of the Dbl family of proteins that function as guanine nucleotide exchange factors for Rho-type GTPases, expressed in caudate nucleus, transforms cells and induces tumors in nude mice | 292 | 23% | 47% | 159 | 1e−09 |
| Sh3d1B | NP_035495.2 | Sh3d1B; Ese2; Sh3p18; Itsn2; mKIAA1256 EH domain and SH3 domain regulator of endocytosis 2, predicted polypeptide contains two EH domains, a coiled coil, and five C-terminal SH3 domains, domains and sequence are similar to intersectin (Itsn), may function in the regulation of endocytosis | 304 | 21% | 46% | 160 | 2e−09 |
| Arhgef10 | NP_766339.1 | Arhgef10; 6430549H08; 6430549H08Rik; mKIAA0294; KIAA0294 Protein containing a RhoGEF (GTPase exchange factor) domain, has weak similarity to a region of rho-specific guanine-nucleotide exchange factor 164 kDa (human ARHGEF17), which is a Rho guanyl-nucleotide exchange factor | 289 | 21% | 45% | 154 | 2e−09 |
| Fgd4 | NP_631978.1 | Fgd4; Frabp; 9330209B17Rik; Frabin; LOC224014; ZFYVE6 FYVE RhoGEF and PH domain containing 4 (frabin), a putative GDP/GTP exchange protein with actin filament-binding activity, may have role in filopodia and lamellipodia formation, may be involved in Rac signaling | 262 | 22% | 42% | 149 | 3e−09 |
| Farp2 | NP_663494.1 | Farp2; Fir; LOC227377; D030026M03Rik; mKIAA0793; KIAA0793 Protein with strong similarity to FERM RhoGEF and pleckstrin domain protein 2 (human FARP2), which is a Rac guanyl-nucleotide exchange factor, member of the FERM domain (Band 4.1 family) family, contains two pleckstrin homology domains and a RhoGEF domain | 434 | 22% | 41% | 152 | 3e−08 |
| 9330140K16Rik | NP_898840.2 | 9330140K16Rik; 9330140K16; ARHGEF4; Asef Protein containing a pleckstrin homology (PH) domain, which mediate protein and lipid binding, a RhoGEF (GTPase exchange factor) | 263 | 19% | 44% | 137 | 3e−08 |

TABLE 6-continued

| Gene | GenBank | Synonyms/Description | Match Length | % Iden | % Sim | High Score | E Val |
|---|---|---|---|---|---|---|---|
| Fgd2 | NP_038738.1 | domain and a Src homology 3 (SH3) domain, which bind proline-rich peptides, has strong similarity to a region of human ARHGEF4 Fgd2; Mm.20867; ZFYVE4 Faciogenital dysplasia homolog 2, a putative rho guanine nucleotide exchange factor, has a rho guanine nucleotide exchange factor domain, two pleckstrin homology domains and an FYVE domain, expressed in spleen and lung | 281 | 22% | 42% | 142 | 4e−08 |
| Fgd3 | NP_056574.1 | Fgd3; Mm.20436; ZFYVE5 Faciogenital dysplasia homolog 3, a member of the FGD1 family of Rho guanine nucleotide exchange factors, may have a role in regulating actin cytoskeletal rearrangements via stimulation of Cdc42 | 260 | 23% | 44% | 139 | 2e−07 |
| BC067047 | BAD32446.1 | BC067047; G630042G04 Protein with strong similarity to human PREX1, which is a guanyl-nucleotide exchange factor, member of the dishevelled, Egl-10, and pleckstrin domain family, contains a pleckstrin homology (PH) domain and a RhoGEF (GTPase exchange factor) domain | 264 | 23% | 45% | 137 | 7e−07 |
| Ect2 | NP_031926.1 | Ect2; Mm.2995; mKIAA4037; KIAA4037 Epithelial cell transforming sequence 2 oncogene, highly expressed in mitotic cells, binds Rho (Arha2) and Rac1, stimulates JNK1 (Mapk8) and p38, induces cyclin D1 (Ccnd1) expression, actin stress fiber and lamellipodia formation, may regulate cytokinesis | 201 | 27% | 42% | 131 | 8e−07 |
| Tiam1 | NP_033410.1 | Tiam1; Mm.1211 T lymphoma invasion and metastasis 1, RAC1 and RHO guanine nucleotide exchange factor that is involved in lamellipodium formation, neurite growth and cell adhesion; deficiency promotes resistance to Ras-induced skin tumors | 235 | 21% | 44% | 130 | 8e−07 |
| Vav1 | NP_035821.2 | Vav1; Vav; Mm.2557; vav-T Vav 1 oncogene, a guanyl-nucleotide exchange factor that is required for antigen receptor-mediated proliferation of B- and T-cells; upregulation of a human VAV1 mutant protein may promote metastasis of lung cancer | 323 | 24% | 42% | 137 | 1e−06 |
| 2210407G14Rik | AAH60724.1 | 2210407G14Rik; E530005C20Rik; DUET; (TRAD) Protein containing a variant SH3 domain, a pleckstrin homology domain, and a RhoGEF domain, has weak similarity to faciogenital dysplasia homolog 3 (mouse Fgd3), which may function in regulating actin cytoskeletal rearrangements via stimulation of Cdc42 | 259 | 23% | 45% | 136 | 1e−06 |
| Arhgef9 | BAC65562.1 | Arhgef9; mKIAA0424; A230067K14; 9630036L12Rik; collybistin; Mm.44841 Cdc42 guanine nucleotide exchange factor (GEF) 9 (collybistin), a putative guanyl-nucleotide exchange factor for Cdc42 that is predominantly expressed in brain, may play a role in synaptogenesis and/or neuronal differentiation | 267 | 22% | 43% | 124 | 1e−06 |
| Cdc42bpb | NP_898837.1 | Cdc42bpb; (DMPK-like) Protein with strong similarity to rat Cdc42bpb, which is a protein kinase, member of the CNH domain and protein kinase C-terminal families, contains protein kinase, pleckstrin homology, P21-Rho-binding and phorbol ester or diacylglycerol binding domains | 149 | 21% | 46% | 124 | 1e−06 |
| Arhgef2 | NP_032513.2 | Arhgef2; GEF; Lfc; (P40); GEFH1; LFP40; Lbcl1; GEF-H1; Mm.7634; mKIAA0651 Rho-Rac guanine nucleotide exchange factor 2, member of the Dbl family of guanyl-nucleotide exchange factors, acts in Rho and Rac signal transduction and control of cell proliferation, overexpression induces oncogenic transformation of fibroblasts | 438 | 23% | 45% | 191 | 2e−06 |
| Fgd6 | NP_444302.3 | Fgd6; Etohd4; ZFYVE24 Protein containing two pleckstrin homology domains, a FYVE zinc finger domain and a RhoGEF domain, has a region of low similarity to FGD1 related F actin binding protein (rat Fgd4), which is a guanyl-nucleotide exchange factor and actin crosslinker | 293 | 20% | 42% | 125 | 6e−06 |

TABLE 6-continued

| Gene | GenBank | Synonyms/Description | Match Length | % Iden | % Sim | High Score | E Val |
|---|---|---|---|---|---|---|---|
| Cit | NP_031734.1 | Cit; Mm.8321; CRIK; CRIK-SK; Citron-K; citron-N; Cit-k Citron Rho interacting kinase, a serine/threonine kinase of the myotonic dystrophy kinase family, binds to Rho and Rac and mediates cytoskeletal reorganization | 284 | 23% | 39% | 125 | 6e−06 |
| Arhgef5 | AAH25127.1 | Arhgef5; (Tim1); Mm.333034; LOC54324 Protein containing a Src homology 3 (SH3) domain, a variant SH3 domain, a RhoGEF (GTPase exchange factor) domain, and a pleckstrin homology (PH) domain, has very strong similarity to a region of rho guanine nucleotide exchange factor 5 (human ARHGEF5) | 219 | 23% | 44% | 113 | 1e−05 |
| Tiam2 | NP_036008.1 | Tiam2; STEF; Racgef1; Mm.29014; mKIAA2016; 3000002F19Rik T-cell lymphoma invasion and metastasis 2, a Rac1-specific guanyl-nucleotide exchange factor, required for neurite outgrowth, may act in neuronal migration and synaptic plasticity via regulation of actin cytoskeleton; human TIAM2 maps to T-cell lymphoma | 205 | 20% | 45% | 115 | 3e−05 |
| Bcr | AAH60270.1 | Bcr; 5133400C09Rik; mKIAA3017 Breakpoint cluster region, a putative negative regulator of the Rho family GTPase Rac that may be involved in vestibular morphogenesis; inhibition or decreased expression of the human BCR-ABL chimeric protein may be therapeutic for some leukemias | 265 | 20% | 42% | 111 | 3e−05 |
| Farp1 | AAH30329.1 | Farp1; Cdep; LOC223254 Protein with high similarity to FERM RhoGEF and pleckstrin domain protein 2 (human FARP2), which is a Rac and Rho guanyl-nucleotide exchange factor, contains two pleckstrin homology (PH) domains and a RhoGEF (GTPase exchange factor) domain | 294 | 20% | 44% | 119 | 5e−05 |
| Fgd1 | NP_032027.2 | Fgd1; Mm.219461; ZFYVE3 Faciogenital dysplasia homolog, guanine nucleotide exchange factor for Cdc42, may be involved in ossification and actin cytoskeletal rearrangement; human FGD1 variants cause faciogenital dysplasia and non-syndromal X-linked mental retardation | 307 | 23% | 42% | 120 | 6e−05 |
| Cdc42bpa | BAC97958.1 | Cdc42bpa; (DMPK-like); A930014J19Rik Protein of unknown function, has strong similarity to a region of rat Cdc42bpa, which is a protein kinase that phosphorylates nonmuscle myosin light chain and acts as a putative downstream effector of Cdc42 in cytoskeletal reorganization | 103 | 22% | 45% | 101 | 8e−05 |
| Mcf2l | NP_835177.1 | Mcf2l; Dbs; C130040020Rik; mKIAA0362; Ost Mcf.2 transforming sequence-like, a guanine nucleotide exchange factor for RhoA (Arha2) that is capable of inducing cellular transformation | 225 | 25% | 47% | 114 | 4e−04 |
| Plekhg3 | NP_722499.2 | Plekhg3; MGC40768; BC030417 Protein containing a RhoGEF domain and a pleckstrin homology domain, which act in protein and lipid binding, has a region of high similarity to a region of common-site lymphoma and leukemia guanine nucleotide exchange factor (mouse Plekhg2) | 274 | 24% | 43% | 113 | 4e−04 |
| BC026778 | NP_941006.1 | BC026778; MGC30363; Gm155 Protein containing a pleckstrin homology (PH) domain, which mediate protein-protein and protein-lipid interactions, and a RhoGEF domain, has weak similarity to a region of human ARHGEF1, which is involved in cell cycle control and cell proliferation | 340 | 22% | 42% | 108 | 5e−04 |
| Srrm2 | NP_780438.1 | Srrm2; 5033413A03Rik; mKIAA0324 Protein with strong similarity to serine-arginine repetitive matrix 2 (human SRRM2), which forms a complex with human SRRM1 that functions as a pre-mRNA splicing coactivator | 374 | 22% | 37% | 112 | 7e−04 |
| Compared with *C. elegans* protein sequences (Documentation) | | | | | | | |
| C02F12.4 | AAK39134.1 | C02F12.4 Protein containing a RhoGEF (GTPase exchange factor) domain, has a region of low similarity | 275 | 23% | 48% | 153 | 2e−08 |

TABLE 6-continued

| Gene | GenBank | Synonyms/Description | Match Length | % Iden | % Sim | High Score | E Val |
|---|---|---|---|---|---|---|---|
| K07D4.7 | AAK71375.1 | to a region of *C. elegans* EXC-5, which is a putative RhoGEF domain protein<br>K07D4.7; K07D4.7A Protein containing a RhoGEF (GTPase exchange factor), a pleckstrin homology (PH), a Src homology 3 (SH3), and a variant SH3 domain, has low similarity to human SGEF, which is responsive to hormone stimulus | 271 | 21% | 46% | 146 | 3e−08 |
| C35B8.2 | AAC46554.4 | C35B8.2 Protein containing a RhoGEF (GTPase exchange factor), a calponin homology (CH), a pleckstrin homology (PH), a C1-like domain, and a phorbol ester or diacylglycerol binding domain, has low similarity to a region of the GTPase exchange factor human VAV2 | 326 | 22% | 45% | 160 | 5e−07 |
| unc-73 | AAC71108.1 | unc-73; F55C7.7A; F55C7.7 Uncoordinated 73, guanine nucleotide exchange factor required for axon guidance and directed cell migrations, helps cells and axons to determine or interpret cellular polarity, binds phospholipids and activates CED-10 | 229 | 24% | 47% | 135 | 5e−07 |
| Y105E8A.24 | CAD21673.1 | Y105E8A.24; Y105E8A.24A Protein containing a RhoGEF (GTPase exchange factor) domain, has a region of weak similarity to a region of Rho-Rac guanine nucleotide exchange factor 2 (human ARHGEF2), which is an exchange factor specific for RhoA (human ARHA) and mediates cell shape | 223 | 23% | 44% | 133 | 9e−07 |
| R02F2.2 | AAL06044.3 | R02F2.2 Protein containing a RhoGEF (GTPase exchange factor) domain, has a region of low similarity to a region of breakpoint cluster region (human BCR), which is a GTPase-activating protein for p21rac with serine/threonine kinase activity | 301 | 23% | 42% | 131 | 2e−06 |
| F13E6.6 | CAA92119.3 | F13E6.6; RhoGEF Rho-guanine nucleotide exchange factor, functions downstream of GPA-12 in a Galpha12-Rho guanine nucleotide exchange factor Rho-dependent signaling pathway in neuronal function and embryonic development | 321 | 23% | 48% | 134 | 6e−06 |

RPL31A - CAA98641.1
RPL31A blast vs human -

| Gene | GenBank | Synonyms/Description | Match Length | % Iden | % Sim | High Score | E Val |
|---|---|---|---|---|---|---|---|
| RPL31 | NP_000984.1 | RPL31 Ribosomal protein L31, a putative component of the large 60S ribosomal subunit, downregulation is associated with cell differentiation and apoptosis, upregulation is seen in colorectal tumors | 111 | 59% | 79% | 351 | 2e−34 |

Compared with *M. musculus* protein sequences (Documentation)

| Gene | GenBank | Synonyms/Description | Match Length | % Iden | % Sim | High Score | E Val |
|---|---|---|---|---|---|---|---|
| Rpl31 | NP_444487.1 | Rpl31; MGC107628 Ribosomal protein L31, a putative component of the large 60S ribosomal subunit; human RPL31 is upregulated in colorectal tumors | 111 | 59% | 79% | 351 | 1e−34 |

Compared with *C. elegans* protein sequences (Documentation)

| Gene | GenBank | Synonyms/Description | Match Length | % Iden | % Sim | High Score | E Val |
|---|---|---|---|---|---|---|---|
| rpl-31 | CAB63331.1 | rpl-31; W09C5.6A; W09C5.6 Protein involved in embryonic and larval development | 109 | 50% | 72% | 289 | 4e−27 |

RPL6B - AAB67529.1
RPL6B blast vs human

| Gene | GenBank | Synonyms/Description | Match Length | % Iden | % Sim | High Score | E Val |
|---|---|---|---|---|---|---|---|
| RPL6 | NP_000961.2 | RPL6; TAXREB107; TXREB1 Ribosomal protein L6, a component of the large 60S ribosomal subunit, binds to the tax-responsive enhancer element in human T-cell leukemia virus type I | 181 | 46% | 63% | 372 | 4e−32 |

Compared with *M. musculus* protein sequences (Documentation)

| Gene | GenBank | Synonyms/Description | Match Length | % Iden | % Sim | High Score | E Val |
|---|---|---|---|---|---|---|---|
| Rpl6 | NP_035420.1 | Rpl6; Mm.588; Taxreb107 Protein with strong similarity to human RPL6, which is a component of the large 60S ribosomal subunit that binds to a human T-cell leukemia virus type I enhancer, member of the ribosomal L6e family, contains a ribosomal protein L6 N-terminal domain | 181 | 46% | 64% | 374 | 6e−33 |

Compared with *C. elegans* protein sequences (Documentation)

| Gene | GenBank | Synonyms/Description | Match Length | % Iden | % Sim | High Score | E Val |
|---|---|---|---|---|---|---|---|
| rpl-6 | AAK29850.1 | rpl-6; R151.3 Member of the ribosomal L6e family that is involved in development and meiosis | 186 | 42% | 56% | 315 | 2e−27 |

TOR1 - AAB39292.1
TOR1 blast vs. human -

| Gene | GenBank | Synonyms/Description | Match Length | % Iden | % Sim | High Score | E Val |
|---|---|---|---|---|---|---|---|
| FRAP1 | NP_004949.1 | FRAP1; FRAP2; FRAP; MTOR; RAFT1; Hs.155952; RAPT1 FK506 binding protein 12-rapamycin associated protein 1, a serine-threonine and 1-phosphatidylinositol 4-kinase that regulates translation, cell cycle, and p53 (TP53) - dependent apoptosis; | 2586 | 39% | 58% | 4525 | 0.0 |

TABLE 6-continued

| Gene | GenBank | Synonyms/Description | Match Length | % Iden | % Sim | High Score | E Val |
|---|---|---|---|---|---|---|---|
| | | inhibition may be therapeutic for various types of cancer | | | | | |
| SMG1 | NP_055907.2 | SMG1; (ATX); LIP; KIAA0421; Hs.352382; 61E3.4 PI-3-kinase-related kinase SMG-1, a protein kinase that participates in nonsense-mediated mRNA decay by phosphorylating hUpf1 (RENT1), binds to and activates atypical protein kinase C lambda (PRKCL) | 643 | 27% | 45% | 595 | 5e−54 |
| ATR | NP_001175.1 | ATR; (FRP1); SCKL; SCKL1 Ataxia telangiectasia and Rad3 related, a PIK-related protein kinase that functions in DNA damage monitoring, checkpoint-mediated cell cycle control, and possibly recombination, overexpression may inhibit differentiation and induce aneuploidy | 1168 | 25% | 42% | 639 | 1e−49 |
| ATM | NP_000042.2 | ATM; (AT1); ATA; ATC; (ATD); (ATDC); (TRIM29); ATE Ataxia telangiectasia mutated, a serine/threonine kinase involved in apoptosis, DNA stability, cell cycle, and radiation response; gene mutation is associated with ataxia telangiectasia and implicated in B cell chronic lymphocytic leukemia | 1056 | 23% | 41% | 499 | 2e−46 |
| PRKDC | NP_008835.5 | PRKDC; DNPK1; HYRC1; DNAPK; XRCC7; DNA-PKcs; p350; HYRC DNA-dependent protein kinase catalytic subunit, a DNA-binding protein kinase involved in DNA double-strand break repair, V(D)J recombination, and radiation response, phosphorylates and activates AKT; mouse Prkdc deficiency is associated with SCID | 532 | 26% | 48% | 383 | 1e−34 |
| TRRAP | NP_003487.1 | TRRAP; TR-AP; PAF400; Hs.203952 Transformation transcription domain-associated protein, ATM superfamily member, subunit of histone acetylase, adenovirus E1A binding, and ESR1 coactivator complexes, transcription coactivator for MYC and E2F, may affect breast cancer cell proliferation | 1352 | 21% | 38% | 259 | 1e−14 |
| PIK3CD | NP_005017.2 | PIK3CD; p110delta; Hs.166116; p110D Phosphatidylinositol 3'-kinase delta catalytic subunit, a kinase which forms a complex with the regulatory subunit p85alpha (PIK3R1) or p85beta (PIK3R2), involved in transmembrane signaling, may play a role in cytoskeletal functions | 339 | 26% | 42% | 181 | 4e−11 |
| PIK3C3 | NP_002638.2 | PIK3C3; VPS34; Vps34 Phosphatidylinositol 3-kinase class 3, phosphorylates PtdIns but not PtdIns4P or PtdIns(4, 5)P2, induces macroautophagy, predicted to be involved in vesicular trafficking | 304 | 26% | 42% | 166 | 9e−10 |
| PIK3CB | NP_006210.1 | PIK3CB; PIK3C1; (PI3K); (p110); p110-BETA; PI3Kbeta Catalytic beta subunit of phosphatidylinositol 3-kinase, a class IA phosphoinositide 3-kinase subunit that forms heterodimers with various regulatory or adaptor subunits, involved in multiple signal transduction pathways during cell proliferation | 266 | 27% | 43% | 165 | 1e−09 |
| PIK3CA | NP_006209.2 | PIK3CA; p110alpha; (PI3K); p110-alpha Phosphatidylinositol 3-kinase catalytic alpha subunit, heterodimerizes with an 85-kDa regulatory subunit that binds the kinase to receptors for signal transduction, expression, activity and gene amplification are involved in cancer progression | 230 | 26% | 44% | 143 | 2e−08 |
| PIK3C2A | NP_002636.1 | PIK3C2A; PI3-K-C2(ALPHA); CPK; PI3-K-C2A; PI3K-C2alpha Phosphoinositide-3-kinase class 2 alpha polypeptide, phosphorylates only PtdIns and PtdIns4P in the absence of phosphatidylserine but phosphorylates PtdIns(4,5)P2 in the presence of phosphatidylserine, exhibits insensitivity to wortmannin | 232 | 25% | 41% | 144 | 6e−08 |
| PIK3CG | NP_002640.2 | PIK3CG; p110gamma; (PI3K); PIK3; PI3CG; PI3Kgamma Phosphoinositide-3-kinase catalytic gamma, a lipid kinase activated by G beta-gamma subunits and H-Ras (HRAS), mediates lysophosphatidylcholine signaling and actin cytoskeletal rearrangement; expression is lost in colorectal adenocarcinoma | 346 | 24% | 42% | 144 | 7e−07 |
| LOC220686 | NP_954977.2 | LOC220686 Member of the phosphatidylinositol 3- and 4-kinase family, has high similarity to a region of human PIK4CA, which is a type II phosphatidylinositol 4-kinase that catalyzes the first step in phosphatidylinositol 4,5-bisphosphate biosynthesis | 196 | 23% | 41% | 112 | 9e−06 |
| PIK3C2B | NP_002637.2 | PIK3C2B; C2-PI3K; PI3K-C2beta; Hs.132463 Phosphoinositide-3-kinase class 2 beta polypeptide, a nuclear enzyme that catalyzes phosphorylation of phosphatidylinositol and phosphatidylinositol 4 monophosphate, may act in signal transduction | 296 | 22% | 41% | 126 | 5e−05 |

TABLE 6-continued

| Gene | GenBank | Synonyms/Description | Match Length | % Iden | % Sim | High Score | E Val |
|---|---|---|---|---|---|---|---|
| LOC375133 | NP_955377.2 | LOC375133 Member of the phosphatidylinositol 3- and 4-kinase family, has high similarity to a region of phosphatidylinositol 4-kinase catalytic alpha polypeptide (human PIK4CA), which is a type II phosphatidylinositol 4-kinase that is inhibited by adenosine | 46 | 46% | 70% | 105 | 5e−05 |
| PIK4CA | NP_477352.1 | PIK4CA; PI4K-ALPHA; pi4K230 Phosphatidylinositol 4-kinase catalytic alpha polypeptide, a type II phosphatidylinositol 4-kinase that catalyzes the first step in phosphatidylinositol 4,5-bisphosphate biosynthesis; activity is enhanced by detergent and inhibited by adenosine | 196 | 23% | 41% | 113 | 2e−04 |
| FLJ12688 | BAB21837.1 | FLJ12688; KIAA1746 Protein containing three HEAT repeats, which appear to act as protein binding surfaces, has a region of weak similarity to a region of *C. elegans* T16G12.5, which is involved in epithelium morphogenesis and regulation of movement and vulva development | 163 | 24% | 44% | 101 | 4e−04 |
| | | Compared with *M. musculus* protein sequences (Documentation) | | | | | |
| Frap1 | NP_064393.1 | Frap1; 2610315D21Rik; FRAP; mTOR; MTOR; FRAP2; RAFT1; RAPT1; flat FK506 binding protein 12-rapamycin associated protein 1, a serine-threonine kinase that regulates translation, cell cycle, and development, involved in starvation responses; inhibition of human FRAP1 may be therapeutic for various types of cancer | 2589 | 39% | 58% | 4510 | 0.0 |
| Atm | NP_031525.1 | Atm; Mm.5088 Ataxia telangiectasia mutated, a serine/threonine kinase involved in apoptosis, DNA stability, cell cycle and radiation response; human ATM mutation is associated with ataxia telangiectasia and implicated in B cell chronic lymphocytic leukemia | 456 | 30% | 49% | 476 | 2e−44 |
| Prkdc | NP_035289.1 | Prkdc; Mm.71; p460; DNAPK; slip; DNAPDcs; DNA-PKcs; scid; DNPK1; HYRC1; XRCC7; DNA-PK DNA-dependent protein kinase catalytic subunit, a DNA-binding protein kinase involved in DNA double-strand break repair and V(D)J recombination; absence is associated with severe combined immunodeficiency | 555 | 25% | 45% | 373 | 6e−33 |
| Atr | AAF61728.1 | Atr Ataxia telangiectasia and Rad3 related, a PIK-related protein kinase required for genomic integrity and early embryonic development, may function in DNA repair or recombination during meiosis, regulates the checkpoint response to ionizing radiation | 304 | 31% | 47% | 329 | 1e−27 |
| Pik3cd | NP_032866.1 | Pik3cd; p100_delta; p110delta; 2410099E07Rik; signalling Phosphatidylinositol 3-kinase catalytic delta polypeptide, a putative lipid kinase expressed in spleen and testis, may play a role in signaling in the immune system; mutation in the corresponding gene causes inflammatory bowel disease | 285 | 27% | 44% | 180 | 2e−11 |
| Pik3c3 | NP_852079.2 | Pik3c3; Vps34; 5330434F23; 5330434F23Rik; Mm.194127 Protein with very strong similarity to rat Pik3c3, member of the phosphoinositide 3-kinase family accessory domain containing family and the phosphatidylinositol 3- and 4-kinase family, contains a phosphoinositide 3-kinase C2 domain | 304 | 27% | 42% | 172 | 6e−11 |
| Pik3cb | NP_083370.1 | Pik3cb; 1110001J02Rik; p110beta Catalytic beta subunit of phosphatidylinositol 3-kinase, a class IA phosphoinositide 3-kinase subunit that forms heterodimers with various regulatory subunits, involved in multiple signal transduction pathways, required for embryonic development | 266 | 28% | 42% | 162 | 6e−08 |
| Pik3ca | NP_032865.1 | Pik3ca; Mm.41943; p110; caPI3K; (PI3K); 6330412C24Rik Phosphatidylinositol 3-kinase catalytic alpha subunit, heterodimerizes with an 85-kDa regulatory subunit that binds the kinase to receptors for signal transduction; human PIK3CA expression, activity, gene amplification are involved in cancer progression | 230 | 26% | 44% | 143 | 1e−07 |
| Pik3c2a | NP_035213.1 | Pik3c2a; Mm.3810; Cpk-m Phosphoinositide-3-kinase C2 domain-containing alpha polypeptide, phosphorylates PtdIns and PtdIns-4-P but not | 232 | 25% | 41% | 141 | 1e−07 |

TABLE 6-continued

| Gene | GenBank | Synonyms/Description | Match Length | % Iden | % Sim | High Score | E Val |
|---|---|---|---|---|---|---|---|
| Pik3cg | NP_064668.1 | PtdIns(4,5)P2, exhibits some insensitivity to wortmannin, contains a C-terminal C2 domain Pik3cg; PI3Kgamma; p110gamma; 5830428L06Rik Phosphoinositide-3-kinase catalytic gamma, a lipid kinase catalyzing Ptdins(3,4,5)P3 formation, involved in mast cell degranulation, neutrophil chemotaxis and activation, and T-cell development; human PIK3CG expression is lost in colorectal adenocarcinoma | 347 | 23% | 41% | 143 | 5e−07 |
| 2610207I05Rik | BAC97946.1 | 2610207I05Rik; mKIAA0421 Member of the FRAP, ATM, TRRAP C-terminal (FATC) domain family, has very strong similarity to a region of PI-3-kinase-related kinase SMG-1 (human SMG1), which is a protein kinase that acts in nonsense-mediated mRNA decay by phosphorylating human RENT1 | 55 | 38% | 64% | 109 | 1e−05 |
| Pik4ca | NP_001001983.1 | Pik4ca; LOC224020 Protein with very strong similarity to rat Pik4ca, which is a phosphatidylinositol (PI) 4-kinase that catalyzes PI 4,5-bisphosphate biosynthesis, member of the phosphoinositide 3-kinase family accessory domain containing and PI 3- and 4-kinase families | 192 | 24% | 41% | 112 | 4e−05 |
| Compared with *C. elegans* protein sequences (Documentation) | | | | | | | |
| let-363 | AAN84885.1 | let-363; B0261.2A; Ce-tor; B0261.2 Lethal 363, target-of-rapamycin-like protein kinase involved in larval development of the gut and gonad, metabolism, and life span regulation, functions with DAF-15 and interacts with the insulin-signaling pathway during dauer formation | 2720 | 30% | 49% | 2952 | e−162 |
| smg-1 | AAC48167.3 | smg-1; C48B6.6A; mab-1; C48B6.6 Suppressor with morphological effect on genitalia 1, PI-3-related protein kinase required for nonsense-mediated mRNA decay, mRNA surveillance, functions in the phosphorylation of SMG-2 | 633 | 27% | 44% | 532 | 4e−47 |
| atm-1 | AAF60692.2 | atm-1; Y48G1BL.F; Y48G1BL.2 May function in a DNA damage checkpoint pathway, has strong similarity to *S. cerevisiae* TEL1 which is a phosphatidylinositol 3-kinase (PI kinase) homolog involved in controlling telomere length | 440 | 23% | 42% | 297 | 4e−24 |
| atl-1 | CAA94790.2 | atl-1; T06E4.3A; Ce-atl1; T06E4.3 ATM-like 1, putative PI-3-like kinase that is required for an early embryonic GOA-1-, GPA-16-dependent DNA replication checkpoint involved in chromosome stability, functions in cell division asynchrony in two-cell embryos by delaying mitotic entry by P1 | 409 | 25% | 42% | 278 | 1e−21 |
| vps-34 | AAF23184.1 | vps-34; B0025.1A; let-512; vps34; B0025.1 Related to yeast vacuolar protein sorting factor 34, phosphatidylinositol 3-kinase required for receptor-mediated endocytosis and membrane transport from the outer nuclear membrane to the plasma membrane | 547 | 24% | 39% | 169 | 9e−10 |
| Y75B8A.24 | CAA22108.1 | Y75B8A.24 Member of the phosphatidylinositol 3- and 4-kinase and phosphoinositide 3-kinase family accessory domain (PIK domain) containing families, has moderate similarity to phosphatidylinositol 4-kinase catalytic alpha peptide (rat Pik4ca) | 181 | 28% | 44% | 146 | 3e−08 |
| age-1 | CAA91377.2 | age-1; daf-23; B0334.8 Aging alteration 1, protein involved in dauer larva formation, longevity, fertility, thermotolerance, response to pathogenic bacteria, and adult motility | 280 | 24% | 42% | 147 | 1e−07 |
| F39B1.1 | CAA93776.1 | F39B1.1 Member of the phosphatidylinositol 3- and 4-kinase and phosphoinositide 3-kinase family accessory domain families, contains C2, phosphoinositide 3-kinase C2, and phox domains and a ubiquitin interaction motif, has low similarity to human PIK3C2A | 274 | 24% | 42% | 143 | 3e−07 |
| F35H12.4 | AAK39229.1 | F35H12.4 Member of the phosphatidylinositol 3- and 4-kinase family, has moderate similarity to phosphatidylinositol 4-kinase beta (human PIK4CB), which is a wortmannin-sensitive lipid kinase that is required for the proper organization of the Golgi complex | 83 | 36% | 57% | 114 | 1e−04 |
| Y48G9A.1 | AAK29920.2 | Y48G9A.1 Protein containing fifteen HEAT repeats, which appear to function as protein-protein interaction surfaces, has low similarity to a region of *S. cerevisiae* | 316 | 21% | 42% | 112 | 8e−04 |

TABLE 6-continued

| Gene | GenBank | Synonyms/Description | Match Length | % Iden | % Sim | High Score | E Val |
|---|---|---|---|---|---|---|---|
| | | Gcn1p, which is a component of a complex required for *S. cerevisiae* Gcn2p activation | | | | | |
| | | Sch9 - NP_012075.1 | | | | | |
| | | Compared with *H. sapiens* protein sequences (Documentation) | | | | | |
| AKT1 | NP_005154.1 | AKT1; (PKB); RAC; RAC-ALPHA; PRKBA; PKBalpha; Akt; c-Akt; MGC99656 V-akt murine thymoma viral oncogene homolog 1, serine-threonine kinase targeted by PDGF-activated PI 3-kinase, involved in cell survival and differentiation and likely insulin signaling, activity is upregulated in breast, prostate, and ovarian cancers | 318 | 49% | 69% | 771 | 1e-82 |
| AKT2 | NP_001617.1 | AKT2; RAC-BETA; PRKBB; PKBBETA v-akt murine thymoma viral oncogene homolog 2, protein kinase that is activated by mitogens and survival factors, may regulate cell proliferation and apoptosis, overexpression is associated with ovarian, breast and pancreatic cancers | 302 | 49% | 70% | 764 | 6e-82 |
| AKT3 | NP_005456.1 | AKT3; PKBG; RAC-GAMMA; PRKBG; DKFZP434N0250; RAC-PK-gamma; RAC-gamma; STK-2 Protein kinase B gamma, a serine/threonine protein kinase that is activated by growth factors and 3-phosphoinositide; insulin-induced activity is upregulated in estrogen receptor negative breast cancer and androgen insensitive prostrate carcinoma | 299 | 49% | 70% | 759 | 2e-81 |
| RPS6KB1 | NP_003152.1 | RPS6KB1; STK14A; p70s6k; S6K1; S6K; PS6K; p70-S6K; p70-alpha; p70(S6K)-alpha Ribosomal protein S6 kinase 70 kD polypeptide 1, an RSK family member that is involved in cell cycle progression and control of cell proliferation; gene amplification is linked to breast cancer | 375 | 46% | 62% | 757 | 2e-80 |
| RPS6KB2 | NP_003943.2 | RPS6KB2; P70-BETA; P70S6KB; p70S6Kb; KLS; STK14B; (SRK); S6K2; P70-beta; S6K-beta2; P70-beta-1; P70-beta-2; p70(S6K)-beta Ribosomal protein S6 kinase 2 (p70 ribosomal S6 kinase beta), rapamycin-sensitive member of the RSK family that plays a role in signal transduction, may be involved in cell cycle control and protein biosynthesis | 347 | 46% | 63% | 738 | 1e-77 |
| SGKL | NP_037389.4 | SGKL; SGK3; (SGK2); CISK; DKFZp781N0293 Serum/glucocorticoid regulated kinase-like, a serine/threonine kinase that stimulates the activity of transporters, including SLC1A3, SLC13A2 and SLC38A3, and Na2+ channels, including SCN5A, phosphorylated and activated by PDK1 | 342 | 43% | 61% | 708 | 3e-75 |
| PRKACB | NP_891993.1 | PRKACB; PKACb; PKA; MGC9320; MGC41879; PKACB Protein kinase cAMP-dependent catalytic beta, participates in neurofibrillary degeneration and hyperphosphorylation of tau in Alzheimer disease, bound to paired helical filaments from Alzheimer brain | 336 | 44% | 65% | 704 | 1e-74 |
| PRKACA | NP_002721.1 | PRKACA; PKACa; Hs.169269; cPKA; Calpha; MGC48865; PKACA Protein kinase cAMP-dependent catalytic alpha, acts in transcriptional regulation, may suppress apoptosis, alternative form Calpha2 may act in sperm development, may serve as a tumor biomarker; reduced activity of mouse Prkaca causes neural tube defects | 312 | 46% | 65% | 698 | 3e-74 |
| RPS6KA5 | NP_004746.2 | RPS6KA5; (MSK1); MSPK1; RLPK; MGC1911 Ribosomal protein S6 kinase A5, a member of the ribosomal protein S6 kinase (RSK) family, contains two kinase domains, phosphorylates histones and activates CREB1 in response to growth factors and stress, activated by ERK2 (PRKM1) or SAPK2 (PRKM11) | 375 | 41% | 62% | 682 | 2e-71 |
| PRKCH | NP_006246.2 | PRKCH; PKCh; PKC-L; (PRKCL); PKCL; MGC5363; MGC26269; nPKC-eta Protein kinase C eta, a Ca2+-independent isoform of protein kinase C, stimulates cell proliferation, inhibits apoptosis through attenuating caspases, acts in cell signaling and epidermal differentiation; decreased expression is linked to colon carcinomas | 339 | 41% | 63% | 677 | 2e-71 |

TABLE 6-continued

| Gene | GenBank | Synonyms/Description | Match Length | % Iden | % Sim | High Score | E Val |
|---|---|---|---|---|---|---|---|
| SGK | NP_005618.2 | SGK; SGK1 Serum glucocorticoid regulated kinase, a serine/threonine protein kinase that inhibits apoptosis and stimulates renal sodium transport, upregulated in response to osmotic stress | 337 | 45% | 63% | 728 | 7e−71 |
| RPS6KA4 | NP_003933.1 | RPS6KA4; RSK-B; (MSK2); RSKB Ribosomal protein S6 kinase polypeptide 4 (mitogen- and stress-activated protein kinase 2), may mediate induction of CREB activation, activated by mitogen-activated protein kinase 1 (MAPK1) and stress-activated protein kinase 2 (MAPK11) | 352 | 43% | 62% | 683 | 1e−70 |
| SGK2 | NP_057360.2 | SGK2; H-SGK2; dJ138B7.2 Serum-glucocorticoid regulated kinase 2, a serine-threonine kinase that may be regulated by 3-phosphoinositide-dependent kinase-1 (PDK1) and by hydrogen peroxide | 337 | 44% | 64% | 726 | 6e−70 |
| RPS6KA1 | NP_001006666.1 | RPS6KA1; (RSK3); (HU-1); (RSK); (RSK1); MAPKAPK1A; p90rsk Ribosomal protein S6 kinase 1, a mitogen activated serine-threonine protein kinase, acts in platelet activation, megakaryocyte differentiation, apoptosis inhibition, and stress response, may be hyperphosphorylated in lung neoplasms | 367 | 42% | 60% | 672 | 1e−69 |
| PRKACG | NP_002723.2 | PRKACG; PKACg; KAPG Protein kinase cAMP-dependent catalytic gamma, testis specific catalytic gamma subunit of cAMP dependent protein kinase, corresponding gene lacks introns and may be a PRKACA derived retrotransposon | 313 | 43% | 64% | 651 | 9e−69 |
| PRKCI | NP_002731.3 | PRKCI; DXS1179E; PKCI; MGC26534; nPKC-iota Protein kinase C iota, an atypical protein kinase C that does not respond to either diacylglycerol or calcium and exhibits an elevated basal activity level, mediates resistance to taxol-induced apoptosis through NF-kB | 346 | 38% | 62% | 645 | 1e−67 |
| RPS6KA3 | NP_004577.1 | RPS6KA3; RSK2; (HU-2); HU-3; (RSK); MAPKAPK1B; ISPK-1; (MRX19); p90-RSK3; pp90RSK2; S6K-alpha3 Ribosomal protein S6 kinase 90 kDa polypeptide 3, required for EGF-stimulated histone H3 and CREB phosphorylation, acts in signal transduction, may regulate transcription; mutation of corresponding gene causes Coffin-Lowry syndrome | 367 | 44% | 61% | 701 | 5e−67 |
| PRKCA | NP_002728.1 | PRKCA; PKCA; PKCalpha; (PRKACA); PKC-alpha Protein kinase C alpha isoform, important for cellular signaling, regulates cell proliferation and migration, and plays a role in RHO protein signal transduction; upregulated in liver of patients with non insulin dependent diabetes mellitus (NIDDM) | 336 | 39% | 61% | 639 | 8e−67 |
| PRKCB1 | NP_002729.2 | PRKCB1; PKCB; PRKCB; PRKCB2; PKCbeta; MGC41878; PKC-beta Protein kinase C beta 1, serine/threonine kinase that acts in the glucose response and proliferation, expression is altered in ALS, colon adenoma, heart failure, Huntington's disease and diabetic nephropathy; rat Prkcb1 is involved in diabetic nephropathy | 346 | 38% | 60% | 637 | 1e−66 |
| RPS6KA2 | NP_001006933.1 | RPS6KA2; (RSK1); (HU-2); MAPKAPK1C; (RSK); (RSK3); Hs.90859; p90-RSK; pp90RSK3; S6K-alpha; p90-RSK2; S6K-alpha2 90 kD ribosomal protein S6 kinase polypeptide 2, protein kinase activated in response to UV irradiation, heat shock or growth factor stimulation through the MAP kinase pathway, phosphorylates histones and the FOS transcription factor | 344 | 46% | 62% | 700 | 2e−66 |
| PKN1 | NP_998725.1 | PKN1; DBK; PKN; (PAK1); (PRK1); PRKCL1; MGC46204 Protein kinase N1, activated by Rac, Rho and fatty acids, stimulates phospholipase D1 (PLD1) and PLC activity, regulates mitosis and cytoskeletal function, may regulate cell adhesion, apoptosis and act in Alzheimer's neurofibrillary tangle formation | 333 | 43% | 62% | 677 | 1e−65 |
| RPS6KA6 | NP_055311.1 | RPS6KA6; RSK4 Ribosomal protein S6 kinase polypeptide 6, a 90 kD putative protein kinase of the S6 kinase family; corresponding gene is commonly deleted in patients with complex X-linked mental retardation | 367 | 44% | 61% | 686 | 3e−65 |

TABLE 6-continued

| Gene | GenBank | Synonyms/Description | Match Length | % Iden | % Sim | High Score | E Val |
|---|---|---|---|---|---|---|---|
| PKN2 | NP_006247.1 | PKN2; PRK2; PRKCL2; PRO2042; MGC71074 Protein kinase N2 (protein kinase C-like 2), a serine-threonine kinase that associates with Rho-GTP (ARHA) and complexes with the Yersinia virulence factor YopM and RSK1 (RPS6KA1), regulates cell-cell adhesion and may act in Rho-signaling and apoptosis | 343 | 42% | 61% | 668 | 2e−64 |
| PRKX | NP_005035.1 | PRKX; PKX1 Protein kinase X-linked, a cAMP-dependent protein kinase catalytic subunit, involved in myeloid cell maturation and ureteric bud development, upregulated in autosomal dominant polycystic kidney disease; gene recombination with PRKY causes Swyer's syndrome | 297 | 44% | 65% | 642 | 3e−64 |
| PRKCZ | NP_002735.3 | PRKCZ; PKCz; PKCzeta; Hs.199054; PKC2 Protein kinase C zeta, a serine-threonine kinase that regulates the activity of numerous signaling pathways and modulates a wide variety of cellular events, decreased expression correlates with insulin resistance in diabetes and glucose intolerance | 344 | 38% | 61% | 622 | 3e−64 |
| PRKCG | NP_002730.1 | PRKCG; PKCC; PKCG; SCA14; MGC57564; PKC-gamma Gamma isoform of protein kinase C, has a potential calcium-binding domain and is important for cellular signaling; increased expression is associated with various cancers; increased proteolysis may be associated with Alzheimer disease | 339 | 40% | 61% | 633 | 2e−61 |
| PKN3 | NP_037487.2 | PKN3; pknbeta; PKNBETA; Hs.44101 Protein kinase N3, a protein kinase regulated by phosphatidylinositol 3-kinase that binds GRAF, GRAF2 and phospholipase D1 (PLD1), upregulated in prostate cancer and involved in lymph node metastasis of prostate cancer cells in nude mice | 339 | 39% | 58% | 597 | 1e−60 |
| PRKCE | NP_005391.1 | PRKCE; PKCE; PKCepsilon; Hs.395751; nPKC-epsilon Protein kinase C epsilon, diacylglycerol-activated and phospholipid dependent isoform of protein kinase C, involved in cell growth and apoptosis, altered expression or localization may correlate with various neoplasms and Alzheimer disease | 350 | 38% | 61% | 649 | 2e−60 |
| PRKCD | NP_997704.1 | PRKCD; PKCD; PKCdelta; MGC49908; nPKC-delta; MAY1 Protein kinase C delta, calcium-independent serine-threonine kinase, promotes apoptosis, phospholipid scrambling, and lamin cleavage, inhibits histamine signaling in myeloid cells, may function as a tumor suppressor | 329 | 38% | 61% | 602 | 4e−59 |
| ADRBK1 | NP_001610.1 | ADRBK1; BARK1; GRK2; beta_ARK; beta-ARK-1; (Ark); BETA-ARK1 Beta-adrenergic receptor kinase 1, kinase that mediates desensitization of G protein-coupled receptors, phosphorylated by PKC, may modulate cardiovascular function; mouse Adrbk1 may be associated with cardiomyopathy and myocardial infarction | 330 | 36% | 56% | 543 | 7e−56 |
| PRKCQ | NP_006248.1 | PRKCQ; PKCt; PKC-theta; Hs.89615; PRKCT; nPKC-theta Protein kinase C theta, involved in T cell activation and protection from apoptosis, may play a role in insulin and multidrug resistance; rat Pkcq may play roles in hyperglycemia, hypertriglyceridemia and insulin resistance | 298 | 41% | 64% | 619 | 3e−55 |
| ADRBK2 | NP_005151.1 | ADRBK2; BARK2; GRK3 Beta adrenergic receptor kinase 2, a protein kinase that specifically phosphorylates activated G protein-coupled receptors resulting in receptor desensitization, may represent a genetic marker for mood disorders | 364 | 36% | 54% | 539 | 3e−55 |
| CDC42BPA | NP_003598.2 | CDC42BPA; MRCKA; MRCK; PK428; KIAA0451; FLJ23347; DKFZp686P1738; DKFZp686L1738 CDC42 binding protein kinase alpha, a protein kinase that binds granulocyte-macrophage colony-stimulating factor receptor alpha subunit (CSF2RA), capable of autophosphorylation, may act in muscle physiology | 360 | 37% | 58% | 542 | 2e−54 |

TABLE 6-continued

| Gene | GenBank | Synonyms/Description | Match Length | % Iden | % Sim | High Score | E Val |
|---|---|---|---|---|---|---|---|
| STK38L | NP_055815.1 | STK38L; NDR2; KIAA0965 Protein with strong similarity to serine/threonine kinase 38 (human STK38), which serves to modulate cell division and cell morphology, member of the protein kinase C-terminal domain containing family, contains a protein kinase domain | 345 | 34% | 57% | 526 | 2e-53 |
| STK38 | NP_009202.1 | STK38; (NDR1); NDR; Hs.8724 Serine/threonine kinase 38, a member of a subfamily of kinases involved in regulation of cell division and cell morphology, regulated by calcium concentrations via EF hand calcium binding S100 proteins | 369 | 33% | 55% | 521 | 7e-53 |
| MAST3 | BAA25487.1 | MAST3; KIAA0561; Hs.173864 Protein with high similarity to human MAST2, which binds protocadherin LKC (human PC-LKC) and may act in contact inhibition, member of the protein kinase C-terminal domain containing family, contains protein kinase and PDZ, DHR, or GLGF domains | 311 | 36% | 58% | 520 | 1e-52 |
| CDC42BPB | NP_006026.2 | CDC42BPB; MRCKB; KIAA1124 CDC42 binding protein kinase beta, putative protein kinase of the myotonic dystrophy kinase family | 352 | 38% | 59% | 523 | 4e-52 |
| STK32C | NP_775846.2 | STK32C; PKE; YANK3; MGC23665 Protein containing a protein kinase domain, has low similarity to cAMP-dependent protein kinase catalytic subunit (*A. niger* PkaC), which is involved in morphogenesis | 289 | 36% | 62% | 495 | 3e-50 |
| PRKY | NP_002751.1 | PRKY Protein kinase Y linked, a putative cAMP dependent serine threonine protein kinase that is encoded on the Y chromosome, may be associated with benign prostatic hyperplasia and carcinoma | 227 | 46% | 67% | 518 | 4e-50 |
| PRKG2 | NP_006250.1 | PRKG2; PKG2; PRKGR2; cGKII Protein kinase cGMP-dependent type II, localizes to the apical plasma membrane and may regulate intestinal ion transport and fluid secretion, expression is greatly reduced in immortalized cells | 297 | 38% | 57% | 495 | 4e-50 |
| MAST1 | NP_055790.1 | MAST1; SAST; SAST170; KIAA0973; Hs.227489; Hs.182628 Protein with strong similarity to mouse Mast1, which binds syntrophins, microtubules and microtubule-associated proteins, member of the protein kinase C-terminal domain containing family, contains a protein kinase domain and a PDZ, DHR, or GLGF domain | 318 | 37% | 58% | 552 | 7e-50 |
| DMPK | NP_004400.4 | DMPK; DMPK1; DM; DMK; DM1; DM1PK Dystrophia myotonica-protein kinase, phosphorylates proteins including histones, inhibits muscle cell apoptosis, regulates muscle contraction, trinucleotide repeat expansion in 3' untranslated region of gene is associated with myotonic dystrophy | 390 | 34% | 53% | 502 | 1e-49 |
| PDPK1 | NP_002604.1 | PDPK1; (PDK1); PR00461; MGC20087; MGC35290; PkB-like 3-phosphoinositide-dependent protein kinase-1, has a pleckstrin homology domain, phosphorylates AKT1, p70s6k, PRKCD, PRKCZ, p21 activated kinase (PAK1), and mediates insulin-induced actin reorganization, activity is inhibited by celecoxib | 311 | 38% | 58% | 494 | 8e-49 |
| LATS1 | NP_004681.1 | LATS1; wts; WARTS Large tumor suppressor 1, putative serine/threonine kinase, binds zyxin (ZYX), binds CDC2 and negatively regulates its activity, acts in cell cycle control, mitosis, and possibly apoptosis, may suppress tumor growth by inducing cycle arrest or apoptosis | 358 | 35% | 51% | 488 | 9e-49 |
| CDC42BPG | NP_059995.1 | CDC42BPG; HSMDPKIN; MRCKgamma; DMPK2; KAPPA-200 Member of the citron homology and protein kinase C-terminal domain-containing families, contains pleckstrin homology, protein kinase, and phorbol ester or diacylglycerol binding domains, has moderate similarity to rat Cdc42bpa, which is a protein kinase | 350 | 38% | 56% | 498 | 1e-48 |
| STK32B | NP_060871.1 | STK32B; STK32; STKG6; YANK2; HSA250839 Protein containing a protein kinase domain, has low similarity to catalytic subunit of cAMP-dependent protein kinase 3 (*S. cerevisiae* Tpk3p), | 335 | 33% | 56% | 478 | 4e-48 |

TABLE 6-continued

| Gene | GenBank | Synonyms/Description | Match Length | % Iden | % Sim | High Score | E Val |
|---|---|---|---|---|---|---|---|
| | | which is a protein kinase that acts in numerous cellular processes | | | | | |
| GRK1 | NP_002920.1 | GRK1; (RK); RHOK; GPRK1; Hs.158325 Rhodopsin kinase, regulates desensitization of the G protein-coupled receptor rhodopsin by phosphorylating it following stimulation by light; mutation of the corresponding gene causes Oguchi disease, a form of stationary night blindness | 303 | 39% | 58% | 509 | 7e-48 |
| LATS2 | NP_055387.1 | LATS2; KPM; FLJ13161 Large Tumor Suppressor 2, member of a subfamily of protein kinases that includes LATS1, a protein kinase that may be involved in cell cycle control; gene may be inactivated in a minority of esophageal squamous cell carcinomas | 357 | 35% | 50% | 479 | 1e-47 |
| MAST2 | NP_055927.1 | MAST2; MTSSK; MAST205; KIAA0807; Hs.101474 Microtubule associated testis specific serine-threonine protein kinase, binding to protocadherin LKC (PC-LKC) suggests involvement in contact inhibition of epithelial cells in colon, liver, and kidney | 318 | 36% | 57% | 531 | 2e-47 |
| MAST4 | BAA20762.1 | MAST4; KIAA0303; Hs.54985 Member of the protein kinase C-terminal domain containing family, contains a protein kinase domain and a PDZ, DHR, or GLGF domain, has a region of high similarity to a region of human MAST2, which binds to protocadherin LKC (human PC-LKC) | 356 | 33% | 54% | 522 | 4e-46 |
| ROCK1 | NP_005397.1 | ROCK1; P160ROCK; Hs.198533; p160ROCK1 Rho-associated coiled-coil containing kinase 1, binds Rho, acts in actin cytoskeleton organization, cell migration, cytokinesis, superoxide anion production, membrane blebbing, upregulated in pancreatic cancer and may play a role in tumor cell migration | 361 | 34% | 57% | 487 | 1e-45 |
| PRKG1 | NP_006249.1 | PRKG1; PKG1; PRKG1B; PRKGR1B; (PGK); cGKI; cGKI-BETA; CGKI; cGKI-alpha; MGC71944 cGMP-dependent protein kinase type 1, relaxes vascular smooth muscle and inhibits platelet aggregation, may be involved cardiac contractility, may be associated with hypertension and atherosclerosis; mouse Prkg1 is associated with erectile dysfunction | 297 | 38% | 58% | 508 | 4e-44 |
| ROCK2 | NP_004841.2 | ROCK2; KIAA0619; ROCK_II Rho-associated coiled-coil containing protein kinase 2, a protein kinase that binds RhoA (human ARHA), regulates the formation of actin stress fibers, actin cytoskeleton organization, and possibly chromatid condensation and membrane blebbing | 347 | 35% | 58% | 489 | 3e-42 |
| STK6 | NP_940839.1 | STK6; (AurA); AIK; Aurora2; (BTAK); (STK15); Hs.333116; (ARK1); AURA; MGC34538 Serine threonine kinase 6 (aurora-A), acts to maintain genomic stability by regulating chromosome segregation and cytokinesis, overexpressed in multiple tumor cell types and possibly involved in tumorigenesis | 279 | 35% | 54% | 421 | 8e-42 |
| GRK5 | NP_005299.1 | GRK5; GPRK5 G protein-coupled receptor kinase 5, a protein kinase that regulates desensitization of G protein-coupled receptors by phosphorylating agonist-stimulated receptors, regulates thrombin activated signaling in endothelial cells | 307 | 37% | 56% | 452 | 5e-41 |
| CAMK1G | NP_065172.1 | CAMK1G; VWS1; DJ272L16.1; Hs.199068; CLICKIII; dJ272L16.1 Calcium/calmodulin-dependent protein kinase IG. a putative serine/threonine protein kinase, highly expressed in brain; corresponding gene is located at a locus associated with Van der Woude syndrome | 334 | 31% | 51% | 413 | 2e-40 |
| CIT | NP_009105.1 | CIT; KIAA0949; STK21; CRIK Citron Rho interacting kinase, a serine/threonine protein kinase that binds to Rho and Rac and mediates the regulation of cytokinesis in neuronal precursor cells | 342 | 37% | 56% | 475 | 2e-39 |
| GRK7 | NP_631948.1 | GRK7; (GPRK7) G protein-coupled receptor kinase 7, catalyses light-dependent phosphorylation of rhodopsin, may play a role in cone opsin desensitization | 321 | 36% | 55% | 455 | 9e-39 |

TABLE 6-continued

| Gene | GenBank | Synonyms/Description | Match Length | % Iden | % Sim | High Score | E Val |
|---|---|---|---|---|---|---|---|
| AURKC | NP_003151.1 | AURKC; AurC; AIE2; AIK3; STK13; aurora-C Serine/threonine kinase 13 (aurora/IPL1-like kinase), may be involved in chromosome segregation, localized to centrosome during mitosis | 277 | 34% | 51% | 387 | 6e−38 |
| GRK6 | NP_002073.2 | GRK6; GPRK6; FLJ32135 G protein-coupled receptor kinase 6, a protein kinase that regulates desensitization of G protein-coupled receptors by phosphorylating agonist-stimulated receptors, including muscarinic acetylcholine receptor 3 (CHRM3) | 326 | 36% | 54% | 444 | 7e−38 |
| GRK4 | NP_892027.2 | GRK4; GPRK4; GPRK2L; GRK4A; GRK4B; IT11; HUMGPRKLG; GRK4a G protein-coupled receptor kinase 4, regulates desensitization of G protein-coupled receptors by phosphorylating agonist-stimulated receptors, involved in renal function; variations in the gene are associated with essential hypertension | 337 | 37% | 53% | 454 | 8e−38 |
| DCAMKL3 | BAB21856.1 | DCAMKL3; KIAA1765 Protein containing a protein kinase domain, has a region of high similarity to a region of doublecortin and CaM kinase-like 1 (human DCAMKL1), which is a microtubule associated kinase that may regulate microtubule polymerization | 295 | 33% | 54% | 375 | 9e−36 |
| STK36 | NP_056505.1 | STK36; Fused; KIAA1278; DKFZp434N0223; FU Serine/threonine kinase 36 (fused homolog, Drosophila), promotes the nuclear localization of Gli zinc-finger transcription factors and regulates the transcriptional activity of GLI2, may function in hedgehog signaling | 268 | 35% | 58% | 380 | 2e−35 |
| CAMK1D | NP_705718.1 | CAMK1D; CKLiK; CaMK1d; LOC57118 Calcium/calmodulin-dependent protein kinase ID, a calcium/calmodulin-dependent protein kinase, stimulated by interleukin 8 (IL8) and during neutrophil differentiation, activates ERK/MAP kinase activity, may act in granulocyte effector functions | 268 | 35% | 56% | 394 | 3e−35 |
| CAMK4 | NP_001735.1 | CAMK4; CaMK-GR; MGC36771 Calcium/calmodulin-dependent protein kinase IV, a protein kinase involved in Ca(2+)-regulated gene expression, including CREBBP-dependent gene expression | 253 | 38% | 58% | 367 | 6e−35 |
| AURKB | NP_004208.1 | AURKB; STK12; AIK2; ARK2; (AIM-1); AIRK2; (AIM1); IPL1; Hs.180655; AurB; STK5 Serine threonine kinase 12, maximally expressed during G2/M phases and may function in cytokinesis and megakaryocyte differentiation, upregulation may cause abnormal cytokinesis and ploidy in colorectal and other neoplasms | 283 | 34% | 51% | 396 | 1e−34 |
| CAMK1 | NP_003647.1 | CAMK1; CaMK1a; CAMKI Calcium-calmodulin dependent protein kinase I, a calcium-calmodulin dependent protein kinase and signal transducer, member of a family of calcium-regulated kinases, involved in the regulation of myogenesis | 270 | 35% | 56% | 378 | 2e−34 |
| MGC42105 | NP_699192.1 | MGC42105; NIM1 NIM1 kinase, a likely member of the AMP-activated kinase family that exhibits protein kinase activity | 243 | 35% | 52% | 347 | 3e−33 |
| SNARK | NP_112214.1 | SNARK; NuaK2; DKFZP434J037; DKFZp686F01113 SNF1/AMP-activated protein kinase, member of the AMPK catalytic subunit family, exhibits AMP-dependent protein kinase activity, enhances cell survival during glucose starvation, may mediate pancreatic islet cell response to metabolic stress | 261 | 33% | 56% | 356 | 1e−32 |
| MARK4 | NP_113605.2 | MARK4; MARKL1; KIAA1860 MAP/microtubule affinity-regulating kinase 4, activated by the beta-catenin/Tcf complex in hepatic cell lines, upregulated in hepatocellular carcinoma, MARK4L alternative form is upregulated in primary glioma and glioblastoma cell lines | 251 | 34% | 53% | 342 | 3e−32 |
| STK33 | NP_112168.1 | STK33 Serine-threonine protein kinase 33, a putative serine-threonine kinase that may be a member of the calcium/calmodulin-dependent protein kinase family | 258 | 34% | 57% | 353 | 5e−32 |
| KIAA0999 | NP_079440.2 | KIAA0999; QSK; FLJ12240; (L19) KIAA0999 protein, protein kinase that preferentially | 246 | 35% | 52% | 341 | 5e−32 |

TABLE 6-continued

| Gene | GenBank | Synonyms/Description | Match Length | % Iden | % Sim | High Score | E Val |
|---|---|---|---|---|---|---|---|
| CAMK2G | NP_751911.1 | phosphorylates the AMARA peptide, yet can also phosphorylate LNR and SAMS peptides, can be activated by STK11-mediated phosphorylation, member of the AMPK-related kinase family CAMK2G; CAMKG; Hs.159519; CAMK; CAMK-II; MGC26678 Calcium/calmodulin-dependent protein kinase II gamma, activated by calmodulin binding, may play roles in insulin secretion and growth control | 257 | 34% | 54% | 341 | 5e−32 |
| MARK2 | NP_059672.1 | MARK2; EMK1; (PAR-1); MGC99619 ELKL motif kinase (microtubule/MAP-affinity regulating kinase), a putative serine/threonine kinase of the EMK kinase family, may have roles in the control of cell polarity, may be associated with cancer | 251 | 33% | 54% | 338 | 8e−32 |
| SNF1LK | NP_775490.1 | SNF1LK; SIK; MSK; LOC150094 Protein with strong similarity to SNF1-like kinase (rat Snf1lk), which is a protein kinase with autophosphorylation activity that may regulate adrenocortical functions, contains protein kinase and protein tyrosine kinase domains | 294 | 30% | 50% | 336 | 2e−31 |
| PSKH2 | NP_149117.1 | PSKH2 Protein with high similarity to protein serine kinase H1 (human PSKH1), which undergoes autophosphorylation on serine residues in a Ca2+-dependent manner and acts in RNA splicing and protein targeting, contains a protein kinase domain | 331 | 29% | 50% | 335 | 2e−31 |
| MARK3 | NP_002367.4 | MARK3; KP78; CTAK1; PAR1A MAP-microtubule affinity regulating kinase 3, a serine-threonine kinase that phosphorylates CDC25C, thereby regulating the interaction of CDC25C with 14-3-3 protein, functions during the DNA damage checkpoint, inhibited by the anticancer agent UCN-01 | 251 | 33% | 54% | 334 | 2e−31 |
| PHKG1 | NP_006204.1 | PHKG1; PHKG Gamma catalytic subunit of phosphorylase kinase, muscle isoform, phosphorylates and thereby activates glycogen phosphorylase, regulates glycogenolysis | 279 | 35% | 51% | 334 | 2e−31 |
| ARK5 | NP_055655.1 | ARK5; NuaK1; KIAA0537 AMP-activated protein kinase family member 5, a serine/threonine kinase that is phosphorylated by AKT and plays a role in cell survival, may function in tolerance to nutrient starvation in tumors | 263 | 32% | 55% | 359 | 5e−31 |
| DCAMKL2 | NP_689832.1 | DCAMKL2; MGC45428; DCDC3; DCK2 Protein with strong similarity to doublecortin kinase 2 (rat RGD1308384), which is a protein kinase that binds microtubules and stabilizes the cytoskeleton against depolymerization, member of the doublecortin family, contains a protein kinase domain | 292 | 30% | 52% | 334 | 7e−31 |
| STK32A | NP_659438.1 | STK32A; YANK1; MGC22688 Protein containing a protein kinase domain, has moderate similarity to a region of S. cerevisiae Sch9p, which is a serine/threonine protein kinase acting in the stress response and a nutrient-sensing signaling pathway and affecting life span | 136 | 44% | 70% | 319 | 8e−31 |
| PRKAA2 | NP_006243.2 | PRKAA2; AMPKa2; (AMPK); PRKAA; AMPK2 Catalytic alpha 2 subunit of the 5'-AMP-activated protein kinase, a metabolic sensor of AMP levels, plays a role in fatty acid beta-oxidation and mediates tolerance to glucose deprivation and tumor growth in pancreatic cancer cells | 302 | 30% | 51% | 330 | 9e−31 |
| BRSK1 | NP_115806.1 | BRSK1; KIAA1811 KIAA1811 protein, a member of the AMPK-related kinase family, activated by STK11-mediated phosphorylation, preferentially phosphorylates the LNR peptide, also phosphorylates AMARA and SAMS peptides, expressed in neuronal tissues | 271 | 31% | 52% | 332 | 2e−30 |
| CAMK2D | NP_001212.2 | CAMK2D; CAMKD; MGC44911 Calcium/calmodulin-dependent protein kinase II delta, member of the multifunctional CAMKII family involved in Ca2+ regulated processes; alternative form delta 3 is specifically upregulated in the myocardium of patients with heart failure | 268 | 33% | 51% | 327 | 2e−30 |
| NEK3 | NP_689933.1 | NEK3; MGC29949; HSPK36; Hs.2236 NIMA (never in mitosis gene a)-related kinase 3, a | 252 | 31% | 54% | 325 | 2e−30 |

TABLE 6-continued

| Gene | GenBank | Synonyms/Description | Match Length | % Iden | % Sim | High Score | E Val |
|---|---|---|---|---|---|---|---|
| DCAMKL1 | NP_004725.1 | putative serine/threonine kinase that may be involved in cell cycle control during mitosis DCAMKL1; KIAA0369; DCLK Doublecortin and CaM kinase-like 1, a microtubule associated kinase that may regulate microtubule polymerization and central nervous system development, contains a kinase domain and a doublecortin domain | 271 | 31% | 52% | 327 | 6e−30 |
| PHKG2 | NP_000285.1 | PHKG2 Phosphorylase kinase gamma 2, activates glycogen phosphorylase (PYGL); mutations in the corresponding gene cause liver glycogen storage disease and may be associated with an increased risk of liver fibrosis and cirrhosis | 292 | 32% | 50% | 335 | 2e−29 |
| CAMK2B | NP_001211.3 | CAMK2B; CAMKB; CAM2; CAMK2; MGC29528 Calcium/calmodulin-dependent protein kinase II beta, a protein kinase that may regulate cell growth, upregulated in the frontal cortex of schizophrenia patients and may regulate small cell lung carcinoma progression | 268 | 33% | 51% | 320 | 2e−29 |
| CAMK2A | NP_057065.2 | CAMK2A; CAMKA; KIAA0968; LOC51618 Calcium: calmodulin-dependent protein kinase II alpha subunit, member of a family of kinases involved in Ca(2+)-regulated processes, participates in TGF-beta (TGFB1) and EGF signal transduction pathways through the phosphorylation of Smad2 (MADH2) | 272 | 31% | 51% | 315 | 6e−29 |
| PSKH1 | NP_006733.1 | PSKH1 Protein serine kinase H1, undergoes autophosphorylation on serine residues in a Ca2+-dependent manner, overexpression leads to nuclear reorganization of splicing factors SFRS1 and SFRS2 and stimulates RNA splicing | 268 | 31% | 54% | 313 | 6e−29 |
| STK17A | NP_004751.1 | STK17A; DRAK1 Serine threonine kinase 17a, contains an N terminal catalytic domain and C terminal regulatory domain, may play a role in cross resistance against DNA damaging anti-cancer drugs, overproduction induces apoptosis | 321 | 29% | 49% | 315 | 1e−28 |
| BRSK2 | NP_003948.1 | BRSK2; STK29; PEN11B C11orf7, (SAD1) Protein with high similarity to human BRSK1, which preferentially phosphorylates the LNR peptide over AMARA and SAMS peptides and is activated by human STK11-mediated phosphorylation, contains a protein kinase and a protein tyrosine kinase domain | 304 | 29% | 50% | 314 | 1e−28 |
| CHEK2 | NP_001005735.1 | CHEK2; (CDS1); CHK2; RAD53; HuCds1; PP1425; bA444G7; HUCDS1; Hs.146329 CHK2 checkpoint homolog, kinase that transmits DNA damage signals from Atm, regulates G2 cell cycle arrest, BRCA1 function, replicative senescence, and TP53 dependent apoptosis, associated with Li Fraumeni Syndrome, breast, colorectal, and gastric cancers | 313 | 32% | 49% | 342 | 2e−28 |
| SNRK | NP_060189.2 | SNRK; KIAA0096; Hs.79025; FLJ20224; HSNFRK; DKFZp779A1866 SNF related kinase, serine-threonine kinase that may play a role in the development of hematopoietic and endothelial cell lineages in the embryo | 279 | 32% | 48% | 310 | 4e−28 |
| PRKD2 | NP_057541.2 | PRKD2; (PKD2); HSPC187; DKFZP586E0820; PKD2_2; DKFZp586E0820 Protein kinase D2, a serine-threonine protein kinase, contains two zinc finger-like cysteine-rich motifs, a pleckstrin homology domain, and a catalytic domain, activated by the cholecystokinin B/gastrin receptor (CCKBR) and phorbol esters | 272 | 34% | 50% | 309 | 5e−28 |
| PRKD1 | NP_002733.1 | PRKD1; PKD; PKCM; PRKCM; PKC-MU; (PKD1) Mu isoform of protein kinase C (protein kinase D), a serine-threonine kinase involved in signal transduction, including activation of the MAPK p42 pathway and inhibition of receptor signaling, forms part of the invadopodia used during tumor invasion | 272 | 33% | 50% | 310 | 6e−28 |
| HUNK | NP_055401.1 | HUNK Hormonally upregulated Neu-associated kinase, a protein kinase with a SNF1 homology domain that may be involved in signal transduction | 246 | 34% | 50% | 304 | 6e−28 |
| NEK1 | NP_036356.1 | NEK1; NY-REN-55; KIAA1901; LOC51037; Hs.414410 NIMA (never in mitosis gene a)-related kinase 1, a predicted protein kinase that | 248 | 33% | 52% | 312 | 1e−27 |

TABLE 6-continued

| Gene | GenBank | Synonyms/Description | Match Length | % Iden | % Sim | High Score | E Val |
|---|---|---|---|---|---|---|---|
| PLK4 | NP_055079.2 | binds kinesin family member 3a (KIF3A), tuberin (TSC2), and alpha catulin (CTNNAL1); may play a role in the etiology of polycystic kidney disease PLK4; SAK; STK18; Hs.172052 Serine/threonine kinase 18, a putative protein kinase belonging to the polo family of mitotic regulators, expressed in proliferating cells during specific phases of the cell cycle; overexpressed in colorectal cancer | 267 | 30% | 49% | 301 | 4e-27 |
| SLK | NP_055535.2 | SLK; (KIAA0204); (STK2); se20-9; bA16H23.1 STE20-like kinase, ubiquitously expressed protein serine-threonine kinase predicted to activate PLK and regulate the mitotic cell cycle, contains a coiled-coil region and a PEST domain, undergoes autophosphorylation | 281 | 33% | 51% | 303 | 5e-27 |
| STK17B | NP_004217.1 | STK17B; DRAK2 Serine/threonine kinase 17b (death-associated protein kinase-related apoptosis-inducing protein kinase 2), a protein kinase localized to the nucleus, undergoes autophosphorylation, functions in the induction of apoptosis | 249 | 33% | 52% | 296 | 5e-27 |
| MGC75495 | AAH63885.1 | MGC75495; Hs.232751 Protein containing protein kinase and protein tyrosine kinase domains, has weak similarity to *S. pombe* Cdk9p, which forms a specific Cdk-cyclin pair with *S. pombe* Pch1p and acts in peptidyl-serine and peptidyl-threonine phosphorylation | 250 | 30% | 53% | 298 | 6e-27 |
| MELK | NP_055606.1 | MELK; KIAA0175; HPK38 Maternal embryonic leucine zipper kinase, a putative protein serine/threonine kinase, interacts with zinc-finger-like protein 9 (ZPR9) | 275 | 28% | 48% | 296 | 1e-26 |
| MAPKAPK5 | NP_620777.1 | MAPKAPK5; PRAK; MAPKAP5 Mitogen-activated protein kinase-activated protein kinase 5, activated by p38 pathway in response to cellular stress and proinflammatory cytokines, phosphorylates HSP27 (HSPB1) and tyrosine hydroxylase (TH), inhibits proliferation | 281 | 32% | 49% | 297 | 2e-26 |
| TSSK2 | NP_443732.2 | TSSK2; STK22B; DGS-G; SPOGA2; FLJ38613 Serine threonine kinase 22B, putative protein kinase expressed in the testis; corresponding gene is located in a chromosomal region that is deleted in DiGeorge syndrome (DGS) and velo cardio facial syndrome (VCFS) | 247 | 32% | 51% | 285 | 5e-26 |
| SNF1LK2 | NP_056006.1 | SNF1LK2; LOH11CR1I; SIK2; KIAA0781; DKFZp434K1115; QIK; Hs.42676 Salt-inducible serine-threonine kinase 2, phosphorylates insulin receptor substrate 1 (IRS1) to perhaps modulate insulin signaling cascade, phosphorylates transducer of regulated cAMP response element-binding protein 2 (TORC2), inhibited by cAMP | 248 | 30% | 51% | 300 | 1e-25 |
| PRKD3 | NP_005804.1 | PRKD3; EPK2; (PKD3); PRKCN; PKC-NU; nPKC-NU; PKCnu Protein kinase C nu, member of the protein kinase C family of serine/threonine kinases involved in the regulation of cellular differentiation and proliferation | 272 | 33% | 49% | 289 | 2e-25 |
| STK10 | NP_005981.2 | STK10; LOK; PRO2729 Serine threonine kinase 10, a member of the STE20 family of serine/threonine kinases, downregulates the MEKK1 (MAP3K1) pathway and negatively regulates CD28 signaling in T cells | 297 | 31% | 51% | 303 | 5e-25 |
| DAPK3 | NP_001339.1 | DAPK3; ZIPK; ZIP; Hs.25619 Death-associated protein kinase 3, serine-threonine protein kinase, regulates cell shape and nuclear morphology via myosin II phosphorylation, upregulated in the frontal cortex of Alzheimer's disease patients | 259 | 32% | 51% | 287 | 5e-25 |
| TRIO | NP_009049.2 | TRIO; Hs.367689; tgat Triple functional domain, RAC and RHO guanine nucleotide exchange factor, interacts with filamin during actin cytoskeleton remodeling and with the tyrosine phosphatase LAR, involved in neurite outgrowth, contains a serine/threonine kinase domain | 352 | 28% | 48% | 288 | 7e-25 |
| PRKAA1 | NP_996790.2 | PRKAA1; AMPKa1; (AMPK); MGC33776; MGC57364 Alpha 1 catalytic subunit of AMP-activated protein kinase, involved in glycolysis, response to starvation, hypoxia, may regulate cystic fibrosis transmembrane conductance regulator (CFTR); rat Prkaa1 is associated with obesity related insulin resistance | 271 | 31% | 52% | 304 | 9e-25 |

TABLE 6-continued

| Gene | GenBank | Synonyms/Description | Match Length | % Iden | % Sim | High Score | E Val |
|---|---|---|---|---|---|---|---|
| NEK2 | NP_002488.1 | NEK2; NLK1; HsPK_21; HsPK21; NEK2A NIMA (never in mitosis gene a)-related expressed kinase 2, a serine/threonine protein kinase, involved in the centrosome cycle and the regulation of mitosis, phosphorylates and inhibits protein phosphatase 1 | 278 | 29% | 49% | 279 | 9e−25 |
| MYLK | NP_444253.2 | MYLK; smMLCK; (MLCK); KRP; Hs.75950; MLCK108; MLCK210; FLJ12216; DKFZp686I10125 Myosin light polypeptide kinase, calcium and calmodulin-dependent kinase, phosphorylates smooth muscle and non-muscle myosin regulatory light chains to activate contraction, telokin corresponds to MYLK C-terminal 154 residues, may modulate MYLK activity | 281 | 28% | 51% | 285 | 1e−24 |
| NEK11 | NP_079076.2 | NEK11; FLJ23495 NIMA (never in mitosis gene a)-related kinase 11, member of the NIMA-related kinase (NEK) family, a protein kinase that may act in the DNA damage checkpoint | 288 | 31% | 49% | 277 | 2e−24 |
| PLK2 | NP_006613.1 | PLK2; SNK Polo-like kinase 2, a protein kinase required for centriole duplication during mitosis, expression is enhanced in thyroid cells following x-ray irradiation | 261 | 27% | 51% | 276 | 2e−24 |
| PLK1 | NP_005021.2 | PLK1; STPK13; PLK Polo-like kinase, regulates CDC2-cyclin B through activation of CDC25C phosphatase, plays a role in multiple mitotic checkpoints, maturation of mitotic centrosomes, and cell proliferation; highly expressed in tumor tissues | 242 | 27% | 53% | 276 | 3e−24 |
| MAPKAPK3 | NP_004626.1 | MAPKAPK3; 3PK; MAPKAP3 Mitogen-activated protein kinase-activated protein kinase 3, putative serine/threonine kinase activated by hyperosmotic stress or tumor necrosis factor (TNF) via phosphorylation by CSBP1/CSBP2 (MAPK14), phosphorylates the small heat shock protein HSP27 | 276 | 29% | 51% | 273 | 6e−24 |
| MAPKAPK2 | NP_116584.2 | MAPKAPK2; MAPKAPK-2; Hs.75074 Mitogen-activated protein kinase-activated protein kinase 2, a protein kinase that is phosphorylated by MAP kinase, activated in response to IFN-gamma (IFNG) and UV, and positively regulates mRNA stability, upregulated in breast cancer | 320 | 28% | 48% | 273 | 7e−24 |
| MARK1 | NP_061120.2 | MARK1; MARK; KIAA1477; (FLJ14146) Microtubule affinity regulating kinase, a serine/threonine kinase that phosphorylates microtubule-associated protein tau, leading to disruption of microtubules | 216 | 31% | 52% | 268 | 8e−24 |
| PLK3 | NP_004064.2 | PLK3; (CNK); FNK; PRK; Hs.153640 Polo-like kinase 3, a serine/threonine kinase that binds and phosphorylates Chk2 (CHEK2) and p53 (TRP53) after DNA damage, regulates centrosome function, downregulated in squamous cell carcinoma and other tumors; rat Plk3 is downregulated in colon tumors | 258 | 28% | 48% | 268 | 1e−23 |
| MAP2K1 | NP_002746.1 | MAP2K1; PRKMK1; MAPKK1; MEK1; MKK1 Mitogen-activated protein kinase kinase 1, a signaling protein that phosphorylates and activates MAP kinase, involved in cell cycle control, antiapoptosis, cell motility, radiation response, and myogenesis, putative target for breast and lung cancer | 215 | 33% | 53% | 266 | 1e−23 |
| DAPK2 | NP_055141.2 | DAPK2; (DRP-1); Hs.129208; (DRP1) Death-associated protein kinase 2, a member of the DAP kinase subfamily of serine-threonine kinases that activates apoptosis in a calcium-calmodulin dependent manner | 287 | 29% | 48% | 268 | 2e−23 |
| CDKL5 | NP_003150.1 | CDKL5; STK9 Cyclin-dependent kinase-like 5 (serine/threonine kinase 9), a putative serine-threonine kinase; gene mutation causes a severe neurodevelopmental disorder with infantile spasms and mental retardation | 207 | 35% | 54% | 266 | 4e−23 |
| STK4 | NP_006273.1 | STK4; KRS2; (MST1); Krs-2; DKFZp686A2068 Serine/threonine kinase 4, a protein kinase that functions in apoptosis, activates caspases and is cleaved and activated by caspases, activity is decreased by EGF stimulation | 264 | 30% | 49% | 264 | 4e−23 |

TABLE 6-continued

| Gene | GenBank | Synonyms/Description | Match Length | % Iden | % Sim | High Score | E Val |
|---|---|---|---|---|---|---|---|
| TSSK4 | NP_777604.2 | TSSK4; STK22E; C14orf20; c14_5117; LOC283629 Protein containing a protein kinase domain, has moderate similarity to mouse Tssk1, which is a testis-specific kinase that forms a complex with mouse Stk22b and binds and phosphorylates mouse Stk22s1 and may act in late spermatid development | 278 | 26% | 49% | 261 | 5e−23 |
| STK3 | NP_006272.1 | STK3; KRS1; MST2; p33QIK; FLJ90748 Serine threonine kinase 3, a protein kinase activated by cell stress, plays a role in apoptosis both upstream and downstream of caspase activation | 425 | 25% | 45% | 264 | 7e−23 |
| CDKL3 | NP_057592.1 | CDKL3; LOC51265; NKIAMRE Cyclin-dependent kinase-like 3, a putative serine/threonine kinase, may contribute to myelodysplasia; gene deletion is detected in leukemic blasts | 208 | 32% | 55% | 258 | 9e−23 |
| LOC340156 | NP_001012418.1 | LOC340156 Protein containing a protein kinase domain, has high similarity to a region of myosin light chain kinase (human MLCK), which is a calcium-calmodulin-dependent protein kinase that acts in the phosphorylation of key regulatory motifs of human MYBPC3 | 266 | 29% | 50% | 260 | 2e−22 |
| CAMKK2 | NP_006540.3 | CAMKK2; CAMKK; KIAA0787; CAMKKB; Hs.197806; MGC15254 Calcium/calmodulin-dependent protein kinase kinase 2 beta, a protein kinase that selectively phosphorylates and activates Ca2+-calmodulin (CaM)-dependent protein kinases I and IV in a Ca2+-CaM-dependent manner, acts in calcium mediated cellular responses | 281 | 27% | 49% | 260 | 3e−22 |
| MASTL | NP_116233.1 | MASTL; THC2; FLJ14813 Protein containing a protein kinase domain, has weak similarity to a region of S. cerevisiae Rim15p, which is a serine/threonine protein kinase that positively regulates expression of S. cerevisiae Ime2p and sporulation | 160 | 40% | 62% | 293 | 4e−22 |
| STK24 | NP_003567.2 | STK24; MST-3; (STK3); MST3; MST3B Serine-threonine kinase 24 (Ste20 yeast homolog), member of the SPS1 subgroup of the STE20-like protein family, a serine-threonine kinase that prefers manganese as a cofactor and uses either GTP or ATP as a phosphate donor | 261 | 28% | 49% | 280 | 4e−22 |
| CHEK1 | NP_001265.1 | CHEK1; CHK1; p56Chk1 Checkpoint homolog 1 (S. pombe), protein kinase, required for mitotic G2 checkpoint in response to radition-induced DNA damage, inhibits mitotic entry after DNA damage via mechanism involving CDC25, alternative form is associated with lung cancer | 214 | 30% | 51% | 250 | 1e−21 |
| TSSK3 | NP_443073.1 | TSSK3; STK22C; SPOGA3; (STK22D) Protein with high similarity to serine/threonine kinase 22b (mouse Tssk2), which is a serine/threonine kinase that is activated at the onset of spermiogenesis and acts in cytodifferentiation of late spermatids to sperms, contains a protein kinase domain | 250 | 29% | 49% | 248 | 1e−21 |
| MAP2K2 | NP_109587.1 | MAP2K2; MEK2; PRKMK2; MKK2; MAPKK2 Mitogen-activated protein kinase kinase 2, a dual-specificity kinase that is involved in signal transduction during cellular growth and differentiation, mitosis, apoptosis, angiogenesis, and immune responses, upregulated in breast cancer | 339 | 28% | 47% | 250 | 2e−21 |
| NEK7 | NP_598001.1 | NEK7; Hs.24119 NIMA (never in mitosis gene a)-related kinase 7, a putative protein serine-threonine kinase and member of a subfamily of NIMA-related kinases | 254 | 28% | 48% | 247 | 2e−21 |
| MKNK1 | NP_003675.2 | MKNK1; MNK1 MAP kinase-interacting serine-threonine kinase 1, phosphorylates translation initiation factor 4E (EIF4E), reduces cap-dependent translation, phosphorylates cytosolic phospholipase A, involved in production of RFLAT-1 (KLF13) during T cell maturation | 402 | 25% | 42% | 255 | 3e−21 |
| MAP3K5 | NP_005914.1 | MAP3K5; MEKK5; ASK1; MAPKKK5; NAP160 Mitogen activated protein kinase kinase kinase 5, activates SAPK, Jun kinase and p38 signaling pathways, acts in stress and cytokine-induced apoptosis, involved in cellular | 255 | 31% | 50% | 254 | 4e−21 |

TABLE 6-continued

| Gene | GenBank | Synonyms/Description | Match Length | % Iden | % Sim | High Score | E Val |
|---|---|---|---|---|---|---|---|
| CASK | NP_003679.1 | differentiation, may play a role in HIV and neurodegenerative disease CASK; hCASK; LIN2 Calcium/calmodulin-dependent serine protein kinase, member of the MAGUK family, involved in recruiting multiprotein complexes at the plasma membrane, may link the extracellular matrix to the actin cytoskeleton, may regulate synaptic vesicle exocytosis | 283 | 28% | 49% | 252 | 5e-21 |
| MKNK2 | NP_951009.1 | MKNK2; MNK2; (GPRK7) MAP kinase interacting serine threonine kinase 2, a protein kinase that phosphorylates translation initiation factor 4E (EIF4E) and negatively regulates translation | 295 | 27% | 45% | 250 | 5e-21 |
| STK25 | NP_006365.2 | STK25; SOK1; YSK1 Serine threonine kinase 25, a member of the Ste20 kinase family, induced by oxidant stress and may regulate an intracellular signaling pathway linked to oxidative stress response | 265 | 29% | 50% | 274 | 6e-21 |
| DAPK1 | NP_004929.1 | DAPK1; DAPK; Hs.153924; DKFZp781I035 Death associated protein kinase 1, a serine-threonine kinase that is a positive mediator of apoptosis; promoter of corresponding gene is hypermethylated in many cancers | 275 | 29% | 51% | 273 | 7e-21 |
| MAP4K3 | NP_003609.2 | MAP4K3; KHS2; (GLK); RAB8IPL1; MAPKKKK3 Mitogen-activated protein kinase kinase kinase kinase 3, a member of the germinal center kinase subfamily of serine-threonine protein kinases, activates the JNK2 pathway and is activated in response to UV and inflammatory cytokines | 305 | 28% | 46% | 252 | 8e-21 |
| PIM1 | NP_002639.1 | PIM1; PIM Pim-1 oncogene, a proto-oncogenic serine/threonine kinase, inhibits apoptosis, may play a role in hematopoesis, may serve as a prognostic marker for prostate cancer; corresponding gene is a target of hypermutation in B-cell diffuse large-cell lymphomas | 268 | 29% | 49% | 245 | 8e-21 |
| MLCK | NP_872299.1 | MLCK; MLCK2; LOC91807; Hs.339846 Myosin light chain kinase (MLCK), a calcium-calmodulin-dependent protein kinase, acts in the phosphorylation of key regulatory motifs of cardiac myosin-binding protein C (MYBPC3), may act in the regulation of cardiac muscle contraction | 249 | 30% | 50% | 246 | 9e-21 |
| PAK1 | NP_002567.3 | PAK1; PAKalpha p21 activated kinase 1, a serine-threonine kinase activated by GTPases CDC42 and RAC1, serves in MAP kinase cascade regulation, cytoskeletal organization, cell migration and apoptosis, increased activity may correlate with breast cancer invasiveness | 295 | 29% | 48% | 246 | 1e-20 |
| PAK3 | NP_002569.1 | PAK3; MRX30; PAK3beta; OPHN3; bPAK; hPAK3; (CDKN1A) p21 (CDKN1A)-activated kinase 3, downstream effector of members of the rho family of GTPases, such as CDC42 and RAC1, kinase activity is stimulated by Rac; mutation of the corresponding gene causes nonsyndromic X-linked mental retardation | 258 | 31% | 49% | 245 | 1e-20 |
| MAPK1 | NP_620407.1 | MAPK1; PRKM1; P41MAPK; P42MAPK; ERK2; (ERK); MAPK2; PRKM2; (p38); (p40); p41; ERT1; p41mapk Mitogen-activated protein kinase 1, a serine-threonine kinase effector of the RAS-MAP kinase pathway, translocates to the nucleus to mediate transcription when activated, involved in the regulation of cell growth, differentiation, migration and apoptosis | 277 | 26% | 49% | 244 | 1e-20 |
| MAP2K6 | NP_002749.2 | MAP2K6; PRKMK6; MEK6; MKK6; SAPKK3; MAPKK6 Mitogen-activated protein kinase kinase 6, a threonine-tyrosine kinase involved in signal transduction, phosphorylates the MAP kinase p38, involved in promoting cell cycle arrest and protection from apoptosis in response to a variety of insults | 271 | 28% | 46% | 243 | 1e-20 |
| ULK3 | NP_056333.1 | ULK3; FLJ90566; DKFZP434C131 Protein containing a protein kinase domain, has low similarity to extracellular signal-regulated kinase 8 (human ERK8), which is a serine/threonine | 205 | 33% | 55% | 241 | 1e-20 |

TABLE 6-continued

| Gene | GenBank | Synonyms/Description | Match Length | % Iden | % Sim | High Score | E Val |
|---|---|---|---|---|---|---|---|
| | | kinase that binds to and is activated by human SRC | | | | | |
| MAP4K2 | NP_004570.2 | MAP4K2; BL44; (GCK); RAB8IP Mitogen-activated protein kinase kinase kinase kinase 2, member of the germinal center kinase subfamily of serine/threonine protein kinases, activates the stress-activated protein kinase pathway, expression is increased in UV-resistant melanoma cells | 295 | 29% | 46% | 247 | 2e−20 |
| CAMKK1 | NP_757344.1 | CAMKK1; CAMKKA; DKFZp761M0423; MGC34095 Protein with strong similarity to calcium-calmodulin-dependent protein kinase kinase 1 alpha (rat Camkk1), which phosphorylates and activates Ca(2+)-calmodulin (CaM)-dependent kinase I and IV but not CaM kinase II, contains a protein kinase domain | 317 | 25% | 44% | 239 | 3e−20 |
| ULK1 | NP_003556.1 | ULK1; UNC51; Unc51.1 Unc-51 (*C. elegans*)-like kinase 1, a member of the Unc51 subfamily of serine threonine kinases, a putative protein kinase that may play a role in vesicle transport and signal transduction during axonal elongation | 385 | 26% | 44% | 296 | 4e−20 |
| ULK2 | NP_055498.2 | ULK2; KIAA0623; Unc51.2 Protein with strong similarity to UNC 51-like kinase 2 (mouse Ulk2), which is a serine-threonine protein kinase, contains a protein kinase and a protein tyrosine kinase domain | 337 | 28% | 47% | 280 | 4e−20 |
| MAP2K3 | NP_659732.1 | MAP2K3; MEK3; MKK3; PRKMK3; MAPKK3 Mitogen activated protein kinase kinase 3, phosphorylates MAP kinase p38, involved in stress and inflammatory responses, senescence, apoptosis, and nontypeable Hemophilus influenzae infection | 281 | 28% | 46% | 240 | 4e−20 |
| CDK2 | NP_001789.2 | CDK2; p33CDK2; p33(CDK2) Cyclin-dependent protein kinase 2, interacts with cyclins to regulate kinase activity and cell cycle progression, regulates DNA replication; decreased expression or inhibition may be therapeutic for many types of cancer | 297 | 28% | 46% | 240 | 4e−20 |
| NEK4 | NP_003148.1 | NEK4; NLK2; (STK2); (NRK2) NIMA (never in mitosis gene a)-related kinase 4, cytosolic tyrosine kinase that has high activity in breast tumor tissue | 247 | 29% | 52% | 248 | 6e−20 |
| MAP3K6 | NP_004663.3 | MAP3K6; MAPKKK6; MGC20114; ASK2 Mitogen-activated protein kinase kinase kinase 6, a protein kinase that interacts with MAPKKK5 (MAP3K5) and weakly activates the JNK pathway, but not the ERK or p38 kinase pathways | 309 | 28% | 45% | 245 | 6e−20 |
| PKMYT1 | NP_004194.3 | PKMYT1; (MYT1); DKFZp547K1610 Membrane-associated tyrosine- and threonine-specific CDC2-inhibitory kinase, controls the cell cycle by phosphorylating and inactivating cyclin-bound CDC2, may play a role in shuttling CDC2-cyclin B1 (CCNB1) complexes between the nucleus and cytoplasm | 288 | 31% | 47% | 241 | 6e−20 |
| MYLK2 | NP_149109.1 | MYLK2; KMLC; (MLCK); skMLCK Skeletal muscle myosin light chain kinase, phosphorylates myosin regulatory light chains in cardiac and skeletal muscle which may modulate contractile activity; gain-of-function mutation is associated with early-onset hypertrophic cardiomyopathy | 270 | 25% | 50% | 240 | 6e−20 |
| MYO3A | NP_059129.2 | MYO3A; DFNB30 Myosin IIIA, a putative ATPase motor, contains a kinase domain and three consensus calmodulin-binding (IQ) motifs, highly expressed in retina where it may function in photoreception, associated with nonsyndromic hearing loss | 297 | 30% | 47% | 247 | 7e−20 |
| NEK6 | NP_055212.2 | NEK6; SID6-1512 NIMA (never in mitosis gene a)-related kinase 6, a protein serine-threonine kinase, phosphorylates and activates the S6 ribosomal protein kinase p70S6K (RPS6KB1) and serum glucocorticoid regulated kinase (SGK), may regulate chromatin condensation | 222 | 28% | 50% | 234 | 7e−20 |
| MAP3K15 | NP_001001671.1 | MAP3K15; bA723P2.3; ELJ16518 Protein containing a protein kinase and a protein tyrosine kinase domain, has high similarity to a region of mitogen activated protein kinase kinase kinase 5 | 289 | 30% | 46% | 244 | 8e−20 |

TABLE 6-continued

| Gene | GenBank | Synonyms/Description | Match Length | % Iden | % Sim | High Score | E Val |
|---|---|---|---|---|---|---|---|
| | | (human MAP3K5), which activates SAPK, Jun kinase and p38 signaling pathways | | | | | |
| RP6-213H19.1 | NP_057626.2 | RP6-213H19.1; MST4; (MASK); LOC51765 Mst3 and SOK1-related kinase, a protein kinase, induces apoptosis, involved in cell growth, appears to activate MAPK but not JNK nor p38 kinase pathways, alternative form MST4a may regulate MST4; gene maps to a region associated with mental retardation | 323 | 27% | 47% | 274 | 9e-20 |
| CRK7 | NP_057591.1 | CRK7; CRKRS; LOC51755; CrkRS; KIAA0904; Hs.123073 CDC2-related protein kinase 7, member of the Cdc2 protein kinase family, contains an SR domain and a proline-rich region, a protein kinase, phosphorylates the C-terminal domain of RNA polymerase II, may link mRNA splicing with transcriptional machinery | 221 | 32% | 50% | 240 | 1e-19 |
| PAK7 | NP_817127.1 | PAK7; (PAK5); KIAA1264; Hs.21864; MGC26232 p21(CDKN1A)-activated kinase 7, protein kinase that interacts with GTP-bound Cdc42 and Rac, activates JNK (MAPK8), promotes neurite outgrowth and filopodium formation | 257 | 27% | 50% | 236 | 1e-19 |
| PAK2 | NP_002568.2 | PAK2; PAK65; PAKgamma p21 (CDKN1A)-activated kinase 2, binds CDC42 and RAC1, activated by caspase cleavage during stress-induced apoptosis leading to activation of the c Jun N terminal kinase (JNK) pathway, and may regulate actin organization and smooth muscle contraction | 258 | 30% | 48% | 235 | 1e-19 |
| TSSK1 | NP_114417.1 | TSSK1; (STK22D); FKSG81; SPOGA4 Serine-threonine kinase 22D (spermiogenesis associated), putative testis-specific serine-threonine kinase, may play a role in sperm function; corresponding gene may be involved in DiGeorge, velocardiofacial, or conotruncal anomaly facial syndromes | 246 | 30% | 49% | 275 | 2e-19 |
| MYO3B | NP_620482.1 | MYO3B; Hs.352249 Myosin IIIB, a member of the class III myosin family of actin-based motor proteins with amino-terminal kinase domains; corresponding gene is a candidate for Bardet-Biedl syndrome | 232 | 34% | 49% | 237 | 2e-19 |
| PAK6 | NP_064553.1 | PAK6; (PAK5) P21(CDKN1A)-activated kinase 6, member of the PAK family of serine-threonine protein kinases, interacts with androgen receptor (AR) and estrogen receptor alpha (ESR1) and suppresses receptor-mediated transcriptional activation | 258 | 26% | 52% | 234 | 3e-19 |
| CDK7 | NP_001790.1 | CDK7; (CAK1); (STK1); CDKN7; (TFIIH); p39MO15 Cyclin-dependent protein kinase 7, trimerizes with CCNH and MNAT1 to form CDK-activating kinase (CAK), phosphorylates CDC2 and the C terminus of RNA polymerase II; inhibition may be therapeutic for colon cancer; may be upregulated in breast cancer | 204 | 32% | 50% | 227 | 3e-19 |
| MAPK3 | NP_002737.1 | MAPK3; ERK1; PRKM3; P44ERK1; P44MAPK; (p44); ERK-1 Mitogen-activated protein kinase 3, a serine-threonine kinase involved in cell surface receptor signaling and cell proliferation, altered activation may be therapeutic for HIV infection, rheumatoid arthritis, and breast, colorectal, and lung cancers | 208 | 27% | 52% | 228 | 4e-19 |
| CDKL2 | NP_003939.1 | CDKL2; (P56); KKIAMRE Cyclin-dependent kinase-like 2, putative protein kinase whose activity is stimulated by epidermal growth factor (EGF), may play a role in sex differentiation | 301 | 28% | 48% | 231 | 5e-19 |
| CDK3 | NP_001249.1 | CDK3 Cyclin-dependent kinase 3, a kinase that binds to cyclin A and is required for progression from G1 to S phase, may have a role in inducing apoptosis | 303 | 28% | 46% | 231 | 5e-19 |
| MAP4K1 | NP_009112.1 | MAP4K1; HPK1; Hs.86575 Mitogen-activated protein kinase kinase kinase kinase 1 (hematopoietic progenitor kinase 1), activates the JNK/SAPK signaling pathway, enhances T cell receptor-mediated apoptosis, modulates NF-kappaB activation and plays a role in the response to stress | 262 | 27% | 52% | 232 | 6e-19 |

TABLE 6-continued

| Gene | GenBank | Synonyms/Description | Match Length | % Iden | % Sim | High Score | E Val |
|---|---|---|---|---|---|---|---|
| NEK8 | NP_835464.1 | NEK8; NEK12A; DKFZp434N0419 NIMA (never in mitosis gene a)-related kinase 8, a putative serine-threonine kinase that may participate in mitotic cell cycle regulation, upregulated in breast cancer; mouse Nek8 gene mutation causes polycystic kidney disease | 250 | 29% | 48% | 247 | 8e−19 |
| MAP3K4 | NP_005913.2 | MAP3K4; MAPKKK4; MTK1; MEKK4; KIAA0213; PRO0412 Mitogen-activated protein kinase kinase kinase 4, phosphorylates MAP2K3, MAP2K6, and MAP2K4, induces MAPK14 and MAPK8 activation, mediates stress activation and cancer cell apoptosis involving MAPK14, BRCA1, and GADD45G | 247 | 29% | 47% | 232 | 1e−18 |
| MAP4K5 | NP_942089.1 | MAP4K5; KHS1; (GCKR); KHS; MAPKKKK5 Mitogen-activated protein kinase kinase kinase kinase 5, a protein kinase of the STE20 family, activates Jun N-terminal kinase, binds to and is activated by TRAF2 during TNF signaling, may mediate stress response and oncogenic transformation by BCR-ABL | 309 | 27% | 45% | 232 | 1e−18 |
| CDC2L5 | NP_003709.2 | CDC2L5; CDC2L; (CHED); KIAA1791 Cell division cycle 2-like 5, contains a PITAIRE motif, putative cyclin-dependent protein kinase that may participate in cholinergic pathways and cell division, may function in megakaryocytopoiesis | 223 | 30% | 50% | 230 | 1e−18 |
| CDKL1 | NP_004187.2 | CDKL1; KKIALRE; (p42) Cyclin-dependent kinase like 1 (CDC2-related kinase 1), member of the proline-directed Ser/Thr kinase family, contains a MAP kinase phosphorylation motif, activated by epidermal growth factor (EGF), phosphorylates histones, upregulated in gliosis | 341 | 25% | 44% | 228 | 1e−18 |
| PIM2 | NP_006866.2 | PIM2; Hs.80205; hPim-2 Pim-2 oncogene, a putative serine-threonine kinase and member of the Pim family of proto-oncogenes, may function in cell proliferation, apoptosis, and male meiosis; reduced expression or gene deletions may have a role in cancer | 260 | 28% | 48% | 226 | 1e−18 |
| TNIK | NP_055843.1 | TNIK; KIAA0551; ZC2; Hs.170204 TRAF2 and NCK interacting kinase, a protein kinase that activates the c-Jun N-terminal kinase pathway and regulates the cytoskeleton | 279 | 29% | 47% | 239 | 2e−18 |
| CDC2 | NP_001777.1 | CDC2; CDK1; p34cdc2 Cell division cycle 2, cyclin-dependent protein kinase that binds B-type cyclins, regulates entry of mitosis and G2 to M-phase transition, promotes cell proliferation; implicated in Alzheimers disease through phosphorylation of amyloid beta and nucleolin | 299 | 26% | 46% | 225 | 3e−18 |
| TSSK6 | NP_114426.1 | TSSK6; SSTK Protein with high similarity to serine threonine kinase 22A (mouse Tssk1), which binds and phosphorylates mouse Stk22s1 and complexes with testis-specific serine kinase 2 (mouse Stk22b), contains a protein kinase domain | 251 | 26% | 49% | 218 | 4e−18 |
| MAPK12 | NP_002960.2 | MAPK12; p38g; SAPK3; ERK6; PRKM12; p38_gamma; P38GAMMA; SAPK-3; (ERK3) Stress activated protein kinase 3, a member of the stress activated protein kinase family, involved in cell cycle arrest and RHO protein signaling, may be involved in intracellular signaling in response to cellular stress | 166 | 31% | 55% | 216 | 4e−18 |
| MAP2K7 | NP_660186.1 | MAP2K7; MAPKK7; MKK7; PRKMK7; JNKK2; Jnkk2 Mitogen activated protein kinase kinase 7, a MAPK kinase that activates Jun N terminal protein kinase (MAPK8) in response to stress, involved in cytokine production, induction of apoptosis, and regulation of cell proliferation | 211 | 32% | 52% | 221 | 5e−18 |
| CDK5 | NP_004926.1 | CDK5; PSSALRE; NCLK Cyclin-dependent protein kinase 5, a serine-threonine kinase that binds regulatory subunit CDK5R1 and phosphorylates Tau (MAPT) and beta-catenin (CTNNB1), upregulation is associated with some diseases; inhibition may be therapeutic for Alzheimer disease | 295 | 25% | 42% | 218 | 5e−18 |
| PIM3 | NP_001001852.1 | PIM3; pim-3 Pim-3 oncogene, a putative serine-threonine protein kinase that regulates cell proliferation and apoptosis in hepatoma cell lines | 270 | 29% | 50% | 236 | 6e−18 |
| PAK4 | NP_005875.1 | PAK4; Hs.20447 p21 (CDKN1A)-activated kinase 4, PAK kinase family member that mediates | 259 | 27% | 49% | 221 | 6e−18 |

TABLE 6-continued

| Gene | GenBank | Synonyms/Description | Match Length | % Iden | % Sim | High Score | E Val |
|---|---|---|---|---|---|---|---|
| | | keratinocyte growth factor receptor (FGFR2) signaling, links activated CDC42 to the actin cytoskeleton and modulates filopodia formation, required for Ras-mediated cell transformation | | | | | |
| PFTK1 | NP_036527.1 | PFTK1; KIAA0834; PFTAIRE1 PFTAIRE protein kinase 1, a CDC2-related serine/threonine protein kinase, may be associated with postmitotic and differentiated state of cells in the nervous system, may function in the process of meiosis as well as neuron differentiation and function | 219 | 29% | 49% | 220 | 6e−18 |
| CAMKV | NP_076951.1 | CAMKV; 1G5; MGC8407; VACAMKL Protein with strong similarity to vesicle-associated calmodulin-binding protein (rat 1G5), which binds calmodulin and appears to lack kinase activity, contains a protein kinase domain | 274 | 25% | 48% | 219 | 8e−18 |
| TLK1 | NP_036422.3 | TLK1; (KIAA0137); PKU-BETA Tousled like kinase 1, a protein kinase that phosphorylates histones and chromatin assembly factors, may regulate chromatin structure, increases cell resistance to ionizing radiation | 429 | 26% | 44% | 250 | 1e−17 |
| TTN | NP_596869.2 | TTN; CMD1G; FLJ32040; (TMD); CMPD4; LGMD2J; CMH9; DKFZp451N061 Titin, a large sarcomeric protein that extends from Z-disk to M-line, maintains resting tension in muscle; autoantibodies are associated with myasthenia gravis, gene mutations are implicated in cardiomyopathy and muscular dystrophy | 302 | 28% | 47% | 240 | 1e−17 |
| CDKL4 | NP_001009565.1 | CDKL4 Protein with high similarity to cyclin-dependent kinase like 1 (CDC2-related kinase 1, human CDKL1), which is a protein serine/threonine kinase that phosphorylates histones and is upregulated in gliosis, contains a protein kinase domain | 200 | 28% | 50% | 212 | 1e−17 |
| CHUK | NP_001269.2 | CHUK; IKK1; NFKBIKA; TCF16; IKK-ALPHA; IKBKA; Hs.159147; IKK-alpha; IKKA Conserved helix-loop-helix ubiquitous kinase, I-kappaB kinase complex catalytic subunit, activates the NF-kappaB transcription factor, involved in keratinocyte differentiation and immune responses; inhibition may be therapeutic for prostate cancer | 305 | 29% | 44% | 222 | 2e−17 |
| GSK3A | NP_063937.2 | GSK3A; Hs.118890; DKFZp686D0638 Glycogen synthase kinase-3 alpha, a serine-threonine kinase that phosphorylates cytoplasmic and nuclear proteins; increased expression is associated with hepatocellular carcinoma | 369 | 22% | 40% | 221 | 2e−17 |
| MAP3K3 | NP_976226.1 | MAP3K3; MAPKKK3; MEKK3 Mitogen activated protein kinase kinase kinase 3, activates the SAPK and ERK pathways and regulates the cell cycle through cyclin D1 (CCND1) expression, selectively upregulated in hepatocellular carcinoma | 500 | 23% | 38% | 221 | 2e−17 |
| MAP2K4 | NP_003001.1 | MAP2K4; JNKK1; MEK4; PRKMK4; SERK1; MKK4; MAPKK4; SEK1; JNKK Mitogen-activated protein kinase kinase 4, involved in JNK and JAK-STAT cascades, mediates apoptosis and response to stress, may act as tumor suppressor; mouse Map2k4 is associated with models of Parkinson and Alzheimer diseases | 383 | 24% | 41% | 217 | 2e−17 |
| TLK2 | NP_006843.2 | TLK2; PKU-ALPHA; Hs.57553; MGC44450 Tousled-like kinase 2, member of the Tlk family of protein kinases, a serine-threonine kinase that exhibits DNA replication-dependent kinase activity that peaks during S-phase, may affect chromatin assembly | 282 | 30% | 50% | 245 | 3e−17 |
| MAPK14 | NP_620581.1 | MAPK14; p38a; CSBP1; CSBP2; CSPB1; PRKM14; PRKM15; (p38); (P38); MXI2; p38alpha; SAPK2a; Exip; EXIP; SAPK2A; p38ALPHA; (RK); Mxi2 Mitogen activated protein kinase 14, serine-threonine protein kinase, acts in signaling in response to cytokines and physiological stimuli, triggers apoptosis in response to stress; inhibition may be therapeutic for breast cancer | 277 | 25% | 47% | 215 | 3e−17 |
| MAP3K2 | NP_006600.2 | MAP3K2; MEKK; LOC51777; MEKK2B Mitogen-activated protein kinase kinase kinase 2, protein serine/threonine kinase, mediates T cell | 230 | 31% | 47% | 215 | 4e−17 |

TABLE 6-continued

| Gene | GenBank | Synonyms/Description | Match Length | % Iden | % Sim | High Score | E Val |
|---|---|---|---|---|---|---|---|
| | | receptor activation of JNK, but not ERK, signaling pathways, activates NF-kappa B and may modulate immune and inflammatory responses | | | | | |
| PCTK3 | NP_997668.1 | PCTK3; (PCTAIRE); PCTAIRE3 PCTAIRE protein kinase 3, a serine/threonine kinase that may be involved in the cell cycle | 221 | 29% | 49% | 213 | 4e−17 |
| PCTK2 | NP_002586.2 | PCTK2; PCTAIRE2 PCTAIRE protein kinase 2 (cdc2-related protein kinase 2), a serine-threonine protein kinase that may regulate transitions in cell cycle | 203 | 30% | 51% | 213 | 4e−17 |
| CDC2L2 | NP_277073.1 | CDC2L2; (PITSLRE); CDC2L3; p58GTA; Hs.169203; Hs.169201; Hs.183418; Hs.169202; Hs.194753; (CDK11-p46); (CDK11-p58); (CDK11-p110) Cell division cycle 2-like 2, a protein kinase of the PITSLRE subclass and p34 (cdc2) superfamily, acts in activated T-cell apoptosis, multiple isoforms result from alternate mRNA splicing; gene deletion is observed in some neuroblastomas and melanomas | 214 | 30% | 48% | 212 | 5e−17 |
| MAP3K1 | AAC97073.1 | MAP3K1; MEKK; MAPKKK1; MEKK1 MAP kinase kinase kinase 1, a protein kinase of the JNK-MAP kinase pathway that responds to stress signals, cytokines, and growth factors, caspase cleavage results in release of a pro-apoptotic fragment, may be involved in inclusion body formation | 286 | 28% | 45% | 226 | 6e−17 |
| IKBKB | NP_001547.1 | IKBKB; IKK-beta; IKKB; IKK2; NFKBIKB; Hs.166208; Hs.226573 Kinase beta of the Inhibitor of kappa light polypeptide gene enhancer in B-cells, subunit of the IkappaB kinase (IKK) complex, phosphorylation of IkappaB targets it for degradation and activates NF-kappaB, involved in immune response to pathogens | 216 | 31% | 49% | 215 | 6e−17 |
| GSK3B | NP_002084.2 | GSK3B Glycogen synthase kinase-3 beta, a serine-threonine protein kinase that regulates the stability of beta-catenin (CTNNB1) in Wnt signaling, involved in embryonic development, interacts with presenilin 1 (PSEN1) and may hyperphosphorylate tau (MAPT) | 208 | 29% | 49% | 211 | 6e−17 |
| MAP2K5 | NP_660144.1 | MAP2K5; MEK5; PRKMK5; MAPKK5; HsT17454 MAP kinase kinase 5, a member of the MAP kinase family that may participate in mitogenic signaling pathways, influences transcription mediated by AP-1 complex, positively modulates cell proliferation, upregulated in metastatic prostrate cancer | 321 | 25% | 40% | 213 | 9e−17 |
| MAPK11 | NP_620478.1 | MAPK11; SAPK2; p38-BETA; PRKM11; P38-2; P38BETA2; P38B; SAPK2B; P38BETA; p38-2 p38Beta Mitogen-activated protein kinase 11, activated by cytokines, stress, MAP2K6, and estradiol, mediates ATF2-dependent gene expression, phosphorylated in selenite-induced apoptosis of prostate cancer cells, may act in transendothelial tumor cell migration | 279 | 25% | 49% | 210 | 9e−17 |
| OXSR1 | NP_005100.1 | OXSR1; (OSR1); KIAA1101; Hs.95220 Oxidative-stress responsive 1, a serine-threonine kinase that binds and threonine phosphorylates p21 activated kinase 1 (PAK1) and is activated by osmotic stress | 300 | 27% | 45% | 217 | 1e−16 |
| MAP3K14 | NP_003945.1 | MAP3K14; (NIK); HSNIK; HS; FTDCR1B Mitogen-activated protein kinase kinase kinase 14 (NFKB-inducing kinase), serine/threonine protein kinase, interacts with TRAF family members, acts in signaling cascades common to receptors of TNF/NGF family; mutation of mouse Map3k14 causes alymphoplasia | 290 | 28% | 48% | 216 | 1e−16 |
| CDC2L1 | NP_001778.1 | CDC2L1; (PITSLRE); (CLK-1); p58CLK-1; p58CDC2L1; PK58; Hs.169204; (p58); (CDK11-p46); (CDK11-p58); (CDK11-p110) Cell division cycle 2 like 1, member of the p34 (CDC2) superfamily that contains a PSTAIRE box, protein kinase involved in apoptosis and cell cycle control; mutation of the corresponding gene is associated with non-Hodgkin lymphoma and melanoma | 201 | 31% | 49% | 208 | 1e−16 |

TABLE 6-continued

| Gene | GenBank | Synonyms/Description | Match Length | % Iden | % Sim | High Score | E Val |
|---|---|---|---|---|---|---|---|
| MINK1 | NP_722549.2 | MINK1; (MINK); B55; MAP4K6; ZC3; MGC21111; hMINK; hMINKbeta Misshapen/NIK-related kinase, a member of the germinal center kinase (GCK) family, may activate the cJUN N terminal kinase (JNK) and p38 MAP kinase pathways | 214 | 31% | 51% | 228 | 2e−16 |
| CDK10 | NP_003665.2 | CDK10; PISSLRE Cyclin dependent kinase 10, member of the CDK family of serine/threonine kinases, binds and inhibits the transcription factor ETS2, involved in cell proliferation, may regulate the G2/M phase of the cell cycle, upregulated in follicular lymphoma | 201 | 31% | 48% | 208 | 2e−16 |
| PCTK1 | NP_148978.1 | PCTK1; PCTGAIRE; PCTAIRE1; Hs.171834; (PCTAIRE) PCTAIRE protein kinase 1, a serine/threonine kinase with cell cycle-regulated activity, phosphorylated by protein kinase A and binds 14-3-3 gamma (YWHAG) and zeta (YWHAZ); gene mutation may be associated with X chromosome-linked heritable disorders | 200 | 30% | 50% | 217 | 3e−16 |
| ULK4 | AAH14794.1 | ULK4; FAM7C1; FLJ20574; REC01035; DKFZp434E1822 Protein containing a protein kinase domain, has low similarity to calcium:calmodulin-dependent protein kinase II alpha subunit (human CAMK2A), which acts in TGF-beta (human TGFB1) and EGF signal transduction pathways through phosphorylation events | 278 | 26% | 44% | 206 | 4e−16 |
| TNNI3K | NP_057062.1 | TNNI3K; CARK; HH498; LOC51086; Hs.414091 TNNI3 interacting kinase (cardiac ankyrin repeat kinase), a nuclear heart-specific kinase that binds troponin | 214 | 29% | 48% | 206 | 4e−16 |
| FLJ25006 | NP_653211.1 | FLJ25006; SgK494 Protein containing a protein kinase domain, has moderate similarity to a region of *C. elegans* CEH-20, which is a homeodomain transcription factor involved in mesoderm development, locomotion, and determination of life span | 172 | 34% | 56% | 233 | 6e−16 |
| RPS6KC1 | NP_036556.2 | RPS6KC1; RSKL1; RPK118; humS6PKh1 Ribosomal protein S6 kinase 52 kD polypeptide 1, a putative serine-threonine kinase that is likely a member of the ribosome protein S6 kinase family, may play a role in protein amino acid phosphorylation and signal transduction | 165 | 35% | 55% | 206 | 6e−16 |
| NEK9 | NP_149107.3 | NEK9; (NEK8); NERCC; MGC16714; DKFZp434D0935; Nek8; NERCC1 NIMA (never in mitosis gene a)-related kinase 9, a serine/threonine protein kinase that binds RAN and phosphorylates BICD2, NEK6, and NEK7, a component of the FACT complex which modulates chromatin structure associated with interphase progression | 261 | 27% | 45% | 205 | 6e−16 |
| NLK | NP_057315.2 | NLK; LOC51701 Nemo-like kinase, a putative protein kinase that localizes to the nucleus | 223 | 27% | 49% | 201 | 8e−16 |
| CDK6 | NP_001250.1 | CDK6; PLSTIRE; MGC59692 Cyclin dependent protein kinase 6, interacts with D-type cyclins and phosphorylates pRB in the G1-phase, involved in cell cycle control and cell proliferation; decreased expression or inhibition may be therapeutic for breast, colon, and lung cancer | 306 | 28% | 46% | 205 | 9e−16 |
| PASK | NP_055963.2 | PASK; STK37; PASKIN; KIAA0135; DKFZP434O051; Hs.79337; Hs.169311; DKFZp686P2031 PAS domain containing serine-threonine kinase, a serine:threonine kinase that contains two PAS domains, likely functions in intracellular signal transduction, may function in the perception of abiotic stimuli | 251 | 29% | 49% | 227 | 2e−15 |
| ERK8 | NP_620590.1 | ERK8; Erk7 Extracellular signal-regulated kinase 8, a serine/threonine kinase that binds to and is activated by SRC | 223 | 31% | 47% | 216 | 3e−15 |
| TTK | NP_003309.2 | TTK; MPS1L1; PYT; ESK; Hs.169840; LOC7272 Dual specificity serine/threonine and tyrosine kinase, may play a role in IL2-induced cell cycle progression of T cells, may play a role in cartilage homeostasis modulated by TNF alpha (TNF) | 283 | 28% | 48% | 205 | 3e−15 |
| TAOK1 | NP_065842.1 | TAOK1; PSK2; MARKK; MAP3K16; FLJ14314; KIAA1361 Protein with very strong similarity to | 264 | 29% | 43% | 199 | 3e−15 |

TABLE 6-continued

| Gene | GenBank | Synonyms/Description | Match Length | % Iden | % Sim | High Score | E Val |
|---|---|---|---|---|---|---|---|
| | | rat LOC286993, which associates with Mek3 (rat Map2k3) and is involved in regulating the p38-containing stress responsive MAP kinase pathway, contains a protein kinase domain and a protein tyrosine kinase domain | | | | | |
| MAPK7 | NP_620603.1 | MAPK7; BMK1; ERK5; PRKM7; ERK4 Mitogen activated protein kinase 7 (big mitogen activated protein kinase), a protein kinase that is involved in signal transduction and cell proliferation; decreased activity is associated with idiopathic dilated cardiomyopathy | 227 | 26% | 47% | 197 | 4e−15 |
| STK39 | NP_037365.1 | STK39; STLK3; DCHT; SPAK Serine-threonine kinase 39, a serine-threonine kinase of the STE20/SPS1 family, activates p38 kinase, induced by androgen, may play a role in androgen signaling, upregulated during progression of androgen-independent growth of prostate cancer cell lines | 217 | 29% | 46% | 198 | 6e−15 |
| RPS6KL1 | NP_113652.1 | RPS6KL1; RSKL2; MGC11287 Protein containing a protein kinase domain and an MIT domain, has a region of moderate similarity to a region of 90 kD ribosomal protein S6 kinase polypeptide 2 (mouse Rps6ka2), which is involved in glycogen synthesis and apoptosis and mast cell activation | 172 | 33% | 53% | 195 | 6e−15 |
| STK11 | NP_000446.1 | STK11; LKB1; PJS Serine threonine kinase 11, a kinase that mediates cell cycle arrest and apoptosis in a p53 (TP53)-dependent pathway; mutations in the corresponding gene cause Peutz-Jeghers syndrome, a hereditary susceptibility to tumor formation | 282 | 29% | 48% | 257 | 1e−14 |
| MAP4K4 | NP_663719.1 | MAP4K4; ZC1; HGK; (NIK); KIAA0687; FLH21957; FLJ20373 Mitogen-activated protein kinase kinase kinase kinase 4, a serine-threonine kinase, activates the c-Jun N-terminal kinase (MAPK8) signaling pathway, does not activate the ERK or p38 (CSBP1) kinase pathways, may be involved in TNF-alpha (TNF) signaling | 279 | 29% | 47% | 231 | 2e−14 |
| MAPK13 | NP_002745.1 | MAPK13; p38d; PRKM13; SAPK4; P38DELTA; p38delta; MGC99536 Mitogen activated protein kinase 13, a p38 MAP kinase that is activated by stress and proinflammatory cytokines, involved in regulation of gene expression in response to upstream regulatory signals | 204 | 29% | 50% | 189 | 2e−14 |
| HIPK1 | NP_938009.1 | HIPK1; Nbak2; KIAA0630; MGC26642; Hs.12259; Hipk1; MGC33446; MGC33548; Myak Protein with very strong similarity to homeodomain interacting protein kinase 1 (mouse Hipk1), which binds homeoproteins and serine phosphorylates mouse Trp53 and mouse Daxx and may act in tumorigenesis, contains a protein kinase domain | 251 | 28% | 47% | 195 | 3e−14 |
| DYRK1B | NP_004705.1 | DYRK1B; MIRK Dual-specificity tyrosine-phosphorylation regulated kinase 1B, phosphorylates threonine on histone H3, acts as a co-activator of transcription factor 1 (TCF1), may be involved in spermatogenesis and the abnormal neurogenesis of Down syndrome | 215 | 32% | 50% | 192 | 3e−14 |
| ALS2CR7 | NP_631897.1 | ALS2CR7; PFTAIRE2 Protein with high similarity to C. albicans Pho85p, which is a putative protein kinase involved in regulation of phosphate utilization, contains a protein kinase domain | 209 | 26% | 46% | 186 | 3e−14 |
| CDK9 | NP_001252.1 | CDK9; PITALRE; CDC2L4; TAK; C-2k Cyclin-dependent kinase 9, binds cyclin T to form the transcription elongation factor P-TEFb, which hyperphosphorylates the carboxy-terminal domain of the RNA polymerase II subunit POLR2A, interacts with HIV-1 Tat to activate viral transcription | 234 | 27% | 46% | 188 | 4e−14 |
| MAPK8 | NP_620637.1 | MAPK8; JNK; JNK1; SAPK1; PRKM8; JNK1A2; SAPK; JNK21B1_2 Mitogen activated protein kinase 8, a serine-threonine kinase that regulates c-Jun (JUN), acts in receptor signaling, cell growth and differentiation, apoptosis, and response to stressors such as DNA damage, reactive oxygen, hypoxia and rRNA damage | 203 | 29% | 49% | 186 | 5e−14 |

TABLE 6-continued

| Gene | GenBank | Synonyms/Description | Match Length | % Iden | % Sim | High Score | E Val |
|---|---|---|---|---|---|---|---|
| MGC4796 | NP_114406.1 | MGC4796; SgK495; SHIK SINK homologous serine-threonine kinase, a putative serine-threonine kinase that negatively regulates transcription mediated by NFKB1 and TP53 | 319 | 26% | 44% | 190 | 7e-14 |
| HIPK3 | NP_005725.2 | HIPK3; PKY; DYRK6; YAK1 Homeodomain interacting protein kinase 3, a serine/threonine protein kinase that interacts with homeodomain transcription factors, inhibits JNK activation, may be involved in apoptosis and cell growth regulation, overexpressed in multidrug-resistant cells | 206 | 29% | 49% | 187 | 9e-14 |
| CDC2L6 | NP_055891.1 | CDC2L6; CDK11; KIAA1028; bA346C16.3 Cyclin-dependent kinase 11, a component of the Mediator transcriptional coactivator complex that is required for induction of RNA polymerase II transcription | 418 | 23% | 38% | 192 | 1e-13 |
| TAOK3 | NP_057365.2 | TAOK3; (DPK); JIK; MAP3K18; DKFZp666H245 STE20-like kinase (JNK-SAPK inhibitory kinase), a serine/threonine kinase and member of the GCK-like subfamily of Ste20 kinases, activated by ligand-bound EGF receptors, inhibits the JNK/SAPK signaling pathway, also interacts with IRE1a (ERN1) | 264 | 28% | 42% | 186 | 1e-13 |
| TAOK2 | NP_057235.2 | TAOK2; PSK; PSK1; TAO1; TAO2; MAP3K17; KIAA0881; Hs.66141 Thousand and one amino acid protein kinase, exhibits MAPKKK and microtubule binding activity, acts in muscarinic acetylcholine receptor signaling pathway, microtubule stabilization, and regulation of cell shape | 249 | 29% | 44% | 186 | 1e-13 |
| DYRK3 | NP_003573.2 | DYRK3; Hs.164267; (RED); REDK; DYRK5 Dual-specificity tyrosine-(Y)-phosphorylation regulated kinase 3, tyrosine autophosphorylated, phosphorylates histone H2B and H3, may function in spermatogenesis | 207 | 28% | 51% | 183 | 1e-13 |
| LIMK1 | NP_002305.1 | LIMK1; LIMK LIM domain kinase 1, a serine-threonine kinase that mediates signaling from Rho to the actin cytoskeleton via phosphorylation of cofilin (CFL1), involved in T cell chemotaxis, activated during mitosis, may be involved in Williams syndrome | 224 | 23% | 47% | 181 | 2e-13 |
| CSK | NP_004374.1 | CSK; CYL C-src tyrosine kinase, a protein tyrosine kinase with SH2 and SH3 domains, inactivates the c-src (SRC) oncoprotein, regulates receptor signaling pathways and possibly T-cell activation, and acts as a tumor antigen in carcinomas | 228 | 27% | 45% | 180 | 2e-13 |
| NEK10 | NP_689747.2 | NEK10; FLJ32685; LOC375328 Protein containing a protein kinase domain, has weak similarity to serine threonine kinase 3 (mouse Stk3), which is a protein kinase that is induced by cell stress and by entry into G0 phase from M phase | 130 | 35% | 55% | 178 | 2e-13 |
| TRIB2 | NP_067675.1 | TRIB2; (TRB2); GS3955; Hs.155418 Protein with high similarity to phosphoprotein regulated by mitogenic pathways (human TRIB1), which is a putative protein kinase possibly induced by mitogenic signaling pathways that interacts with and may regulate human ALOX12 | 219 | 26% | 44% | 179 | 3e-13 |
| HIPK4 | NP_653286.2 | HIPK4; FLJ32818 Protein containing a protein kinase domain, has a region of high similarity to a region of homeodomain interacting protein kinase 2 (human HIPK2), which binds to and represses the transcriptional activity of homeodomain proteins | 227 | 27% | 50% | 183 | 4e-13 |
| ICK | NP_057597.2 | ICK; LCK2; (KIAA0936); MRK; MGC46090 Intestinal cell kinase, a putative serine/threonine kinase that contains a MAP kinase-like dual phosphorylation site which may be necessary for activity | 197 | 27% | 48% | 178 | 4e-13 |
| IKBKE | NP_054721.1 | IKBKE; IKKE; IKKI; KIAA0151; IKK-i IkappaB epsilon protein kinase, member of IkappaB kinase complex, induced by lipopolysaccharide and TNF, involved in developing endotoxin tolerance, constitutively expressed in synovial cells of patients with rheumatoid arthritis and osteoarthritis | 233 | 27% | 44% | 179 | 7e-13 |

TABLE 6-continued

| Gene | GenBank | Synonyms/Description | Match Length | % Iden | % Sim | High Score | E Val |
|---|---|---|---|---|---|---|---|
| RAGE | NP_055041.1 | RAGE; MOK; RAGE1 Renal tumor antigen, a member of the MAP kinase superfamily, a serine threonine protein kinase containing the classic MAP kinase TEY motif, may play a role in signal transduction, may be a target for T-cell-based immunotherapy of renal cell carcinoma | 214 | 28% | 48% | 177 | 7e–13 |
| | | Compared with *M. musculus* protein sequences (Documentation) | | | | | |
| Akt1 | NP_033782.1 | Akt1; Akt; (PKB); PKB_Akt; Mm.6645; PKBalpha Thymoma viral proto-oncogene 1, serine-threonine protein kinase involved in insulin signaling, glucose metabolism, and cell survival and differentiation; human AKT1 is upregulated in breast, prostate, and ovarian cancers | 318 | 49% | 69% | 767 | 4e–82 |
| Akt2 | NP_031460.1 | Akt2; Mm.8901; (PKB); PKBbeta; 2410016A19Rik; MGC14031 v-akt thymoma viral oncogene homolog 2, a putative serine/threonine kinase that plays a role in apoptosis, glucose transport and glucose metabolism, may regulate cell differentiation; human AKT2 is associated with ovarian, breast and pancreatic cancers | 302 | 49% | 70% | 764 | 6e–82 |
| Akt3 | NP_035915.2 | Akt3; D930002M15Rik Protein kinase B gamma, a protein kinase that is activated by insulin; human AKT3 insulin-induced activity is upregulated in estrogen receptor negative breast cancer and androgen insensitive prostrate carcinoma | 299 | 49% | 70% | 759 | 2e–81 |
| Rps6kb2 | NP_067460.1 | Rps6kb2; (S6K2); Mm.20917; (70 kDa) Ribosomal protein S6 kinase 2 (p70 ribosomal S6 kinase beta), rapamycin-sensitive member of the RSK family that plays a role in signal transduction and translational regulation | 347 | 46% | 63% | 748 | 1e–79 |
| Sgk3 | NP_573483.1 | Sgk3; Cisk; 2510015P22Rik; A330005P07Rik Serum/glucocorticoid regulated kinase 3 (cytokine-independent survival kinase), activated by Egf and Igf1 via PX domain-mediated phosphatidylinositol 3-phosphate binding and endosomal localization, promotes Il3-dependent survival of hematopoietic cells | 346 | 43% | 61% | 714 | 6e–76 |
| Sgk2 | NP_038759.1 | Sgk2; SGK2; Sgk1 Serum-glucocorticoid regulated kinase 2, a putative serine-threonine kinase | 343 | 43% | 64% | 719 | 1e–75 |
| Prkacb | NP_035230.1 | Prkacb; Pkacb; Mm.16766 Protein kinase cAMP-dependent catalytic beta, required for long-term potentiation in the Schaffer collateral CA1 pathway and the mossy fiber pathway, acts in fear response; human PRKACB is associated with hyperphosphorylation of tau in Alzheimer disease | 312 | 46% | 66% | 701 | 1e–74 |
| Prkaca | NP_032880.1 | Prkaca; Pkaca; Mm.19111; (Cs); PKA Protein kinase cAMP-dependent catalytic alpha, plays a role in growth and sperm motility, reduced activity causes neural tube defects that lead to spina bifida; human PRKACA may serve as a tumor biomarker | 313 | 45% | 66% | 691 | 2e–73 |
| Prkch | NP_032882.2 | Prkch; Pkch; Mm.8040; nPKC_eta Protein kinase C eta, a Ca2+-independent isoform of protein kinase C, induces apoptosis and cell cycle arrest, regulates cytoskeleton, mediates phorbol ester-induced interleukin-2 (Il2) production, may act in epithelial cell growth and differentiation | 340 | 40% | 63% | 677 | 2e–71 |
| Sgk | NP_035491.1 | Sgk; Sgk1 Serum glucocorticoid regulated kinase, a putative serine/threonine protein kinase, may increase aldosterone-induced sodium absorption in the renal duct, upregulated in response to osmotic stress | 337 | 45% | 64% | 729 | 5e–71 |
| Rps6ka5 | NP_705815.1 | Rps6ka5; Msk1; LOC73086; Mm.220417; 3110005L17Rik; MGC28385; 6330404E13Rik; MSK1; RLPK; MSPK1 Ribosomal protein S6 kinase A5, a serine-threonine kinase activated by the Erk and p38 MAP kinases, phosphorylates histones and activates the Creb1 transcription factor in | 375 | 41% | 61% | 676 | 1e–70 |

TABLE 6-continued

| Gene | GenBank | Synonyms/Description | Match Length | % Iden | % Sim | High Score | E Val |
|---|---|---|---|---|---|---|---|
| | | response to mitogenic stimulus, also mediates UV induced activation of Akt1 | | | | | |
| Rps6ka4 | NP_064308.1 | Rps6ka4; Msk2; mMSK2; Mm.20914; MSK2; 1110069D02Rik; (90 kDa) Ribosomal protein S6 kinase polypeptide 4 (mitogen- and stress-activated protein kinase 2), may be involved in the activation of transcription factors and the MAP kinase pathway, required for stress-induced phosphorylation of CREB (Creb1) and Atf1 | 352 | 42% | 62% | 672 | 2e−70 |
| Prkcl | NP_032883.1 | Prkcl; Pkcl; Mm.4801; 2310021H13Rik; (Prkci); (Pkci); mKIAA4165; KIAA4165 Protein kinase C lambda, an atypical protein kinase C that binds cytoskeletal proteins, functions in transcription regulation, neuronal survival, glucose transport, response to UV light and insulin receptor (Insr) signaling | 346 | 38% | 62% | 645 | 1e−67 |
| Rps6ka3 | NP_683747.1 | Rps6ka3; Rsk2; MPK-9; pp90RSK2; S6K-alpha3 Ribosomal protein S6 kinase polypeptide 3, a serine-threonine kinase required for activation of Elk1 and serum response transcription factors, phosphorylates Creb1; mutations in the human RPS6KA3 gene cause Coffin-Lowry syndrome | 344 | 46% | 62% | 700 | 5e−67 |
| Rps6ka2 | NP_035429.1 | Rps6ka2; Mm.32033; Rsk3; pp90rsk; (S6K2); (90 kDa); Rps6ka-rs1; (p90rsk); D17Wsu134e; LOC436439 90 kD ribosomal protein S6 kinase polypeptide 2, protein kinase activated in response to insulin or heat shock, plays a role in JNK-mediated activation of glycogen synthase, p53 (Tp53)-mediated apoptosis and mast cell activation | 344 | 45% | 62% | 698 | 5e−67 |
| Prkcb1 | NP_032881.1 | Prkcb1; Pkcb; Prkcb; Mm.4182; PKC-betaII; PKC-betaI; Pkcb2; PkcbetaII; A130082F03Rik Protein kinase C beta 1, regulates glucose import and proliferation; expression of human PRKCB1 is altered in ALS, colon adenoma, heart failure, Huntington's disease and diabetic nephropathy, rat Prkcb1 is involved in diabetic nephropathy | 346 | 38% | 60% | 637 | 1e−66 |
| Prkca | NP_035231.1 | Prkca; Pkca; Mm.1266; PKC-alpha Protein kinase C alpha isoform, important for cellular signaling, regulates cell proliferation and migration, plays a role in Rho protein signal transduction, and may be involved in triggering cardiac hypertrophy | 612 | 29% | 47% | 634 | 7e−66 |
| Rps6ka1 | NP_033123.1 | Rps6ka1; Mm.29910; rsk; Rsk1; (p90rsk) Ribosomal protein S6 kinase 1, a mitogen activated serine-threonine protein kinase, acts in response to proliferative and stress signals (including hydrogen peroxide and UV radiation); human RPS6KA1 may be hyperphosphorylated in lung neoplasms | 367 | 40% | 59% | 629 | 3e−65 |
| Prkcz | NP_032886.1 | Prkcz; Pkcz; Mm.28561; zetaPKC; R74924; C80388 Protein kinase C zeta, an atypical serine-threonine kinase that regulates the activity of numerous signaling pathways and modulates a wide variety of cellular events; decreased expression of human PRKCZ correlates with insulin resistance in diabetes | 344 | 38% | 61% | 624 | 4e−65 |
| Pkn1 | NP_796236.2 | Pkn1; DBK; Pkn; PAK1; PRK1; (Stk3); Prkcl1; F730027O18Rik; PKN Protein kinase N1, involved in Rho-mediated retraction of neurite extensions, may play a role in the response to heat stress | 333 | 42% | 62% | 669 | 1e−64 |
| Rps6ka6 | NP_080225.1 | Rps6ka6; 2610524K04Rik; RSK4 Ribosomal protein S6 kinase polypeptide 6, a predicted protein kinase that is an inhibitor of the fibroblast growth factor-RAS-extracellular signal-regulated kinase pathway, may play a role in embryonic development | 344 | 44% | 62% | 668 | 2e−63 |
| Pkn2 | NP_848769.1 | Pkn2; PRK2; Stk7; Prkcl2; 6030436C20Rik; PRKCL2 Protein kinase N2, a putative serine-threonine kinase that binds SH3 domains, may play a role in Rho-GTP signal transduction | 344 | 42% | 60% | 651 | 4e−62 |

TABLE 6-continued

| Gene | GenBank | Synonyms/Description | Match Length | % Iden | % Sim | High Score | E Val |
|---|---|---|---|---|---|---|---|
| Prkcq | NP_032885.1 | Prkcq; Pkcq; PKC-0; Mm.2921; A130035A12Rik; PKC-theta Protein kinase C theta, may regulate mitosis, preadipocyte differentiation and spermatogenesis; human PRKCQ may have roles in insulin and multidrug resistance and rat Pkcq may have roles in hyperglycemia, hypertriglyceridemia and insulin resistance | 332 | 38% | 61% | 619 | 5e−61 |
| Prkcc | NP_035232.1 | Prkcc; Pkcc; PKCgamma; Mm.7980; PKC-gamma Gamma isoform of protein kinase C, involved in cellular signaling, mediates neuropathic pain syndrome; increased expression of human PRKCG is associated with various cancers; increased proteolysis of human PRKCG may be associated with Alzheimer disease | 339 | 40% | 60% | 626 | 1e−60 |
| Prkcd | NP_035233.1 | Prkcd; D14Ertd420e; Pkcd; Mm.2314; PKC[d]; PKCdelta Protein kinase C delta, calcium-independent serine-threonine kinase, promotes apoptosis of keratinocytes, mediates transmembrane receptor signals controlling cell proliferation and differentiation | 334 | 38% | 61% | 612 | 2e−60 |
| Prkce | NP_035234.1 | Prkce; Pkce; PKC[e]; Mm.12808; R75156; 5830406C15Rik Protein kinase C epsilon, diacylglycerol-activated:phospholipid dependent isoform of PKC, involved in cell growth, may be involved in apoptosis; altered expression or localization of human PRKCE correlates with various neoplasms and Alzheimer disease | 345 | 39% | 61% | 646 | 3e−60 |
| Pkn3 | NP_722500.1 | Pkn3; MGC31699 Protein with strong similarity to protein kinase PKNbeta (human PKN3), which binds human GRAF and phospholipase D1 (human PLD1), member of the Hr1 repeat and protein kinase C-terminal domain containing families, contains a protein kinase domain | 339 | 39% | 58% | 600 | 7e−60 |
| Prkx | NP_058675.1 | Prkx; Pkare; PKX1 Protein kinase X-linked, putative cAMP-dependent protein kinase catalytic subunit that may be involved in a cAMP-mediated signaling pathway linked to neurogenesis; gene recombination between human PRKX and human PRKY causes Swyer's syndrome | 302 | 41% | 63% | 588 | 6e−58 |
| Adrbk1 | NP_570933.1 | Adrbk1; BARK1; Grk2; Bark-1; Adrbk-1; GRK2; (Ark); GRK-2; betaARK1 Beta-adrenergic receptor kinase 1, a kinase that may mediate desensitization of G protein-coupled receptors, modulates myocardial function and involved in cardiomyopathy; human ADRBK1 may be associated with hypertension and cardiomyopathy | 388 | 35% | 53% | 552 | 7e−57 |
| Adrbk2 | NP_796052.1 | Adrbk2; Gprk3; Grk3; 4833444A01Rik; GRK3; Bark-2; Adrbk-2 Beta adrenergic receptor kinase 2, member of a family of protein kinases that specifically phosphorylate activated G protein-coupled receptors, resulting in receptor desensitization, likely regulates cardiac function, respiration, analgesia and olfaction | 310 | 39% | 57% | 544 | 3e−56 |
| Stk38 | NP_598876.1 | Stk38; 5830476G13Rik; 9530097A09Rik; Mm.183034; (Ndr1) Protein with very strong similarity to serine/threonine kinase 38 (human STK38), which is a protein serine or threonine kinase, member of the protein kinase C-terminal domain containing family, contains a protein kinase domain | 371 | 35% | 55% | 531 | 4e−54 |
| Stk38l | NP_766322.1 | Stk38l; Ndr54; B230328I19; 4930473A22Rik; (Ndr2) Protein with strong similarity to serine/threonine kinase 38 (human STK38), which is a serine/threonine kinase that is regulated by calcium concentrations, member of the protein kinase C-terminal domain containing family, contains a protein kinase domain | 345 | 33% | 57% | 518 | 1e−52 |
| Stk32a | NP_848864.1 | Stk32a; YANK1; A930015B13Rik Protein containing a protein kinase domain, has low | 300 | 37% | 59% | 514 | 2e−52 |

TABLE 6-continued

| Gene | GenBank | Synonyms/Description | Match Length | % Iden | % Sim | High Score | E Val |
|---|---|---|---|---|---|---|---|
| | | similarity to catalytic subunit C alpha of cAMP-dependent protein kinase (human PRKACA), which acts in transcriptional regulation that may mediate apoptosis suppression and may act in sperm development | | | | | |
| Cdc42bpb | NP_898837.1 | Cdc42bpb; (DMPK-like) Protein with strong similarity to rat Cdc42bpb, which is a protein kinase, member of the CNH domain and protein kinase C-terminal families, contains protein kinase, pleckstrin homology, P21-Rho-binding and phorbol ester or diacylglycerol binding domains | 352 | 37% | 58% | 514 | 5e−51 |
| Stk32c | NP_067277.1 | Stk32c; PKE; Pkek; YANK3; Pke; LOC57740 Protein containing a protein kinase domain, has low similarity to *S. cerevisiae* Tpk2p, which is the catalytic subunit of cAMP-dependent protein kinase 2, protein kinase A or PKA | 325 | 34% | 58% | 495 | 8e−50 |
| Prkg2 | NP_032952.2 | Prkg2; Mm.44410; CGKII; Prkgr2 Protein kinase, cGMP-dependent type II, localizes to the apical plasma membrane amd may regulate intestinal ion transport and fluid secretion | 297 | 38% | 57% | 491 | 1e−49 |
| Mast1 | NP_064329.1 | Mast1; SAST; SAST170; 9430008B02Rik; Sast Syntrophin-associated serine/threonine kinase, interacts with syntrophins via PDZ domains, associates with microtubules and microtubule-associated proteins, may link the dystrophin (Dmd) - utrophin (Utrn) network with microtubule filaments | 318 | 37% | 58% | 549 | 2e−49 |
| Pdpk1 | NP_035192.1 | Pdpk1; Mm.10504; (Pdk1) 3-phosphoinositide-dependent protein kinase-1, phosphorylates and activates protein kinase B (Akt), p70 and p90 ribosomal S6 kinases, PKC zeta (Prkcz), mediates actin reorganization in response to insulin, required for normal embryonic development | 311 | 38% | 58% | 489 | 3e−49 |
| Stk32b | NP_071861.1 | Stk32b; STKG6; Stk32; YANK2; 2510009F08Rik Protein containing a protein kinase domain, has low similarity to *S. cerevisiae* Tpk3p, which is a catalytic subunit of cAMP-dependent protein kinase 3, protein kinase A or PKA | 338 | 35% | 57% | 486 | 7e−49 |
| Lats1 | AAD16883.1 | Lats1 Large tumor suppressor 1, a putative protein kinase, regulates cell proliferation and cell cycle, involved in endocrine system function and tumor growth inhibition | 467 | 31% | 48% | 491 | 1e−48 |
| Mast2 | NP_032667.1 | Mast2; Mtssk; MAST205; Mm.9287; mKIAA0807 Microtubule associated testis specific serine-threonine protein kinase, may be involved in the organization of manchette microtubules in spermatids, may have a role in spermatid maturation | 321 | 36% | 57% | 537 | 4e−48 |
| Dm15 | NP_115794.1 | Dm15; Mm.6529; DMPK; DM; Mm.34648 Dystrophia myotonica kinase B15, a protein kinase that may act in muscle contraction and myoblast differentiation, associated with progressive myopathy; trinucleotide repeat expansion in human DMPK gene is associated with myotonic dystrophy | 306 | 38% | 58% | 484 | 1e−47 |
| Lats2 | NP_056586.1 | Lats; 4932411G09Rik Large tumor suppressor 2, a putative protein kinase that is member of a subfamily of protein kinases that includes Lats1; human LATS2 gene may be inactivated in a minority of esophageal squamous cell carcinomas | 437 | 33% | 45% | 471 | 1e−46 |
| Grk1 | NP_036011.1 | Grk1; RK; Rhok; GPRK1; GRK1 Rhodopsin kinase, may regulate desensitization of the G protein-coupled receptor rhodopsin by phosphorylating it following stimulation by light; mutation of human RHOK causes Oguchi disease, a form of stationary night blindness | 304 | 40% | 58% | 497 | 5e−46 |
| Rock1 | NP_033097.1 | Rock1; P160ROCK1; Mm.6710; Rock-I; 1110055K06Rik Rho-associated coiled-coil containing kinase 1, binds Rho, acts in actin cytoskeleton organization, axon outgrowth, | 361 | 34% | 57% | 485 | 1e−45 |

TABLE 6-continued

| Gene | GenBank | Synonyms/Description | Match Length | % Iden | % Sim | High Score | E Val |
|---|---|---|---|---|---|---|---|
| | | growth cone dynamics, neurite retraction and cell rounding, and membrane blebbing; human ROCK1 is upregulated in pancreatic cancer | | | | | |
| Prkg1 | NP_035290.1 | Prkg1; CGKI; Prkgr1b; Prkg1b; LOC381235 cGMP-dependent protein kinase type 1, relaxes vascular smooth muscle and inhibits platelet aggregation, involved in penile erection; human PRKG1 may be associated with hypertension and atherosclerosis | 297 | 38% | 58% | 508 | 4e-44 |
| Aurka | NP_035627.1 | Aurka; IAK; Ark1; Ayk1; Stk6; AIRK1; Aurora-A; Mm.11738 Serine-threonine kinase 6 (centrosome-associated serine-threonine kinase), a putative protein kinase that may be involved in the control of chromosome segregation during meiosis and mitosis | 271 | 36% | 55% | 424 | 4e-42 |
| Rock2 | NP_033098.1 | Rock2; p160_ROCK-2; Mm.35815; Rock-II; B230113H15Rik; mKIAA0619 Rho-associated coiled-coil containing protein kinase 2, a serine-threonine protein kinase that binds RhoA (mouse Arha2), regulates myosin phosphatase and may be involved in neurogenesis and organogenesis | 347 | 35% | 57% | 484 | 1e-41 |
| Camk1g | NP_659066.1 | Camk1g; MGC30513; CLICK-III Calcium/calmodulin-dependent protein kinase I gamma, a membrane-anchored neuronal Ca2+/calmodulin-dependent protein kinase | 395 | 30% | 49% | 421 | 8e-41 |
| Gprk5 | NP_061357.2 | Gprk5; Mm.10188; GRK5 G protein-coupled receptor kinase 5, a protein kinase regulating G protein-coupled receptor desensitization by phosphorylating agonist-stimulated receptors, including muscarinic receptors, regulates cardiac function, thermoregulation and pain perception | 307 | 37% | 56% | 447 | 2e-40 |
| Aurkc | NP_065597.1 | Aurkc; AIE1; AIK3; Stk13; Mm.12877 Putative serine/threonine kinase, may be involved in chromosome segregation and spermatogenesis | 284 | 33% | 51% | 399 | 3e-39 |
| Aurkb | NP_035626.1 | Aurkb; Aik2; (Aim1); Ark2; AurB; IPL1; Stk5; AIM-1; AIRK2; STK-1; (Stk12); Mm.3488 Serine threonine kinase 12, may function in cytokinesis and megakaryocyte differentiation, localizes to the midbody; upregulation of human STK12 may cause abnormal cytokinesis and ploidy in colorectal and other neoplasms | 284 | 34% | 52% | 393 | 3e-38 |
| Gprk2l | NP_062370.1 | Gprk2l; Mm.10312; GRK; Gprk4; Grk4; GRK4; A830025H08Rik G protein-coupled receptor kinase 4, may regulate desensitization of G protein-coupled receptors by phosphorylating activated receptors; variation in human GPRK2L is associated with essential hypertension | 299 | 37% | 55% | 441 | 4e-38 |
| Cit | NP_031734.1 | Cit; Mm.8321; CRIK; CRIK-SK; Citron-K; citron-N; Cit-k Citron Rho interacting kinase, a serine/threonine kinase of the myotonic dystrophy kinase family, binds to Rho and Rac and mediates cytoskeletal reorganization | 319 | 38% | 56% | 463 | 1e-37 |
| Pnck | NP_036170.1 | Pnck; (Punc); Bstk3; Camk1b; CaMKlb2; caMKlb1 Pregnancy upregulated non-ubiquitously expressed CaM kinase, a putative calcium and calmodulin-dependent protein kinase, may function in central nervous system and mammary gland development; human PNCK may have a role in mammary gland carcinogenesis | 250 | 33% | 56% | 379 | 4e-37 |
| Stk36 | NP_778196.1 | Stk36; FU; MGC58023; B930045J24; 1700112N14Rik; STK36 Serine/threonine kinase 36 (fused homolog, *Drosophila*), may function in hedgehog signaling | 268 | 35% | 58% | 379 | 9e-36 |
| Camk4 | NP_033923.1 | Camk4; Mm.2951; CaMKIV_Gr; CaMKIV; Calspermin; A430110E23Rik Calcium/calmodulin-dependent protein kinase IV, a putative protein kinase involved in Ca(2+)-regulated gene expression, including Creb1-induced gene expression; alternate splicing forms calspermin, a testis-specific calmodulin-binding protein | 253 | 39% | 59% | 373 | 1e-35 |

TABLE 6-continued

| Gene | GenBank | Synonyms/Description | Match Length | % Iden | % Sim | High Score | E Val |
|---|---|---|---|---|---|---|---|
| Dcamkl3 | NP_766516.1 | Dcamkl3; BC056929; C730036H08 Protein containing a protein kinase domain, has low similarity to skeletal muscle myosin light chain kinase (human MYLK2), which phosphorylates myosin regulatory light chains and is associated with early-onset hypertrophic cardiomyopathy upon mutation | 268 | 33% | 56% | 373 | 1e-35 |
| Camk1d | NP_796317.1 | Camk1d; CKLiK; A630059D12Rik; E030025C11Rik; CAMK1D; Mm.44142 Calcium/calmodulin dependent protein kinase ID, a predicted calcium/calmodulin-dependent protein kinase, expression in liver is downregulated by dietary cholesterol through transcription factors Srebf1 and Srebf2 | 268 | 35% | 56% | 394 | 3e-35 |
| Stk33 | CAC39171.1 | Stk33; 4921505G21Rik Serine-threonine protein kinase 33, a putative serine-threonine kinase that may be a member of the calcium/calmodulin-dependent protein kinase family | 259 | 34% | 56% | 364 | 4e-35 |
| 1200013B22Rik | NP_083054.1 | 1200013B22Rik; Snark; mKIAA0537 Protein with strong similarity to SNF1/AMP-activated protein kinase (human SNARK), which exhibits AMP-dependent protein kinase activity and enhances cell survival during glucose starvation, contains protein kinase and protein tyrosine kinase domains | 261 | 34% | 56% | 372 | 1e-34 |
| Camk1 | NP_598687.1 | Camk1; D6Ertd263e Protein with very strong similarity to calcium-calmodulin dependent protein kinase I (rat Camk1), which is a calcium-calmodulin dependent protein kinase that functions in protein kinase signaling cascades, contains a protein kinase domain | 270 | 35% | 56% | 382 | 2e-34 |
| 4921509C19Rik | NP_941057.1 | 4921509C19Rik; Gm1005; LOC381393 Protein containing a protein tyrosine kinase domain, has low similarity to mouse MARK2, which is a putative serine-threonine kinase that may be involved in the control of cell polarity | 248 | 38% | 53% | 358 | 4e-34 |
| E130304F04Rik | NP_780747.1 | E130304F04Rik Protein containing a protein kinase domain and a protein tyrosine kinase domain, has low similarity to mouse Akt3, which is a protein kinase that is activated by insulin (mouse Ins1) and exhibits increased activity in breast, prostate, and ovarian cancers | 286 | 32% | 49% | 343 | 2e-32 |
| Mark4 | NP_758483.1 | Mark4; MARK4; Mark11; 2410090P21Rik MAP/microtubule affinity-regulating kinase 4, a protein serine/threonine kinase that is involved in the response to permanent focal cerebral ischemia; human MARK4 is upregulated in hepatocellular carcinoma, primary glioma and glioblastoma cell lines | 251 | 34% | 53% | 342 | 3e-32 |
| Camk2g | NP_848712.1 | Camk2g; CaMK-II; Camkg; 5930429P18Rik Protein with high similarity to Ca2+/calmodulin-dependent protein kinase II alpha (rat Camk2a), which is involved in TGF-beta (Tgfb1) receptor signaling and may be important for regulation of neuronal excitability, contains a protein kinase domain | 257 | 34% | 54% | 341 | 3e-32 |
| BC033915 | NP_081774.2 | BC033915; LOC270153; 5730525O22Rik; mKIAA0999; MGC90906; MGC91236 Protein with strong similarity to human KIAA0999, which is a protein kinase that phosphorylates the AMARA, LNR, and SAMS peptides and can be activated by human STK11-mediated phosphorylation, contains a protein kinase and protein tyrosine kinase domain | 306 | 31% | 49% | 344 | 8e-32 |
| Mark2 | NP_031954.1 | Mark2; Emk; Par-1; MARK2; mKIAA4207; KIAA4207 ELKL motif kinase (microtubule/MAP-affinity regulating kinase), a putative serine/threonine kinase of the EMK kinase family, may have roles in the control of cell polarity; human MARK2 may be associated with cancer | 251 | 33% | 54% | 337 | 1e-31 |
| Mark3 | NP_067491.1 | Mark3; ETK-1; Emk2; 1600015G02Rik; mKIAA1860; A430080F22Rik Protein with strong similarity to human MARK3, which acts in DNA damage checkpoint, contains a | 251 | 33% | 54% | 336 | 1e-31 |

TABLE 6-continued

| Gene | GenBank | Synonyms/Description | Match Length | % Iden | % Sim | High Score | E Val |
|---|---|---|---|---|---|---|---|
| | | UBA (ubiquitin associated) or TS-N domain, a protein kinase domain, a C-terminal kinase associated domain 1 and a protein tyrosine kinase domain | | | | | |
| Dcamkl2 | NP_081815.3 | Dcamkl2; 6330415M09Rik Protein with strong similarity to doublecortin kinase 2 (rat RGD1308384), which is a protein kinase that binds microtubules and stabilizes the cytoskeleton against depolymerization, member of the doublecortin family, contains a protein kinase domain | 315 | 30% | 50% | 340 | 2e−31 |
| Mark1 | NP_663490.1 | Mark1; Emk3; B930025N23Rik; mKIAA1477; KIAA1477 Protein with very strong similarity to rat Mark1, which is a serine/threonine kinase, contains a C-terminal kinase associated domain 1, a protein kinase domain, a protein tyrosine kinase domain and a UBA (ubiquitin associated) or TS-N domain | 251 | 34% | 54% | 334 | 3e−31 |
| Prkaa2 | NP_835279.1 | Prkaa2; (AMPK); PRKAA; 2310008I11Rik; A830082D05 Catalytic alpha 2 subunit of the 5′-AMP-activated protein kinase, a metabolic sensor of AMP levels, involved in fatty acid beta-oxidation and stimulates glucose transport during exercise, activated by the anti-diabetic drugs, rosiglitazone and metformin | 257 | 33% | 54% | 332 | 7e−31 |
| Dcamkl1 | NP_064362.1 | Dcamkl1; Cpg16; DCLK; CPG16; 1700113D08Rik; mKIAA0369; 2810480F11Rik Doublecortin and calcium-calmodulin-dependent protein kinase-like 1, a protein kinase that may play a role in central nervous system development, contains a kinase domain and a doublecortin domain | 271 | 32% | 52% | 332 | 9e−31 |
| B230104P22Rik | NP_001004363.1 | B230104P22Rik; Mm.25874; LOC77976; MGC90816 Protein with strong similarity to AMP-activated protein kinase family member 5 (human ARK5), which is a serine-threonine kinase that may act in tolerance to nutrient starvation in tumors, contains a protein kinase and protein tyrosine kinase domain | 263 | 32% | 55% | 356 | 1e−30 |
| BB049667 | NP_808566.2 | BB049667; 6530411J22 Protein containing a protein tyrosine kinase domain, has low similarity to NIMA (never in mitosis gene a)-related kinase 11 (human NEK11), which is a protein kinase that may act in the DNA damage checkpoint | 250 | 32% | 53% | 327 | 2e−30 |
| Camk2d | NP_076302.1 | Camk2d; [d]-CaMKII; 2810011D23Rik; 8030469K03Rik; MGC60852; mKIAA4163; KIAA4163 Protein with strong similarity to calcium-calmodulin-dependent protein kinase II delta (rat Camk2d), which is involved in Ca2+ regulated processes, contains a protein kinase domain | 268 | 33% | 51% | 327 | 2e−30 |
| Brsk1 | NP_001003920.1 | Brsk1; Gm1100; SADB; MGC99905 Protein with very strong similarity to KIAA1811 protein (human BRSK1), which is activated by human STK11-mediated phosphorylation and preferentially phosphorylates the LNR peptide, contains protein kinase and protein tyrosine kinase domains | 271 | 31% | 52% | 332 | 3e−30 |
| Chek2 | NP_057890.1 | Chek2; CHK2; (Cds1); Rad53; HUCDS1; Mm.42149; Chk2 CHK2 checkpoint homolog, kinase that may transmit DNA damage signals from Atm, may prevent mitosis through phosphorylation of Cdc25c; human CHEK2 is associated with Li Fraumeni Syndrome, breast, colorectal, and gastric cancers | 300 | 33% | 51% | 344 | 8e−30 |
| Phkg2 | NP_081164.1 | Phkg2; 1500017I02Rik; Mm.30991 Protein with very strong similarity to phosphorylase kinase gamma 2 (rat Phkg2), which is a calcium/calmodulin-dependent protein kinase that activates glycogen phosphorylase, contains a protein kinase domain | 292 | 32% | 51% | 342 | 2e−29 |
| Nek1 | BAD32570.1 | Nek1; kat; LOC382011; Mm.204943; D8Ertd790e NIMA (never in mitosis gene a)-related expressed kinase 1, dual specificity kinase that phosphorylates serine, threonine, | 245 | 33% | 52% | 320 | 3e−29 |

TABLE 6-continued

| Gene | GenBank | Synonyms/Description | Match Length | % Iden | % Sim | High Score | E Val |
|---|---|---|---|---|---|---|---|
| Camk2b | NP_031621.2 | and tyrosine residues, binds spermatid-specific protein Nurit, may function in meiosis, spermatogenesis, axon growth, and transport Camk2b; Mm.4857; (Camk2d); MGC90738 Calcium/calmodulin-dependent protein kinase II beta, putative signal transducer that may contribute to learning; human CAMK2B is upregulated in the frontal cortex of schizophrenia patients and may regulate small cell lung carcinoma progression | 268 | 33% | 51% | 317 | 3e−29 |
| Snrk | NP_598502.1 | Snrk; 2010012F07Rik; Mm.30079; E030034B15; SNRK; MGC28970; mKIAA0096 Protein with very strong similarity to SNF related kinase (rat Snrk), which is a protein kinase that may play a role in the regulation of low potassium-induced apoptosis, contains a protein kinase and a protein tyrosine kinase domain | 279 | 33% | 48% | 317 | 5e−29 |
| Camk2a | NP_803126.1 | Camk2a; Mm.8037; Mm.30350; CaMKII; CAMKII-alpha; alpha-CaMKII; R74975; mKIAA0968 Calcium: calmodulin-dependent protein kinase II alpha, member of a family of kinases involved in Ca(2+)-regulated processes, required for neuronal transmission and long term potentiation involved in memory and learning | 272 | 31% | 51% | 315 | 6e−29 |
| Pskh1 | NP_775608.1 | Pskh1; E130013P03Rik; AW539964; E130013P03; Mm.27627 Protein with very strong similarity to protein serine kinase H1 (human PSKH1), which is a calcium-dependent protein kinase that may be involved in autophosphorylation, RNA splicing and protein targeting, contains a protein kinase domain | 268 | 31% | 54% | 313 | 6e−29 |
| Phkg1 | NP_035209.1 | Phkg1; Phkg; Mm.3159 Gamma catalytic subunit of phosphorylase kinase, muscle isoform, phosphorylates and thereby activates glycogen phosphorylase, regulates glycogenolysis | 281 | 34% | 51% | 327 | 1e−28 |
| 4833424K13Rik | NP_001009930.1 | 4833424K13Rik; SADA; Brsk2 Protein with high similarity to human BRSK1, which is a protein kinase that preferentially phosphorylates the LNR peptide and can also phosphorylate AMARA and SAMS peptides, contains a protein tyrosine kinase domain | 304 | 29% | 50% | 317 | 1e−28 |
| Nek3 | NP_035978.1 | Nek3; Mm.41413 NIMA (never in mitosis gene a)-related expressed kinase 3, a cytoplasmic protein kinase, expression and activity are elevated in quiescent cells but remain relatively constant throughout the cell cycle | 252 | 31% | 52% | 307 | 2e−28 |
| AI325941 | NP_849231.1 | AI325941; (Prkd2); (PKD2) Protein with strong similarity to protein kinase D2 (human PRKD2), which is a serine-threonine kinase, contains two phorbol ester or diacylglycerol binding domains (C1 domains), which bind two zinc ions, and a pleckstrin homology (PH) domain | 293 | 32% | 50% | 311 | 4e−28 |
| Snf1lk | NP_034961.1 | Snf1lk; Msk; MSK; (Sik) SNF1-like kinase (salt-inducible kinase), a protein kinase that exhibits histone phosphorylation activity, may play a role in heart and muscle development and G2/M transition during the mitotic cell cycle | 263 | 30% | 52% | 307 | 4e−28 |
| Melk | NP_034920.2 | Melk; MPK38; mKIAA0175 Maternal embryonic leucine zipper kinase, a protein kinase, may function in T-cell activation and embryonic development | 275 | 28% | 49% | 313 | 5e−28 |
| Stk17b | NP_598571.2 | Stk17b; Drak2; 3110009A03Rik Serine/threonine kinase 17b, a protein that negatively regulates T cell receptor signaling and T cell activation | 249 | 33% | 53% | 304 | 6e−28 |
| C130083N04Rik | AAW79567.1 | C130083N04Rik; (Prkaa1) Protein of unknown function, has very strong similarity to a region of alpha 1 catalytic subunit of AMP-activated protein kinase (rat Prkaa1), which regulates fatty acid synthesis and is | 256 | 33% | 55% | 331 | 1e−27 |

TABLE 6-continued

| Gene | GenBank | Synonyms/Description | Match Length | % Iden | % Sim | High Score | E Val |
|---|---|---|---|---|---|---|---|
| | | associated with obesity related insulin resistance | | | | | |
| 4930509O22 | NP_766092.1 | 4930509O22 Protein containing a protein kinase domain, has low similarity to sperm motility kinase 1 (mouse Smok1), which is a protein kinase and component of a signaling cascade that may control sperm motility | 273 | 33% | 53% | 326 | 1e−27 |
| Smok1 | CAB61344.1 | Smok1; Tcr; Tcr1; Smok; Tcr-1 Sperm motility kinase 1, member of the Smok family of protein kinases, a component of a signaling cascade that may control sperm motility | 265 | 30% | 51% | 301 | 1e−27 |
| Plk4 | NP_035625.1 | Plk4; Sak; Stk18; 1700028H20; Mm.3794 Serine/threonine kinase 18, a protein kinase belonging to the polo family of mitotic regulators, required for degradation of cyclin B and exit from mitosis; human STK18 is overexpressed in colorectal cancer | 266 | 30% | 50% | 301 | 4e−27 |
| Hunk | NP_056570.1 | Hunk; Bstk1; Mak-v; Mm.25120 Hormonally upregulated Neu-associated kinase, SNF1-related serine-threonine kinase involved in pregnancy, cell proliferation, and lactation, and possibly regulation of endocytosis | 246 | 34% | 49% | 297 | 4e−27 |
| Prkcm | NP_032884.1 | Prkcm; PKD; Pkcm; Mm.990 Mu isoform of protein kinase C (protein kinase D), a serine-threonine kinase, may act in diacylglycerol and phorbol ester signal transduction, B cell receptor signaling, and Golgi to plasma membrane transport; human PRKCM may be used during tumor invasion | 272 | 33% | 50% | 302 | 5e−27 |
| Mapkapk5 | NP_034895.1 | Mapkapk5; Mm.22612; MAPKAP5; MK5; PRAK MAP kinase activated protein kinase 5, a serine/threonine kinase activated by MAP kinases ERK and p38 but not by JNK | 281 | 32% | 49% | 300 | 7e−27 |
| Slk | NP_033315.1 | Slk; 9A2; Etk4; SMAK; Stk2; mSLK; mKIAA0204; SLK; Mm.7693 STE20-like kinase, undergoes cleavage by caspase 3 (Casp3) during apoptosis, releasing an N-terminal kinase domain that promotes apoptosis and cytoskeletal rearrangement and a C-terminal domain that disassembles actin stress fibers | 275 | 32% | 52% | 297 | 1e−26 |
| Mastl | NP_080255.2 | Mastl; THC2; 2700091H24Rik; C88295 Protein containing a protein kinase domain, has weak similarity to a region of *S. cerevisiae* Rim15p, which is a serine/threonine protein kinase that positively regulates *S. cerevisiae* Ime2p expression and sporulation | 160 | 39% | 63% | 292 | 1e−26 |
| Mknk1 | NP_067436.1 | Mknk1; Mm.42074; MNK1; Mnk1; 2410048M24Rik MAP kinase-interacting serine-threonine kinase 1, kinase that binds growth factor-regulated and stress-activated Erk and p38 MAP kinases and is activated by them, phosphorylates translation initiation factor 4E (Eif4e) | 360 | 28% | 46% | 300 | 2e−26 |
| Snf1lk2 | NP_848825.2 | Snf1lk2; Sik2; G630080D20Rik; SIK2 RIKEN cDNA G630080D20 gene, a serine-threonine kinase expressed mainly in adipose tissues, phosphorylates insulin receptor substrate 1 (Irs1), represses CRE-mediated transcriptional activation, activity is increased in adipose tissue in diabetes | 248 | 29% | 51% | 300 | 1e−25 |
| Prkcn | NP_083515.2 | Prkcn; MGC47171; 4930557O20Rik; 5730497N19Rik Protein with strong similarity to protein kinase C nu (human PRKD3), which regulates cell differentiation and proliferation, contains two phorbol ester or diacylglycerol binding (C1 domain), protein kinase and pleckstrin homology (PH) domains | 272 | 32% | 49% | 290 | 1e−25 |
| Camkk1 | NP_061371.1 | Camkk1; Camkk; CaMKKalpha; CaMkkalpha; 4732414G09Rik Calcium-calmodulin-dependent protein kinase 1 alpha, upregulated during retinoic acid-induced differentiation of neutrophils | 280 | 28% | 50% | 285 | 2e−25 |
| Smok2 | CAB61342.1 | Smok2 Sperm motility kinase 2, a member of the Smok family of protein kinases that are expressed in late spermiogenesis and are | 263 | 30% | 50% | 297 | 3e−25 |

TABLE 6-continued

| Gene | GenBank | Synonyms/Description | Match Length | % Iden | % Sim | High Score | E Val |
|---|---|---|---|---|---|---|---|
| | | components of the signal cascade that control sperm motility | | | | | |
| Dapk3 | NP_031854.1 | Dapk3; Mm.10294; ZIPK Death-associated kinase 3, serine-threonine kinase, self-associates and binds transcription factor Atf4, functions as an apoptosis activator when overexpressed; human DAPK3 is upregulated in the frontal cortex of Alzheimer's disease patients | 259 | 30% | 51% | 280 | 5e−25 |
| Tssk4 | NP_081949.1 | Tssk4; 1700020B19Rik; 4933424F08Rik; TSSK4 Protein containing protein kinase and protein tyrosine kinase domains, has moderate similarity to serine threonine kinase 22A (mouse Tssk1), which is a testis-specific kinase that complexes with mouse Stk22b and binds and phosphorylates mouse Stk22s1 | 260 | 27% | 51% | 277 | 5e−25 |
| Trio | AAH51169.1 | Trio; Mm.138088 Triple functional domain (PTPRF interacting), a putative Rho guanine nucleotide exchange factor, regulates skeletal muscle development and neural tissue organization | 252 | 31% | 50% | 283 | 7e−25 |
| Dapk2 | NP_034149.2 | Dapk2; Mm.41755 Death-associated kinase 2, a member of the DAP kinase apoptotic signaling family that activates apoptosis in a calcium-calmodulin dependent manner | 288 | 30% | 49% | 281 | 7e−25 |
| Cdkl3 | NP_722480.1 | Cdkl3; MGC28957; B230379H01Rik Protein with high similarity to cyclin-dependent kinase like 1 (human CDKL1), which is activated by epidermal growth factor (EGF), phosphorylates histones, and is upregulated in gliosis, contains protein tyrosine kinase and protein kinase domains | 208 | 34% | 54% | 275 | 9e−25 |
| Tssk1 | NP_033461.1 | Tssk1; Tsk1; Tssk; TSK-1; Stk22a; Mm.18470 Testis-specific serine kinase 1, a serine-threonine kinase that binds and phosphorylates Stk22s1, likely to play a role in late spermatid development; human STK22D gene may be involved in DiGeorge, velocardiofacial, or conotruncal anomaly facial syndromes | 247 | 30% | 50% | 274 | 1e−24 |
| Plk2 | NP_690017.1 | Plk2; Snk Polo-like kinase 2, a putative serine-threonine protein kinase that is induced along with other early-growth-response proteins, required for embryonic growth and skeletal development, and entry into the S phase of the mitotic cell cycle | 261 | 26% | 51% | 276 | 2e−24 |
| 4933423E17 | NP_808374.1 | 4933423E17 Protein containing a protein kinase domain, has moderate similarity to sperm motility kinase 1 (mouse Smok1), which is a component of a signaling cascade that may be involved in spermatogenesis and cell motility | 239 | 30% | 50% | 269 | 6e−24 |
| Mapkapk3 | NP_849238.1 | Mapkapk3; 3PK; MAPKAP3; MapkKapk3; MapKapk3 Mitogen-activated protein kinase-activated protein kinase 3, a protein kinase whoase activity is stimulated by interferon-alpha and requires mitogen activated protein kinase 14 (Mapk14) | 276 | 29% | 51% | 272 | 8e−24 |
| Ulk3 | AAH37093.1 | Ulk3; 1200015E14Rik Protein containing a protein tyrosine kinase domain, a protein kinase domain, and a MIT domain, has low similarity to mouse Dapk3, which is a serine-threonine kinase that self-associates and binds activating transcription factor 4 (mouse Atf4) | 266 | 32% | 53% | 297 | 9e−24 |
| Map2k1 | NP_032953.1 | Map2k1; Prkmk1; Mm.1059; MAPKK; MAPKK1; Mek1; MEK1; (MEKK1) Mitogen-activated protein kinase kinase 1, a signaling protein that phosphorylates and activates MAP kinase, involved in cell cycle control, antiapoptosis, and response to radiation; human MAP2K1 is a putative target for breast and lung cancer | 215 | 33% | 53% | 266 | 1e−23 |
| Mapkapk2 | NP_032577.1 | Mapkapk2; Mm.29725; (Rps6kc1); (MK2) MAP kinase-activated protein kinase 2, a protein kinase phosphorylated by MAP kinase, positively regulates mRNA stability, important for cell migration, Tnf alpha production, and | 320 | 28% | 48% | 269 | 2e−23 |

TABLE 6-continued

| Gene | GenBank | Synonyms/Description | Match Length | % Iden | % Sim | High Score | E Val |
|---|---|---|---|---|---|---|---|
| | | the inflammatory response; human MAPKAPK2 is upregulated in breast cancer | | | | | |
| Tssk3 | NP_536690.1 | Tssk3; Tsk-3; Stk22c; Stk22d; Tssk-3; Tssk3b; 1700014N07Rik; 4930594I21Rik Serine-threonine kinase 22C (spermiogenesis associated), a putative kinase that is expressed specifically in the interstitial Leydig cells post-puberty, which suggests a role in spermatogenesis | 250 | 30% | 49% | 263 | 2e-23 |
| Cdkl5 | BAC34965.1 | Cdkl5; Stk9 Cyclin-dependent kinase-like 5 (serine/threonine kinase 9), a putative serine-threonine kinase; gene mutation may be associated with congenital cateracts observed in the Xcat mutant; human CDKL5 gene mutation causes a severe neurodevelopmental disorder | 207 | 35% | 54% | 266 | 3e-23 |
| Stk4 | NP_067395.1 | Stk4; (Mst1); Ysk3; Kas-2 Serine/threonine kinase 4, a protein kinase that forms a complex with NORE and Ras, is cleaved and activated by caspases during apoptosis, mediates apoptosis via p53 (Trp53), induces cell-matrix detachment and activates JNK1 (Mapk8) and JNK3 (Mapk10) | 264 | 30% | 49% | 264 | 4e-23 |
| Tssk2 | NP_033462.1 | Tssk2; Tsk2; DGS-G; SPOGA2; Stk22b; Mm.14777 Serine threonine kinase 22b, a serine/threonine kinase involved in the cytodifferentiation of late spermatids into sperm; human STK22B is located in a chromosomal region that is deleted in DiGeorge syndrome (DGS) and velo cardio facial syndrome (VCFS) | 248 | 31% | 50% | 261 | 5e-23 |
| Plk1 | NP_035251.2 | Plk1; Plk; STPK13 Polo-like kinase, a serine/threonine protein kinase that plays a role in mitotic cell cycle control, apoptosis, activation of the anaphase promoting complex/cyclosome (APC), and cell proliferation; human PLK is highly expressed in tumor tissues | 242 | 27% | 54% | 281 | 7e-23 |
| Rps6kb1 | NP_082535.1 | Rps6kb1; p70s6k; p70-85s6k; S6K1; 2610318I15Rik; (70 kDa); p70__85s6k Ribosomal protein S6 kinase 70 kD polypeptide 1, an RSK family member that is involved in cell cycle progression, cell proliferation, glucose homeostasis, and embryonic growth; human RPS6KB1 gene amplification is linked to breast cancer | 111 | 51% | 69% | 256 | 8e-23 |
| Stk3 | NP_062609.1 | Stk3; Mess1; 0610042I06Rik; Mm.4678; p33QIK; Mst3; (MST); mess1 Serine threonine kinase 3, a protein kinase induced by cell stress and by entry into G0 phase from M phase | 421 | 24% | 44% | 269 | 1e-22 |
| Plk3 | NP_038835.1 | Plk3; Cnk; Fnk; PRK; Mm.69521 Polo-like kinase 3, a putative serine/threonine kinase of the polo family, regulates cytokinesis and induces apoptosis; human PLK3 is downregulated in squamous cell carcinoma and other tumors; rat Plk3 is downregulated in colon tumors | 258 | 27% | 47% | 258 | 1e-22 |
| Nek11 | NP_766049.1 | Nek11; 4932416N14; 4932416N14Rik Protein with high similarity to NIMA (never in mitosis gene a)-related kinase 11 (human NEK11), which is a protein kinase that may act in the DNA damage checkpoint, contains a protein kinase domain and a protein tyrosine kinase domain | 250 | 30% | 51% | 261 | 2e-22 |
| Camkk2 | NP_663333.1 | Camkk2; 6330570N16Rik; LOC207565; Mm.87620; mKIAA0787 Calcium/calmodulin-dependent protein kinase kinase 2 beta, required for some types of hippocampal long-term memory formation | 281 | 27% | 49% | 260 | 2e-22 |
| Stk10 | NP_033314.1 | Stk10; Mm.8235; Lok; Gek1; mKIAA4026; KIAA4026 Serine threonine kinase 10, a member of the STE20 family of serine/threonine kinases; gene deletion results in increased lymphoid cell adhesion | 297 | 32% | 51% | 306 | 3e-22 |
| Nek2 | NP_035022.1 | Nek2; Mm.5379 NIMA (never in mitosis gene a)-related expressed kinase 2, a | 234 | 30% | 51% | 255 | 4e-22 |

TABLE 6-continued

| Gene | GenBank | Synonyms/Description | Match Length | % Iden | % Sim | High Score | E Val |
|---|---|---|---|---|---|---|---|
| Chek1 | NP_031717.2 | serine/threonine protein kinase, predicted to be involved in chromosome condensation, meiosis, and gametogenesis Chek1; Chk1; Mm.16753; rad27 Checkpoint kinase 1 homolog (*S. pombe*), protein kinase, acts in DNA damage checkpoint, inhibits cell proliferation, required for embryonic development, may be involved in gamma radiation response; human CHEK1 variant is associated with lung cancer | 214 | 29% | 51% | 253 | 5e−22 |
| Stk24 | NP_663440.1 | Stk24; LOC223255; MGC6330; MST-3; STK3; MST3; MST3B; 1810013H02Rik Protein with very strong similarity to serine-threonine kinase 24 (Ste20 yeast homolog, human STK24), which is a serine-threonine kinase that prefers manganese as a cofactor, contains a protein kinase domain and a protein tyrosine kinase domain | 261 | 28% | 49% | 278 | 7e−22 |
| Pim2 | NP_613072.1 | Pim2; (Pim-2); DXCch3 Proviral integration site 2, a serine-threonine kinase that negatively regulates apoptosis through phosphorylation of mouse Bad, involved in cellular transformation; deletion of human PIM2 may have a role in cancer | 226 | 32% | 52% | 252 | 8e−22 |
| Pim1 | NP_032868.2 | Pim1; Pim-1 Proviral integration site 1, a serine/threonine protein kinase, inhibits apoptosis and promotes cell proliferation, may act in hematopoesis; corresponding gene serves as a proviral integration target site in leukemia and is associated with lymphomagenesis | 264 | 30% | 50% | 250 | 2e−21 |
| Sbk1 | NP_663562.1 | Sbk1; Sbk; LOC233866 Protein with very strong similarity to SH3-binding kinase (rat Sbk), which is a SH3-binding protein kinase with an SH3-binding domain that may act in brain development, contains a protein kinase domain | 210 | 34% | 51% | 248 | 2e−21 |
| Obscn | NP_001003914.1 | Obscn; UNC89; MGC51514; Mm.248843; Loc380698; Gm878; BC046431 Obscurin, a putative Rho guanine nucleotide exchange factor, may play a role in myofibrillogenesis and sarcomere organization during cardiac development and cardiac hypertrophy | 266 | 29% | 50% | 286 | 3e−21 |
| Map3k5 | NP_032606.1 | Map3k5; ASK1; Mekk5; Mm.6595; MAPKKK5; 7420452D20Rik Mitogen activated protein kinase kinase kinase 5, activates Jun kinase, likely plays a role in stress or cytokine-induced apoptosis, involved in cellular differentiation; human MAP3K5 may play a role in HIV and neurodegenerative disease | 333 | 28% | 47% | 258 | 3e−21 |
| Mknk2 | NP_067437.1 | Mknk2; Mnk2; Gprk7; 2010016G11Rik; Mm.42126 MAP kinase interacting serine threonine kinase 2, a serine/threonine kinase that is activated by Mapk1, Mapk11, and Mapk14, phosphorylates initiation factor-4E (Eif4e), and likely regulates translation | 295 | 27% | 46% | 251 | 3e−21 |
| D830007F02Rik | NP_780650.1 | D830007F02Rik; 6030449M12; (MLCK) Protein with high similarity to myosin light chain kinase (MLCK, human LOC91807), which is a calcium-calmodulin-dependent protein kinase that acts in peptidyl-serine phosphorylation, contains a protein kinase domain | 249 | 29% | 49% | 249 | 3e−21 |
| Map2k2 | NP_075627.2 | Map2k2; Prkmk2; MEK2; (MK2) Mitogen-activated protein kinase kinase 2, a dual-specificity kinase that is involved in signal transduction during cellular growth and differentiation, meiosis, mitosis, and immune responses; human MAP2K2 is upregulated in breast cancer | 203 | 32% | 54% | 245 | 3e−21 |
| Cask | NP_033936.1 | Cask; Lin-2; Mm.10735; DXPri1; DXRib1; Pals3; mLin-2; LIN-2; MGC7449 Calcium/calmodulin-dependent serine protein kinase, member of the MAGUK family, forms a trimeric complex with Mint1 (Apba3) and | 283 | 28% | 49% | 252 | 5e−21 |

TABLE 6-continued

| Gene | GenBank | Synonyms/Description | Match Length | % Iden | % Sim | High Score | E Val |
|---|---|---|---|---|---|---|---|
| | | Lin7 that may play a role in receptor targeting at the neuronal plasma membrane | | | | | |
| Nek7 | NP_067618.1 | Nek7; Mm.143817 NIMA (never in mitosis gene a)-related expressed kinase 7, a protein serine-threonine kinase and member of a subfamily of NIMA-related kinases, may play a role in regulation of mitosis | 254 | 28% | 48% | 244 | 5e−21 |
| Mylk | NP_647461.2 | Mylk; (MLCK); telokin; KRP; Mlck; MLCK108; MLCK210; A930019C19Rik; 9530072E15Rik Myosin light polypeptide kinase, a calcium and calmodulin-dependent kinase that plays a role in chemotaxis and may regulate cell shape and synaptic vesicle transport; 17 kDa C-terminal segment is expressed as a separate protein, telokin, in smooth muscle | 280 | 28% | 50% | 273 | 6e−21 |
| Pak1 | NP_035165.1 | Pak1; Mm.29955; Paka; PAK-1 p21 activated kinase 1, a protein kinase involved in cell-matrix adhesion and perhaps actin filament reorganization, neuronal migration and neurite outgrowth; increased human PAK1 activity may correlate with breast cancer invasiveness | 295 | 30% | 48% | 249 | 8e−21 |
| Map2k3 | NP_032954.1 | Map2k3; Mm.18494; MKK3; Prkmk3; MEK3; mMKK3b Mitogen activated protein kinase kinase 3, phosphorylates MAP kinase p38, involved in immune, inflammatory, and stress responses, also has roles in glucose transport and ischemic kidney injury; human MAP2K3 acts in nontypeable *H. influenzae* infection | 281 | 28% | 47% | 246 | 8e−21 |
| Nek6 | NP_067619.1 | Nek6; 1300007C09Rik; Mm.143818 NIMA (never in mitosis gene a)-related expressed kinase 6, a putative serine-threonine kinase | 254 | 28% | 48% | 243 | 8e−21 |
| Dapk1 | NP_083929.1 | Dapk1; DAPK; 2810425C21Rik; 2310039H24Rik; D13Ucla1; DAP-Kinase Death associated protein kinase 1, a serine-threonine kinase that inhibits TNF-induced apoptosis; human DAPK1 gene promoter is hypermethylated in many cancers | 275 | 29% | 50% | 272 | 1e−20 |
| Ulk2 | NP_038909.2 | Ulk2; Mm.27664; Unc51.2; mKIAA0623; A830085I22Rik UNC 51-like kinase 2, a member of the UNC-51-like family of serine/threonine protein kinases | 293 | 29% | 49% | 285 | 2e−20 |
| Map4k2 | NP_033032.1 | Map4k2; Rab8ip; Mm.25860; GCK; BL44 Mitogen-activated protein kinase kinase kinase kinase 2, member of the germinal center kinase subfamily of serine/threonine protein kinases, interacts with Rab8; expression of human MAP4K2 is increased in UV-resistant melanoma cells | 333 | 28% | 44% | 249 | 2e−20 |
| Pkmyt1 | NP_075545.1 | Pkmyt1; AW209059; (Myt1); 6230424P17; PKMYT1 Protein with strong similarity to membrane-associated tyrosine- and threonine-specific CDC2-inhibitory kinase (human PKMYT1), which controls the cell cycle by phosphorylating and inactivating cyclin-bound human CDC2, contains a protein kinase domain | 293 | 29% | 48% | 245 | 2e−20 |
| Mapk1 | NP_036079.1 | Mapk1; Prkm1; ERK; Erk2; MAPK2; PRKM2; p41mapk; p42mapk; C78273; 9030612K14Rik Mitogen-activated protein kinase 1, a serine-threonine kinase effector of the RAS-MAP kinase pathway, translocates to the nucleus to mediate transcription when activated, involved in cell cycle control, apoptosis, glucose transport, synaptic transmission | 277 | 26% | 49% | 243 | 2e−20 |
| Mapk3 | NP_036082.1 | Mapk3; Prkm3; Mm.8385; Erk1; (p44); Erk-1; p44erk1; p44mapk; Esrk1 Mitogen activated protein kinase 3, a serine-threonine kinase involved in receptor signaling and cell proliferation; altered activation of human MAPK3 may be therapeutic for HIV infections, rheumatoid arthritis, and breast, colorectal, and lung cancers | 208 | 27% | 53% | 240 | 2e−20 |
| Ulk1 | NP_033495.2 | Ulk1; Mm.34216; Unc51.1; mKIAA0722 Unc-51 (*C. elegans*)-like kinase 1, a member | 340 | 27% | 45% | 294 | 3e−20 |

TABLE 6-continued

| Gene | GenBank | Synonyms/Description | Match Length | % Iden | % Sim | High Score | E Val |
|---|---|---|---|---|---|---|---|
| | | of the Unc51 subfamily of serine threonine kinases, a protein kinase involved in the early steps of cerebellar granule cell neurite extension, may be part of a signaling cascade | | | | | |
| Myo3a | NP_680779.1 | Myo3a; 9030416P08Rik Myosin IIIA, putative hybrid motor and signaling protein, expressed in the cochlea and predicted to be involved in hearing | 297 | 30% | 48% | 249 | 4e−20 |
| 1810024B03Rik | NP_941032.1 | 1810024B03Rik; LOC329509 Protein containing a protein kinase domain, has a region of high similarity to a region of *C. elegans* PAR-1, which is a serine-threonine protein kinase required for cytoplasmic partitioning and for cell-cell fusion events during vulval morphogenesis | 123 | 39% | 59% | 228 | 5e−20 |
| 2610018G03Rik | NP_598490.1 | 2610018G03Rik; Mst4; Mm.46254 Protein with very strong similarity to mst3 and SOK1-related kinase (human RP6-213H19.1), which is a protein kinase that induces apoptosis and may be associated with mental retardation, contains a protein kinase domain and a protein tyrosine kinase domain | 316 | 26% | 47% | 269 | 9e−20 |
| Map3k6 | NP_057902.2 | Map3k6; Mm.36640; MAPKKK6 Protein with strong similarity to human MAP3K6, which binds MEKK5/ASK1 (human MAP3K5) and weakly activates the JNK pathway, but not the ERK or p38 MAP kinase pathways, contains a protein kinase domain and a protein tyrosine kinase domain | 267 | 30% | 48% | 242 | 1e−19 |
| Pak2 | NP_796300.1 | Pak2; gammaPAK; PAK; PAK-2; D16Ertd269e; LOC224105; A130002K10Rik; mKIAA4182; KIAA4182 p21 (CDKN1A)-activated kinase 2, a member of the PAK family of protein kinases, binds GTP-bound Cdc42 and is involved in the response to heat, radiation, DNA damage and hyperosmotic stresses | 258 | 30% | 48% | 235 | 1e−19 |
| Pak3 | NP_032804.1 | Pak3; PAK-B; Mm.3392; mPAK-3; Pak65beta; Pak65alpha; (Stk4) p21 (CDKN1A)-activated kinase 3, downstream effector of members of the rho family of GTPases, such as Cdc42 and Rac1, associates with phospholipase C gamma (Plcg1) and Nck (Nck1); mutations in human PAK3 cause nonsyndromic X-linked mental retardation | 259 | 30% | 47% | 235 | 1e−19 |
| Cdk7 | NP_034004.1 | Cdk7; Mm.21056; Crk4; Cdkn7 Cyclin-dependent protein kinase 7, interacts with Ccnh and Mat1 to phosphorylate and activate members of the CDC2 family of protein kinases; inhibition of human CDK7 may be therapeutic for colon cancer; human CDK7 may be upregulated in breast cancer | 203 | 33% | 50% | 230 | 1e−19 |
| Pak7 | NP_766446.1 | Pak7; Pak5; 6430627N20; 2900083L08Rik p21 (CDKN1A)-activated kinase 7, putative protein serine-threonine kinase that is highly expressed in the brain, predicted to be involved in filopodia formation and neurite outgrowth | 257 | 27% | 50% | 235 | 2e−19 |
| Map2k6 | NP_036073.1 | Map2k6; Mm.14487; MKK3b; Prkmk6; MEK6; MKK6; SAPKK3 Mitogen-activated protein kinase kinase 6, a threonine-tyrosine kinase involved in the response to osmotic shock, plays a role in muscle development and may regulate cell proliferation | 271 | 27% | 46% | 233 | 2e−19 |
| Stk25 | NP_067512.2 | Stk25; Ste20-like; Mm.28761; Ysk1; C86992; 1500019J11Rik Serine threonine kinase 25, a putative protein kinase of the Ste20 kinase family, may be involved in a protein kinase cascade linked to oxidative stress response | 265 | 29% | 49% | 259 | 4e−19 |
| Cdk2 | NP_904326.1 | Cdk2; Mm.260; Mm.118; Cdk2alpha; Cdk2beta; A630093N05Rik Cyclin-dependent protein kinase 2, interacts with cyclins to regulate kinase activity and cell cycle progression, induces apoptosis, may control DNA replication; decreased expression or inhibition of human CDK2 may be therapeutic for many types of cancer | 213 | 32% | 51% | 229 | 4e−19 |

TABLE 6-continued

| Gene | GenBank | Synonyms/Description | Match Length | % Iden | % Sim | High Score | E Val |
|---|---|---|---|---|---|---|---|
| Nek8 | NP_543125.1 | Nek8; 4632401F23Rik; jck NIMA (never in mitosis gene a)-related expressed kinase 8, a putative serine-threonine kinase required for normal kidney development; gene mutation causes polycystic kidney disease and upregulation of human NEK8 is linked to breast cancer | 250 | 29% | 48% | 248 | 6e−19 |
| Crk7 | NP_081228.1 | Crk7; Pksc; CrkRS; 1810022J16Rik; Mm.260516 Protein with strong similarity to CDC2-related protein kinase 7 (human CRK7), which phosphorylates the C-terminal domain of RNA polymerase II and may link mRNA splicing with the transcriptional machinery, contains a protein kinase domain | 221 | 31% | 50% | 233 | 6e−19 |
| Map3k4 | NP_036078.1 | Map3k4; Mm.28587; Mekk4; D17Rp17e; MTK1; Rp17a; MAPKKK4; D17Rp17; RP17; mKIAA0213; Mek4b Mitogen-activated protein kinase kinase kinase 4, binds Cdc42 and Rac1, activates Mapk8 and Mapk9 through phosphorylation and activation of Map2k4, but does not activate Mapk3 nor Mapk14 | 247 | 29% | 48% | 232 | 8e−19 |
| Cdkl2 | NP_058608.1 | Cdkl2; KKIAMRE; Kkm; 5330436L21Rik Cyclin-dependent kinase-like 2, putative serine/threonine protein kinase found in brain neurons | 220 | 29% | 52% | 227 | 8e−19 |
| Pftk1 | NP_035204.1 | Pftk1; Mm.6456; mKIAA0834 PFTAIRE protein kinase 1, a Cdc2a-related serine/threonine protein kinase, may be associated with postmitotic and differentiated state of cells in the nervous system, may function in the process of meiosis as well as neuron differentiation and function | 218 | 28% | 48% | 223 | 1e−18 |
| Cdc2l5 | BAD32543.1 | Cdc2l5; 2310015O17Rik Cell division cycle 2-like 5 (cholinesterase-related cell division controller), a protein required for normal megakaryocytopoiesis, may function in cell division | 223 | 30% | 50% | 230 | 2e−18 |
| Map4k1 | NP_032305.1 | Map4k1; Hpk1; mHPK1; Mm.3313 Mitogen-activated protein kinase kinase kinase kinase 1 (hematopoietic progenitor kinase 1), binds Blnk and SLP-76 (Lcp2), activates the JNK/SAPK pathway, inhibits T cell receptor-induced AP-1 activation and may be involved in the immune response | 260 | 27% | 51% | 226 | 2e−18 |
| Map2k5 | NP_035970.1 | Map2k5; Mm.19947; MEK5; Mapkk5; Prkmk5 MAP kinase kinase 5, a member of the MAP kinase family that may participate in mitogenic signaling pathways and is a positive modulator of cell proliferation; human MAP2K5 is upregulated in metastatic prostrate cancer | 274 | 26% | 42% | 224 | 2e−18 |
| Cdkl1 | NP_899117.1 | Cdkl1; 4933411O17Rik; Mm.132325 Protein with strong similarity to cyclin-dependent kinase like 1 (CDC2-related kinase 1, human CDKL1), which is a protein serine-threonine kinase that phosphorylates histones and is upregulated in gliosis, contains a protein kinase domain | 298 | 26% | 45% | 222 | 3e−18 |
| Tssk6 | NP_114393.1 | Tssk6; Sstk; Mm.69431; MGI_2148775 Protein with high similarity to serine threonine kinase 22b (mouse Tssk2), which is a serine/threonine kinase involved in the cytodifferentiation of late spermatids into sperm, contains a protein kinase domain | 251 | 26% | 49% | 219 | 3e−18 |
| Cdc2a | NP_031685.2 | Cdc2a; Mm.4761; Cdk1; p34_CDC2_; Cdc2; CDK1 Cell division cycle 2a, cyclin-dependent protein kinase that has a key role in regulating entry into mitosis and the G2 to M-phase transition, promotes cell proliferation, involved in meiosis; human CDC2 is implicated in Alzheimers disease | 299 | 27% | 46% | 223 | 5e−18 |
| Map2k7 | NP_036074.1 | Map2k7; Mm.3906; MKK7; Prkmk7; sek2; Jnkk2; 5930412N11Rik Mitogen activated protein kinase kinase 7, a MAPK kinase that activates Jun N terminal protein kinase (Mapk8) in response to stress, involved in cell | 211 | 33% | 52% | 220 | 5e−18 |

TABLE 6-continued

| Gene | GenBank | Synonyms/Description | Match Length | % Iden | % Sim | High Score | E Val |
|---|---|---|---|---|---|---|---|
| | | proliferation and the inflammatory response, has a predicted role in the induction of apoptosis | | | | | |
| Cdk5 | NP_031694.1 | Cdk5; Mm.4818; Crk6 Cyclin-dependent protein kinase 5, a serine-threonine kinase that binds regulatory subunit Cdk5r; upregulation of human CDK5 is associated with some diseases; inhibition of human CDK5 may be therapeutic for Alzheimer disease | 295 | 25% | 42% | 218 | 5e−18 |
| Map4k5 | NP_958927.1 | Map4k5; KHS; GCKR; MAPKKKK5; 4432415E19Rik Protein with strong similarity to mitogen-activated protein kinase kinase kinase kinase 5 (human MAP4K5), which activates Jun N-terminal kinase, member of the citron homology (CNH) domain-containing family, contains a protein kinase domain | 311 | 27% | 45% | 227 | 6e−18 |
| Pim3 | NP_663453.1 | Pim3; LOC223775; Kid1; MGC27707; MGC37517 Proviral integration site 3, a putative serine-threonine protein kinase, activated in lymphomas in which Pim1 and Pim2 are inactivated, has a contributing role in embryonic and postnatal body growth, may function in hematopoietic growth factor signaling | 265 | 29% | 50% | 233 | 7e−18 |
| Camkv | NP_663596.1 | Camkv; BC017634; MGC28873; LOC235604; 1G5 Protein with very strong similarity to vesicle-associated calmodulin-binding protein (rat 1G5), which has similarity to serine-threonine protein kinases but apparently lacks kinase activity, contains a protein kinase domain | 274 | 25% | 48% | 219 | 8e−18 |
| Tlk1 | NP_766252.1 | Tlk1; 4930545J15; 4930545J15Rik Protein with very strong similarity to tousled like kinase (human TLK1), which is a putative serine-threonine kinase that phosphorylates histones and may increase cell resistance to ionizing radiation, contains a protein kinase domain | 339 | 29% | 45% | 251 | 9e−18 |
| Ccrk | NP_444410.1 | Ccrk; (p42); CDCH; PNQLARE; MGC38901; 4932702G04Rik Protein with high similarity to cyclin-dependent kinase 3 (human CDK3), which is a kinase that binds to cyclin A and is required for progression from G1 to S phase and may have a role in inducing apoptosis, contains a protein kinase domain | 210 | 30% | 49% | 216 | 9e−18 |
| Nek4 | NP_035979.1 | Nek4; Mm.57013 NIMA (never in mitosis gene a)-related expressed kinase 4, member of NIMA kinase family which controls entrance into mitosis, may play a role as a cell cycle regulator, highly expressed in testis; human NEK4 displays high activity in breast tumor tissue | 246 | 28% | 51% | 245 | 1e−17 |
| BC048082 | NP_808590.1 | BC048082; MGC56865; MGC56903 Protein with strong similarity to extracellular signal-regulated kinase 7 (rat Erk7), which is a constitutively active nuclear MAP kinase that binds chloride intracellular channel 3 and inhibits cell proliferation, contains a protein kinase domain | 221 | 33% | 50% | 221 | 1e−17 |
| Chuk | NP_031726.1 | Chuk; Mm.3996; IKK-alpha; IKK1; Chuk1; IKK-1; IKK[a]; IKKalpha; Ikbka; ikBKA; IKK-A Conserved helix-loop-helix ubiquitous kinase, an I-kappaB kinase, activates the NF-kappaB, involved in keratinocyte and B-cell differentiation and lymphoid organogenesis; inhibition of human CHUK may be therapeutic for prostate cancer | 284 | 30% | 46% | 223 | 2e−17 |
| Mapk14 | NP_036081.1 | Mapk14; Csbp1; (p38); Mm.4437; Mxi2; CSBP2; PRKM14; PRKM15; p38-alpha; Crk1; p38MAPK; MGC102436 Mitogen activated protein kinase 14, serine-threonine protein kinase, acts in signaling in response to cytokines and physiological stimuli, triggers apoptosis in response to stress; inhibition of human MAPK14 may be therapeutic for breast cancer | 277 | 25% | 47% | 216 | 2e−17 |

| Gene | GenBank | Synonyms/Description | Match Length | % Iden | % Sim | High Score | E Val |
|---|---|---|---|---|---|---|---|
| Pctk3 | NP_032821.1 | Pctk3; Mm.28130; PCTAIRE-3 PCTAIRE protein kinase 3, serine/threonine kinase that may be involved in the cell cycle | 221 | 29% | 50% | 216 | 2e−17 |
| Map2k4 | NP_033183.1 | Map2k4; Serk1; (SAPK); Mm.4412; MEK4; MKK4; (Sek1); JNKK1; PRKMK4 Mitogen-activated protein kinase kinase 4, involved in response to cellular stress, may trigger apoptosis, associated with models of Parkinson and Alzheimer diseases, activation may cause long lasting neurodegenerative effects | 282 | 27% | 45% | 216 | 2e−17 |
| Tlk2 | NP_036033.1 | Tlk2; PKUalpha; Tlk; Mm.4557; tlk Tousled-like kinase 2, a putative serine threonine protein kinase, interacts with 14-3-3 zeta (Ywhaz), may be involved in cell cycle-related functions or spermatogenesis | 282 | 30% | 50% | 245 | 3e−17 |
| Mapk12 | NP_038899.1 | Mapk12; SAPK3; Erk6; Mm.38343; Prkm12; P38gamma; Sapk3 Stress activated protein kinase 3, involved in RHO protein signaling, may be involved in intracellular signaling in response to cellular stress | 249 | 27% | 49% | 214 | 3e−17 |
| Pctk2 | NP_666351.1 | Pctk2; MGC25109; 6430598J10Rik Protein with high similarity to PCTAIRE protein kinase 1 (human PCTK1), which is a serine-threonine kinase with cell cycle-regulated activity and may be associated with X chromosome-linked heritable disorders, contains a protein kinase domain | 203 | 30% | 51% | 213 | 3e−17 |
| Map3k3 | NP_036077.1 | Map3k3; Mm.27041; Mekk3; MAPKKK3; mKIAA4031; KIAA4031 Mitogen-activated protein kinase kinase kinase 3, an Erk and JNK pathway activator, phosphorylates IKKbeta (Ikbkb) leading to NF-kappaB activation, is required for embryonic angiogenesis; human MAP3K3 is selectively upregulated in hepatocellular carcinoma | 251 | 30% | 45% | 215 | 4e−17 |
| 4932414J04 | NP_766380.1 | 4932414J04 Protein containing a protein kinase domain, has moderate similarity to a region of microtubule-MAP affinity regulating kinase (rat Mark2), which is a serine-threonine kinase that acts in microtubule stability and the control of cell polarity | 142 | 32% | 55% | 204 | 4e−17 |
| Oxsr1 | AAH60645.1 | Oxsr1; (Osr1); 2210022N24Rik; 2810422B09Rik Oxidative-stress responsive 1, a predicted serine-threonine kinase that binds cation-chloride co-transporters Scl12a1, Slc12a2, and Scl12a6 to play a likely role during initiation of the cellular stress response | 301 | 27% | 44% | 221 | 6e−17 |
| Gsk3b | NP_062801.1 | Gsk3b; GSK-3beta; GSK-3; C86142; 7330414F15Rik; 8430431H08Rik; GSK3 Glycogen synthase kinase-3 beta, a serine-threonine protein kinase that acts in Wnt signaling and regulates the stability of cyclin D1 (Ccnd1), interacts with Axin, involved in embryonic development, may be involved in colon carcinogenesis | 208 | 29% | 49% | 211 | 6e−17 |
| Map3k1 | NP_036075.1 | Map3k1; Mekk; Mm.15918; (MEKK1); MAPKKK1 MAP kinase kinase kinase 1, a protein kinase of the JNK-MAP kinase pathway that responds to stress signals, cytokines, and growth factors, caspase cleavage results in release of a pro-apoptotic fragment, induces cardiac hypertrophy | 286 | 28% | 44% | 225 | 8e−17 |
| Ikbkb | NP_034676.1 | Ikbkb; IKK2; IKK-2; IKK[b]; IKK-beta Kinase beta of Inhibitor of kappaB, subunit of the IkappaB kinase (IKK) complex, phosphorylation of IkappaB targets it for degradation and activates NF-kappaB (RelA), required for embryonic liver development, may be involved in insulin resistance | 216 | 31% | 49% | 214 | 8e−17 |
| Ulk4 | BAB30285.1 | Ulk4; 4932415A06Rik Protein containing three HEAT repeats, which appear to function as protein-protein interaction surfaces, and a protein kinase domain, has a region of low similarity to a region of calcium-calmodulin dependent protein kinase ID (mouse Camk1d) | 295 | 26% | 43% | 213 | 8e−17 |

TABLE 6-continued

| Gene | GenBank | Synonyms/Description | Match Length | % Iden | % Sim | High Score | E Val |
|---|---|---|---|---|---|---|---|
| Mapk11 | NP_035291.3 | Mapk11; Mm.116702; Mk11; p38-beta; Prkm11; P38b; Sapk2; p38-2; Sapk2b; p38beta; p38beta2 Mitogen-activated protein kinase 11, involved in cell differentiation, immune and stress responses, and DNA damage repair; human MAPK11 may act in transendothelial tumor cell migration | 279 | 25% | 49% | 209 | 1e−16 |
| Cdc2l1 | NP_031687.2 | Cdc2l1; (p58); Cdc2l2; Mm.4414; CDK11-p46; CDK11-p58; CDK11-p110 Cell division cycle 2 like 2, a protein kinase that binds Src-homology 2 (SH2) domains, appears to be involved in cell cycle regulation during embryonic development; mutation of the human CDC2L1 gene is associated with non-Hodgkin lymphoma and melanoma | 201 | 31% | 49% | 208 | 1e−16 |
| Mink1 | NP_795712.1 | Mink1; Map4k6; (Mink); B55; MINK; Ysk2 Mitogen-activated protein kinase kinase kinase kinase 6 (misshapen/NIK-related kinase), a member of the germinal center kinase family, activates the JUN N terminal kinase (JNK) and p38 MAP kinase pathways, may be involved in postnatal cerebral development | 214 | 31% | 51% | 228 | 2e−16 |
| Pctk1 | NP_035179.1 | Pctk1; PCTAIRE-1; Pctairel; Crk5; Mm.4597 PCTAIRE motif protein kinase 1, a serine/threonine kinase that binds calpactin 1 light chain (S100a10) and with 14-3-3 eta (Ywhah), theta (Ywhaq) and zeta (Ywhaz); mutations in human PCTK1 may be associated with X chromosome-linked heritable disorders | 287 | 27% | 46% | 221 | 3e−16 |
| Cdk10 | NP_919428.1 | Cdk10; Mm.31090 Protein with very strong similarity to cyclin dependent kinase 10 (human CDK10), which binds and inhibits the transcription factor human ETS2 and has a role in cell proliferation and is associated with follicular lymphoma, contains a protein kinase domain | 201 | 31% | 48% | 206 | 3e−16 |
| Tnni3k | NP_796040.2 | Tnni3k; Cark; D830019J24Rik Protein containing three ankyrin (Ank) repeats, which may mediate protein-protein interactions, has strong similarity to a region of TNNI3 interacting kinase (cardiac ankyrin repeat kinase, human TNNI3K), which binds troponin | 214 | 29% | 47% | 207 | 4e−16 |
| Map3k2 | NP_036076.1 | Map3k2; Mm.5067; Mekk2; Mekk2b Mitogen-activated protein kinase kinase kinase 2, protein serine/threonine kinase involved in T cell receptor signaling, Galpha13 (Gna13) - induced JNK1 (Mapk8) activation and NF-kappaB pathway activation via IKKalpha (Chuk) and IKKbeta (Ikbkb) | 413 | 24% | 38% | 206 | 4e−16 |
| Nlk | NP_032728.2 | Nlk; Mm.9001 Nemo-like kinase, a putative serine/threonine kinase related to MAP, ERK and CDK kinases and is required for normal bone marrow stromal cell differentiation, may play a role in transcription regulation | 223 | 27% | 49% | 201 | 8e−16 |
| Cdk6 | NP_034003.1 | Cdk6; Crk2; AI504062; 5830411I20 Cyclin dependent protein kinase 6, phosphorylates pRB in the G1-phase, involved in cell cycle control and control of cell proliferation; decreased expression or inhibition of human CDK6 may be therapeutic for breast, colon, and lung cancer | 332 | 27% | 44% | 204 | 1e−15 |
| Nek9 | NP_660120.1 | Nek9; C130021H08Rik Protein with strong similarity to human NEK9, which is a serine-threonine protein kinase that binds RAN and is a component of the FACT complex, contains two regulator of chromosome condensation (RCC1) repeats and a protein kinase domain | 264 | 27% | 45% | 206 | 2e−15 |
| Mylk2 | AAH19408.1 | Mylk2; 9830004H17Rik; LOC228785 Protein containing a protein kinase domain, has very strong similarity to a region of skeletal muscle myosin light chain kinase (rat Mylk2), which may modulate contractile activity | 192 | 27% | 51% | 194 | 3e−15 |
| Mapk7 | NP_035971.1 | Mapk7; Mm.38172; ERK5; BMK1; PRKM7; Erk5-T Mitogen activated protein kinase 7 (big mitogen activated protein kinase), a redox-sensitive transcriptional activator that | 227 | 26% | 47% | 197 | 4e−15 |

TABLE 6-continued

| Gene | GenBank | Synonyms/Description | Match Length | % Iden | % Sim | High Score | E Val |
|---|---|---|---|---|---|---|---|
| | | interacts with MEK5 (PRKMK5); decreased activity of human MAPK7 is associated with idiopathic dilated cardiomyopathy | | | | | |
| Mapk13 | NP_036080.1 | Mapk13; Serk4; Mm.27970; SAPK4 Mitogen activated protein kinase 13, a p38 MAP kinase that has roles in the inflammatory and stress responses, may be involved in developmental processes | 340 | 27% | 43% | 199 | 5e−15 |
| Stk39 | NP_058562.1 | Stk39; DCHT; SPAK; Spak; Mm.29404; PASK; Mm.198414 Serine-threonine kinase 39, a putative serine/threonine kinase of the STE20/SPS1 family, translocates from cytosol to cytoskeleton in response to hyperosmotic shock; human STK39 may be a marker for progression to hormone-independent prostate cancer | 217 | 29% | 46% | 198 | 6e−15 |
| Hipk2 | NP_034563.1 | Hipk2; Mm.20934; Stank; 1110014O20Rik; B230339E18Rik Homeodomain interacting protein kinase 2, protein kinase that binds to and represses the transcriptional activity of homeodomain proteins | 264 | 29% | 47% | 199 | 1e−14 |
| Cdk9 | NP_570930.1 | Cdk9; PITALRE Cyclin-dependent kinase 9, binds cyclin T to form the transcription elongation factor P-TEFb, which hyperphosphorylates RNA polymerase II subunit POLR2A, plays a role in mediating cardiac hypertrophy and may be involved in muscle cell differentiation | 234 | 28% | 46% | 192 | 1e−14 |
| A430105I05Rik | BAC30618.1 | A430105I05Rik; LOC414088 Protein containing a protein tyrosine kinase domain and a protein kinase domain, has low similarity to NIMA (never in mitosis gene a)-related expressed kinase 6 (mouse Nek6), which is a putative serine-threonine kinase | 264 | 29% | 43% | 191 | 1e−14 |
| Pask | NP_543126.1 | Pask; Paskin; Mm.31408; mKIAA0135 PAS domain containing serine-threonine kinase, a putative serine-threonine kinase that contains a PAS domain, may function in intracellular signal transduction and the perception of abiotic stimuli | 242 | 30% | 48% | 222 | 2e−14 |
| Dyrk1b | NP_034222.1 | Dyrk1b; Mirk Dual-specificity tyrosine-phosphorylation regulated kinase 1B, autophosphorylates tyrosine, phosphorylates threonine on histone H3, may function in spermatogenesis | 215 | 32% | 50% | 192 | 2e−14 |
| Hipk1 | NP_034562.1 | Hipk1; Mm.20827; Myak; 1110062K04Rik Homeodomain interacting protein kinase 1, interacts with homeoproteins, serine phosphorylates tumor protein p53 (Trp53) and Fas death domain associated protein (Daxx), undergoes autophosphorylation, may act in tumorigenesis through regulation of Trp53 | 251 | 28% | 47% | 195 | 3e−14 |
| Ttk | NP_033471.1 | Ttk; Mm.1904; PYT; esk; Esk1 Dual specificity serine/threonine and tyrosine kinase, a substrate for cyclin-dependent-kinase Cdk2, may induce centrosome duplication together with Cdk2 and play a role in cell cycle control | 282 | 27% | 47% | 195 | 3e−14 |
| Pak4 | NP_081746.1 | Pak4; 5730488L07Rik; Mm.21876; mKIAA1142 p21(CDKN1A)-activated kinase 4, a putative protein kinase, binds Grb2 and keratinocyte growth factor receptor (Fgfr2), involved in keratinocyte growth factor (Fgf7) signaling | 257 | 27% | 48% | 214 | 4e−14 |
| Hipk3 | NP_034564.1 | Hipk3; Mm.20333; HIPK3; PKY; DYRK6; FIST3 Homeodomain interacting protein kinase 3, a serine/threonine kinase and corepressor of transcription, interacts with homeodomain transcription factors and death receptors; human HIPK3 is overexpressed in multidrug-resistant cells | 220 | 29% | 49% | 190 | 5e−14 |
| Mapk8 | NP_057909.1 | Mapk8; Prkm8; JNK1; JNK; SAPK1 Mitogen activated protein kinase 8, a serine-threonine kinase that regulates c-Jun (JUN), acts in receptor and ceramide signaling, cell growth and differentiation, apoptosis, and response to | 203 | 29% | 49% | 186 | 5e−14 |

TABLE 6-continued

| Gene | GenBank | Synonyms/Description | Match Length | % Iden | % Sim | High Score | E Val |
|---|---|---|---|---|---|---|---|
| | | stressors such as DNA damage, reactive oxygen and hypoxia | | | | | |
| 4932415M13 | NP_808267.1 | 4932415M13 Protein containing a protein kinase domain, has low similarity to sperm motility kinase 1 (mouse Smok1), which is a component of a signaling cascade that may be involved in spermatogenesis and cell motility | 142 | 31% | 52% | 180 | 5e−14 |
| Stk11 | NP_035622.1 | Stk11; Lkb1; Mm.29947; R75140 Serine threonine kinase 11, protein that acts in the vascular endothelial growth factor (Vegf) signaling pathway, has role in activation of apoptosis; mutations in the human STK11 gene cause Peutz-Jeghers syndrome | 282 | 28% | 48% | 252 | 7e−14 |
| Map3k14 | NP_058592.1 | Map3k14; aly; (Nik) Mitogen-activated protein kinase kinase kinase 14 (NF-kappaB-inducing kinase), serine/threonine protein kinase that interacts with TRAF family members, acts in signaling cascades common to receptors of TNF/NGF family; mutation causes alymphoplasia | 328 | 26% | 46% | 214 | 7e−14 |
| 2310004N11Rik | NP_083076.2 | 2310004N11Rik Protein with very strong similarity to SINK homologous serine-threonine kinase (human MGC4796), which is a putative serine-threonine kinase that negatively regulates transcription mediated by human NFKB1 and human TP53, contains a protein kinase domain | 207 | 29% | 48% | 188 | 7e−14 |
| Apeg1 | NP_031489.2 | Apeg1; BPEG; SPEGbeta; SPEGalpha; D1Bwg1450e; mKIAA1297; SPEG Aortic preferentially expressed gene 1, may serve in muscle development, expression of alternative form SPEGalpha is induced during differentiation of myoblasts to myotubes, alternative form SPEGbeta has kinase activity capable of autophosphorylation | 265 | 27% | 48% | 224 | 8e−14 |
| Dyrk3 | NP_663483.1 | Dyrk3; LOC226419; Mm.39299 Dual-specificity tyrosine-(Y)-phosphorylation regulated kinase 3, protein kinase that serine phosphorylates CREB and inhibits apoptosis | 207 | 29% | 51% | 184 | 9e−14 |
| Map4k4 | NP_032722.1 | Map4k4; Mm.987; NIK; (Nik); HGK Mitogen-activated protein kinase kinase kinase kinase 4, a serine-threonine kinase that interacts with MEKK1 (Map3k1) and activates the c-Jun N-terminal kinase (Mapk8) signaling pathway, also interacts with Nck; required for somite and hindgut development | 278 | 29% | 46% | 222 | 1e−13 |
| Nrk | NP_038752.1 | Nrk; NRK; NESK; Nesk Nik related kinase, an embryonic specific kinase of the group I germinal center kinase family, activates the JNK signaling pathway | 295 | 25% | 43% | 191 | 1e−13 |
| Taok2 | BAC98045.1 | Taok2; PSK; PSK1; TAO1; TAO2; MAP3K17; KIAA0881; mKIAA0881; 1110033K02Rik; B230344N16 Protein with high similarity to serine_threonine protein kinase TAO1 (rat LOC286993), which binds MEK3 and is involved in regulating the p38-containing stress responsive MAP kinase pathway, contains protein kinase and protein tyrosine kinase domains | 249 | 29% | 44% | 186 | 1e−13 |
| Cdk4 | NP_034000.1 | Cdk4; Mm.6839; (Crk3) Cyclin dependent kinase 4, activated by binding to cyclin D1(CCND1) resulting in Rb1 phosphorylation, required for cell cycle progression; decreased expression or inhibition of human CDK4 may be therapeutic for breast, colorectal, and lung cancer | 261 | 28% | 44% | 182 | 2e−13 |
| Tec | NP_038717.1 | Tec; Mm.2350 Cytoplasmic tyrosine kinase Dscr28C related (tec protein tyrosine kinase), a non-receptor protein tyrosine kinase that is involved in T cell receptor signaling and B cell development, activated by protein tyrosine phosphatase D1 (Ptpn21) | 229 | 26% | 48% | 181 | 2e−13 |
| Csk | NP_031809.2 | Csk C-src tyrosine kinase, a protein tyrosine kinase that functions as a negative regulator of Src family kinases, plays a role in T-cell signaling and differentiation, neural tube | 228 | 27% | 45% | 180 | 2e−13 |

TABLE 6-continued

| Gene | GenBank | Synonyms/Description | Match Length | % Iden | % Sim | High Score | E Val |
|---|---|---|---|---|---|---|---|
| | | development, and embryogenesis; human CSK is a tumor antigen in carcinomas | | | | | |
| Ick | NP_064371.1 | Ick Intestinal cell kinase, a putative serine/threonine kinase that contains a MAP kinase-like dual phosphorylation site which may be necessary for activity | 198 | 27% | 49% | 180 | 3e−13 |
| Mapk4 | NP_766220.1 | Mapk4; (Erk3); (Prkm4); p63Mapk; A330097D03; A330097D03Rik Protein with high similarity to mitogen-activated protein kinase 6 (rat Mapk6), which is a serine-threonine protein kinase that is involved in cell surface receptor linked signal transduction, contains a protein kinase domain | 223 | 26% | 45% | 177 | 5e−13 |
| Ikbke | NP_062751.2 | Ikbke; Ikki; IKK-i IkappaB epsilon protein kinase, member of IkappaB kinase complex, induced by lipopolysaccharide and TNF, phosphorylates Nfkbia, activates NF kappa B, may have a role in the immune response; human IKKE is associated with rheumatoid arthritis | 233 | 27% | 44% | 179 | 6e−13 |
| Limk1 | NP_034847.1 | Limk1 LIM-domain containing protein kinase, serine-threonine kinase, mediates signaling from Rho to the cytoskeleton via phosphorylation of cofilin 1 (Cfl1), may have a role in Listeria-induced phagocytosis; human LIMK1 may be involved in Williams syndrome | 225 | 24% | 47% | 177 | 7e−13 |
| Rps6kl1 | NP_666356.2 | Rps6kl1; MGC38756; A830084F09Rik Protein containing a MIT domain and a protein kinase domain, has a region of moderate similarity to a region of 90 kD ribosomal protein S6 kinase polypeptide 2 (mouse Rps6ka2), which is a protein kinase acting in glycogen synthase activation and apoptosis | 186 | 33% | 53% | 214 | 1e−12 |
| Mapk6 | NP_056621.2 | Mapk6; ERK3; Prkm6; (Mapk4); (Prkm4); Mapk63; (Erk3); D130053K17Rik Mitogen-activated protein kinase 6, a serine-threonine protein kinase regulated during development and activated in response to growth factors; downregulation of human MAPK6 may cause decreased cell proliferation associated with prostatic cancer | 227 | 26% | 45% | 175 | 1e−12 |
| Rage | NP_036103.1 | Rage; Mm.27161; MOK; RAGE1; MGC46883; MGC107277 Renal tumor antigen, a member of the MAP kinase superfamily, a serine threonine protein kinase, may play a role in signal transduction; human RAGE may be a target for T-cell-based immunotherapy of renal cell carcinoma | 212 | 27% | 46% | 174 | 1e−12 |
| Raf1 | NP_084056.1 | Raf1; Raf-1; v-Raf; 6430402F14Rik; c-Raf; Craf1; (D830050J10Rik) V-Raf-1 leukemia viral oncogene 1, a serine/threonine kinase acting in signal transduction processes controlling cell proliferation; altered expression of human RAF1 is associated with breast, colon, and lung cancer | 211 | 24% | 48% | 174 | 1e−12 |
| Trib2 | NP_653134.2 | Trib2; TRB-2 Protein with high similarity to phosphoprotein regulated by mitogenic pathways (human TRIB1), which is a putative protein kinase that interacts with and may regulate 12-lipoxygenase (human ALOX12), contains a protein kinase domain | 183 | 27% | 46% | 172 | 1e−12 |
| Mak | NP_032573.1 | Mak; Mm.8149; RCK; A930010O05Rik Male germ cell-associated kinase, a serine/threonine kinase that may be involved in meiosis during spermatogenesis or sensory signal transduction; human MAK is upregulated in prostate cancer cells | 364 | 21% | 41% | 177 | 2e−12 |
| Pdikl1 | NP_666268.1 | Pdikl1; MGC36635; BC027088 Protein with high similarity to serine-threonine kinase 35 (human STK35), which is a serine-threonine kinase that is translocated from nucleus to actin stress fibers by interaction with CLP-36 (human PDLIM1), contains a protein kinase domain | 343 | 25% | 40% | 174 | 2e−12 |

TABLE 6-continued

| Gene | GenBank | Synonyms/Description | Match Length | % Iden | % Sim | High Score | E Val |
|---|---|---|---|---|---|---|---|
| Mapk10 | NP_033184.1 | Mapk10; Mm.4936; (SAPK); Serk2; JNK3; p493F12; p54bSAPK; SAPK(beta); JNK3B2; JNK3B1 Mitogen-activated protein kinase 10, phosphorylates c-Jun (Jun), interacts with beta arrestin 2 (Arrb2), and plays a role in excitatory-induced or stress-induced neuronal apoptosis; decreased human MAPK10 expression is observed in brain tumor cell lines | 207 | 28% | 48% | 173 | 2e–12 |
| Irak4 | NP_084202.2 | Irak4; NY-REN-64; 9330209D03Rik; 8430405M07Rik; IRAK-4 Interleukin-1 receptor associated kinase 4, a putative protein kinase, involved in innate immune response and Toll/IL-1 receptor signaling via NFkappaB and JNK cascades; mutation in human IRAK4 causes an increased susceptibility to bacterial infections | 209 | 30% | 45% | 173 | 2e–12 |
| Dyrk1a | NP_031916.1 | Dyrk1a; Mm.4041; mmb; Mnbh; Dyrk; D16Ertd493e; 2310043O08Rik; D16Ertd272e Dual-specificity tyrosine phosphorylation-regulated kinase, a serine-threonine kinase that regulates body and brain size, cognitive and motor skills and neurogenesis; human DYRK1A is overexpressed in Down's syndrome | 246 | 29% | 46% | 175 | 3e–12 |
| Dyrk4 | NP_997093.1 | Dyrk4; Dyrk4a; Dyrk4b Protein containing a protein kinase domain, has moderate similarity to dual-specificity tyrosine phosphorylation regulated kinase 3 (human DYRK3), which is tyrosine autophosphorylated and phosphorylates histones H2B and H3 and may act in spermatogenesis | 213 | 27% | 46% | 172 | 3e–12 |
| Mapk9 | NP_997575.1 | Mapk9; Prkm9; Jnk2; JNK2; p54aSAPK Mitogen activated protein kinase 9, a stress-activated protein kinase, activated by proinflammatory cytokines and cell stress, acts on apoptosis regulators Trp53 and Bcl2, negatively regulates Mapk8 phosphorylation, plays a role in T-cell differentiation | 169 | 27% | 51% | 169 | 3e–12 |
| Tbk1 | NP_062760.2 | Tbk1; 1200008B05Rik TANK-binding kinase 1, a putative IkappaB kinase, forms a ternary complex with TANK and TRAF2 to activate NFkappaB, acts as inhibitor of apoptosis | 239 | 26% | 44% | 173 | 4e–12 |
| Compared with *C. elegans* protein sequences (Documentation) | | | | | | | |
| sgk-1 | CAB03485.1 | sgk-1; tag-74; W10G6.2 Serum and glucocorticoid-inducible kinase homolog 1, protein kinase that is involved in the DAF-2 insulin-like receptor signaling pathway, forms a complex with AKT-1 and AKT-2 to regulate development, life span, and stress response, phosphorylates DAF-16 | 336 | 44% | 63% | 734 | 2e–78 |
| akt-2 | CAA20936.1 | akt-2; F28H6.1A; F28H6.1 Akt kinase family 2, serine/threonine protein kinase that forms a multimeric complex with AKT-1 and SGK-1, transduces signal from AGE-1 to antagonize DAF-16 transcription factor | 300 | 47% | 70% | 722 | 5e–77 |
| Y47D3A.16 | CAB55075.1 | Y47D3A.16 Protein that may be involved in regulation of developmental timing and body size | 347 | 47% | 65% | 762 | 6e–75 |
| akt-1 | AAC62467.1 | akt-1; C12D8.10B; C12D8.10 AKT kinase 1, serine-threonine protein kinase that is involved in larval development that transduces signal from AGE-1 to antagonize DAF-16 transcription factor, forms a complex with AKT-2 and SGK-1 | 355 | 45% | 65% | 744 | 2e–73 |
| pkc-1 | CAB00101.2 | pkc-1; kin-13; F57F5.5 Protein kinase C 1, calcium-independent, diacylglycerol-activated protein kinase C (nPKC) | 340 | 43% | 64% | 691 | 1e–72 |
| rsk-1 | CAA99896.2 | rsk-1; T01H8.1A; T01H8.1 Protein with high similarity to ribosomal protein S6 kinase 1 (human RPS6KA1), which is a mitogen activated protein kinase, member of the protein kinase C-terminal domain containing family, contains two protein kinase and a protein tyrosine kinase domain | 344 | 48% | 64% | 728 | 7e–70 |
| C54G4.1 | CAA99814.2 | C54G4.1 Protein with high similarity to ribosomal protein S6 kinase A5 (human RPS6KA5), member of the protein kinase C-terminal domain containing family, contains two protein kinase domains | 349 | 41% | 61% | 636 | 5e–66 |

TABLE 6-continued

| Gene | GenBank | Synonyms/Description | Match Length | % Iden | % Sim | High Score | E Val |
|---|---|---|---|---|---|---|---|
| kin-1 | CAD45613.1 | kin-1; ZK909.2C; CeCatalpha; ZK909.2 Putative cAMP-dependent protein kinase that is expressed at high levels during larval but not embryonic development | 291 | 45% | 67% | 655 | 7e−64 |
| kin-11 | AAA68709.2 | kin-11; E01H11.1C; pkc-2; PKC2; E01H11.1 Protein kinase 11, serine/threonine protein kinase | 306 | 41% | 62% | 610 | 1e−63 |
| pkc-3 | AAA79341.1 | pkc-3; F09E5.1 Protein kinase C 3, serine/threonine protein kinase that functions in embryogenesis, morphogenesis, pharyngeal and vulva development, required for asymmetric protein distribution, regulates cortical cytoskeleton and promotes cortical flow | 346 | 38% | 63% | 610 | 5e−63 |
| R04A9.5 | AAA83287.2 | R04A9.5; R04A9.5A Member of the protein kinase C-terminal domain containing family, contains two homeobox domains (homeodomains) and a protein kinase domain, has a region of high similarity to a region of ribosomal protein S6 kinase 2 (mouse Rps6kb2) | 305 | 43% | 65% | 633 | 5e−62 |
| tpa-1 | AAC26916.1 | tpa-1; B0545.1A; B0545.1 Tpa resistance abnormal 1, protein kinase C required for acute stimulation of egg-laying by serotonin, mediates PMA and activated GPA-12 induced growth arrest | 317 | 40% | 62% | 638 | 3e−61 |
| grk-2 | AAA64322.2 | grk-2; W02B3.2 G protein-coupled receptor kinase-2, putative G protein-coupled receptor kinase required for normal chemosensory response in the adult | 387 | 34% | 54% | 550 | 4e−56 |
| F47F2.1 | AAK72061.2 | F47F2.1; F47F2.1B Protein with high similarity to protein kinase X-linked (human PRKX), which is a cAMP-dependent protein kinase catalytic subunit involved in signaling during macrophage and granulocyte development, contains a protein kinase domain | 300 | 38% | 59% | 543 | 1e−55 |
| F46F6.2 | CAA90339.4 | F46F6.2 Protein that is a putative target of DAF-16 | 334 | 37% | 58% | 564 | 9e−55 |
| kin-4 | CAB05684.1 | kin-4; C10C6.1 Protein containing a protein kinase domain and a PDZ, DHR, or GLGF domain, which are found in signaling proteins, has moderate similarity to syntrophin-associated serine/threonine kinase (mouse Mast1), which binds syntrophins, microtubules and MAPS | 312 | 36% | 58% | 534 | 2e−51 |
| sax-1 | AAK82913.2 | sax-1; R11G1.4A; R11G1.4 Sensory axon defects 1, serine/threonine protein kinase required for maintenance of nerve ring morphology, inhibits primary neurite outgrowth and secondary neurite formation | 383 | 33% | 53% | 507 | 3e−51 |
| K08B12.5 | AAB52260.3 | K08B12.5 Protein involved in growth rate regulation, morphogenesis of an epithelium, locomotory behavior, and body morphogenesis including the male tail | 382 | 35% | 53% | 513 | 5e−51 |
| C09G4.2 | AAM75371.1 | C09G4.2; C09G4.2C Protein containing three protein kinase domains and two cyclic nucleotide-binding domains, has moderate similarity to cGMP-dependent protein kinase type 1 (human PRKG1), which relaxes vascular smooth muscle and inhibits platelet aggregation | 297 | 39% | 60% | 489 | 3e−49 |
| let-502 | AAB42348.1 | let-502; C10H11.9 Lethal 502, Rho-binding serine/threonine protein kinase that functions in cellularization, cytokinesis, embryonic elongation, larval development, body development, male tail morphogenesis, and regulation of locomotion | 342 | 36% | 56% | 485 | 4e−48 |
| M03C11.1 | CAA88953.1 | M03C11.1 Protein containing a protein kinase domain, has low similarity to cAMP-dependent protein kinase catalytic subunit C alpha (human PRKACA), which is a putative tumor biomarker involved in transcription regulation and possibly apoptosis or sperm development | 293 | 36% | 59% | 460 | 3e−46 |
| T20F10.1 | CAB04745.1 | T20F10.1 Protein involved in locomotory behavior and growth rate regulation | 354 | 31% | 51% | 444 | 6e−44 |
| egl-4 | AAD36954.1 | egl-4; F55A8.2A; odr-9; cgk-1; chb-1; F55A8.2 Egg laying defective 4, cGMP-dependent protein kinase that may function in several neuronal signaling pathways and may act in both TGFB-mediated and insulin-like signaling pathways, regulates odorant adaptation, locomotion, life span, and body size | 293 | 38% | 57% | 482 | 4e−42 |
| grk-1 | CAA88047.1 | grk-1; F19C6.1 Protein with high similarity to G protein-coupled receptor kinase 6 (rat Gprk6), which is a protein kinase that regulates desensitization of G protein-coupled receptors, contains a protein kinase | 318 | 37% | 58% | 475 | 2e−40 |

TABLE 6-continued

| Gene | GenBank | Synonyms/Description | Match Length | % Iden | % Sim | High Score | E Val |
|---|---|---|---|---|---|---|---|
| F28C10.3 | AAB00607.1 | domain and a regulator of G protein signaling domain<br>F28C10.3 Protein containing a protein kinase domain, has low similarity to protein kinase C lambda (rat Pkcl), which is a protein kinase C that activates human Erk1 and human Erk2 and is involved in glucose transport and actin cytoskeleton organization regulation | 281 | 35% | 55% | 379 | 2e−36 |
| air-2 | AAB52459.2 | air-2; let-603; B0207.4 Aurora/Ip11-related 2, component of the aurora B kinase complex, required for mitotic and meiotic chromosome segregation and involved in the release of chromosome cohesion | 245 | 35% | 54% | 361 | 6e−35 |
| ceh-20 | AAM29686.1 | ceh-20; F31E3.2A; F31E3.1; F31E3.2 *C. elegans* homeobox 20, homeodomain transcription factor involved in embryonic development, larval development, mesoderm development, vulval development, locomotion, and determination of adult life span | 282 | 35% | 53% | 362 | 2e−34 |
| pdk-1 | AAD42307.1 | pdk-1 Phosphoinositide dependent kinase 1, serine/threonine protein kinase involved in dauer larva development, aging, and the response to hypoxia, interacts with SGK-1, AKT-1, and AKT-2 | 365 | 28% | 45% | 362 | 2e−33 |
| par-1 | CAB54263.1 | par-1; H39E23.1A; zyg-14; H39E23.1 Partitioning defective 1, serine/threonine kinase required for embryonic polarity, early cytoplasmic partitioning, P granule stabilization, and vulval cell-cell fusion events, inhibits CCCH finger protein degradation and vulval precursor cell induction | 446 | 27% | 44% | 373 | 3e−33 |
| air-1 | AAA96180.2 | air-1; (let-412); K07C11.2 Aurora/ip11-related 1, serine/threonine protein kinase associated with mitotic chromosomes, required for cytokinesis, polar body extrusion and recruitment, involved in germ line development and post-embryonic cell division | 266 | 34% | 58% | 386 | 6e−33 |
| PAR2.3 | AAA50618.1 | PAR2.3; PAR2.3A; aak-1; aka-2 Protein containing protein kinase and protein tyrosine kinase domains, has moderate similarity to human PRKAA2, which is a metabolic sensor of AMP levels, and plays a role in fatty acid beta-oxidation, glucose metabolism, and regulation of cell growth | 262 | 32% | 52% | 346 | 1e−32 |
| R06A10.4 | AAB96730.1 | R06A10.4 Protein containing a protein kinase domain, has moderate similarity to protein serine kinase H1 (human PSKH1), which undergoes Ca2+-dependent autophosphorylation and stimulates nuclear splicing factor reorganization and RNA splicing upon overexpression | 254 | 34% | 56% | 338 | 9e−32 |
| kin-29 | AAK97497.1 | kin-29; sns-8; sma-11; F58H12.1 Kinase 29, putative serine/threonine protein kinase that regulates chemoreceptor expression and sensory signaling, functions in a TGFbeta pathway to regulate body size and dauer formation | 245 | 35% | 53% | 336 | 1e−31 |
| aak-2 | AAM69095.1 | aak-2; T01C8.1A; T01C8.1 AMPKalpha homlog 2, AMP-activated protein kinase that acts as a sensor of AMP levels promoting the extension of life span, required for dauer formation | 288 | 31% | 52% | 334 | 3e−31 |
| cmk-1 | BAA82674.1 | cmk-1; K07A9.2 Calcium/calmodulin-dependent protein kinase 1, CAM kinase that stimulates cyclic AMP response element-dependent transcription, required in larvae for gene expression, morphology, and function of adult AFD thermosensory neurons | 270 | 32% | 55% | 350 | 5e−30 |
| piak | AAC68917.1 | piak; W04B5.5 Serine/threonine protein kinase with similarity to phosphoinositide-dependent protein kinases, but not affected by phosphoinositides; may act as a "survival kinase" | 298 | 29% | 51% | 321 | 5e−30 |
| F49C5.4 | CAB04433.3 | F49C5.4 Protein containing a protein kinase and a protein tyrosine kinase domain, has moderate similarity to *S. pombe* Cmk1p, which is a calmodulin-dependent protein kinase | 239 | 35% | 53% | 329 | 3e−29 |
| B0496.3 | AAU05598.1 | B0496.3; B0496.3B Protein containing a protein tyrosine kinase domain and a protein kinase domain, has weak similarity to *C. albicans* Gin4p, which is involved in septum formation during germ tube formation | 261 | 31% | 50% | 310 | 6e−28 |
| unc-43 | CAA94244.2 | unc-43; K11E8.1C; dec-8; K11E8.1 Uncoordinated 43, calcium/calmodulin dependent serine/threonine kinase type II (CaMKII) that activates a MAP kinase cascade to regulate pathogen response, likely | 255 | 33% | 54% | 322 | 3e−27 |

TABLE 6-continued

| Gene | GenBank | Synonyms/Description | Match Length | % Iden | % Sim | High Score | E Val |
|---|---|---|---|---|---|---|---|
| C44C8.6 | AAC68944.1 | involved in egg-laying and locomotory behavior, operates upstream of DAF-3 and DAF-5 C44C8.6; C44C8.6A Protein with high similarity to MAP kinase-activated protein kinase (human MAPKAPK3), which is phosphorylated by CSBP1, CSBP2, ERK2(MAPK1), and SAPK (MAPK8) MAP kinases, contains a protein kinase domain | 263 | 31% | 50% | 291 | 2e−26 |
| W03G1.6 | AAD14754.1 | W03G1.6; W03G1.6A Protein containing a protein kinase domain, a protein tyrosine kinase domain, and a C-terminal kinase associated domain 1, has moderate similarity to maternal embryonic leucine zipper kinase (mouse Melk), which is a protein kinase | 244 | 31% | 51% | 289 | 3e−26 |
| B0511.4 | AAC17652.1 | B0511.4 Protein containing a protein kinase domain, has low similarity to camKI-like protein kinase (human CAMK1D), which is a protein kinase stimulated by human IL8 that activates ERK/MAP kinase activity and may act in granulocyte effector functions | 272 | 30% | 49% | 289 | 4e−26 |
| sad-1 | CAA94127.2 | sad-1; F15A2.6 Synapses of amphids defective 1, serine/threonine protein kinase that functions cell autonomously to promote presynaptic differentiation and localizes to synapse-rich regions of the axon | 260 | 30% | 52% | 307 | 6e−26 |
| W09C5.5 | CAB04940.1 | W09C5.5 Protein containing a protein kinase domain and two phorbol esters or diacylglycerol binding domains (C1 domains), has moderate similarity to mu isoform of protein kinase C (human PRKD1), which is a serine-threonine kinase involved in signal transduction | 236 | 34% | 54% | 291 | 6e−26 |
| titin | AAN61517.1 | titin; 2MDa_1; F12F3.2 Protein containing 12 fibronectin type III domains, 28 immunoglobulin (Ig) domains, 16 immunoglobulin V-set domains, 45 immunoglobulin I-set domains, and a protein kinase domain, has a region of weak similarity to C. elegans UNC-89 | 277 | 30% | 52% | 310 | 2e−25 |
| Y38H8A.4 | CAA16343.1 | Y38H8A.4 Protein containing a protein kinase domain, has moderate similarity to serine threonine kinase 22b (mouse Tssk2), which is involved in the cytodifferentiation of late spermatids into sperm | 305 | 28% | 47% | 283 | 2e−25 |
| F32D8.1 | CAA98453.2 | F32D8.1 Protein containing a protein tyrosine kinase domain and a protein kinase domain, has moderate similarity to calcium-calmodulin-dependent protein kinase ID (human CAMK1D), which is a protein kinase that activates ERK-MAP kinase activity | 306 | 28% | 50% | 325 | 4e−25 |
| R166.5 | CAD59152.1 | R166.5; R166.5B Protein that is a downstream target of a VHL-1 pathway | 282 | 31% | 48% | 284 | 7e−25 |
| zyg-8 | CAB54507.2 | zyg-8; Y79H2A.G; Y79H2A.11; Y75B8A.A; Y75B8A.36 Microtubule-associated protein with Doublecortin and kinase domains, required for microtubule assembly and stabilization and for proper spindle positioning | 261 | 32% | 51% | 282 | 7e−25 |
| unc-22 | CAA98082.2 | unc-22; ZK617.1B; ZK617.1 Serine-threonine protein kinase that may regulate muscle contraction, putative member of immunoglobulin superfamily | 253 | 30% | 51% | 288 | 1e−24 |
| ZK524.4 | CAA96698.1 | ZK524.4 Protein containing a protein kinase domain, has a region of high similarity to a region of SNRK protein kinase (rat SNRK), which may play a role in regulation of low potassium-induced apoptosis in cultured cerebellar granule neurons | 253 | 31% | 53% | 278 | 3e−24 |
| K12C11.4 | AAK18971.1 | K12C11.4 Protein containing seven ankyrin (Ank) repeats, a death domain, and a protein kinase domain, has low similarity to death associated protein kinase 1 (human DAPK1), which is a serine-threonine kinase that is a positive mediator of apoptosis | 274 | 28% | 49% | 276 | 5e−24 |
| W02B12.12 | CAA91402.1 | W02B12.12; W02B12.12A Protein containing a protein kinase domain, has low similarity to mouse Tssk1, which is a testis-specific kinase that forms a complex with testis-specific serine kinase 2 (mouse Tssk2) and binds and phosphorylates mouse Slk | 247 | 29% | 49% | 269 | 6e−24 |
| plk-1 | AAM22025.1 | plk-1; C14B9.4B POLO kinase 1, serine/threonine protein kinase that functions in cytokinesis and spindle assembly | 245 | 27% | 53% | 269 | 7e−24 |
| R02C2.6 | AAO21432.1 | R02C2.6 Protein containing a protein kinase domain, has low similarity to camKI-like protein kinase (human CAMK1D), which is a granulocyte-specific protein kinase that activates ERK-MAP kinase | 231 | 30% | 50% | 268 | 7e−24 |

TABLE 6-continued

| Gene | GenBank | Synonyms/Description | Match Length | % Iden | % Sim | High Score | E Val |
|---|---|---|---|---|---|---|---|
| DC2.7 | AAD14728.2 | activity and may play a role in granulocyte effector functions DC2.7; DC2.7A Protein containing two protein kinase domains, has weak similarity to ribosomal protein S6 kinase A5 (human RPS6KA5), which phosphorylates histones and activates human CREB1 after stress or growth factors and is activated by human PRKM1 or human PRKM11 | 231 | 31% | 51% | 271 | 2e−23 |
| plk-2 | AAF36014.1 | plk-2; Y71F9B.7 Putative serine/threonine protein kinase with strong similarity to *Drosophila* POLO, human PLK, yeast Cdc5p, and other members of the polo family, which are involved in activation of the anaphase-promoting complex in late mitosis | 248 | 27% | 51% | 262 | 4e−23 |
| Y43D4A.G | CAB60347.1 | Y43D4A.G; Y43D4A.6 Protein containing a protein kinase domain, has low similarity to serine threonine kinase 12 (rat Aurkb), which is a serine/threonine kinase that phosphorylates myosin II regulatory light chain and is involved in cytokinesis | 291 | 27% | 47% | 260 | 1e−22 |
| ZC373.4 | CAA88976.1 | ZC373.4 Protein containing a protein kinase domain, has a region of moderate similarity to a region of myosin light polypeptide kinase (human MYLK), which is a calcium/calmodulin-dependent kinase that acts on regulatory myosin light chains to activate contraction | 269 | 31% | 52% | 287 | 2e−22 |
| T25E12.4 | CAB07478.1 | T25E12.4; T25E12.4A Protein with high similarity to mu isoform of protein kinase C (protein kinase D, human PRKD1), contains two phorbol ester or diacylglycerol binding domains (C1 domains), a pleckstrin homology (PH) domain, and a protein kinase domain | 240 | 32% | 52% | 262 | 4e−22 |
| ckk-1 | AAA19242.2 | ckk-1; CaM-KK; C05H8.1 Ca2+/calmodulin-dependent protein kinase kinase 1, calcium and calmodulin-dependent protein kinase kinase, component of a phosphorylation cascade that stimulates cyclic AMP response element-dependent transcription | 284 | 26% | 46% | 255 | 4e−22 |
| plk-3 | AAC14425.1 | plk-3; F55G1.8 Polo-like kinase 2, putative serine/threonine protein kinase | 314 | 25% | 46% | 253 | 8e−22 |
| Y38F1A.10 | CAA21637.2 | Y38F1A.10; Y38F1A.L Protein with high similarity to human PAK3, which is a kinase downstream of human CDC42 and human RAC1 and is associated with nonsyndromic X-linked mental retardation upon gene mutation, contains a protein kinase and a protein tyrosine kinase domain | 262 | 30% | 47% | 252 | 9e−22 |
| pak-1 | AAA68805.2 | pak-1; C09B8.7A; CePAK; C09B8.7 P21 activated kinase 1, putative serine/threonine kinase that may regulate hypodermal cell shape changes during embryonic elongation | 466 | 26% | 42% | 255 | 1e−21 |
| F23C8.8 | AAD03136.1 | F23C8.8; F23C8.D Protein containing a protein kinase domain, has low similarity to serine threonine kinase 22b (mouse Tssk2), which is a serine/threonine kinase involved in the cytodifferentiation of late spermatids into sperm | 256 | 28% | 45% | 245 | 2e−21 |
| Y50D7A.3 | AAF59648.4 | Y50D7A.3 Protein containing a protein kinase domain, has moderate similarity to phosphorylase kinase gamma 2 (rat Phkg2), which is a calcium-calmodulin-dependent protein kinase that activates glycogen phosphorylase | 322 | 28% | 46% | 276 | 3e−21 |
| D1044.8 | AAK68286.2 | D1044.8 Protein containing a protein kinase domain, has a region of low similarity to NIMA (never in mitosis gene a)-related kinase 6 (human NEK6), which is a protein serine-threonine kinase | 277 | 28% | 46% | 251 | 3e−21 |
| phi-35 | AAB54139.1 | phi-35; ZC581.1 Protein involved in larval development, regulation of locomotion, and regulation of movement | 341 | 26% | 45% | 249 | 3e−21 |
| cds-1 | CAB60407.2 | cds-1; chk-2; Ce-cds-1; Ce-chk-2; Y60A3A.12 Required for pairing of homologous chromosomes during meiosis | 327 | 30% | 47% | 291 | 4e−21 |
| cdk-4 | CAB16923.2 | cdk-4; F18H3.5B; F18H3.5 Cyclin-dependent kinase family 4, protein required for postembryonic G1 progression | 229 | 33% | 51% | 247 | 4e−21 |
| T08D2.7 | CAB07420.2 | T08D2.7; Ce-cds-2 Strongly similar to *C. elegans* CDS-1; similar to *D. melanogaster* Dmnk-related kinase; may be required for meiotic recombination | 298 | 30% | 49% | 295 | 9e−21 |
| C05D10.2 | AAA20987.2 | C05D10.2; C05D10.2A Protein with high similarity to extracellular signal-regulated kinase 7 (rat Erk7), which is a constitutively active nuclear MAP kinase | 264 | 28% | 47% | 243 | 9e−21 |

TABLE 6-continued

| Gene | GenBank | Synonyms/Description | Match Length | % Iden | % Sim | High Score | E Val |
|---|---|---|---|---|---|---|---|
| | | that binds to chloride intracellular channel 3 and inhibits cell proliferation, contains a protein kinase domain | | | | | |
| mek-2 | AAA85118.1 | mek-2; let-537; Y54E10B_152.B; Y54E10B_152.C; Y54E10BL.6 MAP kinase kinase or ERK kinase 1, serine/threonine kinase required for vulval induction and meiotic cell cycle progression, involved in bacterial pathogen defense, sex myoblast migration, olfaction, and muscle proteolysis, and RAS-mediated signaling | 195 | 34% | 50% | 240 | 9e−21 |
| Y60A3A.1 | CAB60406.1 | Y60A3A.1 Protein with very strong similarity to *C. elegans* UNC-51, which is a serine/threonine protein kinase involved in axon morphogenesis and elongation, contains a protein kinase domain and a protein tyrosine kinase domain | 294 | 32% | 49% | 302 | 1e−20 |
| unc-51 | CAA86114.1 | unc-51; Y60A3.Y; Y60A3.W Serine/threonine protein kinase involved in axon morphogenesis and elongation | 294 | 32% | 49% | 302 | 1e−20 |
| kin-18 | AAA19437.1 | kin-18; T17E9.1A; Sulu; T17E9.1 Putative protein kinase that may regulate a signal transduction pathway in the pharynx to control pharyngeal pumping rate, involved in embryogenesis, body morphogenesis, and positive growth regulation | 275 | 31% | 45% | 246 | 2e−20 |
| nsy-1 | AAK31527.2 | nsy-1; esp-8; F59A6.1 Neuronal symmetry 1, protein that acts through a MAP kinase cascade to regulate pathogen response, controls gonadal programmed cell death in response to Salmonella enterica, regulates the OFF/ON position of the AWC olfactory neurons | 243 | 31% | 53% | 247 | 3e−20 |
| cdk-1 | CAA81590.1 | cdk-1; ncc-1; CECDC2A; T05G5.3 Cyclin-dependent kinase 1, putative cyclin dependent kinase required for cell cycle progression, meiosis and mitosis, functions in embryogenesis | 313 | 28% | 45% | 239 | 7e−20 |
| chk-1 | AAF59485.2 | chk-1; Y39H10A.7A; Y39H10A.7; Y39H10A.A; Y39H10A_224.A Checkpoint kinase 1, kinase required for early GOA-1-, GPA-16-dependent DNA replication checkpoint, functions in cell division asynchrony in two-cell embryos, involved in larval development, embryogenesis, and body morphogenesis | 210 | 31% | 52% | 245 | 1e−19 |
| R02C2.1 | AAO21431.1 | R02C2.1 Protein containing a protein kinase domain, has low similarity to *C. elegans* CMK-1, which is a calcium/calmodulin-dependent protein kinase | 279 | 28% | 47% | 242 | 1e−19 |
| ZC404.9 | AAA97966.1 | ZC404.9 Member of the citron homology (CNH) domain-containing family, contains a protein kinase domain and a protein tyrosine kinase dopmain, has moderate similarity to human MAP4K5, which activates Jun N-terminal kinase | 280 | 29% | 48% | 240 | 1e−19 |
| Y39G10AR.4 | AAK39610.1 | Y39G10AR.4; Y39G10AR.U Protein containing a protein kinase domain and a protein tyrosine kinase domain, has a region of moderate similarity to a region of NIMA-related expressed kinase 8 (mouse Nek8), which is a putative serine-threonine kinase required for kidney development | 289 | 26% | 46% | 238 | 1e−19 |
| Y39G10AR.3 | AAT81178.1 | Y39G10AR.3; Y39G10AR.V Protein containing a protein kinase domain and a protein tyrosine kinase domain, has a region of low similarity to a region of NIMA-related kinase 9 (human NEK9), which is a serine/threonine protein kinase and FACT complex component that binds human RAN | 289 | 26% | 46% | 238 | 2e−19 |
| mpk-1 | AAA18956.1 | mpk-1; F43C1.2B; sur-1; F43C1.2 MAP kinase 1, serine/threonine kinase required for vulval induction and meiotic progression, involved in bacterial pathogen defense, oogenesis, embryogenesis, muscle proteolysis, fluid homeostasis, sex myoblast migration, and RAS-mediated signaling | 320 | 24% | 46% | 229 | 1e−18 |
| prk-1 | AAA50639.2 | prk-1; C06E8.3A; C06E8.3 Protein containing a protein kinase domain, has a region of moderate similarity to proviral integration site 3 (kinase induced by depolarization 1) (rat Pim3), which is a serine-threonine protein kinase that may play a role in neurogenesis | 304 | 27% | 45% | 229 | 1e−18 |
| pmk-2 | AAM98017.2 | pmk-2; F42G8.3B; F42G8.3 P38 map kinase family 2, mitogen-activated protein kinase that may be involved in response to osmotic and other cellular stresses | 258 | 26% | 49% | 222 | 4e−18 |

TABLE 6-continued

| Gene | GenBank | Synonyms/Description | Match Length | % Iden | % Sim | High Score | E Val |
|---|---|---|---|---|---|---|---|
| gck-1 | AAC69038.1 | gck-1; T19A5.2A; T19A5.2 Protein containing a protein tyrosine kinase domain and a protein kinase domain, has low similarity to MAP-microtubule affinity regulating kinase 3 (human MARK3), which is a serine-threonine kinase that functions during the DNA damage checkpoint | 248 | 27% | 51% | 251 | 5e-18 |
| tlk-1 | CAD45580.2 | tlk-1; C07A9.3B; C07A9.3 Tousled-like kinase 1, predicted to regulate transcription elongation by phosphorylation of AMA-1 at S2 of the C-terminal domain, methylates histone H3 at K36 | 421 | 27% | 44% | 242 | 1e-17 |
| ZC504.3 | CAA90342.1 | ZC504.3 Protein with high similarity to C. elegans B0495.2, which is a serine/threonine cyclin-dependent protein kinase that functions in genome stability of somatic cells, contains a protein kinase domain | 339 | 25% | 46% | 225 | 1e-17 |
| F19H6.1 | CAA90762.2 | F19H6.1 Protein involved in growth rate regulation, morphogenesis of an epithelium, locomotory behavior, and hermaphrodite genital morphogenesis | 242 | 26% | 47% | 216 | 1e-17 |
| K08F8.1 | CAA91283.1 | K08F8.1; K08F8.1A Protein involved in lipid storage | 267 | 28% | 49% | 236 | 2e-17 |
| C04A11.3 | CAB03829.1 | C04A11.3 Protein involved in regulation of movement | 213 | 30% | 54% | 221 | 2e-17 |
| Y42A5A.4 | CAB63367.1 | Y42A5A.4 Protein with high similarity to cyclin-dependent kinase like 1 (CDC2-related kinase 1, human CDKL1), which is activated by epidermal growth factor (human EGF) and phosphorylates histones and is associated with gliosis, contains a protein kinase domain | 248 | 29% | 49% | 215 | 2e-17 |
| R02C2.2 | AAC48229.2 | R02C2.2 Protein containing a protein kinase domain, has a region of moderate similarity to a region of human CHEK1, which is a protein kinase that inhibits mitotic entry after DNA damage via a mechanism that involves the phosphatase CDC25 | 207 | 29% | 48% | 213 | 2e-17 |
| C24A8.4 | AAK39183.2 | C24A8.4; C24A8.4A Putative rhodopsin-like G protein-coupled receptor and serine/threonine kinase that is a downstream target of a VHL-1 pathway | 254 | 28% | 50% | 237 | 3e-17 |
| F14H12.4 | AAK68327.1 | F14H12.4; F14H12.4B Protein with high similarity to serine threonine kinase 3 (human STK3), which is a protein kinase activated by cell stress that acts in apoptosis via caspase activation, contains a protein kinase and protein tyrosine kinase domain | 254 | 28% | 50% | 237 | 3e-17 |
| mkk-4 | CAA88264.1 | mkk-4; F42G10.2 MKK (MAP kinase kinase) homolog 4, predicted protein kinase that acts as a member of the MAP kinase cascade that is required for normal distribution of synaptic vesicles at the presynaptic terminal, operates in the same pathway with PMK-3 and DLK-1 | 225 | 28% | 50% | 213 | 3e-17 |
| gsk-3 | AAD45354.1 | gsk-3; sgg-1; Y18D10A.F; Y18D10A.5 Glycogen synthase kinase 3, a serine/threonine protein kinase required for early embryonic development and proper spindle orientation and polarization of the EMS and P2 blastomeres | 213 | 29% | 51% | 214 | 4e-17 |
| jkk-1 | AAA81711.2 | jkk-1; F35C8.3 JNK kinase 1, serine/threonine protein kinase and member of the JNK signaling pathway that appears to be required for maintenance of normal life span | 290 | 26% | 44% | 216 | 5e-17 |
| C44H4.6 | CAB01863.1 | C44H4.6 Protein containing a protein kinase domain, has moderate similarity to glycogen synthase kinase-3 beta (mouse Gsk3b), which is a serine-threonine protein kinase involved in embryonic development | 209 | 29% | 48% | 209 | 5e-17 |
| pmk-1 | AAB00664.1 | pmk-1; B0218.3 p38 Map kinase 1, serine/threonine protein kinase that functions in pathogen and hyperosmotic response, regulates gonadal programmed cell death in response to Salmonella enterica | 165 | 29% | 57% | 208 | 5e-17 |
| wee-1.3 | CAB16484.1 | wee-1.3; spe-37; Y53C12A.1 Putative serine/threonine/tyrosine protein kinase required for embryonic morphogenesis, germ line proliferation, initiating meiosis during spermatogenesis, and lipid storage | 275 | 26% | 49% | 215 | 6e-17 |
| M04C9.5 | CAB06021.1 | M04C9.5 Protein containing a protein kinase domain, has low similarity to S. pombe Pit1p, which is a putative serine/threonine protein kinase that plays a role in sporulation | 191 | 31% | 50% | 207 | 1e-16 |
| B0414.7 | AAK68678.1 | B0414.7; B0414.7B Serine/threonine protein kinase of the MAP kinase kinase (MEK kinase) subfamily, has similarity to S. cerevisiae Ssk2p and Ssk22p | 236 | 28% | 47% | 211 | 2e-16 |

TABLE 6-continued

| Gene | GenBank | Synonyms/Description | Match Length | % Iden | % Sim | High Score | E Val |
|---|---|---|---|---|---|---|---|
| dlk-1 | CAB06544.3 | dlk-1; F33E2.2A; F33E2.2 DAP (Death associated protein kinase) like kinase 1, predicted protein kinase that is a member of the MAP kinase cascade required for normal distribution of synaptic vesicles at the presynaptic terminal, activates MKK-4 | 204 | 30% | 52% | 209 | 3e−16 |
| lit-1 | CAB05827.2 | lit-1; W06F12.1A; W06F12.1 Loss of intestine 1, serine/threonine protein kinase that functions to establish anteroposterior polarity of dividing embryonic cells, phosphorylates POP-1 on serine and threonine | 209 | 29% | 52% | 206 | 4e−16 |
| mig-15 | CAC42384.1 | mig-15; ZC504.4C; ZC504.4 Protein related to mammalian Nck-interacting kinase, involved in axonal outgrowth and guidance through integrin binding, and in lipid storage | 214 | 30% | 51% | 243 | 5e−16 |
| B0495.2 | AAA62523.1 | B0495.2 Serine/threonine cyclin-dependent protein kinase of the PITSLRE CDC2-like protein kinase family that functions in genome stability of somatic cells | 345 | 26% | 42% | 218 | 5e−16 |
| C45B11.1 | CAA98429.1 | C45B11.1; C45B11.1A Protein containing a P21-Rho-binding domain, which are also known as a Cdc42 or Rac interactive binding (CRIB) domain, a protein tyrosine kinase domain, and a protein kinase domain, has moderate similarity to p21(CDKN1A)-activated kinase 4 (human PAK4) | 266 | 27% | 47% | 205 | 5e−16 |
| prk-2 | CAA84323.2 | prk-2; F45H7.4 Pim-related kinase 2, protein involved in lipid storage | 282 | 24% | 44% | 204 | 5e−16 |
| pct-1 | AAL00852.1 | pct-1; C07G1.3B; C07G1.3 Protein containing a protein kinase domain, has a region of high similarity to PCTAIRE protein kinase 1 (human PCTK1), which is a cell-cycle regulated serine-threonine protein kinase that may be associated with X chromosome-linked heritable disorders | 206 | 27% | 50% | 202 | 5e−16 |
| lin-2 | CAA90760.2 | lin-2; F17E5.1A; F17E5.1 Component of the LIN-2, LIN-7, LIN-10 cell junction complex, involved in vulval development, probable ortholog of human and rat CASK proteins (putative scaffold proteins of the cytoskeletal membrane involved in signal transduction coordination) | 403 | 20% | 44% | 210 | 7e−16 |
| Y106G6A.1 | CAA21594.1 | Y106G6A.1 Protein containing a protein kinase domain, has a region of low similarity to a region of mitogen activated protein kinase kinase kinase 3 (human MAP3K3), which activates the SAPK (MAPK8) and ERK (MAPK3) but not the p38 MAP kinase (MAPK14) pathway | 213 | 29% | 52% | 202 | 9e−16 |
| Y106G6D.4 | CAA20977.2 | Y106G6D.4 Protein containing a protein kinase domain, has low similarity to glycogen synthase kinase 3 (*C. elegans* GSK-3), which is a serine-threonine protein kinase required for early embryonic development and proper spindle orientation and polarization | 321 | 28% | 43% | 205 | 1e−15 |
| pmk-3 | AAB92065.2 | pmk-3; F42G8.4 P38 map kinase family 3, mitogen-activated protein kinase, member of the MAP kinase cascade that is required for normal distribution of synaptic vesicles at the presynaptic terminal, likely involved in response to osmotic and other cellular stresses | 243 | 26% | 52% | 204 | 1e−15 |
| zyg-1 | AAB54253.2 | zyg-1; F59E12.2 Zygote defective/embryonic lethal 1, protein required, possibly maternally, for centrosome separation and centriole duplication, contributes to localization of proteins to the centriole | 242 | 26% | 48% | 197 | 4e−15 |
| F09C12.2 | AAN63410.1 | F09C12.2 Protein with high similarity to *S. pombe* Spk1p, which is a mitogen-activated protein kinase acting in the mating and sporulation pathways, contains a protein kinase domain | 205 | 28% | 47% | 194 | 6e−15 |
| hpk-1 | AAM54186.1 | hpk-1; F20B6.8B; F20B6.8 Protein containing a protein kinase domain, has high similarity to a region of homeodomain interacting protein kinase 2 (mouse Hipk2), which is a protein kinase that binds to and represses the transcriptional activity of homeodomain proteins | 228 | 31% | 50% | 215 | 7e−15 |
| T07F12.4 | AAA68420.2 | T07F12.4 Protein containing a protein kinase domain, has low similarity to *S. pombe* Pef1p, which is a putative cyclin-dependent serine-threonine protein kinase that is involved in G1 to S phase transition | 260 | 28% | 47% | 192 | 2e−14 |

TABLE 6-continued

| Gene | GenBank | Synonyms/Description | Match Length | % Iden | % Sim | High Score | E Val |
|---|---|---|---|---|---|---|---|
| kin-21 | CAA94238.2 | kin-21; Cehd-3; W08D2.8 Putative tyrosine protein kinase, has similarity to human and *D. melanogaster* fps/fes-related protein kinases | 211 | 27% | 47% | 189 | 2e−14 |
| kgb-2 | AAB88368.2 | kgb-2; ZC416.4 Protein with strong similarity to *C. elegans* KGB-1, which is a putative protein serine-threonine kinase involved in oogenesis and spermatogenesis, contains a protein kinase domain | 206 | 29% | 49% | 189 | 2e−14 |
| F39H11.3 | CAB03083.2 | F39H11.3 Protein involved in reproduction and morphogenesis of an epithelium | 266 | 27% | 45% | 190 | 4e−14 |
| kgb-1 | AAK39276.2 | kgb-1; T07A9.3 Kinase that GLHs bind 1, putative protein serine/threonine kinase that is involved in oogenesis and spermatogenesis, member of a MAPK pathway that regulates response to heavy metal stress | 268 | 27% | 47% | 190 | 4e−14 |
| gck-3 | CAC14417.2 | gck-3; Y59A8B.23 Germinal center kinase-3, volume sensitive kinase that inhibits activation of the ClC anion channel CLH-3 in a phosphorylation dependent manner | 224 | 26% | 48% | 187 | 5e−14 |
| cdk-5 | CAB04875.1 | cdk-5; T27E9.3 Protein with high similarity to cyclin-dependent protein kinase 5 (rat Cdk5), which is a serine-threonine kinase that associates with the regulatory subunit p35 (rat Cdk5r) and phosphorylates neuronal proteins, contains a protein kinase domain | 295 | 24% | 41% | 184 | 6e−14 |
| H01G02.2 | CAB07422.2 | H01G02.2 Protein containing a protein kinase domain, has moderate similarity to cyclin-dependent protein kinase 7 (rat Cdk7), which is a component of TFIIH, acts in transcription from Pol II promoter, and may act as part of the CDK-activating kinase | 232 | 25% | 44% | 182 | 6e−14 |
| cdk-7 | AAD38186.1 | cdk-7; (Y39G10AL.3) Putative cyclin-dependent protein kinase, phosphorylates RNA polymerase II, required for mRNA transcription, cell cycle progression, meiosis, and mitosis | 198 | 30% | 46% | 180 | 9e−14 |
| Y39G10AL.3 | AAK68887.2 | Y39G10AL.3 Protein with very strong similarity to *C. elegans* CDK-7, which is a putative cyclin-dependent protein kinase that phosphorylates RNA polymerase II and is required for transcription and cell cycle progression, contains a protein kinase domain | 198 | 30% | 46% | 180 | 9e−14 |
| W06B3.2 | CAA18361.3 | W06B3.2; W06B3.2A Protein containing a protein kinase domain, has low similarity to mitogen-activated protein kinase 3 (human MAPK3), which transduces signals from cell surface receptors and is involved in cell proliferation and defense responses | 290 | 25% | 43% | 185 | 2e−13 |
| mpk-2 | AAA98016.3 | mpk-2; C04G6.1A; C04G6.1 Protein containing a protein kinase domain, has low similarity to *C. albicans* Mkc1p, which is a serine/threonine protein kinase | 208 | 28% | 46% | 184 | 2e−13 |
| VZC374L.1 | CAB08354.1 | VZC374L.1 Protein with high similarity to mitogen-activated protein kinase kinase 4 (human MAP2K4), which is a putative tumor suppressor involved in the response to cellular stress and apoptosis activation, contains a protein kinase domain | 235 | 26% | 48% | 179 | 2e−13 |
| sek-1 | BAC11708.1 | sek-1; esp-2; R03G5.2 SAPK/ERK kinase 1, putative MAP kinase kinase that acts through a kinase cascade to regulate pathogen response and determination of asymmetric cell fate, functions in response to hyperosmotic stress | 294 | 26% | 45% | 184 | 3e−13 |
| Y116A8C.38 | CAB55139.2 | Y116A8C.38 Protein containing a Src homology 2 (SH2) domain, which are regulatory modules of intracellular signaling, a protein kinase domain and a protein tyrosine kinase domain, has low similarity to *C. elegans* T04B2.2, which functions in lipid storage | 250 | 26% | 44% | 181 | 4e−13 |
| Y116A8C.24 | CAB55129.1 | Y116A8C.24 Protein containing a protein kinase domain, a protein tyrosine kinase domain, and a Src homology 2 (SH2) domain, which are regulatory modules of intracellular signaling, has low similarity to *C. elegans* T04B2.2, which is involved in lipid storage | 250 | 26% | 44% | 181 | 4e−13 |
| jnk-1 | AAA98724.2 | jnk-1; B0478.1A; B0478.1 Jnk homolog 1, mitogen-activated serine/threonine protein kinase, positive regulator of life span acting in a pathway parallel to the insulin-like pathway converging on DAF-16 | 355 | 23% | 42% | 181 | 5e−13 |
| F26E4.5 | CAB03003.2 | F26E4.5 Protein containing a Src homology 2 (SH2) domain, which are regulatory modules of intracellular signaling, a protein kinase domain, and a protein tyrosine kinase domain, has moderate | 263 | 24% | 46% | 180 | 5e−13 |

TABLE 6-continued

| Gene | GenBank | Synonyms/Description | Match Length | % Iden | % Sim | High Score | E Val |
|---|---|---|---|---|---|---|---|
| | | similarity to *C. elegans* T04B2.2, which is involved in lipid storage | | | | | |
| lin-45 | AAF36042.1 | lin-45; Y73B6A.5A; raf-1; Y73B6A.5 Lineage abnormal 45, RAF-like serine/threonine kinase involved in bacterial pathogen defense, L1 larval viability, vulval and male spicule development, sex myoblast migration, olfaction, muscle proteolysis, and RAS-mediated signaling | 229 | 25% | 45% | 178 | 9e−13 |
| mbk-2 | CAA94353.1 | mbk-2; F49E11.1B; F49E11.1 Minibrain kinase 2, dual-specificity protein kinase that drives the transition from egg to embryo, regulates the formation of asymmetric germ plasm, spindle positioning and the degradation of specific proteins during the meiosis to mitosis transition | 652 | 22% | 39% | 197 | 1e−12 |
| cdk-9 | CAB07238.3 | cdk-9; H25P06.2B; H25P06.2 Cyclin-dependent kinase family 9, essential putative protein kinase and transcription elongation factor essential for expression of many early embryonic genes and required for embryonic development | 233 | 26% | 44% | 173 | 1e−12 |
| T06C10.3 | AAA82300.1 | T06C10.3 Protein containing a Src homology 2 (SH2) domain, which are regulatory modules of intracellular signaling, a protein kinase domain, and a protein tyrosine kinase domain, has moderate similarity to *C. elegans* T04B2.2, which acts in lipid storage | 224 | 28% | 46% | 175 | 2e−12 |
| Y52D3.1 | CAA19523.1 | Y52D3.1 Protein involved in embryogenesis | 244 | 28% | 44% | 177 | 5e−12 |
| B0285.1 | CAA84302.3 | B0285.1 Member of the protein kinase family that is involved in embryogenesis, body morphogenesis, positive growth regulation, and regulation of movement | 331 | 21% | 42% | 174 | 5e−12 |
| kin-3 | AAC16993.1 | kin-3; CKIIalpha; B0205.7 Casein kinase II, alpha subunit | 236 | 26% | 47% | 198 | 6e−12 |
| ZC123.4 | AAU87802.1 | ZC123.4; ZC123.4B Protein containing a protein kinase domain, has weak similarity to CDC-like kinase 1 (human CLK1), which is a protein serine-threonine kinase that may play a role in cell cycle control and cell proliferation | 228 | 29% | 48% | 187 | 6e−12 |
| flr-4 | BAA89795.1 | flr-4; F09B12.6 Fluoride-resistant 4, predicted serine/threonine kinase involved in fluoride uptake and timing of development, involved in regulation of the defecation cycle periods in a cell-functional aspect and not in a developmental aspect | 282 | 26% | 45% | 171 | 1e−11 |
| csk-1 | AAK29898.3 | csk-1; Y48G1C.2 Protein tyrosine kinase that suppresses SRC-1 or KIN-22 induced growth inhibition and tyrosine phosphorylation in yeast | 261 | 26% | 44% | 175 | 2e−11 |
| F21F3.2 | AAB42279.1 | F21F3.2 Protein containing a protein kinase domain, has low similarity to *S. cerevisiae* Rim11p, which is required for induction of IME2 by Ime1p | 298 | 27% | 40% | 169 | 2e−11 |
| F35C8.1 | AAX55692.1 | F35C8.1 Protein containing a protein kinase domain, has a region of moderate similarity to mitogen-activated protein kinase kinase 6 (rat Map2k6), which is a threonine-tyrosine kinase that activates MAP kinase p38 following heat shock and interleukin 1 beta | 99 | 36% | 57% | 157 | 3e−11 |
| F35C8.2 | AAX55693.1 | F35C8.2 Protein containing a protein kinase domain, has low similarity to a region of mitogen-activated protein kinase kinase 6 (rat Map2k6), which is a protein threonine-tyrosine kinase that phosphorylates and activates MAP kinase p38 in response to heat shock | 76 | 39% | 61% | 153 | 4e−11 |
| E02D9.1 | AAS80347.1 | E02D9.1; E02D9.1C Protein involved in positive regulation of growth rate, locomotory behavior, gametogenesis, and hermaphrodite genital morphogenesis | 240 | 28% | 45% | 164 | 6e−11 |
| R03D7.5 | CAA86858.2 | R03D7.5 Protein containing a protein kinase domain, has low similarity to *S. cerevisiae* Rim11p, which is a protein kinase required for induction of *S. cerevisiae* Ime2p by *S. cerevisiae* Ime1p | 325 | 25% | 40% | 160 | 6e−11 |
| C46C2.1 | CAA92591.3 | C46C2.1; C46C2.1A Protein involved in growth rate regulation and egg-laying | 182 | 28% | 50% | 163 | 8e−11 |
| R151.4 | AAP82638.1 | R151.4; R151.4A Protein containing a protein tyrosine kinase domain and a protein kinase domain, has low similarity to *C. elegans* PHI-35, which is involved in body morphogenesis and larval development and locomotory behavior and suppressing polyglutamine aggregation | 206 | 26% | 49% | 158 | 8e−11 |

TABLE 6-continued

| Gene | GenBank | Synonyms/Description | Match Length | % Iden | % Sim | High Score | E Val |
|---|---|---|---|---|---|---|---|
| kin-23 | AAF00546.1 | kin-23; W04G5.6A; Cehd-7; W04G5.6 Putative receptor tyrosine protein kinase, has similarity to human and *D. melanogaster* fibroblast growth factor receptor-related protein kinases | 223 | 27% | 45% | 159 | 1e−10 |
| ZC449.3 | AAM69076.1 | ZC449.3; ZC449.3B Protein containing a protein kinase domain, has moderate similarity to mitogen-activated protein kinase kinase 4 (mouse Map2k4), which may be involved in the response to cellular stress and may trigger apoptosis | 217 | 29% | 43% | 156 | 1e−10 |
| E02H4.3 | CAA94122.2 | E02H4.3; E02H4.3A Protein containing a protein kinase domain, has a region of high similarity to CDC-like kinase 2 (human CLK2), which is a dual specificity protein kinase that associates with serine- and arginine-rich (SR) proteins and may thus regulate mRNA splicing | 516 | 24% | 41% | 200 | 2e−10 |
| par-4 | AAD45355.1 | par-4 Partitioning defective 4, probable serine/threonine kinase required for polarized cytoplasmic flow and the asymmetric distribution of P granules and other factors during embryogenesis | 265 | 23% | 45% | 166 | 2e−10 |
| Y59A8B.14 | CAC15862.2 | Y59A8B.14 Protein with very strong similarity to *C. elegans* PAR-4, which is a probable serine/threonine kinase required for the asymmetric distribution of P granules and other factors during embryogenesis, contains a protein kinase domain | 265 | 23% | 45% | 166 | 2e−10 |
| C36B7.2 | AAK68228.1 | C36B7.2 Protein containing a protein kinase domain, has low similarity to a region of dual-specificity tyrosine phosphorylated and regulated kinase 3 (human DYRK3), which phosphorylates histone H2B and H3 and may function in spermatogenesis | 232 | 27% | 46% | 159 | 2e−10 |
| C24A1.3 | AAB70312.2 | C24A1.3; C24A1.3A Protein containing nine ankyrin repeats, which may mediate protein-protein interactions, a protein tyrosine kinase domain, and a protein kinase domain, has moderate similarity to TNNI3 interacting kinase (human TNNI3K), which is a troponin-binding kinase | 214 | 27% | 46% | 159 | 2e−10 |
| F11E6.8 | CAB02923.1 | F11E6.8 Protein containing a protein kinase and protein tyrosine kinase domain, has low similarity to v-src avian sarcoma viral oncogene homolog (human SRC), which is a tyrosine kinase involved in cell proliferation, cell adhesion, and cytoskeletal organization | 233 | 26% | 45% | 157 | 2e−10 |
| K03E5.3 | AAC17568.2 | K03E5.3; K03E5.3A Protein involved in morphogenesis of an epithelium, locomotory behavior, larval development, cuticle biosynthesis, and body morphogenesis | 207 | 29% | 46% | 153 | 2e−10 |
| C49C3.10 | CAB05163.1 | C49C3.10; C49C3.10A Protein containing a protein kinase domain, has low similarity to jun N-terminal kinase 2 (human MAPK9), which regulates c-Jun (JUN) in response to proinflammatory cytokines or cellular stress and also triggers apoptosis | 140 | 31% | 48% | 153 | 2e−10 |
| F57B9.8 | AAA21175.2 | F57B9.8 Protein containing a protein kinase, a protein tyrosine kinase, and a Src homology 2 (SH2) domain, which are regulatory modules of intracellular signaling, has moderate similarity to *C. elegans* T04B2.2, which is involved in lipid storage | 283 | 24% | 46% | 158 | 3e−10 |
| F01D4.3 | CAB02882.2 | F01D4.3 Protein containing a protein kinase domain, a protein tyrosine kinase domain, and a Src homology 2 (SH2) domain, has moderate similarity to *C. elegans* T04B2.2, which is involved in lipid storage | 242 | 26% | 45% | 155 | 4e−10 |
| sma-6 | AAD12261.1 | sma-6; C32D5.2 Small 6, receptor serine/threonine protein kinase involved in body size regulation and male tail development | 220 | 24% | 45% | 154 | 4e−10 |
| T25B9.4 | CAA94372.1 | T25B9.4 Protein containing a protein tyrosine kinase and a protein kinase domain, and a Src homology 2 (SH2) domain, which are regulatory modules of intracellular signaling, has low similarity to *C. elegans* F22B3.8, which is involved in positive growth regulation | 225 | 24% | 48% | 179 | 6e−10 |
| ZK593.9 | CAA93423.1 | ZK593.9 Protein containing a Src homology 2 (SH2) domain, which are regulatory modules of intracellular signaling, a protein tyrosine kinase domain, and a protein kinase domain, has low similarity to protein kinase 22 (*C. elegans* KIN-22) | 201 | 26% | 49% | 173 | 6e−10 |
| C36B1.10 | CAB02275.1 | C36B1.10 Protein containing a protein kinase domain, has low similarity to glycogen synthase kinase-3 beta (human GSK3B), which is a serine- | 224 | 26% | 43% | 150 | 6e−10 |

TABLE 6-continued

| Gene | GenBank | Synonyms/Description | Match Length | % Iden | % Sim | High Score | E Val |
|---|---|---|---|---|---|---|---|
| | | threonine protein kinase that regulates beta-catenin (CTNNB1) stability in Wnt signaling and acts in embryonic development | | | | | |
| W04G5.10 | CAC42353.1 | W04G5.10 Protein containing a protein kinase domain and a protein tyrosine kinase domain, has moderate similarity to *C. elegans* OLD-1, which is a putative receptor tyrosine protein kinase that extends life span when overproduced | 236 | 28% | 46% | 171 | 8e−10 |
| Y47G6A.5 | AAF60657.1 | Y47G6A.5; Y47G6A.5A Protein containing a Src homology 2 (SH2), a Src homology 3 (SH3), a variant SH3, a protein tyrosine kinase and a protein kinase domain, has moderate similarity to *C. elegans* SRC-1, which is a protein tyrosine kinase that acts in cell division | 315 | 24% | 45% | 159 | 8e−10 |
| F53G12.6 | AAB54162.2 | F53G12.6 Protein containing a protein kinase, a protein tyrosine kinase, and a Src homology 2 (SH2) domain, has low similarity to fer tyrosine kinase (mouse Fert2), which is a tyrosine kinase that regulates the mitotic cell cycle and the hyperosmotic response | 203 | 27% | 48% | 152 | 8e−10 |
| mek-1 | AAA79746.2 | mek-1; K08A8.1A; kin-17; mkk7; K08A8.1 MAP kinase kinase or Erk kinase 1, protein that is a member of a MAPK pathway that regulates response to heavy metal stress and to pathogens | 153 | 30% | 46% | 146 | 9e−10 |
| Y69E1A.3 | CAA22261.1 | Y69E1A.3; Y69E1A.C Protein containing a protein kinase domain, a protein tyrosine kinase domain, and a Src homology 2 (SH2) domain, has low similarity to protein kinase 14 (*C. elegans* KIN-14), which is involved in positive regulation of body size | 246 | 23% | 42% | 150 | 1e−09 |
| unc-89 | AAP68958.1 | unc-89; C09D1.1B; phm-1; C09D1.1; C24G7.5 Uncoordinated 89, protein expressed as four major isoforms required for M line assembly in muscles, involved in the regulation of movement | 182 | 31% | 51% | 191 | 2e−09 |
| vab-1 | AAK77620.1 | vab-1; M03A1.1A; M03A1.1 Variable abnormal morphology 1, putative receptor tyrosine kinase involved in epidermal morphogenesis, acts to negatively regulate oocyte maturation and ovulation upon sperm depletion, functions in ventral cord asymmetry and axon guidance | 223 | 26% | 44% | 153 | 2e−09 |
| T25B9.5 | CAA94373.1 | T25B9.5 Protein containing a protein tyrosine kinase domain, a protein kinase domain and a Src homology 2 (SH2) domain, which are regulatory modules of intracellular signaling has low similarity to *C. elegans* T04B2.2, which is involved in lipid storage | 247 | 24% | 43% | 149 | 2e−09 |
| F52B5.2 | CAA99854.2 | F52B5.2 Protein containing a protein kinase domain, has low similarity to *C. albicans* Cdc28p, which is a serine-threonine protein kinase involved in the cell cycle | 174 | 29% | 47% | 148 | 2e−09 |
| Y106G6E.1 | CAB76732.1 | Y106G6E.1 Protein containing a protein kinase domain, has low similarity to *C. elegans* GSK-3, which is a serine/threonine protein kinase that is required for proper spindle orientation and polarization of the EMS blastomere | 230 | 26% | 40% | 147 | 2e−09 |
| kin-24 | CAA94277.1 | kin-24; cehd-8; K07F5.4 Protein kinase 24, putative FER (fps/fes-related)-like tyrosine protein kinase | 222 | 27% | 47% | 168 | 4e−09 |
| mbk-1 | CAA93756.2 | mbk-1; T04C10.1 Minibrain kinase 1, member of the DYRK/minibrain kinase family that functions in sensory neurons to regulate chemotaxis to specific volatile odorants but is not essential for viability | 210 | 30% | 47% | 150 | 4e−09 |
| F46F5.2 | AAC78196.1 | F46F5.2 Protein containing a Src homology 2 (SH2) domain, which are regulatory modules of intracellular signaling, a protein kinase domain, and a protein tyrosine kinase domain, has moderate similarity to *C. elegans* T04B2.2, which is involved in lipid storage | 178 | 28% | 48% | 144 | 4e−09 |
| C53A5.4 | CAB03982.1 | C53A5.4 Protein containing a protein kinase domain, has moderate similarity to *C. elegans* C04G2.2, which is a protein involved in lipid storage | 308 | 24% | 41% | 147 | 6e−09 |
| src-1 | AAK29735.3 | src-1; Y92H12A.1; Y92H12A.F; Y92H12A.G SRC oncogene related 1, protein tyrosine kinase component of a signaling pathway between embryonic blastomeres P2 and EMS that controls the axis of cell division and differentiation into endoderm of EMS, upstream of LET-99 in spindle positioning | 257 | 23% | 44% | 147 | 6e−09 |
| ksr-2 | CAB70239.2 | ksr-2; F58D5.4A; F58D5.4 Protein required for Ras-mediated signaling during meiotic progression, may | 276 | 22% | 43% | 148 | 7e−09 |

TABLE 6-continued

| Gene | GenBank | Synonyms/Description | Match Length | % Iden | % Sim | High Score | E Val |
|---|---|---|---|---|---|---|---|
| | | be a serine/threonine kinase, and has similarity to *H. sapiens* and *D. melanogaster* KSR (kinase suppressor of ras) protein kinases | | | | | |
| mom-4 | CAB60998.1 | mom-4; F52F12.3 More mesoderm 1, serine/threonine protein kinase that is involved in control of the axis of cell division and differentiation of the EMS blastomere, may specify intestinal cell face | 203 | 27% | 50% | 143 | 9e−09 |
| Y65B4A.9 | AAK29951.1 | Y65B4A.9; Y65B4A.A Protein involved in reproduction | 158 | 24% | 48% | 139 | 9e−09 |
| prp-4 | CAA95814.1 | prp-4; F22D6.5 Yeast PRP (splicing factor) related 4, protein involved in growth rate regulation, locomotory behavior, and gametogenesis | 233 | 25% | 45% | 166 | 1e−08 |
| W01B6.2 | CAA92625.1 | W01B6.2 Protein with high similarity to *C. elegans* C04G2.2, which is involved in lipid storage, contains a protein kinase domain | 359 | 23% | 43% | 147 | 1e−08 |
| C18H7.4 | AAF98610.1 | C18H7.4 Protein containing a protein tyrosine kinase domain, a protein kinase domain, and a Src homology 2 (SH2) domain, which are regulatory modules of intracellular signaling, has low similarity to fer (fps/fes related) tyrosine kinase (mouse Fert2) | 292 | 23% | 42% | 143 | 1e−08 |
| Y81G3A.3 | CAA22515.1 | Y81G3A.3 Member of the RWD domain containing family, contains a protein kinase domain, has weak similarity to eukaryotic initiation factor 2 alpha kinase 4 (mouse Eif2ak4), which phosphorylates the alpha subunit (mouse Eif2s1) of translation initiation factor eIF2 | 245 | 24% | 42% | 145 | 2e−08 |
| daf-4 | AAC02726.1 | daf-4; C05D2.1A; C05D2.1 Dauer formation 4, type II TGFbeta receptor kinase, involved in regulation of dauer formation, body size, and male tail development, plays a role in initiating necrotic cell death, regulates chemosensory receptor expression | 213 | 25% | 48% | 141 | 2e−08 |
| F23C8.7 | AAD03135.1 | F23C8.7; F23C8.E Protein containing a protein kinase, a protein tyrosine kinase, and a Src homology 2 (SH2) domain, has moderate similarity to *C. elegans* T04B2.2, which is involved in lipid storage | 229 | 24% | 45% | 140 | 2e−08 |
| T14E8.1 | AAA82385.2 | T14E8.1; T14E8.1A Protein containing a protein kinase and a protein tyrosine kinase domain, has a region of moderate similarity to a region of met proto-oncogene (human MET), which is a receptor tyrosine kinase that acts in cell proliferation and migration | 214 | 28% | 45% | 144 | 3e−08 |
| kin-22 | | kin-22; Cehd-4; F49B2.5 Protein kinase 22, protein tyrosine kinase that may be involved in pharynx morphogenesis | 306 | 21% | 42% | 138 | 3e−08 |
| old-2 | CAA90147.1 | old-2; kin-28; tkr-2; ZK938.5 Overexpression longevity determinant 2, putative tyrosine protein kinase | 232 | 26% | 45% | 138 | 3e−08 |
| ksr-1 | AAK39225.1 | ksr-1; sur-3; F13B9.4; F13B9.5 Kinase suppressor of activated ras 1, RAF-like serine/threonine kinase scaffold protein required for MPK-1 phosphorylation and MEK localization, involved in bacterial pathogen defense, larval and vulval development, and RAS-mediated signaling | 171 | 26% | 46% | 136 | 4e−08 |
| ZK354.2 | AAM97988.1 | ZK354.2; ZK354.2B Protein with strong similarity to *C. elegans* Y65B4A.9 which is involved in reproduction, contains a protein kinase domain | 158 | 23% | 46% | 136 | 4e−08 |
| C36B7.1 | AAK68227.1 | C36B7.1 Protein containing a protein kinase domain, has low similarity to *P. carinii*, Cdc2_carinii which is a cyclin-dependent kinase with a potential role in the cell cycle | 227 | 26% | 42% | 135 | 5e−08 |
| cam-1 | CAD36478.1 | cam-1; C01G6.8A; kin-8; Cehd-17; D2013.4; C01G6.8 Canal associated neuron abnormal migration 1, putative receptor tyrosine protein kinase involved in vulva development, locomotion, cell migration, and asymmetric cell division, suggested to directly bind EGL-20 thus inhibiting Wnt signaling | 355 | 24% | 43% | 143 | 1e−07 |
| R11E3.1 | AAK39263.2 | R11E3.1 Protein containing a protein tyrosine kinase domain and a protein kinase domain, has low similarity to *C. elegans* T04B2.2, which is involved in lipid storage | 252 | 25% | 45% | 139 | 1e−07 |
| F36H12.9 | AAC26933.1 | F36H12.9 Protein with high similarity to *C. elegans* B0218.5, which is involved in lipid storage, contains a protein kinase domain | 248 | 26% | 45% | 137 | 1e−07 |
| R13H9.6 | AAK85495.1 | R13H9.6 Protein with high similarity to *C. elegans* B0218.5, which is involved in lipid storage, contains a protein kinase domain | 248 | 26% | 45% | 136 | 1e−07 |

TABLE 6-continued

| Gene | GenBank | Synonyms/Description | Match Length | % Iden | % Sim | High Score | E Val |
|---|---|---|---|---|---|---|---|
| F22B3.8 | CAA92740.3 | F22B3.8 Protein involved in positive growth regulation | 260 | 25% | 45% | 135 | 1e−07 |
| C25A8.5 | AAB03183.1 | C25A8.5 Protein containing a Src homology 2 (SH2) domain, which are regulatory modules of intracellular signaling, a protein tyrosine kinase domain, and a protein kinase domain, has moderate similarity to *C. elegans* T04B2.2, which is involved in lipid storage | 224 | 24% | 45% | 134 | 1e−07 |
| ZK622.1 | AAA81104.1 | ZK622.1 Protein containing a Src homology 2 (SH2) domain, which are regulatory modules of intracellular signaling, a protein tyrosine kinase domain, and a protein kinase domain, has moderate similarity to *C. elegans* T04B2.2, which is involved in lipid storage | 225 | 28% | 45% | 133 | 1e−07 |
| Y39G8C.2 | CAC35855.1 | Y39G8C.2; Y39G8C.C Protein containing a protein kinase domain, has moderate similarity to *C. elegans* B0218.5, which is involved in lipid storage | 165 | 30% | 48% | 127 | 1e−07 |
| abl-1 | CAA90691.2 | abl-1; M79.1A; Cehd-15; M79.1 ABL related 1, putative tyrosine protein kinase that prevents apoptosis in the germ line after radiation induced damage, acts as a negative regulator of CEP-1 and checkpoint pathway genes CLK-2(RAD-5), HUS-1 and MRT-2 | 498 | 20% | 39% | 138 | 2e−07 |
| W09C3.1 | AAC24410.1 | W09C3.1 Protein containing a protein kinase domain, has moderate similarity to *C. elegans* R10D12.10, which is involved in lipid storage | 211 | 27% | 45% | 131 | 2e−07 |
| Y51B9A.9 | CAA19542.1 | Y51B9A.9 Protein containing a protein kinase domain, has low similarity to jnk homolog 1 (*C. elegans* JNK-1), which is a mitogen-activated serine-threonine protein kinase that is involved in the regulation of locomotion and response to metal ions | 214 | 23% | 42% | 128 | 2e−07 |
| pik-1 | CAB05550.2 | pik-1; K09B11.1 Protein containing a protein kinase, a protein tyrosine kinase, and a death domain, has low similarity to interleukin-1 receptor associated kinase 4 (human IRAK4), which is involved in Toll/IL-1 receptor signaling upstream of human IRAK1 | 317 | 23% | 39% | 134 | 3e−07 |
| K09B11.5 | CAB63235.1 | K09B11.5 Protein containing a protein kinase, a protein tyrosine kinase, and a Src homology 2 (SH2) domain, has low similarity to megakaryocyte-associated tyrosine kinase (human MATK), which is a non-receptor protein kinase that regulates cell proliferation | 193 | 23% | 45% | 129 | 3e−07 |
| lin-18 | AAA82618.2 | lin-18; Ceryk; C16B8.1 Abnormal cell lineage 18, putative receptor that functions redundantly with LIN-17 to determine orientation of the vulval P7.p lineage, regulates the pattern of POP-1 localization in the P7.p and P6.pp vulval cell lineage | 115 | 35% | 53% | 128 | 3e−07 |
| F53C3.1 | AAC67453.2 | F53C3.1 Protein containing a protein kinase domain, has moderate similarity to *C. elegans* B0218.5, which is involved in lipid storage | 162 | 27% | 48% | 124 | 3e−07 |
| C30F8.4 | AAK85457.1 | C30F8.4; C30F8.4A Protein containing a protein tyrosine kinase domain and a protein kinase domain, has low similarity to protein tyrosine kinase 2 beta (mouse Ptk2b), which is a focal adhesion kinase that plays a role in G protein signal transduction | 227 | 25% | 45% | 131 | 4e−07 |
| C01C4.3 | AAM51508.1 | C01C4.3; C01C4.3B Protein containing a protein kinase domain, has low similarity to SH3-binding kinase (rat Sbk), which is a serine-threonine protein kinase that may act in brain development | 216 | 25% | 44% | 128 | 4e−07 |
| T21G5.1 | AAB52900.3 | T21G5.1 Protein containing a protein tyrosine kinase domain, a protein kinase domain and a Src homology 2 (SH2) domain, which are regulatory modules of intracellular signaling, has moderate similarity to *C. elegans* T04B2.2, which is involved in lipid storage | 152 | 28% | 49% | 127 | 4e−07 |
| F54H5.2 | AAB38092.1 | F54H5.2 Protein containing a protein kinase domain, has moderate similarity to *C. elegans* C04G2.2, which is involved in lipid storage | 233 | 28% | 45% | 128 | 5e−07 |
| kin-26 | AAA82302.1 | kin-26; Cehd-22; T06C10.6 Putative tyrosine protein kinase, has similarity to human and *D. melanogaster* FER (fps/fes-related) protein kinases | 345 | 23% | 41% | 132 | 6e−07 |
| D2045.7 | CAA84698.2 | D2045.7 Serine/threonine protein kinase with similarity to human myristoylated and palmitoylated protein kinase MPSK1, has similarity to *D. melanogaster* cAMP-dependent protein kinase | 269 | 26% | 43% | 132 | 6e−07 |
| F11D5.3 | AAK68319.1 | F11D5.3; F11D5.3A Protein containing an F5 or 8 type C (discoidin) domain, a protein kinase domain, | 203 | 24% | 43% | 128 | 6e−07 |

TABLE 6-continued

| Gene | GenBank | Synonyms/Description | Match Length | % Iden | % Sim | High Score | E Val |
|---|---|---|---|---|---|---|---|
| | | and a protein tyrosine kinase domain, has low similarity to discoidin domain receptor 2 (human DDR2), which is a receptor protein tyrosine kinase activated by collagen | | | | | |
| old-1 | CAA91146.1 | old-1; (tkr-1); C08H9.5 Overexpression longevity determinant 1, putative receptor tyrosine protein kinase that functions in life span regulation | 239 | 25% | 43% | 127 | 7e−07 |
| kin-31 | AAB37087.3 | kin-31; B0523.1 Protein containing a Src homology 2 (SH2) domain, which are regulatory modules of intracellular signaling, a protein kinase domain, and a protein tyrosine kinase domain, has moderate similarity to *C. elegans* T04B2.2, which acts in lipid storage | 245 | 22% | 43% | 125 | 7e−07 |
| K06H7.8 | AAF99989.1 | K06H7.8 Protein containing a protein kinase domain, has moderate similarity to *C. elegans* C04G2.2, which is involved in lipid storage | 302 | 24% | 42% | 129 | 8e−07 |
| R09D1.12 | CAA93871.2 | R09D1.12 Protein containing a protein tyrosine kinase domain and a protein kinase domain, has moderate similarity to *C. elegans* OLD-1, which is a putative receptor tyrosine protein kinase that extends life span upon overproduction | 255 | 23% | 40% | 124 | 8e−07 |
| W01B6.5 | CAA92623.2 | W01B6.5 Protein containing a protein kinase domain and a protein tyrosine kinase domain, has moderate similarity to *C. elegans* F22B3.8, which is involved in positive growth regulation | 194 | 27% | 48% | 153 | 9e−07 |
| T04B2.2 | CAA92609.1 | T04B2.2 Protein involved in lipid storage | 190 | 26% | 47% | 153 | 1e−06 |
| F59A3.8 | AAB37822.2 | F59A3.8 Protein containing a Src homology 2 (SH2) domain, which are regulatory modules of intracellular signaling, a protein tyrosine kinase domain, and a protein kinase domain, has low similarity to *C. elegans* T04B2.2, which is involved in lipid storage | 244 | 27% | 46% | 130 | 1e−06 |
| F38E1.3 | AAA83477.1 | F38E1.3 Protein containing a protein kinase domain, has low similarity to *C. elegans* B0218.5, which is involved in lipid storage | 168 | 27% | 45% | 127 | 1e−06 |
| R05H5.4 | CAA88727.1 | R05H5.4 Protein containing a protein tyrosine kinase domain and a protein kinase domain, has low similarity to fer (fps/fes related) tyrosine kinase (mouse Fert2), which may mediate cell-cell signaling and act in cell size-dependent cytoskeletal reorganization | 223 | 25% | 45% | 127 | 1e−06 |
| W02A2.D | CAB05307.1 | W02A2.D; W02A2.4 Protein containing a protein kinase domain and a protein tyrosine kinase domain, has low similarity to *C. elegans* T04B2.2, which is involved in lipid storage | 193 | 23% | 46% | 122 | 1e−06 |
| kin-15 | AAA28151.1 | kin-15; M176.6A; M176.6 Putative receptor tyrosine protein kinase, has similarity to human and *D. melanogaster* fibroblast growth factor receptor-related protein kinases | 118 | 32% | 51% | 121 | 1e−06 |
| M05D6.1 | CAA91411.1 | M05D6.1 Protein containing a protein kinase domain, has low similarity to casein kinase 1 delta (rat Csnk1d), which is a serine/threonine protein kinase possibly involved in DNA repair | 154 | 29% | 49% | 121 | 1e−06 |
| F35C11.3 | CAA90241.1 | F35C11.3 Protein containing a protein kinase domain, has low similarity to casein kinase 1 delta (human CSNK1D), which is a serine/threonine protein kinase involved in DNA repair that may play a role in circadian rhythms and is elevated in Alzheimer's | 154 | 29% | 49% | 121 | 1e−06 |
| kin-5 | CAA93112.1 | kin-5; T13H10.1 Protein containing a protein kinase, a protein tyrosine kinase, and a Src homology 2 (SH2) domain, which are regulatory modules of intracellular signaling, has moderate similarity to protein kinase 14 (*C. elegans* KIN-14), which regulates body size | 208 | 27% | 49% | 151 | 2e−06 |
| ire-1 | CAA88100.2 | ire-1; ire1; C41C4.4 IRE1 kinase-related 1, serine/threonine protein kinase and stress-activated endoribonuclease that is involved in the unfolded protein response signaling pathway and trafficking of glutamate receptors, required for larval development | 317 | 24% | 41% | 130 | 2e−06 |
| B0218.5 | AAB00666.1 | B0218.5 Protein involved in lipid storage | 257 | 25% | 44% | 125 | 2e−06 |
| T05C12.1 | CAA91303.1 | T05C12.1 Protein involved in lipid storage | 237 | 26% | 41% | 124 | 2e−06 |
| C56C10.6 | AAA68774.2 | C56C10.6 Protein containing a protein kinase domain, has low similarity to casein kinase 1 gamma 3 (rat Csnk1g3), which is a serine-threonine protein kinase that may play roles in cell growth and in morphogenesis | 233 | 27% | 45% | 124 | 2e−06 |

TABLE 6-continued

| Gene | GenBank | Synonyms/Description | Match Length | % Iden | % Sim | High Score | E Val |
|---|---|---|---|---|---|---|---|
| pek-1 | CAA92117.1 | pek-1; CePEK; PERK; F46C3.1 Human PERK kinase homolog 1, protein kinase that may regulate translation initiation by phosphorylating initiation factor eIF-2alpha, involved in the stress response and required for larval development | 175 | 26% | 44% | 124 | 2e−06 |
| C03B1.5 | AAA81740.3 | C03B1.5 Protein containing a protein kinase domain, has low similarity to a region of serine-threonine kinase 24 (human STK24), which is a serine-threonine kinase that prefers manganese as a cofactor | 273 | 25% | 44% | 168 | 3e−06 |
| Y69F12A.1 | AAF60861.1 | Y69F12A.1 Protein containing a protein kinase domain, has moderate similarity to C. elegans B0218.5, which is involved in lipid storage | 186 | 28% | 44% | 120 | 3e−06 |
| T27C10.6 | AAK73898.3 | T27C10.6 Protein containing six ankyrin (Ank) and six leucine rich repeats and a protein kinase domain, has a region of low similarity to a region of mitogen-activated protein kinase kinase kinase 10 (human MAP3K10), which activates human JNK and induces apoptosis | 374 | 24% | 38% | 151 | 4e−06 |
| F55C5.7 | CAB01572.2 | F55C5.7 Protein containing a protein kinase domain, an MIT domain, and a phox protein (PX) domain, which bind phosphoinositides, has weak similarity to uncharacterized ribosomal protein S6 kinase 52 kD polypeptide 1 (human RPS6KC1) | 189 | 29% | 44% | 124 | 4e−06 |
| C55C3.4 | AAA96169.1 | C55C3.4 Protein containing a protein tyrosine kinase domain, a protein kinase domain, and a Src homology 2 (SH2) domain, has moderate similarity to C. elegans T04B2.2, which is involved in lipid storage | 228 | 24% | 45% | 123 | 4e−06 |
| kin-14 | CAA95813.1 | kin-14; F22D6.1 Protein kinase 14, protein involved in positive regulation of body size | 356 | 22% | 42% | 131 | 5e−06 |
| C35E7.10 | AAC17525.1 | C35E7.10; C35E7.10A Protein containing a protein tyrosine kinase domain, a protein kinase domain, and a Src homology 2 (SH2) domain, has moderate similarity to C. elegans T04B2.2, which is involved in lipid storage | 232 | 25% | 44% | 122 | 5e−06 |
| R107.4 | CAD45599.1 | R107.4; R107.4B Protein with similarity over the N terminus to serine/threonine protein kinases, putative paralog of C. elegans Y39G8B.F, expressed in the anal sphincter cell and intestinal muscle cells in L1 larvae, involved in lipid storage | 262 | 27% | 41% | 134 | 7e−06 |
| Y52D5A.2 | AAF60752.2 | Y52D5A.2 Protein containing a protein tyrosine kinase domain, a protein kinase domain and a Src homology 2 (SH2) domain, which are regulatory modules of intracellular signaling, has low similarity to C. elegans T04B2.2, which is involved in lipid storage | 325 | 22% | 38% | 121 | 7e−06 |
| scd-2 | AAC19236.2 | scd-2; alk; T10H9.2 Suppressor of constitutive dauer formation 2, anaplastic lymphoma kinase homolog that is proposed to inhibit or destabilize differentiation of synapses, functions in the group 2 pathway for dauer larvae formation | 405 | 21% | 43% | 133 | 8e−06 |
| | | URE2 - NP_014170.1 URE2 blast vs human - | | | | | |
| GSTT1 | NP_000844.1 | GSTT1 Glutathione S-transferase T1, theta class GST subunit forms GSTT1-1 homodimers, adds glutathione to electrophiles, dehalogenates dihaloalkanes to toxic intermediates; a common null mutation has been linked to p53 (TP53) mutation rates and cancer risk | 172 | 26% | 42% | 93 | 0.001 |
| | | Compared with M. musculus protein sequences (Documentation) | | | | | |
| Gstt1 | NP_032211.2 | Gstt1; Mm.2746; Gstt1-1 Glutathione S-transferase T1, theta class GST subunit forms GSTT1-1 homodimers, adds glutathione to electrophiles, dehalogenates dihaloalkanes to toxic intermediates; a common null mutation of the human GSTT1 gene has been linked to cancer risk | 91 | 34% | 56% | 109 | 1e−05 |

Example 4

Identification of Sir2-Independent Calorie Restriction Pathway

Figure 17A:
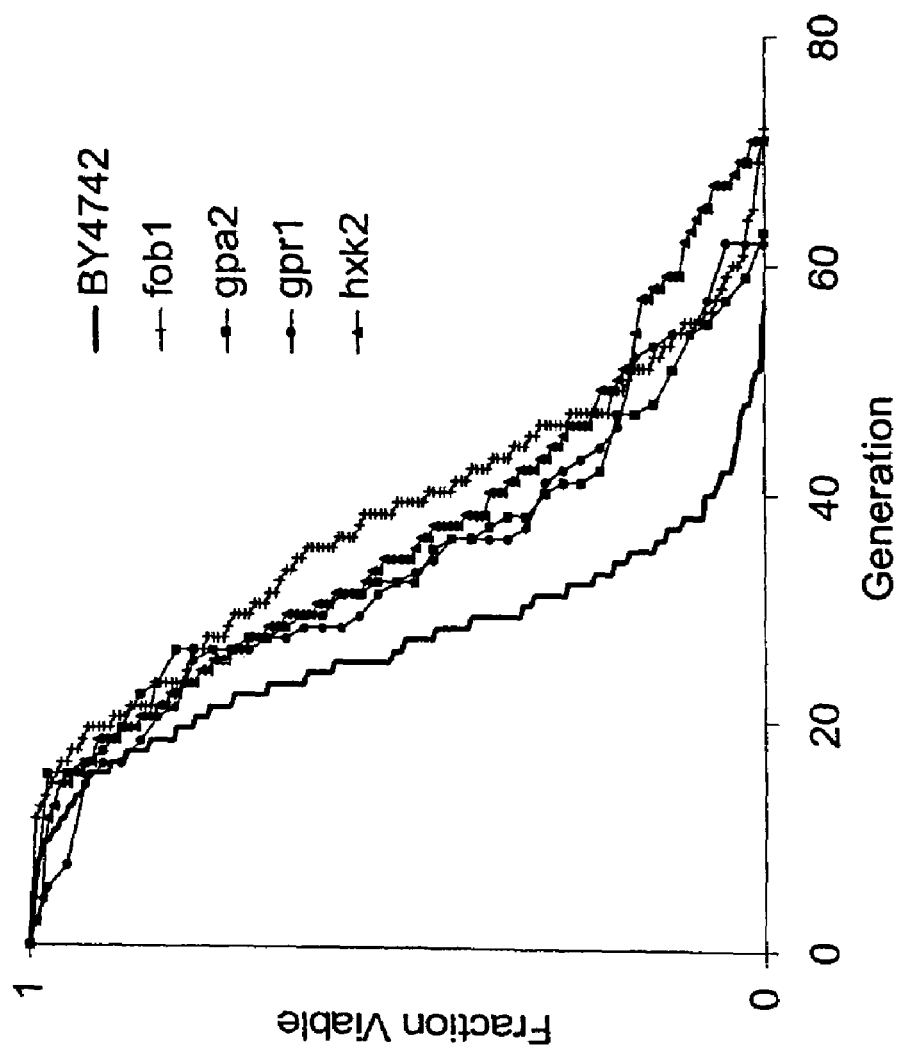
FIG. 17A illustrates mortality curves and mean RLS for various single-gene deletion mutants, including representative genetic models of CR.

FIG. 17A illustrates mortality curves and mean RLS for various single-gene deletion mutants, including representative genetic models of CR. Genetic models of CR, including hxk2Δ, gpa2Δ, and gpr1Δ, are created in the "BY4742" genetic background, and assayed to determine life spans for each. Mean RLS values are shown for hxk2Δ, gpa2Δ, and gpr1Δ. As previously reported, each of these result in a 30-40% increase in life span in the BY4742 strain. For comparison, the mean RLS for a fob1Δ strain is determined. Although the fob1Δ strain is not a genetic model for CR pathway, this deletion strain also exhibits 30-40% increase in longevity. For FIGS. 25-26, the BY4742 is utilized as a reference strain.

Figure 17C:
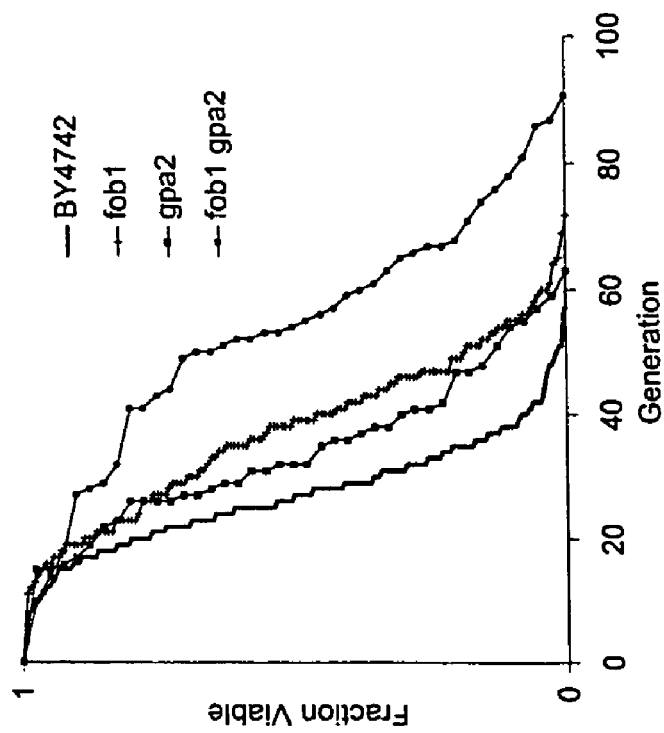
FIG. 17C compares mortality curves of a fob1-gpa2-double-deletion mutant, fob1-deletion mutant, and gpa2-deletion mutant.
Figure 17B:
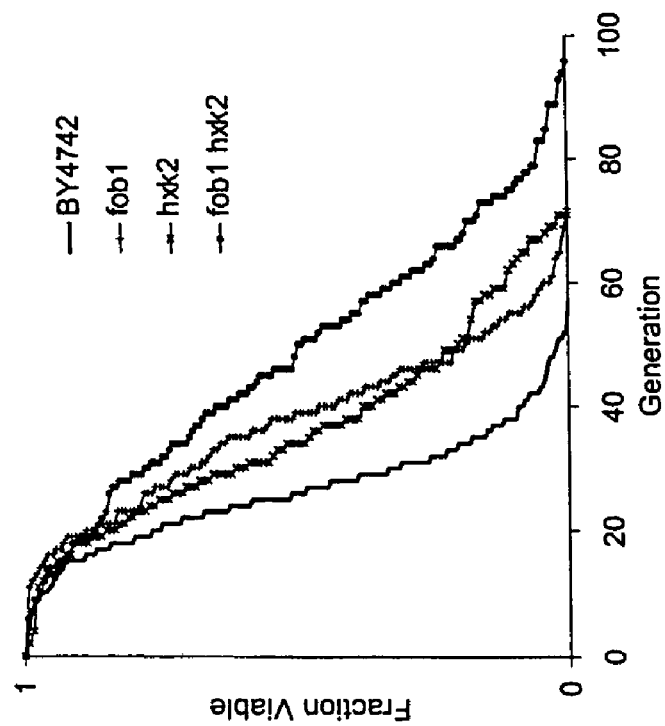
FIG. 17B compares mortality curves of a fob1-hxk2-double-deletion mutant, fob1-deletion mutant, and hxk2-deletion mutant.

FIG. 17B compares mortality curves of a fob1-hxk2-double deletion mutant, fob1 deletion mutant, and hxk2 deletion mutant. In FIG. 17B, both fob1Δ mutant and hxk2Δ mutant exhibit longer mean life spans than that of the "wildtype" BY4741 reference strain as observed in FIG. 18A. However, the combined effect of CR and FOB1 deletion has not been evaluated before by others, so a fob1Δ-hxk2Δ-double mutant is generated to determine a mean RLS. Unexpectedly, the mean RLS values for a fob1Δ-hxk2Δ-double mutant greatly exceeds that of either single mutants, suggesting an additive effect on longevity that results by combining a FOB1 deletion with CR.

A similar effect of additive longevity is observed when FOB1 deletion is combined with a GPA2 deletion mutant which acts in the CR pathway. FIG. 17C compares mortality curves of a fob1-gpa2-double deletion mutant, fob1 deletion mutant, and gpa2 deletion mutant. Similar to deletions of both FOB1 and HXK2, the fob1Δ-gpa2Δ-double mutant exhibits an average life span nearly double that of "wildtype" cells. With mean and maximum life spans of 54.5 and 94 generations, respectively, the fob1Δ-gpa2Δ and fob1Δ-hxk2Δ double mutants are the longest-lived yeast strains reported to date. The observation that CR further increases the already prolonged life span of a fob1Δ mutant is inconsistent with a hypothesis that CR increases life span solely by activation of sir2. Since over-expression of sir2 is sufficient to increase the life span of a wildtype, but does not further extend the life span of a fob1Δ strain, then CR, presumably acting through sir2, should not further extend the life span of a fob1Δ strain. This result supports the existence of a sir2-independent, CR-responsive pathway that enhances longevity, which is tested as follows.

Figure 17E:
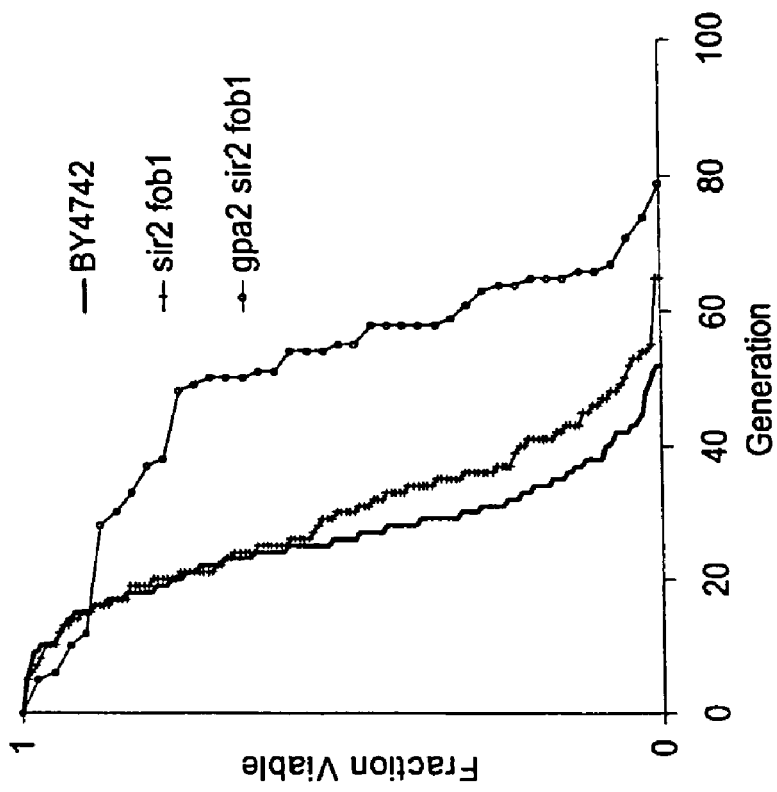
FIG. 17E compares mortality curves of a sir2Δ-fob1Δ-gpa2Δ strain, fob1Δ-gpa2Δ strain, and sir2Δ-fob1Δ strain.
Figure 17D:
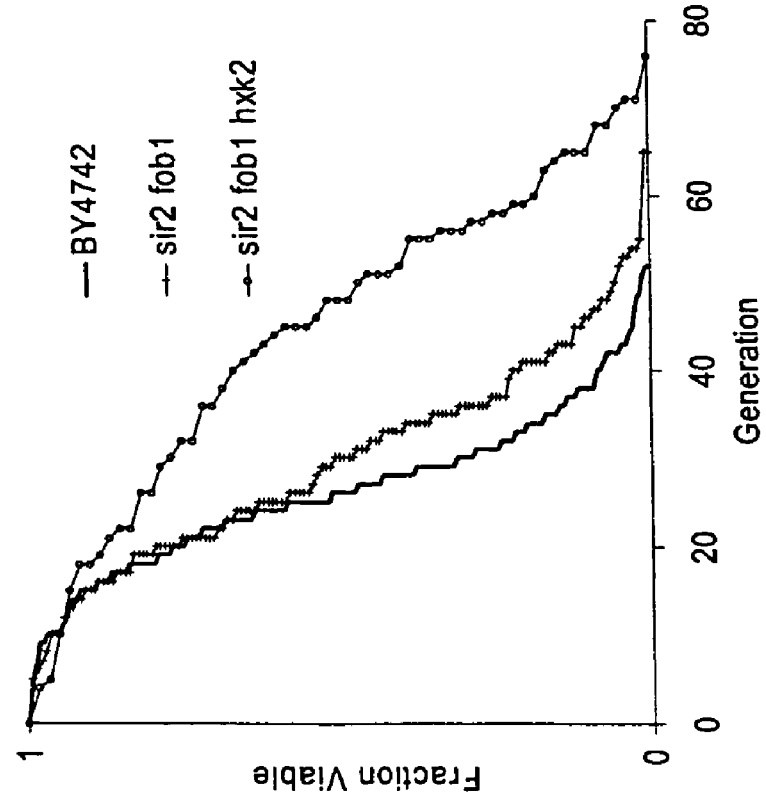
FIG. 17D compares mortality curves of a sir2Δ-fob1Δ-hxk2Δ strain, fob1Δ-hxk2Δ strain, and sir2Δ-fob1Δ strain.

FIG. 17D compares mortality curves of a sir2Δ-fob1Δ-hxk2Δ strain, fob1Δ-hxk2Δ strain, and sir2Δ-fob1Δ strain. Surprisingly, in the sir2Δ fob1Δ double mutant cells, deletion of HXK2 resulted in a robust life span extension. FIG. 17E compares mortality curves of a sir2Δ-fob1Δ-gpa2Δ strain, fob1Δ-gpa2Δ strain, and sir2Δ-fob1Δ strain. The life span of a sir2Δ-fob1Δ-gpa2Δ triple mutant cells is similarly determined, and results in life span significantly longer than that of sir2Δ-fob1Δ-double mutant cells. In fact, the life spans of sir2Δ-fob1Δ-hxk2Δ or sir2Δ-fob1Δ-gpa2Δ cells did not differ significantly (p~0.4) from fob1Δ-hxk2Δ or fob1Δ-gpa2Δ cells, respectively. Thus CR clearly enhances longevity in a genetic context lacking both SIR2 and FOB1, but not in the absence of SIR2 alone. These findings demonstrate that sir2 is dispensable for life span extension by CR, at least in the context of reduced ERC levels (as a result of fob1Δ) in this long-lived strain background.

Figure 18:
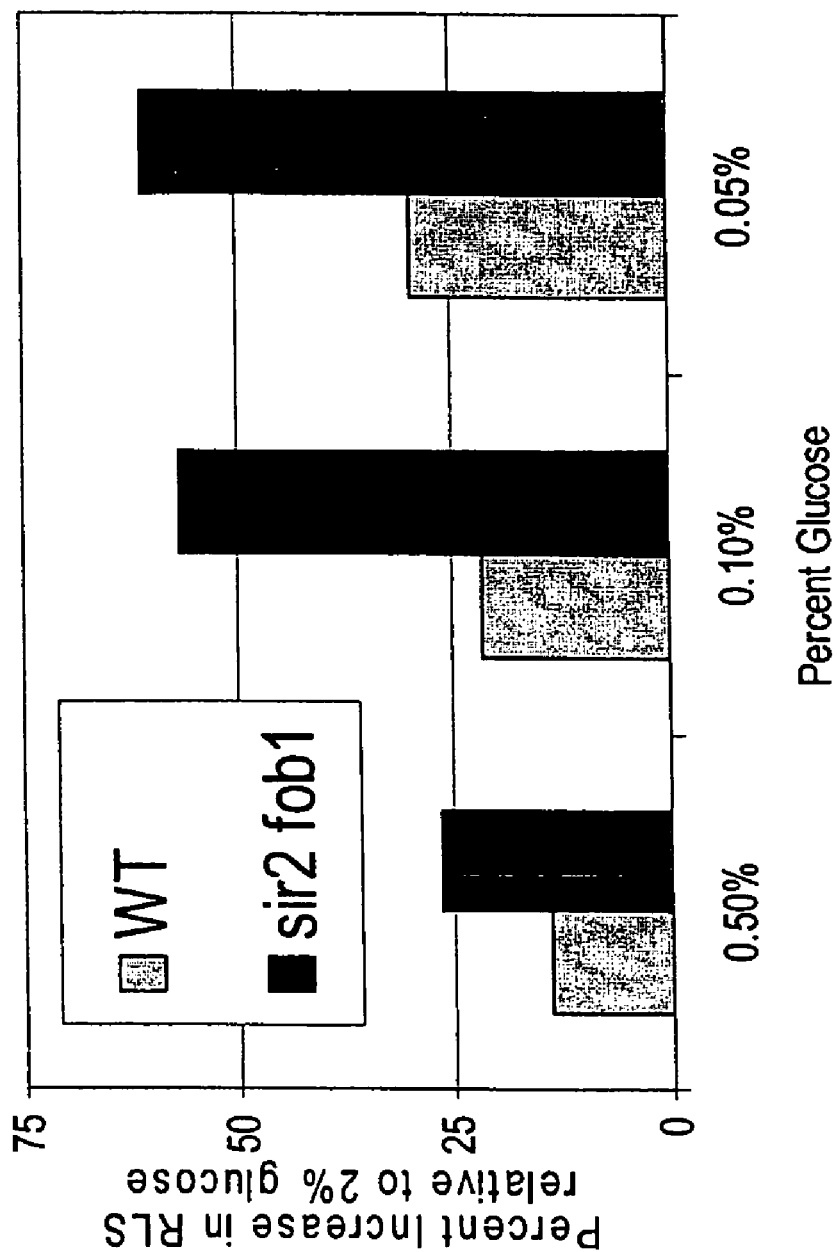
FIG. 18 illustrates the responsiveness of a sir2-fob1-double-deletion mutant to calorie restriction.

FIG. 18 illustrates the responsiveness of a sir2-fob1-double deletion mutant to calorie restriction. One way to induce calorie restriction (CR) in yeast cells is by reducing glucose concentration of growth media from 2% to 0.5% (or lower) that results in a 30-40% increase in life span. Although genetic models of CR, such as hxk2Δ and gpa2Δ, are used for convenience as surrogates for CR, growth at low glucose concentrations can be varied over a range of values to control the degree of CR. In FIG. 18, the life spans of "wild type" and sir2Δ-fob1Δ-double mutant cells on 2%, 0.5%, 0.1%, and 0.05% glucose are determined. Wildtype cells show an increase in mean life span ranging from 15-25%, with maximal increases observed at 0.05% glucose. The effect of growth on low glucose is more pronounced in the sir2Δ-fob1Δ-double mutant, with a mean life span increase by 30% on 0.5% glucose and by 70% on 0.05% glucose. Thus, CR is more effective at enhancing longevity in the sir2Δ-fob1Δ-double mutant than in the presence of SIR2.

Finally, the combined effects of SIR2 over-expression and CR in the BY4742 background is tested. Over-expression of SIR2 results in a significant life span extension, and calorie restriction of SIR2-overexpressing cells results in a further increase in life span, supporting that CR and SIR2 can promote longevity by influencing different pathways.

Finally, the combined effects of SIR2 over-expression and CR in the BY4742 background is tested. Over-expression of SIR2 results in a significant life span extension, and calorie restriction of SIR2-overexpressing cells results in a further increase in life span, supporting that CR and SIR2 can promote longevity by influencing different pathways.

From these experiments, it appears that at least two pathways regulate aging in yeast: one pathway is regulated by ERC accumulation and the other pathway is undefined at a molecular level, but responsive to CR. In a long-lived "wildtype" background, such as the BY4742 strain, both processes influence longevity. The existence of an ERC-independent aging pathway in yeast modulated by CR suggests the existence of similar mechanism for aging in higher eukaryotes. CR is the only intervention shown to extend life span in a wide range of eukaryotes, including mammals. Nevertheless, in *C. elegans*, increased expression of the sir2 ortholog, sir-2.1, has been found to extend life span in a manner dependent on the Daf-16 transcription factor. Similarly, the mammalian sir2 ortholog, SirT1, has recently been reported to regulate the activity of murine Foxo3A. These experiments confirm a role for sir2 proteins in eukaryotic aging, linking Sirtuin activity to insulin/IGF-1 signaling pathways. Evidence has accumulated in both *C. elegans* and mice that CR can further extend the life span of long-lived insulin/IGF-1 pathway mutants, suggesting that CR and insulin/IGF-1 act in two distinct pathways to regulate aging. Both pathways may be conserved throughout eukaryotic aging mechanisms.

Example 5

Epistasis Analysis of LL Variants

Each variant classified as LL by methods of the present invention can be further classified into one or more life-span-regulating pathways. New combinations of deletion strains can be generated so that genes that confer longer life spans in identified LL variants can be sorted into distinct life-span-regulating pathways. Various combination of well-characterized genetic models described above can be used as suitable genetic backgrounds, including fob1Δ strain, sir2Δ strain, fob1Δ-sir2Δ-double-deletion strain, hxk2Δ strain, gpa2Δ strain, gpr1Δ strain, fob1Δ-hxk2Δ-double-deletion strain, fob1Δ-gpa2Δ-double-deletion strain, and fob1Δ-gpr1Δ-double-deletion strain. Methods for generating new genetic variants, such as homologous recombination, yeast mating, and sporulation, are well-known by persons in the art.

For example, for each LL-deletion variant identified by the present methods, such LL variants can be combined with FOB1 deletion strains to produce novel double-deletion strains, referred to as "LLΔ-fob1Δ" variants, and also combined with fob1Δ-sir2Δ-double-deletion strains to produce novel triple-deletion strains, referred to as "LLΔ-fob1Δ-sir2Δ" variants. The RLSs for each "LLΔ-fob1Δ" double variant and "LLΔ-fob1Δ-sir2Δ" triple variant generated can be determined to generate mortality curves for each LL variant. Any "LLΔ-fob1Δ" double variants that exhibit life spans comparable to a "wildtype" strain, and that do not further extend the life span of a fob1Δ, most likely lack a gene that acts in the ERC-dependent pathway. Any LLΔ-fob1Δ-sir2Δ-triple variants that exhibit life spans comparable to a "wild-type" strain, most likely lack a gene that acts in the ERC pathway. For those "LLΔ-fob1Δ" double variants and "LLΔ-fob1Δ-sir2Δ" triple variants that exhibit life spans which substantially exceeds the "wildtype" RLS, then such variants are likely to represent genes in an alternative pathway, such as a sir2-independent CR pathway. A substantial life-span extension includes an increase in RLS of at least 80%, 85%, 90%, 95%, and 100% relative to a "wildtype" reference.

Example 6

Identification of Sir2 Regulators Using LL Variants

Because Sir2 orthologs in C. elegans are known to regulate aging pathways and to regulate transcription factors that are purported to participate in aging mechanisms in mammalian systems, regulators of Sir2 are very likely to be conserved broadly among diverse eukaryotic systems. Yeast genes and orthologs identifiable by methods of the present invention ("present methods") can be assayed to determine whether encoded gene products are able to regulate Sir2 histone deacetylase activity. For example, whether an identified gene can alter Sir2 activity can be determined by measuring Sir2-dependent silencing at the telomeres and rDNA within LL variants. Yeast strains containing reporter genes positioned at either loci, telomeres or rDNA, can be crossed for example, with LL-deletion variants so that LL variants containing reporter genes at these loci can be generated. Such LL-deletion variants can be monitored for Sir2-dependent transcriptional silencing, and levels of marker gene expression in LL-deletion variants can be compared to levels of a "wild type" reference to determine the effect of a deleted gene in question on Sir2-dependent transcriptional silencing.

In addition, for each LL-deletion variant identified by present methods, such LL-deletion variants can be combined with FOB1 deletion strains to produce novel double-deletion strains, referred to as "LLΔ-fob1Δ" variants, and also combined with fob1Δ-sir2Δ-double-deletion strains to produce novel triple-deletion strains, referred to as "LLΔ-fob1Δ-sir2Δ" variants. The degree of Sir2-dependent transcriptional silencing for each "LLΔ-fob1Δ" double variant and "LLΔ-fob1Δ-sir2Δ" triple variant can be determined. A "LLΔ-fob1Δ-sir2Δ" variant that does not exhibit an increased life span compared to an increased life span observed for a LL variant with only a single-gene deletion in question ("LLΔ") indicates that the gene is likely to act within a Sir2-dependent pathway. Genes (LLΔ) identified in LL-deletion variants are candidates for Sir2 regulators, which are predicted to be conserved in higher eukaryotes. Various methods for generating new genetic variants are known by persons skilled in the art. Exemplary reporter genes include ADE2 or URA3 that can be positioned near telomeres, and ADE2, URA3 or MET15 that can be positioned within rDNA sites.

Example 7

Translation Inhibition and Aging

Many of the genes, which when deleted result in extended replicative life span, encode proteins that regulate or are directly involved in ribosome biogenesis. RPL31A, RPL6B and RPS21A encode components of the ribosome and REI1 is implicated in formation of the 60S subunit of the ribosome. Ribosomal genes are often duplicated in the yeast genome. Thus deletion of RPL31A reduces but does not eliminate formation of functional ribosomes since RPL31B encodes a gene product with redundant function. Thus, in these deletions, we are likely reducing the number of ribosomes, but not eliminating ribosomal function altogether (an event that would be lethal). Polysome profiling, which measures the quantity of ribosomes in yeast cells and their degree of association with mRNA, supports this assertion. Δrpl31b or Δrei1 cells contain less ribosomes associated with mRNA and a striking reduction in the free cytoplasmic 60S (but not the free 40S) subunit of the ribosome. Since Rpl31b is a known component of the 60S subunit this result is not surprising.

Also identified in our genome-wide RLS screen were signaling components that link nutrient levels to ribosome biogenesis, including TOR1 and URE2. Deletion of SCH9 and components of the protein kinase A (PKA) pathway also result in extended RLS. These genes encode products in signaling pathways that also link nutrient levels to ribosome biogenesis. However the downstream effects of PKA and Sch9 signaling are numerous and no one has connected life span extension by reduced PKA or Sch9 activity to ribosome biogenesis. We speculate these two events are linked and moreover that reduction in ribosome biogenesis may be the primary mechanism by which CR (which results in less PKA, Sch9 and TOR activity) extends yeast RLS. Indeed we find that ribosome levels are reduced in Δsch9 cells as measured by polysome profiling, consistent with predictions based on gene expression profiling. Tor1 is a protein kinase intimately linked to yeast cell growth. Yeast in rich media are exposed to high levels of nitrogen and carbon (e.g. glucose), which results in TOR activation, ultimately leading to enhanced ribosome biogenesis and increased growth rates.

A number of drugs antagonize TOR activity including rapamycin and several derivatives thereof. In addition, the drug methionine sulfoximine (MSX), an inhibitor of glutamine synthase, results in decreased glutamine levels. Intracellular glutamine levels reflect nitrogen availability, and intracellular levels of this metabolite are monitored by TOR. Increased glutamine levels therefore result in increased TOR activity. Thus exposure of cell to MSX results in decreased TOR activity. We find that exposure of yeast cells to MSX extends replicative life span in yeast, confirming our observation the Δtor1 strains have increased RLS and suggesting that MSX and derivatives thereof may be effective anti-aging compounds in eukaryotic organisms.

There are approximately 150 yeast genes that are known to be involved in ribosome biogenesis and function. We will perform the following experiments to address their possible roles in yeast replicative aging: (1) perform RLS (replicative life span) analysis on all deletion strains, (2) examine growth rate of all deletion strains in rich and calorie restricted conditions as a measure of their relative contribution to ribosome function, and (3) perform polysome analysis on all deletion strains that exhibit extended replicative life span.

How does decreased ribosomal biogenesis lead to enhanced replicative life span? We consider two general explanations. First, lengthened RLS may result from a general decrease in the synthesis and activity of ribosomes. This model derives from the observation that the yeast cell overproduces ribosomes in times of plenty. Indeed a significant proportion of ribosomes in the yeast cell are not associated with mRNA as indicted by polysome profiling of young wild-type cells. Ribosome production accounts for up to half of the cells energy usage under conditions of rapid growth. One possibility is that there is a tradeoff between reproduction (growth rate) and aging in yeast, as has been speculated for mammals. In other words, the yeast cell overproduces ribosomes to maximize growth rate and thus production of new cells. Therefore, the yield of daughter cells on a population level (clonal reproduction) would be maximized at the expense of aging in single "mother" cells. The ability of a single mother cell to divide more than 15 times may be superfluous under these conditions since rapid division ensures that the vast majority of cells in the population are young. Alternatively, extra ribosomes may be produced and stored in times of plenty, so that they can be used in later times of starvation when energy may not be sufficient to generate new ribosomes. If it is true that enhanced RLS derives from the benefits of reduced ribsome biogenesis, then drugs that precipitate this effect, may prolong life span. Possible drugs include cycloheximide and edeine, which inhibit either translation or translation initiation (see section on drugs).

A second explanation is that the benefit of reduced ribosome biogenesis is specific to decreased or altered translation of one or more messages that encode proteins delimiting yeast replicative aging. If this is the case, it will be important to determine which messages are altered. Even in this case, drugs which generally inhibit translation are likely provide an aging benefit, since mutations with this effect (e.g. $\Delta$sch9) increase life span.

Example 8

Small Molecules that Delay Yeast Aging

Based on our genome-wide screen of yeast replicative aging, we can predict two classes of drugs that are likely to increase life span. The first class consists of inhibitors of upstream components of the TOR, SCH9, or PKA pathways. These include rapamycin and methionine sulfoximine (MSX, an inhibitor of glutamine synthase). The second class consists of inhibitors of the relevant downstream targets of these pathways, speculatively including cycloheximide, edeine, and amino acid alcohols (e.g methioninol and threoninol). These compounds inhibit translation through various known mechanisms. We have determined that MSX administration significantly increases life span at 50 uM, 100 uM, 1 mM, and 2.5 mM. Maximal life span extension in these preliminary experiments is obtained at 1 mM, results in a 25-30% increase in mean replicative life span. We will test the effect of both translation inhibitors on yeast replicative life span as well. Derivatives of these drugs may also delay aging as might any compound found to slow translation. In general, once pathways are determined that regulate yeast replicative aging, we will test any compounds known to regulate that pathway and derivatives thereof.

Any compound found to prolong yeast RLS will be tested in other eukaryotic organisms and in yeast chronological life span analysis. We will administer the compound to *C. elegans* and determine whether life span is extended in this organism (see section on *C. elegans*). Also we will perform studies using mice as a model system to determine whether prolonged exposure to a compound in question results in prolonged life span or health span in mammals.

Aging studies in *C. elegans*. If a yeast strain lacking a gene exhibits extended mean and/or maximum replicative life span, one can infer that the protein encoded by that gene restricts life span in the single-celled eukaryote. This raises the question of whether decreased function of an orthologous protein will result in prolonged life span in another eukaryotic organism. Thus we will test orthologs of yeast aging genes identified in our genome-wide RLS screen in the nematode *C. elegans*. Over half of the yeast aging genes identified have orthologs in *C. elegans*. In some cases, more than one *C. elegans* protein bears significant homology to a yeast aging gene, and in these cases we will examine the effects of each potential ortholog.

One (or both) or two approaches will be taken to examine *C. elegans* genes. We will use RNAi, with the double-stranded RNA delivered to the worms through expression in their bacterial food source *E. coli*. This approach is used routinely and interfering RNAs specific to most *C. elegans* genes have already been created. As a second approach, we will generate or obtain worms with inactivating mutations in potential aging genes. Life span studies will be performed in a variety of manners. For the RNAi approach, we will shift worms in the L4 larval stage to *E. coli* expressing the double-stranded RNA. This will lead to downregulation of gene expression of the potential aging gene after development and thus avoid most developmental defects and possible dauer formation, which complicates aging studies. Alternatively, we will administer the RNAi to adult worms and monitor life span of their progeny. In this case, worms will be exposed to the RNAi both during development and as adults. Finally, we will administer candidate compounds identified in yeast studies to determine their potential effects on aging in worms.

Example 9

Aging Studies in a Mitotically Active Simple Eukaryote

Since *C. elegans* exists as a completely post-mitotic adult (with the exception of the germ line), we recognize that *C. elegans* may not be an optimal choice for testing candidate aging genes identified from a replicative life span screen in yeast. To address this issue, we may examine orthologs of candidate aging genes in a different, mitotically active simple eukaryote. Possible organisms under consideration are the flatworm Planaria and the fruit fly *Drosophila melanogaster*.

Example 10

Aging Studies in Mice

An important question will be to determine whether aging genes identified in yeast also affect life span or health span in mammals. Therefore we will initiate aging studies in mice, where gene knockouts of orthologs of identified yeast/worm aging genes can be created. We will choose a subset of the genes identified in our yeast studies, emphasizing those that also regulate aging in worms or another multicellular model. Given the evolutionary divergence of worms and yeast, we feel strongly that gene sets regulating aging in both organisms, are highly likely to regulate aging in mammals as well.

Experiments will be performed by generating conditional knock-outs of orthologs of yeast and worm aging genes. By flanking the gene in question with lox sites, we can control when the gene is excised by temporal or tissue-specific administration of Cre, an enzyme that excises DNA between two lox sites. Therefore, we can allow mice to undergo fetal development and then generate the gene deletion post-natally by ubiquitous delivery of Cre. This will allow us to avoid developmental defects associated with loss of a candidate aging gene that would impair aging studies. Post-natal administration can be performed in a variety of documented methods including but not limited to the use of a tet-regulated promoter driving expression of Cre present in the germ line of the mouse. Should post-natal administration result in lethality or other phenotypes which preclude aging analysis, we will perform life span analysis in mice heterozygous for the gene in question.

In addition to monitoring mouse life span, we will examing a variety of aging biomarkers including but not limited to changes in cognitive ability, fat mass and body weight, body temperature, strength, as well as alopecia and blood serum levels of a variety of compounds including insulin, IGF, glucose, leptin, DHEA, growth hormone, and molecules diagnostic of immune response. Additionally we will perform gene expression array analysis looking at genome-wide changes in gene expression during the mouse aging process (see specific section). Changes in expression of many genes known to occur during aging and by monitoring these genes, we can measure rates of aging. By using such a biomarkers, we can (1) determine whether a gene deletion is likely to affect life span prior to the completion of aging studies and (2) monitor changes in health span that occur with age.

Finally, we will examine the effects of prolonged administration of drugs on mouse aging and aforementioned biomarkers of aging. Drugs that are effective in yeast and worms will be chosen for studies in mice.

Example 11

Gene Expression Array Analysis

We will use genome-wide gene expression array analysis in all three organisms (yeast, worms and mice), as well as potentially on human cells in culture, to (1) determine aging rates and (2) identify downstream targets of aging genes that might underlie delayed aging phenotypes. This analysis will be performed on yeast examining gene expression changes in strains lacking genes which exhibit long RLS. We will also perform array analysis on yeast exposed to environmental conditions (e.g., calorie restriction defined as media containing 0.05% glucose) or in the presence of compounds such as MSX which result in extended yeast RLS.

In worms, we will monitor changes in genome-wide gene expression in worms lacking aging genes. This analysis may be performed both in young worms and throughout the aging process. In addition, we will examine environmental conditions that extend life span and compounds as described above. Similar experiments will be performed in young and aging mice. Again, this will allow us to monitor the rate of aging by looking at changes in gene expression known to occur during murine aging and to identify critical targets of aging genes.

Example 12

Polymorphisms and Human Aging

Loss-of-function mutations resulting in prolonged life span or health span in yeast, worms and mice might be phenocopied by polymorphisms that have arisen in the human population. Thus, we will determine whether aging genes identified in yeast, worms or mice are enriched for particular polymorphisms in unusually old individuals relative to the normal population. An enhancement in the relative proportion of a particular allele of a potential aging gene would provide evidence for the gene regulating aging in humans.

Although the present invention has been described in terms of particular embodiments, it is not intended that the invention be limited to these embodiments. Modifications within the spirit of the invention will be apparent to those skilled in the art. The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and practical applications, and thereby enable others skilled in the art to best utilize the invention and various embodiments with various modifications as are suited to particular uses contemplated. It is intended that the scope of the invention be defined by the following claims and their equivalents. Each recited range includes all combinations and sub-combinations of ranges, as well as specific numerals contained therein.

All publications and patent applications cited in this specification are herein incorporated by reference in their entirety for all purposes as if each individual publication or patent application were specifically and individually indicated to be incorporated by reference for all purposes.

What is claimed:

1. A high throughput method for screening a genetic variant for a long-lived phenotype of interest, the method comprising:

providing a set of unknown genetic variants, iteratively, for each genetic variant in the set of genetic variants;

selecting a number N of cells for the genetic variant;

quantitatively measuring replicative life span (RLS) for each of the N cells of the genetic variant and determining the mean replicative life span of the N cells; and classifying the genetic variant as positive, negative, or ambiguous for a long-lived phenotype of interest, wherein the variant is positive if the mean RLS value exceeds a positive threshold value, negative if the mean RLS value is below a negative threshold value, and ambiguous if the mean RLS value is neither above the positive threshold value nor below the negative threshold value.

2. The method of claim 1 further comprising establishing the negative threshold value by determining the mean life span value of a statistically reliable set of a wildtype reference, and establishing the positive threshold value by determining the mean life span value of a statistically reliable set of variants exhibiting a life span substantially greater than that of the wildtype reference.

3. The method of claim 2 wherein the positive variant has a mean replicative life span substantially greater than the mean replicative life span of a wildtype reference, and wherein the negative variant has a mean replicative life span less than the mean replicative life span of the wildtype reference.

4. The method of claim 3 wherein the mean replicative life span of the positive variant is at least about 20% greater than the mean replicative life span of the wildtype reference.

5. The method of claim 1 wherein the number of cells N is an integer greater than 3 and less than 20 and the variant is a yeast strain containing a mutation that affects the expression of at least one gene.

6. The method of claim 1 wherein determining the number of cells N further comprises minimizing the classification of a positive variant having a mean replicative life span substantially greater than that of a wildtype reference as a negative variant; and minimizing the classification of a negative variant having a mean replicative life span less than that of the wildtype reference as a positive variant.

7. The method of claim 1 wherein measuring replicative life span further comprises: establishing a first dataset that includes replicative life span values for N cells of a variant, wherein the replicative life span value for each cell of N is included; establishing a second dataset by selecting a subset of the first dataset, wherein the second dataset includes between one and N-1 of the highest replicative life span values observed for the first dataset; determining the mean replicative of the second dataset; and utilizing the mean replicative life span of the second dataset in classifying the variant.

8. The method of claim 1 wherein the method further comprises: iteratively computing mean replicative life span for one or more additional genetic variants; computing a median replicative life span for the set of genetic variants; computing an average median mean replicative life span for the set of genetic variants; and normalizing the mean replicative life span for each variant.

9. The method of claim 8 wherein normalizing further comprises multiplying the computed mean replicative life span for each variant by a coefficient value, wherein the coefficient value is computed by dividing the median replicative life span for the set of genetic variants by the average median mean replicative life span for the set of genetic variants.

10. A method for identifying genes having life-span-regulating activity, the method comprising: identifying a gene that is differentially expressed in a variant classified as positive or negative according to the method of claim 1 relative to a wild-type reference; comparing the replicative lifespan (RLS) of the variant with the RLS measured under conditions in which expression of the gene is suppressed, wherein the gene has life-span regulating activity if the RLS is significantly different when expression of the gene is suppressed.

* * * * *

UNITED STATES PATENT AND TRADEMARK OFFICE
CERTIFICATE OF CORRECTION

PATENT NO. : 7,622,271 B2  Page 1 of 1
APPLICATION NO. : 11/107542
DATED : November 24, 2009
INVENTOR(S) : Brian K. Kennedy and Matthew R. Kaeberlein It is certified that error appears in the above-identified patent and that said Letters Patent is hereby corrected as shown below:

Column 1, line 14, delete "by" insert --under U.S.--.

Column 1, line 14, delete "by Grant No. P30 AG0133280" insert --under Grants P30 AG0133280 and 2T32AG000057--.

Column 1, line 14, delete "from the" insert --awarded by--.

Column 1, line 15, after "The" insert --U.S.--.

Signed and Sealed this

Ninth Day of February, 2010

David J. Kappos
*Director of the United States Patent and Trademark Office*